US009233154B2

(12) United States Patent
Blander et al.

(10) Patent No.: US 9,233,154 B2
(45) Date of Patent: Jan. 12, 2016

(54) T-HELPER CELL TYPE 17 LINEAGE-SPECIFIC ADJUVANTS, COMPOSITIONS AND METHODS

(71) Applicant: Icahn School of Medicine at Mount Sinai, New York, NY (US)

(72) Inventors: Julie Magarian Blander, North Haven, CT (US); Miriam Torchinsky, New York, NY (US)

(73) Assignee: Icahn School of Medicine at Mount Sinai, New York, NY (US)

(*) Notice: Subject to any disclaimer, the term of this patent is extended or adjusted under 35 U.S.C. 154(b) by 0 days.

(21) Appl. No.: 14/106,477

(22) Filed: Dec. 13, 2013

(65) Prior Publication Data

US 2014/0178400 A1 Jun. 26, 2014

Related U.S. Application Data

(62) Division of application No. 13/133,817, filed as application No. PCT/US2009/067356 on Dec. 9, 2009, now Pat. No. 8,628,762.

(60) Provisional application No. 61/121,449, filed on Dec. 10, 2008.

(51) Int. Cl.

| | |
|---|---|
| ***A61K 39/39*** | (2006.01) |
| ***A61K 39/00*** | (2006.01) |
| ***A61K 39/395*** | (2006.01) |

(52) U.S. Cl.

CPC ............ *A61K 39/39* (2013.01); *A61K 39/0011* (2013.01); *A61K 39/39533* (2013.01); *A61K 2039/5154* (2013.01); *A61K 2039/5156* (2013.01); *A61K 2039/57* (2013.01)

(58) Field of Classification Search

CPC ............... C12N 5/0639; C12N 5/0636; C12N 2500/70; C12N 2500/72; C12N 2500/74; A61K 2039/5154; A61K 2039/5156; A61K 2039/5158; A61K 2039/57; A61K 39/0011; A61K 39/00; A61K 47/48815; A61K 2039/55522; A61K 38/164

See application file for complete search history.

(56) References Cited

U.S. PATENT DOCUMENTS

| | | | |
|---|---|---|---|
| 4,458,066 | A | 7/1984 | Caruthers et al. |
| 4,925,673 | A | 5/1990 | Steiner et al. |
| 5,013,556 | A | 5/1991 | Woodle et al. |
| 5,284,656 | A | 2/1994 | Platz et al. |
| 5,451,569 | A | 9/1995 | Wong et al. |
| 5,972,899 | A | 10/1999 | Zychlinsky et al. |
| 6,497,876 | B1 | 12/2002 | Maraskovsky et al. |
| 6,602,709 | B1 | 8/2003 | Albert et al. |
| 6,651,655 | B1 | 11/2003 | Licalsi et al. |
| 7,074,413 | B2 | 7/2006 | Dietzschold et al. |
| 7,988,963 | B1 | 8/2011 | Banchereau et al. |
| 8,124,067 | B2 | 2/2012 | Penninger et al. |
| 8,628,762 | B2 | 1/2014 | Blander et al. |
| 2006/0147427 | A1 | 7/2006 | Penninger et al. |
| 2006/0147456 | A1 | 7/2006 | Lebecque et al. |
| 2008/0267994 | A1 | 10/2008 | Hochrein et al. |
| 2009/0263421 | A1 | 10/2009 | Spetz-Holmgren et al. |

FOREIGN PATENT DOCUMENTS

| | | |
|---|---|---|
| WO | WO 90/01069 | 2/1990 |
| WO | WO 01/32887 | 5/2001 |
| WO | WO 2006/120439 | 11/2006 |

OTHER PUBLICATIONS

Gerosa et al., J. Exp. Med. vol. 205 No. 6 1447-1461 May 19, 2008.*

International Search Report and Written Opinion in International Application No. PCT/US2009/067356, mailed May 21, 2010, 11 pages.

Bettelli et al., "Induction and effector functions of T(H)17 cells," Nature, 2008, 453:1051-1057.

Bettelli et al., "Reciprocal developmental pathways for the generation of pathogenic effector TH17 and regulatory T cells," Nature, 2006, 441(7090):235-8.

Blachere et al., "Apopototic cells deliver processed antigen to dendritic cells for cross-presentation," PLoS Biol., 2005, 3(6):1070-1078.

Blander et al., "Regulation of Phagosome Maturation by Signals from Toll-Like Receptors," Science, 2004, 304: 1014-8.

Blander et al., "Toll-dependent selection of microbial antigens for presentation by dendritic cells," Nature, 2006, 440(7085):808-12.

Bonham et al., "Marked Prolongation of Cardiac Allograft Survival by Dendritic Cells Genetically Engineered with NF- κB Oligodeoxyribonucleotide Decoys and Adenoviral Vecotrs Enclding CTLA4-1g," J Immunol., 2002, 169(6):3382-91.

Brown et al., "Chemical Synthesis and Cloning of a Tyrosine tRNA Gene," Methods Enzymol., 1979, 68:109-51.

Cariello et al., "Fidelity of Thermococcus litoralis DNA polymerase (VentTM) in PCR determined by denaturing gradient gel electrophoresis," Nucleic Acids Res., 1991, 19(15):4193-4198.

Caserta et al., "Q-VD-OPh, a broad spectrum casepase inhibitor with potent antiapoptotic properties," Apoptosis, 2003, 8(4):345-352.

Chien et al., "Deoxyribonucleic Acid Polymerase from the Extreme Thermophile Thermus aquaticus," J Bacteriol., 1976, 127(3):1550-1557.

(Continued)

*Primary Examiner* — Daniel C Gamett

(74) *Attorney, Agent, or Firm* — Fish & Richardson P.C.

(57) ABSTRACT

The present invention relates to compositions and methods for the modulation of $T_H17$ responses. The invention provides compositions for the induction of $T_H17$ responses containing a TLR agonist and an apoptotic cell-associated agent or containing a microbe-infected apoptotic cell. The compositions of the present invention may also contain dendritic cells capable of inducing $T_H17$ responses. In other embodiments, the invention provides compositions for the inhibition of $T_H17$ responses containing one or more blocking agents. Methods and compositions for the modulation of $T_H17$ responses and for the treatment of $T_H17$-associated diseases and for cancer are also provided.

16 Claims, 26 Drawing Sheets

(56) References Cited

OTHER PUBLICATIONS

Couper et al., "IL-10: The Master Regulator of Immunity to Infection," J Immunol., 2008, 180(9):5771-7.
Crane et al., "Role of EspF in host cell death induced by enteropathogenic *Escherichia coli*," Cell Microbiol., 2001, 3(4):197-211.
Debs et al., "Lung-Specific Delivery of Cytokines Induces Sustained Pulmonary and Systemic immunomodulation in Rats," J Immunol., 1988, 140(10):3482-3488.
Deng et al., "Dissecting virulence: systematic and functional analyses of a pathogenicity island," PNAS, 2004, 101(10):3597-3602.
Dong, "TH17 cells in development: an updated view of their molecular identity and genetic programming," Nature Rev Immunol., 2008, 8(5):337-48.
Helmich et al., "The Role of Adoptively Transferred CD8 T Cells and Host Cells in the Control of the Growth of the EG7 Thymoma: Factors That Determine the Relative Effectiveness and Homing Properties of Tc1 and Tc2 Effectors," J Immunol., 2001, 166(11):6500-8.
Holmgren et al., "Mucosal immunity and vaccines," Nature Med., 2005, 11(4):S45-S53.
Hubbard et al., "Anti-Neutrophil-Elastase Defenses of the Lower Respiratory Tract in α1—Antitrypsin Deficiency Directly Augmented with an Aerosol of α1—Antitrypsin," Ann Intern Med., 1989, 111(3):206-12.
Ivanov et al., "The Orphan Nuclear Receptor RORgammat Directs the Differentiation Program of Proinflammatory IL-17+ T Helper Cells," Cell, 2006, 126:1121-1133.
Ivanov et al., "Transcriptional regulation of Th17 cell differentiation," Semin Immunol., 2007, 19:409-417.
Iwasaki et al., "Toll-like receptor control of the adaptive immune responses," Nature Immunology, 2004, 5(10):987-95.
Jinushi et al., "MFG-EB-mediated uptake of apopototic cells by APCs links the pro- and antiinflammatory activities of GM-CSF," J. Clin Invest., 2007, 117(7):1902-1913.
Johann et al., "Recognition of apoptotic cells by macrophages activates the peroxisome proliferator-activated receptor-γ and attenuates the oxidative burst," Cell Death Differ., 2006, 13(9):1533-1540.
Kamanaka et al., "Expression of lnterleukin-10 in Intestinal Lymphocytes Detected by an Interleukin-10 Reporter Knockin tiger Mouse," Immunity, 2006, 25(6):941-952.
Kang et al., "Low-dose peptide tolerance therapy of lupus generates plasmacytoid dendritic cells that cause expansion of autoantigen-specific regulatory T cells and contraction of inflammatory Th17 cells," J Immunol., Jun. 15, 2007, 178(12):7849-7858.
Kaper et al., "Pathogenic *Escherichia coli*," Nature Rev Microbiol., 2004, 2:123-140.
Karlin et al., "Applications and statistics for multiple high-scoring segments in molecular sequences," Proc. Natl. Acad. Sci., 1993, 90(12):5873-5877.
Karlin et al., "Methods for assessing the statistical significance of molecular sequence features by using general scoring schemes," Proc. Natl. Acad. Sci., 1990, 27:2264-2268.
Kawai et al., "TLR signaling," Semin Immunol., 2007, 19:24-32.
Kenny et al., "Co-ordinate regulation of distinct host cell signalling pathways by multifunctional enteropathogenic *Escherichia coli* effector molecules," Mol Microbiol., 2002, 44(4):1095-1107.
Kiyono et al., "The mucosal immune system: features of inductive and effector sites to consider in mucosal immunication and vaccine development," Reg Immunol., 1992, 4:54-62.
Kobayashi et al., "TIM-1 and TIM-4 Glycoproteins Bind Phosphalidylserine and Mediate Uptake of Apoptotic Cells," Immunity, 2007, 27:927-940.
Lecomte et al., "Selective inactivation of the 3' to 5' exonuclease activity of *Escherichia coli* DNA polymerase I by heat," Nucleic Acids Res., 1983, 11(21):7505-15.
LeibundGut-Landmann et al., "Syk- and CARD9-dependent coupling of innate immunity to the induction of T helper cells that produce interleukin 17," Nature Immunol., 2007, 8(6):630-8.
Lundberg et al., "High-fidelity amplification using a thermostable DNA polymerase isolated from Pyrococcus furiosus," Gene, 1991, 108:1-6.
Manetti et al., "Natural Killer Cell Stimulatory Factory (interleukin 12 [IL-12]) Induces T Helper Type 1 (Th1)-specific immune Responses and Inhibits the Development of IL-4-producing Th Cells," J. Exp. Med., 1993, 177:1199-1204.
Mangan et al., "Transforming growth factor-B induces development of the T(H)17 lineage," Nature, 2006, 441:231-4.
Marthinon et al., "Inflammatory Caspases: Linking an Intracellular Innate Immune System to Autoinflammatory Diseases," Cell, 2004, 117:561-574.
McGeachy et al., "TGF-B and IL-6 drive the production of IL-17 and IL-10 by Tcells and restrain Th-17 cell-mediated pathology," Nat Immunol., 2007, 8(12):1390-7.
McGhee et al., "The mucosal immune system: from fundamental concepts to vaccine development," Vaccine, 1922, 10(2):75-88.
McNamara et al., "A novel praline-rich protein, EspF, is secreted from enteropathogenic *Escherichia coli* via the type III export pathway," FEMS Microbiology Letters, 1998, 166:71-78.
McNamara et al., "Translocated EspF protein from enteropathogenic *Escherichia coli* disrupts host intestinal barrier function," J Clinical Investigation, 2001, 107(5):621-9.
Medzhitov, "Recognition of microorganisms and activation of the immune response," Nature, 2007, 449:819-26.
Miyanishi et al., "Identification of Tim4 as a phosphatidylserine receptor," Nature, 2007, 450:435-9.
Myers et al., "Reverse Transcription and DNA Amplification by a Thermus thermophilus DNA Polymerase," Biochemistry, 1991, 30(31):7661-6.
Nagai et al., "Targeting of Enteropathogenic *Escherichia coli* EspF to Host Mitochondria is Essential for Bacterial Pathogenesis," J Biol Chem., 2006, 280(4):2998-3011.
Narang et al., "Improved Phosphotriester Method for the Synthesis of Gene Fragments," Methods Enzymol., 1979, 68:90-8.
Needleman et al., "A General Method Applicable to the Search for Similarities in the Amino Acid Sequence of Two Proteins'," J. Mal. Biol., 1970, 48:443-453.
Nordstrom et al., "Characterization of Bacteriphage T7 DNA Polymerase Purified to Homogeneity by Antithioredoxin immunoadsorbent Chromatography," J Biol Chem., 1981, 256(6):3112-3117.
Nougyrede et al., "Enteropathogenic *Escherichia coli* EspF is targeted to mitochondria and is required to initiate the mitochondrial death pathway," Cell Microbiol., 2004, 6(11):1097-1111.
Nurieva et al., "Essential autocrine regulation by IL-21 in the generation of inflammatory T cells," Nature, 2007, 448:480-3.
O'Garra et al., "Differentiation of human T(H)-17 cells does require TFT-β!" Nat Immunol., 2008, 9(6):588-90.
Omura et al., "A New Alkaloid AM-2282 of Streptomyces Origin Taxonomy, Fermentation, Isolation and Preliminary Characterization," J Antibiot., 1977, 30:275-82.
O'Neill, "Therapeutic targeting of Toll-like receptors for inflammatory and infectious diseases," Current Opinion in Pharmacol., 2003, 3:396-403.
Palucka et al., "Dendritic Cells Loaded with Killed Allogeneic Melanoma Cells can Induce Objective Clinical Responses and MART-1 Specific CO8+ T-cell Immunity," J Immunother., 2006, 29(5):545-57.
Pappu et al., "TL 1A-DR3 interation regulates Th17 cell function and Th17-mediated autoimmune disease," J. Exp. Med., 2008, 205(5):1049-1062.
Patil et al., "Broad spectrum caspase inhibitor rescues retinal ganglion cells after ischemia," Neuroreport, 2004, 15(6):981-4.
Reeck et al., "Homology in Proteins and Nucleic Acids: A Terminology Muddle and a Way out of it," Cell, 1987, 50:667.
Sakaguchi, "Naturally Arising CD4+ Regulatory T Cells for Immunologic Self-Tolerance and Negative Control of Immune Responses," Ann. Rev. Immunol., 2004, 22:531-62.
Savill et al., "Apoptotic PS to Phagocyte TIM-4: Eat Me," Immunity, 2007, 27(6):830-2.
Serhan and Savill, "Resolution of inflammation: the beginning programs the end," Nat Immunol., 2005, 6(12):1191-7.

(56) References Cited

OTHER PUBLICATIONS

Stockinger et al., "Differentiation and function of Th17 T cells," Current Opinion in Immunology, 2007, 19:281-286.
Stockinger et al., "Th17 T cells: linking innate and adaptive immunity," Semin. Immunol., 2007, 19(6):353-361.
Stumhofer et al., "Interleukins 27 and 6 induce STAT3-mediated T cell production of interleukin 10," Nat Immunol., 2007, 8(12):1363-71.
Szabo et al., "A Novel Transcription Factor, T-bet, Directs Th1 Lineage Commitment," Cell, 2000, 100:655-669.
Takagi et al., "Characterization of DNA Polymerase from *Pyrococcus* sp. Strain DOD1 and Its Application to PCR," Appl Environ Microbiol., 1997, 63(11):4504-4510.
Takeda et al., "Toll-Like Receptors," Annu. Rev. lmmunol., 2003, 21:335-76.
Tesseur et al., "Highly sensitive and specific bioassay for measuring bioactive TGF-B," BMC Cell Biol., 2006, 7:15.
Uhlig et al., "Characterization of Foxp3+CD4+CD25+ and IL-10-Secreting CD4+CD25+ T Cells during Cure of Colitis," J Immunol., 2006, 177(9):5852-60.
Vallance et al., "Host Susceptibility to the Attaching and Effacing Bacterial Pathogen Citrobacter rodentium" Infect Immun., 2003, 71(6):3443-3453.
Veldhoen et al., "TGFβ in the Context of an Inflammatory Cytokine Milieu Supports De Novo Differentiation of IL-17-Producing T Cells," Immunity, 2006, 24:179-189.
Viswanathan et al., "Enteropathogenic *E. coli*-induced barrier function alteration is not a consequence of host cell apoptosis," Am J. Physiol Gastrointest Liver Physiol., 2008, 294(5):G1165-70.
Wang et al., "Toll-like receptor 3 mediates West Nile virus entry into the brain causing lethal encephalitis," Nat Med., 2004, 10(12):1366-73.
Weaver et al., "IL-17 Family Cytokines and the Expanding Diversity of Effector T Cell Lineages," Annu. Rev. lmmunol., 2007, 25:821-52.
Yang et al., "A novel systemically active caspase inhibitor attenuates the toxicities of MPTP, malonate, and 3NP in vivo," Neurobiol Dis., 2004,17(2):250-259.
Zhao et al., "Induction of anti-human lmmunodeficienty virus type 1 (HIV-1) COB(+) and CD4(+) T-cell reactivity by dendritic cells loaded with HIV-1 X4-infected apoptotic cells," J. Virol., 2002, 76(6):3007-3014.
Zheng and Rudensky, "Foxp3 in control of the regulatory T cell lineage," Nat Immunol., 2007, 8(5):457-62.
Zheng et al., "Interleukin-22 mediates early host defense against attaching and effacing bacterial pathogens," Nature Med., 2008, 14(3):282-9.

* cited by examiner

Apoptotic Neutrophils
Apoptotic B cells
apoptotic neutrophils
apoptotic neutrophils +IL-6
apoptotic neutrophils/ E.coli
apoptotic A20
apoptotic A20+IL-6
apoptotic A20/LPS blasts
IFN-γ
IL-17
Foxp3

T-HELPER CELL TYPE 17 LINEAGE-SPECIFIC ADJUVANTS, COMPOSITIONS AND METHODS

CROSS REFERENCE TO RELATED APPLICATIONS

This application is a divisional of U.S. Ser. No. 13/133,817filed Oct. 3, 2011 which is a U.S. National Phase application under 35 U.S.C. §371 of International Patent Application No. PCT/US2009/067356, filed Dec. 9, 2009, and claims the benefit of U.S. Provisional Patent Application Ser. No. 61/121,449, filed Dec. 10, 2008, all of which are hereby incorporated by reference in their entireties. The International Application published in English on Jun. 17, 2010 as WO 2010/068680 under PCT Article 21(2).

FIELD OF THE INVENTION

The present invention relates to compositions and methods for the modulation of $T_H17$ responses. The invention provides compositions for the induction of $T_H17$ responses containing a TLR agonist and an apoptotic cell-associated agent or containing a microbe-infected apoptotic cell. The compositions of the present invention may also contain dendritic cells capable of inducing $T_H17$ responses. In other embodiments, the invention provides compositions for the inhibition of $T_H17$ responses containing one or more blocking agents. Methods and compositions for the modulation of $T_H17$ responses and for the treatment of $T_H17$-associated diseases and for cancer are also provided

BACKGROUND OF THE INVENTION

The citation and/or discussion of cited references in this section and throughout the specification is provided merely to clarify the description of the present invention and is not an admission that any such references is "prior art" to the present invention.

Adaptive immune responses rely on differentiation of CD4 T helper cells into subsets with distinct effector functions best suited for host defense against an invading pathogen. Interleukin (IL)-17 producing T-helper cells ($T_H17$) are a recently identified subset, separate from the T helper type 1 ($T_H1$) and T helper type 2 ($T_H2$) subsets[1]. The $T_H17$ response is a pro-inflammatory T cell response that is associated with the release of IL-17 and IL-23 cytokines. It has been closely associated with immunity in response to TLR-activated microbial infections and has been reported in a variety of autoimmune conditions including inflammatory bowel disease, colitis, systemic sclerosis, psoriasis, rheumatoid arthritis, diabetes, and cystic fibrosis. Studies have shown that inhibitory antibodies to IL-17 or mice deficient in IL-17 responses are able to suppress or prevent the $T_H17$ response in disease models for gastrointestinal immunity, experimental autoimmune encephalitis (EAE), and rheumatoid arthritis.

Generation of $T_H17$ responses is also thought to be favored at mucosal sites for protective immunity. Importantly, mucosal sites represent a primary target for delivery of vaccines, because most infections affect or start from a mucosal surface. Moreover, often in these infections, application of a vaccine directly to the mucosal surface is required to induce an effective, protective immune response [Holmgren, J. and C. Czerkinsky, Nat Med (2005) 11(4 Suppl):S45-53], since induction of peripheral immune responses by parenteral immunization does not result in significant mucosal immunity [Kiyono, H., et al. Reg Immunol, (1992) 4(2):54-62; McGhee, J. R., et al., Vaccine, (1992) 10(2):75-88].

The effort that has been focused thus far on inducing effective immune responses in mucosal tissues has met with considerable challenge, since most protein antigens (Ags) are rather weak immunogens when given via the mucosal route. The coadministration of mucosal adjuvants, such as cholera toxin (CT), has been shown to effectively support Ag-specific mucosal immune responses, however, the inherent toxicity of cholera toxin is a major hindrance to its use in humans. Thus, the development of other, effective and reliable mucosal adjuvants, that preferably induce $T_H17$ responses, is of central importance for new generation vaccines [McGhee, J. R., et al. Vaccine (1992) 10(2)75-88]. However, it is important to recognize that tight regulation of these $T_H17$ responses must also be achieved, since $T_H17$ responses are also associated with driving a number of autoimmune diseases. Thus, it is critical that the factors that govern differentiation of $T_H17$ cells in vitro be better understood, so that $T_H17$ responses may be carefully regulated.

SUMMARY OF THE INVENTION

In certain embodiments of the present invention, a microbe-infected apoptotic cell that expresses an exogenous immune antigen is provided.

In other embodiments of the present invention an isolated $T_H17$-inducing dendritic cell (DC) that secretes interleukin-6 (IL-6) and transforming growth factor beta (TGF-β), is provided, wherein the combined amount of IL-6 and TGF-β is effective for inducting a $T_H17$ response. In certain embodiments, the present invention provides an isolated $T_H17$-inducing dendritic cell (DC) wherein, the $T_H17$-inducing DC is loaded with an apoptotic cell which includes a TLR ligand or an inactivated microbe, and wherein the microbe expresses an exogenous immune antigen. In still other embodiments, the present invention provides a composition including a $T_H17$-inducing dendritic cell (DC) and interleukin-6, wherein the DC is loaded with an apoptotic cell, and wherein the apoptotic cell expresses an exogenous immune antigen.

In certain aspects of the present invention, a method for inducing a $T_H17$ response in a mammal is provided, which involves administering to a mammal in need of such induction a microbe-infected apoptotic cell of the invention is an effective amount for inducing the $T_H17$ response.

In other aspects, the present invention provides a method for inducing a $T_H17$ response in a mammal, which involves administering to a mammal in need of such induction a $T_H17$-inducing DC of the invention in an effective amount for inducing the $T_H17$ response. In certain aspects, the method further involves administering to a DC in vitro a microbe-infected apoptotic cell in an effective amount for generating a $T_H17$-inducing DC of the invention. In yet other aspects, the microbe-infected apoptotic cell expresses an exogenous immune antigen.

In certain embodiments, a method for generating the $T_H17$-inducing DC of the invention involves administering to a DC in vitro a Toll-like receptor (TLR) agonist and an apoptotic cell-associated agent in a combined amount effective for generating the $T_H17$-inducing DC. In some embodiments, the TLR agonist and the apoptotic cell-associated agent are either in direct physical association or are combined in a manner that allows internalization as a single entity by the DC in vitro. In still other embodiments of the invention, methods of generating a TH17-inducing DC involve administering to a DC in vitro, as a single entity or in a combined form, at least one member selected from the group consisting of a Toll-like receptor (TLR) ligand, a TLR ligand mimic, a synthetic or chemical TLR ligand, a cell or particle including a pathogen-associated molecular pattern, a microbial pathogen, a TLR agonist, a bacterium, and a virus or viral-like particle, and at least one member selected from the group consisting of an apoptotic cell, a microbe-infected apoptotic cell, an apoptotic cell mimic, phosphatidylserine, a phosphatidylserine mimic, an apoptotic cell-associated agent, a mimic of cell surface calreticulin translocation, and a polypeptide that is a marker of apoptosis, in a combined amount effective for generating the $T_H17$-inducing DC.

In certain aspects of the present invention, a vaccine composition is provided which includes: a) a microbe-infected apoptotic cell, b) an immune antigen, and c) a pharmaceutically acceptable carrier or diluent, wherein the combined amount of a) and b) is effective for eliciting an immune response directed toward the immune antigen. In some aspects, the microbe-infected apoptotic cell expresses the immune antigen, and the immune antigen is an exogenous immune antigen.

In some embodiments of the present invention, a vaccine composition is provided that includes: a) a $T_H17$-inducing dendritic cell (DC) that secretes interleukin-6 (IL-6) and transforming growth factor beta isoform 1 (TGF-62 ), b) an immune antigen, and c) a pharmaceutically acceptable carrier or diluent, wherein a combined amount of IL-6 and TGF-β secreted by the DC and the immune antigen is effective for eliciting a $T_H17$ response to the immune antigen. In certain embodiments, methods for generating the $T_H17$-inducing DC include pre-treating a DC in vitro with a Toll-like receptor (TLR) agonist and an apoptotic cell-associated agent in a combined amount effective for generating the $T_H17$-inducing DC. In other embodiments, the TLR agonist and the apoptotic cell-associated agent are combined in a manner that allows internalization as a single entity by the DC in vitro. In still other embodiments, the DC is treated with the apoptotic cell-associated agent and administered with recombinant interleukin-6 (IL-6). In yet other embodiments, the $T_H17$-inducing DC is pre-treated in vitro with the immune antigen or with a peptide fragment derived from the immune antigen.

In certain embodiments, vaccine compositions provided by the present invention further include a microbe-infected apoptotic cell, and a combined amount of the microbe-infected apoptotic cell, a) and b) is effective for eliciting an immune response.

In certain aspects of the present invention, methods for treating of preventing cancer in a mammal are provided, which involve administering to a mammal in need of such treatment a vaccine composition of the invention in an effective amount for treating or preventing cancer, wherein the antigen is a tumor-specific antigen. In some aspects, the cancer is an epithelial or mixed epithelial carcinoma. In certain of these aspects, the epithelial or mixed epithelial carcinoma is a member selected from the group consisting of ovarian cancer, breast cancer, pancreatic cancer, lung carcinoma, laryngeal carcinoma, adenoid cystic carcinoma, epithelial carcinomas of the upper aerodigestive tract, hepatocellular carcinoma, colorectal carcinoma, lymphoepithelial carcinoma, squamous cell carcinoma, renal cell carcinoma, mixed epithelial and stromal tumors of the kidney, and renal angiomyoadenomatous tumors.

In other aspects, the present invention provides a method for inducing in a patient a $T_H17$-driven immune response to an antigen, which involves administering to a patient in need of such treatment the vaccine composition according to certain of the above aspects of the present invention in an effective amount for inducing a $T_H17$-driven immune response.

In certain aspects of the present invention, a method is provided for modulating an immune response of a mammal, which involves administering to a mammal in need of such treatment a vaccine composition according to certain of the above aspects of the present invention in an effective amount for modulating the immune response of the mammal.

In some embodiments of the present invention, a method for inhibiting a $T_H17$ response in a mammal is provided, which involves administering to a mammal in need of such treatment a blocking agent that inhibits immune recognition of an apoptotic cell-associated agent in an effective amount for inhibiting the $T_H17$ response in the mammal. In yet other embodiments, a method for inhibiting a $T_H17$ response in a mammal, involves administering to a mammal in need of such treatment a blocking agent that inhibits immune recognition of a Toll-like receptor (TLR) adjuvant in an effective amount for inhibiting the $T_H17$ response in the mammal.

In certain embodiments of the invention, a method for inducing regulatory T cell development and immune tolerance in a mammal is provided, which involves administering to a mammal in need of such treatment a blocking agent that inhibits immune recognition of a Toll-like receptor (TLR) ligand in an effective amount for inducing the regulatory T cell development and immune tolerance in the mammal, wherein the TLR ligand is a component of an infected apoptotic cell.

In yet other embodiments, a method for inducing immune tolerance in a mammal is provided, which involves administering to a mammal in need of such treatment an apoptotic cell-associated agent in an effective amount for inducing regulatory T cell development and immune tolerance in the mammal. In still other embodiments, a method for inducing immune tolerance in a mammal is provided, which involves administering to a mammal in need of such treatment a blocking agent that inhibits immune recognition of a Toll-like receptor (TLR) adjuvant in an effect amount for inducing immune tolerance in the mammal.

In certain aspects, the present invention provides a methods for inducing immune tolerance in a mammal, which involves administering to a mammal in need of such treatment a blocking agent that inhibits immune recognition of a Toll-like receptor (TLR) adjuvant or blocks TLR signal transduction in an effective amount for inducing immune tolerance in the mammal.

In one embodiment of the present invention, a composition is provided having a first blocking agent that inhibits immune recognition of an apoptotic cell-associated agent, and a second blocking agent that inhibits immune recognition of a Toll-like receptor (TLR) adjuvant.

In yet other embodiments, a pharmaceutical formulation is provided including a first clocking agent that inhibits immune recognition of an apoptotic cell-associated agent, and a second clocking agent that inhibits immune recognition of a Toll-like receptor (TLR) adjuvant, and pharmaceutically acceptable diluent or carrier. In certain of these embodiments, the first blocking agent specifically inhibits dendritic-cell-mediated immune recognition of the apoptotic cell-associated agent. In other embodiments, the second blocking agent specifically inhibits dendritic-cell-mediated immune recognition of the TLR adjuvant.

The present invention provides in some embodiments, a method for the treatment of a $T_H17$-driven disease or condition in a mammal, which involves administering to a mammal in need of such treatment a pharmaceutical formulation of the invention in an effective amount for treating the $T_H17$-driven disease or condition, wherein the disease or condition is a member selected from the group consisting of inflammatory bowel disease. Crohn's disease, colitis, systemic sclerosis (scleroderma), atopic dermatitis, psoriasis, rheumatoid arthritis, diabetes, cystic fibrosis, allergic airway disease, atopic asthma, allergic asthma, Sjogren's Syndrome, and systemic lupus erythematosus.

In certain aspects, the invention provides a vaccine composition including: a) a first quantity of a blocking agent which inhibits immune recognition of an apoptotic cell-associated agent, b) a second quantity of a blocking agent which inhibits immune recognition of Toll-like receptor (TLR) adjuvant, c) a third quantity of an immune antigen, and d) a pharmaceutically acceptable carrier or diluent, wherein the combined quantities of a), b) and c) are effective for inhibiting a $T_H17$ response. In certain aspects, the combined quantities of a), b) and c) are effective for inducing a T regulatory cell response. In other aspects, the immune antigen is a rumor-specific antigen.

The present invention provides, in certain embodiments, a method for treating or preventing cancer in a subject, which involves administering to a subject in need of such treatment a vaccine composition of the present invention in an effective amount for treating or preventing cancer, wherein the antigen is a tumor-specific antigen. In certain of these embodiments, the subject is a human or mammal. In other aspects, the human is a patient. In other aspects, the cancer is a member selected from the group consisting of Hodgkin lymphoma, follicular lymphoma, multiple myeloma, monoclonal gammopathy and T cell leukemia/lymphoma.

In some aspect of the invention, a method for treatment of $T_H17$-driven disease or condition is provided, which involves administering to a mammal in need of such treatment a vaccine composition according to the present invention in a effective amount for treating a $T_H17$-driven disease that is a member selected from the group consisting of inflammatory bowel disease, Crohn's disease, colitis, systemic sclerosis (scleroderma), atopic dermatitis, psoriasis, rheumatoid arthritis, diabetes, cystic fibrosis, allergic airway disease, atopic asthma, allergic asthma, Sjogren's Syndrome, and systemic lupus erythematosus.

In any of the above embodiments of the invention, the apoptotic cell-associated agent includes any one of the agents selected from the group consisting of an apoptotic cell, an apoptotic cell mimic, phosphatidylserine, a microbe-infected apoptotic cell, a phosphatidylserine mimic, a mimic of cell surface calreticulin translocation, and a polypeptide that is a marker of apoptosis.

In any of the above embodiments of the invention, the TLR adjuvant includes any one of the agents selected from the group consisting of a TLR ligand, a TLR ligand mimic, a synthetic or chemical TLR ligand, a cell or particle including a pathogen-associated molecular pattern, a microbial pathogen, a bacterium, and a virus or viral particle.

In any of the above aspects of the invention, the mammal may be a human and a patient may be a human.

In any of the above embodiments of the invention, a microbe may be selected from the group consisting of attenuated live *Mycobacterium bovis, Salmonella typhi*, and *Vibrio cholerae.*

In any of the above embodiments of the invention, the vaccine composition is delivered by an oral or mucosal route.

In any of the above aspects of the invention, the $T_H17$ or immune response is a mucosal immune response.

DETAILED DESCRIPTION

Figure 1:
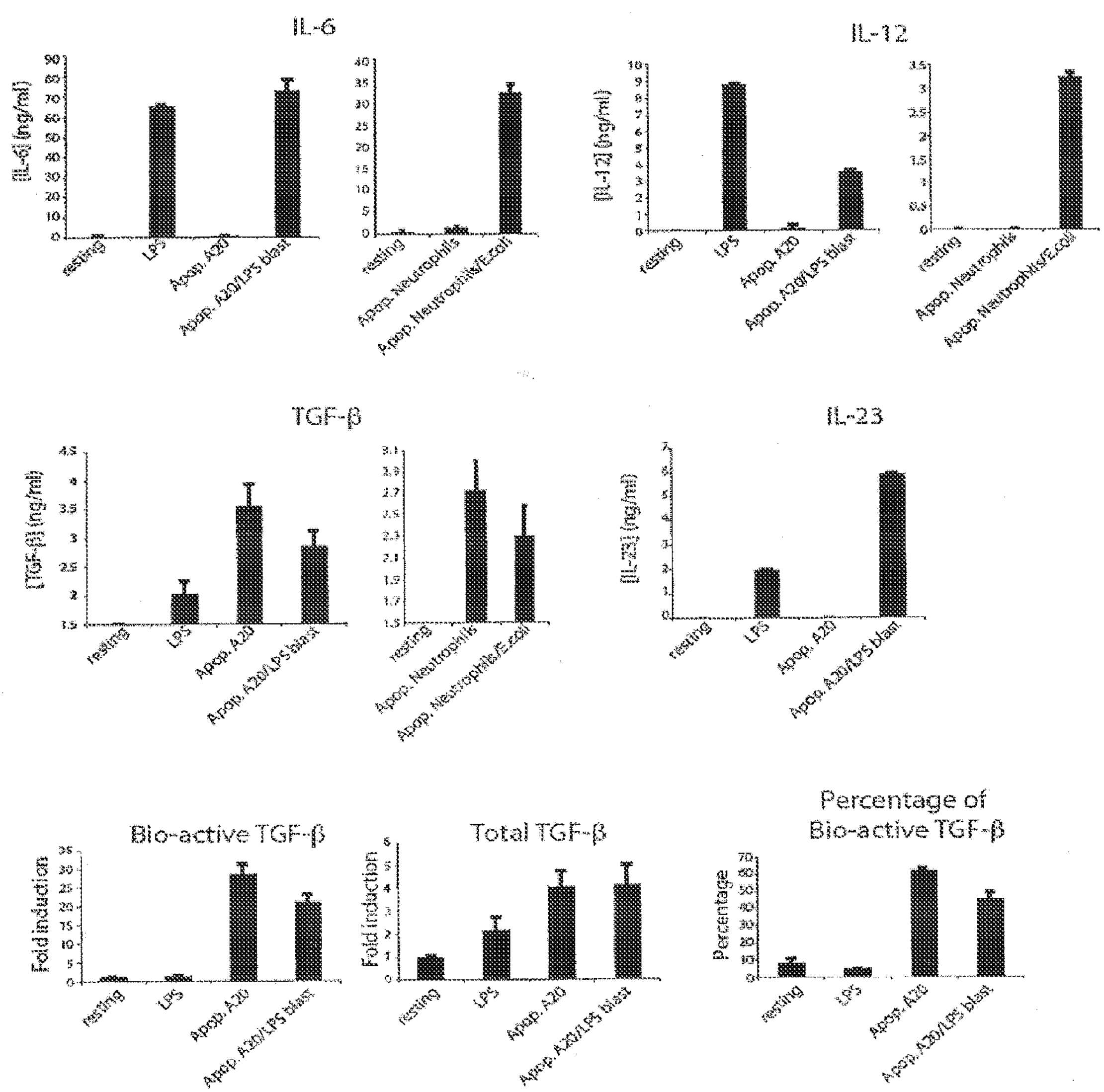
FIG. 1 shows protein levels of cytokines produced by bone marrow dendritic cells following in vitro stimulation with LPS, apoptotic A20/LPS blasts, or apoptotic neutrophils/*E. coli.*

The present invention relates to the surprising discovery of naturally-occurring, specific combination of immune adjuvants that induces a $T_H17$ response in vitro and in vivo. More specifically, the present invention provides methods for regulating $T_H17$ responses based on this discovery. In certain embodiments, the compositions of the present invention are useful for inducing $T_H17$ responses. In other embodiments, the compositions of the invention are useful for inhibiting $T_H17$ responses and for inducing immune tolerance.

Also provided by the present invention are pharmaceutical formulations and vaccine compositions useful for modulating $T_H17$ responses.

Characteristics of CD4 T Cell Subsets

CD4 T cells upon activation and expansion develop into different T helper ($T_H$) cell subsets with different cytokines profiles and distinct effector functions. Appropriate differentiation of $T_H$ into effector subsets best suited for host defense against an invading pathogen is of critical importance to the immune system. CD4 T cells differentiate into at least four known subsets, three effector subsets ($T_H1$, $T_H2$ and $T_H17$) and one T regulatory subset ($T_{reg}$).

Based on the cytokines that they produce, T cells were historically divided into $T_H1$ and $T_H2$ cells, and this has provided a framework to understand how specific cytokine milieus produced by cells of the innate immune system guide the development of adaptive immunity. $T_H1$ cells, which are potently induced by dendritic cells (DC) secreting IL-12, are characterized by the expression of the lineage-specific transcription factor T-bet (T box 21) and the production of IFN-γ. $T_H2$ cells, which depends on IL-4 during differentiation and lack of IL-12, produce IL-4, IL-5, IL-9, and IL-13 and are characterized by the expression of the transcription factor GATA-3. Importantly, in the past five years, a third subset of IL-17-producing effector T helper cells, called $T_H17$ cells, has been discovered and characterized.

$T_H17$ cells produce IL-17, IL-17F and IL-22. By secreting these effector cytokines, $T_H17$ cells induce a massive tissue reaction due to the broad distribution of the IL-17 and IL-22 receptors. $T_H17$ cells also secrete IL-21 to communicate with the cells of the immune system. Synergy between the cytokines transforming growth factor beta isoform 1 (TGF-β) and interleukin (IL)-6 induces development of $T_H17$ cells in mice[10-12] and humans[13], while IL-23 supports expansion of these cells[10-12]. IL-23 consists of two subunits, the p19 subunit and the p35 subunit. The p35 subunit is also used by IL-12, which is a heterodimer consisting of the p35 and the p40 subunit. The differentiation factors (TGF-βplus IL-6 or IL-21), the growth and stabilization factor (IL-23), and the transcription factors (STAT3, ROR-γt (ROR-c), and ROR-a) involved in the development of $T_H17$ cells have only recently been identified. The participation of TGF-β in the differentiation of $T_H17$ cells places the $T_H17$ lineage in close relationship with CD4$^+$ CD25$^+$ Foxp3$^+$ regulatory T cells ($T_{reg}$) since TGF-β also induces differentiation of naive T cells in Foxp3$^+$ $T_{reg}$ in the peripheral immune compartment. The investigation of the differentiation, effector function, and regulation of $T_H17$ cells has opened up a new framework for understanding T cell differentiation. While the important of $T_H17$ cells in clearing pathogens during host defense reaction and in inducing tissue inflammations in autoimmune disease has been appreciated [Reviewed in Kota, T. et al. (2009) Annual Review of Immunology, 27:485-517], the exact nature of the stimuli that induce their differentiation in vivo is not known.

$T_{reg}$ cells are specialized subpopulation of T cells that act to suppress motivation of the immune system and thereby maintain immune system homeostasis and tolerance to self-antigens. Development of $T_{reg}$ cells, which are capable of suppressing autoimmune disease, is therefore reciprocally related to $T_H17$ cells,[10] which can drive immune responses, including autoimmune responses. $T_{reg}$ cells can be identified by their unique expression of the transcription factor forkhead box P3 (Foxp3).[19] Importantly, there are two phenotypically identical populations of CD4$^+$CD25$^+$ $T_{reg}$—natural and adaptive. Natural CD4$^+$CD25$^+$ $T_{reg}$ cells arise in the thymus under homeostatic conditions to safeguard against autoimmunity. Adaptive CD4$^+$CD25$^+$ $T_{reg}$ cells arise during inflammatory processes such as infections and cancers and suppress immunity through heterogeneous mechanisms that include direct contact or the production of soluble factors such as IL-10 and TGF-β.

$T_{reg}$ cells are thought to be involved in cancer. The tumor itself and cells in the tumor microenvironment, such as DC, induce the differentiation of $T_{reg}$ cells through various mechanisms including the production of TGF-β and the expression of the costimulatory molecule B7-H1. At least some tumor-associated $T_{reg}$ cells are specific for tumor antigens, although once activated, they can also suppress tumor antigen-independent immune responses through bystander mechanisms. It has been demonstrated that $T_{reg}$ cells actively accumulate in the human ovarian cancer microenvironment, inhibiting tumor-specific cytotoxicity and cytokine production by tumor-specific $CD8^+$ T cells in vitro and in vivo. Importantly, certain studies have shown that the number of $CD4^+CD25^+$ $Foxp3^+$ T cells correlates inversely with clinical outcomes in several epithelial carcinomas, including ovarian cancer, breast cancer, and hepatocellular carcinoma. [Curiel et al. (2007) Clin Invest. 117(5):1167-1174]. In one study, there was an inverse correlation between the number of $T_{reg}$ cells in the tumor and patient survival, which was corroborated independently by the demonstration that high levels of Foxp3 in the tumor microenvironment predicted reduced survival in patients with ovarian cancer. Thus, in ovarian cancer, for example, it would be useful to be able to inhibit development of $T_{reg}$ responses, for example, through the induction of $T_H17$ responses. The present invention provides such methods.

While the presence of $T_{reg}$ cells is thought to be harmful in some cancers, as discussed above, in others it may be helpful. For example, the situation in hematologic malignancies differs. Increased numbers of tumor-infiltrating $Foxp3^+$ T cells predicts improved survival in individuals with follicular lymphoma, and reduced numbers of $Foxp3^+$ cells predicts poor survival in individuals with Hodgkin lymphoma. Both the number and the functions of $Foxp3^+$ $T_{reg}$ cells was reduced in patients with multiple myeloma or monoclonal gammopathy of uncertain significance, and $T_{reg}$ cell function decreased as tumor burden increased in a small series of patients with cutaneous T cell leukemia/lymphoma. Therefore, it is possible that the effects of $T_{reg}$ cells or the differentiation of $Foxp3^+$ cells in functional $T_{reg}$ cells fundamentally differs in lymphoid malignancies compared with epithelial carcinomas. These studies indicate that in certain circumstances, it would be useful to be able to induce $T_{reg}$ cell responses, likely through the modulation of $T_H17$ responses, in order to treat cancer. The present invention provides such methods.

In certain embodiments, the epithelial or mixed epithelial carcinomas that may be treated by methods of the present invention include ovarian cancer, breast cancer, pancreatic cancer, lung carcinoma, laryngeal carcinoma, adenoid cystic carcinoma, epithelial carcinomas of the upper aerodigestive tract, hepatocellular carcinoma, colorectal carcinoma, lymphoepithelial carcinoma, squamous cell carcinoma, renal cell carcinoma, mixed epithelial and stromal tumors of the kidney, and renal angiomyoadenomatous tumors.

Generation of $T_H17$ Cells $T_H17$ cells have been known to be induced in vitro by TGF-β and IL6[1-5]. However, it was not known what conditions in vivo would induce this combination of cytokines. Furthermore, it is enigmatic that a combination of pro-inflammatory and anti-inflammatory cytokines would be required to generate an effector $T_H17$ response. The present invention shows that the relevant physiological stimulus triggering this combination of $T_H17$-inducing cytokines is the recognition and phagocytosis of infected apoptotic cells by DC. Phagocytosis of infected apoptotic cells uniquely triggers the combination of IL-6 and TGF-β through recognition of a pathogen associated molecular pattern (PAMP) (e.g., Toll-like receptor (TLR) ligands)[6] and an apoptotic-cell associated agent (such as, e.g., phosphatidylserine exposed on apoptotic cells[7]), respectively. Conversely, phagocytosis of apoptotic cells in the absence of microbial signals induces differentiation of the closely related regulatory T-cells ($T_{reg}$), which are important for controlling autoimmunity[8].

A surprising discovery of the present invention was that the TLR ligand (or other PAMP) and the apoptotic-cell associated agent must be associated as a single entity (e.g., as a microbe-infected apoptotic cell) in order to generate a $T_H17$-inducing DC. Coadministration of the TLR ligand and apoptotic cell-associated agent did not generate a $T_H17$-inducing DC. Moreover, blocking apoptosis during infection of the intestinal epithelium with the rodent pathogen *Citrobacter rodentium*[9], impaired the characteristic $T_H17$ response in the lamina propria. The results of the present disclosure demonstrate that infected apoptotic cells are a critical component of the innate immune signals instruction $T_H17$ differentiation, and point to pathogens particularly adept at triggering apoptosis that might preferentially induce $T_H17$-mediated immunity.

The coding sequences and amino acid sequences for human and murine IL-6, IL-10, IL-12 p35 and p40 subunits, IL-22, IL-23a p19 subunit, TGF-β1, Foxp3, TNFsf15, IL-17A, IL-17F, Tbet (TBX21), Ror-c (Ror-γt), β-actin, and HPRT are known and have been described. The coding sequences are set forth in the sequence identifiers as follows: hIL-6 (NM_000600) (SEQ ID No: 1), mIL6 (NM_031168) (SEQ ID NO: 2), hIL10 (NM_000572) (SEQ ID NO: 3), mIL10 (NM_010548) (SEQ ID NO: 4), hIL-12a(p35 subunit) (NM_000882) (SEQ ID NO: 5), hIL-12b (p40 subunit) (NM_002187) (SEQ ID NO: 6), mIL-12a p35 subunit (NM_008351) (SEQ ID NO: 7), mIL-12b p40 subunit (NM_008352) (SEQ ID NO: 8), hIL-22 (NM_020525) (SEQ ID NO: 9), mIL-22 (NM_016971) (SEQ ID NO: 10), hIL-23a p19 subunit (NM_016584) (SEQ ID NO: 11), mIL-23a p19 subunit (NM_031252) (SEQ ID NO: 12), hTGFβ (NM_000660) (SEQ ID NO: 13), mTGFβ (NM_011577) (SEQ ID NO: 14), hFoxp3 (NM_014009) (SEQ ID NO: 15), mFoxp3 (NM_054039) (SEQ ID NO: 16), hTMFsf15 (NM_005118) (SEQ ID NO: 17), nTNFsf15 (NM_177371) (SEQ ID NO: 18), hIL-17A (NM_002190) (SEQ ID NO: 19), mIL-17A (NM_010552) (SEQ ID NO: 20), hIL-17F (NM_052872) (SEQ ID NO: 23), mIL-17F (NM_145856) (SEQ ID NO: 24), hTbet (TBX21) (NM_013351) (SEQ ID NO: 25), mTbet (Tbx21) (NM_019507) (SEQ ID NO: 26), hRORc (NM_005060) (SEQ ID NO: 27), mRORc (NM_011281) (SEQ ID NO: 28), hHPRT (NM_000194) (SEQ ID NO: 29), mHPRT (NM_013556) SEQ ID NO: 30), hβ-actin (NM_001101) (SEQ ID NO: 31), and mβ-actin (NM_007393) (SEQ ID NO: 32).

The amino acid sequences are set forth in the sequence identifiers as follows: hIL-6 (NP_000591) (SEQ ID NO: 33), mIL6 (NP_112445) (SEQ ID NO: 34), hIL10 (NP_000563) (SEQ ID NO: 35), mIL10 (NP_034678) (SEQ ID NO: 36), hIL-12a(p35 subunit) (NP_00873) (SEQ ID NO: 37), hIL-12b (p40 subunit) (NP_002178) (SEQ ID NO: 38), mIL-12a p35 subunit (NP_032377) (SEQ ID NO: 39), mIL-12b p40 subunit (NP_032378) (SEQ ID NO: 40), hIL-22 (NP_065386) (SEQ ID NO: 41), mIL-22 (NP_058667) (SEQ ID NO: 42), hIL-23a p19 subunit (NP_057668) (SEQ IS NO: 92), mIL-23a p19 subunit (NP_112542) (SEQ ID NO: 93), hTGFβ (NP_000651) (SEQ ID NO: 43), mTGFβ (NP_035707) (SEQ ID NO: 44), hFox3 (NP_054728) (SEQ ID NO: 45), mFoxp3 (NP_473380) (SEQ ID NO: 46), hTNFsf15 (NP_005109) (SEQ ID NO: 47), mTNFsf15 (NP_796345) (SEQ ID NO: 48), hIL-17A (NP_002181) (SE ID NO: 49), mIL-17A (NP_034682) (SEQ ID NO: 50), hIL-17F (NP_443104) (SEQ ID NO: 51), mIL-17F (NP_665855) (SEQ ID NO: 52, hTbet (TBX21) (NP_037483) (SEQ ID NO: 53), mTbet (Tbx21) (NP_062380) (SEQ ID NO: 54), hRORc (RORγτ) (NP_005051) (SEQ ID NO: 55), mRORc (RORγτ) (NP_035411) (SEQ ID NO: 56), hHPRT (NP_000185) (SEQ ID NO: 57), mHPRT (NP_038584) (SEQ ID NO: 58), hβ-actin (NP_001092) (SEQ ID NO: 59), and mβ-actin (NP_031419) (SEQ ID NO: 60).

Compositions and Methods for Inducing a $T_H17$ Response in a Mammal

In certain embodiments, the invention relates to compositions for inducing $T_H17$ responses which include a Toll-like receptor (TLR) agonist. The innate immune system in mammals senses the invasion of microorganisms using pattern recognition receptors (PRRs), such as the family of TLRs, which recognize conserved microbial components, termed pathogen-associated molecular patterns (PAMPs). Activation of TLRs leads to the induction of inflammatory responses and the development of antigen-specific adaptive immunity. [Reviewed in Takeda, K. et al. (2003) Annual Review of Immunology, 21:335-376]. TLRs are characterized by an extracellular domain composed of leucine-rich-repeat motifs for ligand binding as well as an IL-1 receptor domain (termed TIR domain). TLR intracellular domains specifically recruit several adaptor proteins including MyD88, TRIF, TIRAP/MAL, TOLLIP, and/or TRAM for downstream signaling. These adaptor proteins subsequently associate with a family of IL-1 receptor associated kinases (IRAK1, 2, M, and 4). Recruitment of numerous downstream signaling proteins lends to activation of a range of transcription factor such as NF-κB, AP-1, and IRFs, which are responsible for specific gene transcription, including the genes for pro-inflammatory cytokines including IL-6, IL-10, IL-17, and TGF-β. Despite significant domain conservation, distinct TLRs or combinations of TLR heterodimers induce gene programs that lead not only to the robust production of general proinflammatory mediators but also to the production of unique effectors, which provide pathogen-tailored immune responses.

Biochemical studies and genetic analyses using transgenic mice have revealed specific ligands for the activation of TLRs. Of the 11 TLRs described, the ligands for 10 of the receptors have been identified. TLR1, TLR2, TLR4 and TLR6 (both as heterodimers and homodimers) recognize different microbial structures, whereas TLR3 recognizes viral double stranded RNA (dsRNA). TLR5 recognizes Flagellin, a protein found in the flagella of gram-negative bacteria. TLR7 and 8 recognize endosomal single-stranded RNA (ssRNA) to detect infection by virus, and TLR9 detects unmethylated CpG motifs, characteristics of bacterial DNA. TLR11, present in mice, but not humans, senses the profilin-like proteins from the protozoan parasite *Toxoplasma gondii* and also recognizes uropathogenic *E. coli*.

In certain embodiments of the invention, the requirement for TLR signaling for the generation of a response to an antigen or microbial pathogen or product is tested in vivo using genetically engineered "knockout" mice. For example, TLR4 knockout ($TLR4^{-/-}$) mice are homozygous null for the full-length TLR4 gene. Accordingly, these mice do not express functional TLR4 protein and therefore cannot detect TLR4 ligands, such as, e.g., lipopolysaccharide (LPS) through TLR4. In other knockout mice, adaptor molecules that are downstream of TLRs in the signaling pathway are targeted for deletion. For example, $MyD88^{-/-}$ mice do not express the MyD88 adaptor protein, and are deficient in most TLR signaling pathways. It has been discovered the some TLRs do not depend entirely, or at all, on MyD88, however, because the signal is transmitted through another adaptor molecule, TRIF. Thus, $TRIF^{31\,/-}$ mice have been generated to determine which TLRs depend on TRIF for signaling (such as, e.g., TLR3). It has also been shown that when $MyD88^{-/-}$ $TRIF^{-/-}$ double knockout mice are used (i.e., they express neither functional MyD88 nor TRIF proteins), all TLR signaling is completely abrogated. [See, Kawai T and Akira S. (2007) Semin Immunol; 19:24-32; Medzhitov R. (2007) Nature; 449:819-26].

TLRs are expressed on a wide variety of cells in mammals, including on cells of the innate (such as antigen-presenting cells (APC)) and adaptive immune systems. The DC is an APC that is of critical importance for the initiation of adaptive immune responses. DC reside systemically, in lymph nodes, and in tissues, where they are poised for early detection of microbial invasion, and to signal the invasion to the adaptive arm of the immune system (i.e., to T and B cells). However, DC reside in an immature state, and in this state they are unable to stimulate T cell activation. It is through recognition of microbial pathogens or products by PRRs (especially TLRs), expressed on their cell surface or intracellularly, that activation of these cells is facilitated (upon, e.g., phagocytosis of the invading pathogen or an associated antigens). Phagocytosis of apoptotic cells by DC is described in detail in Blander, J. M. and Medzhitov., R, Science (2004) 304 (5673): 1014.

Upon TLR ligation, DC undergo a program of maturation whereby they upregulate costimulatory molecules (e.g., CD80, CD86, CD40 and major histocompatibility complex (MHC) type I and type II molecules), which are critical for T cell activation, and they migrate to the draining lymph node associated with the assaulted tissue. In the draining lymph node, the mature DC present peptides from the phagocytosed pathogen in the context of surface MHC molecules to naïve T cells in the draining lymph node, leading to T cell activation. "Naïve T cells" are T cells which have never encountered the antigen for which their unique T cell receptor is specific.

Importantly, in the draining lymph nodes, mature DC secrete cytokines that regulate naïve CD4 T cell activation and differentiation into effector subsets. For example, in response to TLR ligation, DC express the cytokine IL-6, a pro-inflammatory cytokine that is critical for T cell activation. Moreover, DC are known to secrete IL-12 in response to certain TLR4 ligands, such as LPS. IL-12 is pro-$T_H1$ cytokine, and culture of naïve CD4 TA cells with IL-12 and APC leads to their differentiation in vitro into $T_H1$ effector cells. [See, Manetti R, et al. (1993) J Exp Med; April 1; 177(4): 1199-204.] DC are also capable of secreting other cytokines, including TGF-β, IL-10, and IL-23, in response to specific stimuli.

In certain embodiments of the invention, the mRNA expression of cytokines and other genes is quantified. For the isolation of RNA, any suitable means known in the art may be used. This includes phenol-chloroform extraction followed by ethanol or 2-propanol precipitation. Certain commercial reagents, such as TRIzol® reagent are well known in the art and may be used according to the manufacturer's instructions for the isolation of RNA.

The present invention, in certain aspects, provides methods for inducing DCs to secrete specific combinations of cytokines, either in vitro or in vivo, based on the discovery of certain stimuli that are capable of inducing such combinations. These stimuli include TLR agonists in combination with apoptotic cells or apoptotic-cell associated agents.

"TLR agonist" or "TLR adjuvant" is understood to mean a natural TLR ligand, a TLR ligand mimic, a synthetic or chemical TLR ligand, a cell or particle including a pathogen-associated molecular pattern, a microbial pathogen, a bacterium, and a virus or viral and viral-like particle. Moreover, it is well known in the art that TLRs may be expressed on the cell surface, or intracellularly, such as, e.g., in endosomes. Moreover, TLRs may function as heterodimers (e.g., as a TLR1/2 and TLR2/6 heterodimers) or as homodimers (e.g., as a TLR4/4 homodimer). TLRs may also function as monomers.

TLR agonists may be synthetic, chemical or nature ligands of TLRs. TLR agonists include, but are not limited to, Pam3CysSerLys4(CSK4) (for TLR1/2); Lipoarabinomannan, LPS *P.gingivalis* as well as LPS from Gram-positive bacteria, peptidoglycan (PGN) (e.g., from *S.aureus*), beat killed forms of microbial pathogens such as *Listeria monocytogenes* (HKLM), lipteichoic acid (LTA) (e.g., from *S.aureus*), triacylated bacterial lipopeptides (for TLR1/2), diacylated lipopeptides (for TLR2/6), and Malp-2 (for TLR2); Poly(I:C) and dsRNA (for TLR3); LPS (from Gram-negative bacteria such as *E. coli*) Monophosphoryl lipid A (MPLAp), heat shock protein (HSP) 60, and extra domain A of fibronectin (EDA) (for TLR4); Flagellin (for TLR5); FSL-1 (for TLR2/6); Imiquimod, Loxoribine, Gardiquimod™, and *E.coli* RNA/LyoVec (for TLR7); ssRNA, polyU, PolyU/LyoVec, Gardiquimod™, and *E.coli* RNA/LyoVec (for TLR8); CpG oligodeoxynucleotides (ODN) (for TLR9); and profilin from *T. gandii* and uropathogenic *E. coli* (for TLR11).

In certain embodiments, the invention relates to compositions for inducing $T_H17$ responses which include an apoptotic cell or apoptotic cell-associated agent. Apoptosis is an active process of cell suicide involving the action of a number of caspase proteins that leads to ordered destruction of the cells and their safe disposal by professional (macrophages and immature DC) and in some cases nonprofessional (such as fibroblasts and epithelial cells) phagocytes. The removal of apoptotic cells in the final step and perhaps the ultimate objective of the apoptotic programs. Apoptosis is a ubiquitous process and plays a key role in many fundamental biological events, including embryonic development, normal tissue homeostasis, development of the immune system and resolution of inflammation. In addition, apoptotic cells are a potential source of self-antigens, and defective clearance of cell corpses has recently been implicated in the pathogenesis of autoimmune disease [Botto et al. (2004) Arthritis Res Ther; 6:147-150].

Dying, apoptotic cells can provide specific signals that enable recruitment and recognition by phagocytes (e.g., DC). Apoptosis is characterized by a variety of morphological feathers such as loss of membrane asymmetry and attachment, condensation of the cytoplasm and nucleus, and internucleosomal cleavage of DNA. One of the earliest indications of apoptosis is the translocation of the membrane phospholipid phosphatidylserine from the inner to the outer leaflet of the plasma membrane. Phosphatidylserine is a key apoptosis mediator. Receptors for phosphatidyl serine continue to be discovered, however, they include the phosphatidylserine receptor as well as Tim proteins, such as Tim1 and Tim4. [Miyanishi M, et al (2007) Nature. 450:435-9; Kobayashi N., et al. (2007) Immunity. 27:927-40]. Thus, the present invention contemplates targeting any receptor shown to be involved in the recognition of phosphatidylserine. Once exposed to the extracellular environment, binding sites on phosphatidylserine become available and can recruit phagocytic cells.

In the present invention, the term "apoptotic cell" is understood to include a cell having lost integrity of its plasma membrane, a cell having exposed phosphatidylserine residues, translocated calreticulin to its cell surface, absorbed soluble proteins such as C1q and thrombospondin, or exhibiting other "eat me" signals (i.e., signals to a phagocytic cell to "eat" or phagocytose the apoptotic cell), a cell having suppressed "do not eat me" (i.e., "do no phagocytose me") signals such as suppression of surface CD47 expression, a cell having complete permeabilization of its outer mitochondrial membrane, a cell having lost mitochondrial membrane potential, a cell having caspase activation, a cell having $\Delta\Psi m$ dissipation, a cell having a nucleus that has undergone complete fragmentation into discrete bodies frequently referred to as "apoptotic bodies" and measured by quantification of hypodiploid events (sub-G1 peak), a cell having nuclear fragmentation (karyorrhexis), a cell labeling positively for terminal deoxynucleotidyl transferase-mediated dUTP nick end labeling (TUNEL), a cell triggered to undergo apoptosis through different biochemical routes (the "intrinsic" or the "extrinsic" pathway, with or without the contributions of mitochondria), a cell exhibiting typical apoptotic morphology define by rounding-up of the cell, retraction of pseudopodes, reduction of cellular volume (pyknosis), chromatin condensation, karyorrhexis, little or no ultrasound modifications of cytoplasmic organelles, plasma membrane blebbing (but maintenance of its integrity until the final stages of the process) and engulfment by phagocytes.

As used herein, the term "apoptotic cell-associated agent" refers to an entire apoptotic cell, or, to molecular components of an apoptotic cell, no phospholipids (e.g., phosphatidylserine) and intracellular proteins such as calreticulin or polypeptides that are exposed outside their normal intracellular compartments during apoptotic, (i.e., on the outer cell membrane), to synthetic apoptotic cell mimics, or to any apoptotic cell derived ligand recognized by a receptor specific to the apoptotic cell derived ligand and expressed by the DC or macrophage. This apoptotic cell-associated agent or mimic would trigger specific receptors triggering the same signaling pathways that an apoptotic cell would otherwise trigger in a DC, macrophage or other phagocytic cell, recognizing that apoptotic cell or engaged in phagocytosis of that apoptotic cell.

In certain embodiments of the invention, cell lines are used to study apoptosis. For example, the B cell lymphoma cell line A20 (ATCC number TIB-208) may be treated with anti-Fas antibody (anti-CD95) to induce apoptosis. The Fas receptor (also known as Apo-1 or CD95) binds the Fas ligand (FasL), a transmembrane protein part of the TNF family. The interaction between Fas and FasL results in the formation of the death-inducing signaling complex (DISC), which contains the FADD, caspase-8 and caspase-10. In some types of cells, processed caspase-8 directly activates other members of the caspase family, and triggers the execution of apoptosis. In other types of cells, the Fas-DISC starts a feedback loop that spirals into increasing release of pro-apoptotic factors from mitochondria and the amplified activation of caspase-8. Thus, cells, such as A20 cells, express Fas ligand and their cell surface undergo apoptotic cell death upon cross-linking of Fas, either by Fas ligand or by anti-Fas antibodies.

In a highly preferred embodiment of the present invention, the TLR ligand is incorporated directly into the apoptotic cell. The TLR ligand may be recognized by cell surface TLR, such as e.g., TLR-1, 2, or 4, or may be recognized by an endosomal TLR, such as, e.g. TLR-3, 7, or 8.

In other embodiments, apoptotic neutrophils are generated in vivo by the intraperitoneal injection of thiogylcollate. Upon thiogylcollate injection, neutrophils are recruited to the inflamed injection site. Once, recruited, neutrophils which are short-lived cells, live only a matter of days, and soon begin undergoing apoptosis. These cells may be isolated and used for study. Thiogylcollate may also be mixed with live *E. coli* and this mixture can be injected intraperitoneally. In this case, neutrophils recruited to the peritoneal cavity will phagocytose the injected *E. coli* and under apoptosis. These latter neutrophils differ from the former (without *E. coli*) in that they have served in the studies supporting the present invention as a model for an infected apoptotic cell since they have phagocytosed *E. coli* and now undergo apoptosis carrying both signatures of TLR ligands and apoptotic cells.

In certain aspects of the invention, cell apoptosis is detected. Apoptosis may be detected by a variety of methods known in the art, including, but not limited to flow cytometric-based analysis of Annexin V expression on the cell surface. Annexin V is a 35-36 kDa. $Ca^{2+}$-dependent, phospholipid binding protein with a high affinity for phosphatidylserine. The translocation of phosphatidylserine precedes other apoptotic processes such as loss of plasma membrane integrity, DNA fragmentation, and chromatin condensation. As such, Annexin V can be conjugated to biotin or to fluorochrome such as FITC, PE, APC, Cy5, or Cy5.5, and used for the easy, flow cytometric indentification of cells in the early stages of apoptosis.

Because phosphatidylserine translocation also occurs during necrosis, Annexin V is not an absolute marker of apoptosis. Therefore, it may be used in conjunction with vital dyes such as 7-amino-actinomycin D (7-AAD) or propidium iodide (PI), which bind to nucleic acids, but only penetrate the plasma membrane when membrane integrity is breached, as occurs in the later stages of apoptosis or in necrosis. Using these methods, cells that are negative for both Annexin V and the vital dye have no indications of apoptosis, since phosphatidylserine translocation has not occurred and the plasma membrane is still intact. Cells that are Annexin V-positive and vital dye-negative, however, are in early apoptosis as phosphatidylserine translocation has occurred, yet the plasma membrane is still intact. Cells that are positive for both Annexin V and the vital dye are either in the late stages of apoptosis or are already dead, as phosphatidylserine translocation has occurred and the loss of plasma membrane integrity is observed. When measured over time, Annexin V and a vital dye can be used to monitor the progression of apoptosis from cell viability, to early-stage apoptosis, and finally to late-stage apoptosis and cell death.

In certain other embodiments of the invention, apoptosis may also be assessed using TUNEL staining. The TUNEL (terminal deoxynucleotide transferase [TdT]-mediated dUTP-digoxigenin nick-end labeling) method is based on the in situ labeling of DNA fragmentation sites in nuclei of intact fixed cells. DNA fragmentation is characteristic of apoptotic cells. TUNEL staining may be performed using the In Situ Cell Death Detection Kit, TMR Red (Roche, Indianapolis, Ind.).

The use of synthetic mimics for the effects of apoptotic cells may be in the form of phosphatidylserine incorporated into liposomes, or agonists for nuclear hormone receptor superfamily member. Peroxisome Proliferators-Activated Receptor (PPAR)-γ. A combination of TLR ligands with PPAR-γ agonists, for example, thiazolidinediones (also referred to as glitazones) such as Rosiglitazone, are examples of such synthetic agonists. Thiazolidinediones are used as therapy against various inflammatory diseases because of their anti-inflammatory and anti-proliferative effects. They are also used for treatment of type 2 diabetes. Moreover, it has been reported that recognition of apoptotic cells by cells of the innate immune system, such as macrophages, results in the activation of PPAR-γ [Johann A. M. et. al (2006) Cell Death Diff; 13:1533-1540].

In certain other embodiments, a mimic of cell surface calreticulin translocation, including but not limited to inhibitors of the protein phosphatase 1/GADD34 complex, may be used to mimic cellular apoptosis.

In certain embodiments of the invention, an apoptotic cell or a microbe-infected apoptotic cell is engineered to express an exogenous immune antigen. As used herein "exogenous" refers to a factor that is present and active in an individual organism or living cell but that originated outside of that organism, as opposed to an "endogenous" factor, which originates from the organism expressing the factor. As used herein, an "exogenous immune antigen" expressed by a microbe or expressed by a microbe-infected apoptotic cell refers to an antigen that is not endogenously expressed by the apoptotic cell. In certain embodiments, it is preferred that the exogenous immune antigen is expressed neither by the apoptotic cell nor by the microbe infecting the appropriate cell. In other embodiments, it is preferred that the exogenous immune antigen is expressed endogenously by the microbe but is not expressed endogenously by the apoptotic cell, DNA introduced to cells via transfection or viral infection (transduction) is a non-limiting example of an exogenous factor. This method can be used to express as exogenous antigen by an apoptotic cell which is otherwise not expressed by the apoptotic cell. Non-limiting examples of an exogenous immune antigen include a tumor-associated antigen, and an antigen expressed by a microbe that could be used to elicit a $T_H17$ immune response to the microbe, e.g., to induce effective host defense against the microbe as well as tissue repair. In certain embodiments of the invention, such as, e.g., vaccine compositions of the invention, an "immune antigen" is provided. As used herein, an "immune antigen" may be any antigen that elicits an immune response, and may be either an exogenously or endogenously express antigen. Endogenous or exogenous (e.g. tumor associated antigen) expressed antigens would be used in the context of apoptotic cells alone as a regulatory T cell adjuvant where a regulatory T cell response is preferentially induced, while an exogenously expressed antigen such as a microbial antigen or a tumor-associated antigen would be used in the context of an apoptotic cell engineered to carry TLR ligands as a $T_H17$ adjuvant where a $T_H17$ immune response is preferentially induced.

Apoptotic cells may be engineered to express such exogenous immune antigens by any suitable method known in the art. Examples of such methods include transfecting a suitable cell line or virus with the gene encoding the desired antigen or transforming a cell, such as, e.g., a bacterium, with the gene encoding the desired antigen using a suitable virus, e.g. a *lentivirus* or an adenovirus. Apoptosis may then be induced in the transfected or transformed cell before use. In other embodiments, a certain apoptotic cell may be selected for use because it endogenously (i.e., naturally) expresses a desired immune antigen. In other embodiments, a cell expressing a desired immune antigen is either infected with a microbe, such as, e.g., *E. coli*, or allowed to internalize an inactivated form of a microbe such as *E. coli*. Apoptosis is then induced following infection or internalization of the microbe. In other embodiments, a cell can be made to express an antigen as a fusion protein with a TLR ligand such as Flagellin. Apoptosis is then induced, where the resultant apoptotic cell expresses the exogenous antigen directly fused to a TLR ligand. Apoptosis may be induced by a number of methods known in the art, including exposure to heat, UV, or fixation. The specific method of apoptosis induction will depend on the type of cell to be treated, and is readily determined by a skilled artisan.

According to certain embodiments of the present invention, the combinatorial use of PPAR-γ agonists and TLR ligands provides a stimulus for $T_H17$ cell development. Specifically, PPAR-γ agonists and TLR ligands may be administered as one entity such as encapsulated within liposomes, e.g., in order to achieve co-internalization by DC into one subcellular compartment such as an endosome or phagosome.

In certain embodiments of the present invention, apoptosis may be inhibited using Q-VD-OPH, a broad-spectrum caspase inhibitor. Q-VD-OPH is not toxic to cell even at extremely high concentrations, and consists of a carboxy terminal phenoxy group conjugated to the amino acids valine and aspartate. The compound is a potent inhibitor of cell death by apoptosis and is significantly more effective in preventing apoptosis than ZVAD-fmk and Boc-D-fmk. It is equally effective in preventing apoptosis mediated by the three major apoptotic pathways, caspase-9 and caspase-3, caspase-8 and caspase-10, and caspase-12. [Caserta T M et al (2003) Apoptosis 8(4): 345-352; Patil K. and Sharma S C (2004) NeuroReport 15:981-984; Yang L et al. (2004) Neurobiology of Disease 17(2): 250-259].

In some aspects, the present invention relates to compositions, pharmaceutical formulations or vaccine compositions that include specific combinations of the TLR agonists and apoptotic cells or apoptotic cell-associated agents described herein. In certain embodiments, TLR agonists and apoptotic cells are combined as a single entity by coadministration in one physical form as described herein. For example, a TLR ligand and an apoptotic cell-associated agent may be incorporated into liposomes such that each liposome carries both an apoptotic cell-associated agent (e.g., phosphatidylserine) and a TLR ligand. This composition endures co-delivery in one physical form and internalization into one subcellular compartment within DC (e.g., endosome or phagosome). In other embodiments, the combination of the two $T_H17$ adjuvants occurs naturally, and is administered as a single agent, such as, for example, a microbe-infected apoptotic cell or an apoptotic cell engineered to carry a TLR ligand. A microbe-infected apoptotic cell according to the present invention expresses markers of apoptosis suitable for eliciting TGF-β secretion by DC and TLR ligands suitable for eliciting IL-6 secretion by the same DC.

Any form or method of delivery, either in vitro or in vivo, that results in co-internalization of both the TLR agonist and the apoptotic cell-associated agent by the same DC, or that results in stimulation of a DC such that the DC is induced to become a $T_H17$-inducing DC by exposure to the TLR agonist and the apoptotic cell-associated agent, is contemplated by the present invention.

Non-limiting examples of microbe-infected cells that may be used in the present invention include cells infected with live attenuated vaccine strains such as *Mycobacterium bovis* BCG vaccine against tuberculosis, *Salmonella typhi* Ty21a vaccine against typhoid fever, and *Vibrio cholerae* CVD 103-HgR vaccine against cholera. Killed bacteria of all strains may also be used after inactivation with heat, UV or fixation. These may then be given to phagocytic cells and apoptosis of the cell induced after internalization of the inactivated microbe. In certain embodiments of the present invention, neutrophils infected with *E. coli* are used. *E coli* infection of neutrophils causes them to become apoptotic, and the *E. coli* provides TLR ligands, thus representing an agent which combines both of the two necessary $T_H17$ adjuvants.

Bacteria that cause significant apoptosis and tissue damage at epithelial surfaces during infection include, but are not limited to, *Shigella dysenteriae, Klebsiella pneumoniae, Pseudomonas aeruginosa*, enteropathogenic and enterohemorrhagic *E. coli* (EPEC and EHEC)

In certain embodiments, the invention relates to compositions that have a DC capable of inducing a $T_H17$ response, wherein the DC secretes IL-6 and TGF-β. The DC compositions may also include a microbe-infected apoptotic cell. The DC may phagocytose the microbe-infected apoptotic cell expressing exogenous immune antigens also administered to the DC. A killed microbe (inactivated, e.g., by heat, UV or fixative) may also be used because the DC will phagocytose this microbe, a method which delivers to the DC not only the relevant adjuvants for $T_H17$ induction but also all the exogenous immune antigens unique to that microbe. Other microbes may include those selected for use as live attenuated vaccine strains such as *Mycobacterium bovis* BCG vaccine against tuberculosis, *Salmonella typhi* Ty21a vaccine against typhoid fever, and *Vibrio cholerae* CVD 103-HgR vaccine against cholera.

In certain embodiments, DC are generated in vitro in bone marrow (BM)-derived GM-CSF DC cultures. Using this method, large numbers of BMDC may be generated by culturing whole BM cells in the presence of GM-CSF. The cultures are grown in RPMI supplemented with GM-CSF and 5% foetal bovine serum (FBS), plus 100 μg/mL penicillin, 100 μg/mL streptomycin, 2 mM L-glutamine, 10 mM HEPES, 1 nM sodium pyruvate, 1X MEM nonessential amino acids, and 2.5 μM β-mercaptoethanol (all from Sigma-Aldrich, St. Louis, Mo.). Semi-adherent cells are then harvested on ice on day 5 and re-plated immediately in fresh GM-CSF medium at $1\times10^6$ cells/well in 24-well tissue culture-treated plates and used for experiments.

In the present invention, other phagocytic cells in addition to DC that are capable of inducing $T_H17$ responses are also contemplated.

In certain embodiments of the present invention, in vitro experiments are carried out to assess the $T_H17$-inducing potential of a DC. In certain embodiments, a DC is co-cultured directly with a T cell in vitro in the presence of a TLR agonist and apoptotic cell-associated stimuli of the present invention. In other embodiments, the DC is first treated with a TLR adjuvant and apoptotic cell-associated stimuli of the present invention, and then the DC conditioned media (CM) is collected and transferred to a well containing CD4 T cells stimulated with T cell activating agents (e.g., anti-CD3 and anti-CD28 antibodies). The ability of a soluble factor secreted by the DC into the conditioned media to induce CD4 T cell differentiation may then be assessed. Such in vitro methods are widely accepted in the art as suitable models for characterizing the requirements for CD4 T cell differentiation in vivo.

In certain embodiments of the present invention, T cell proliferation may be determined by measuring tritiated thymidine ($^3$H-Thymidine) incorporation into dividing cells. As T cells proliferate, they incorporate the labeled nucleic acid into the dividing cells. The resulting radioactivity of the divided cells can be detected using a beta liquid scintillation counter. In the examples of the present disclosure, following 72 hours of co-culture, 1 μCi of $^3$H-thymidine is added to each culture well. Then, 18 hours after pulsing with $^3$H-thymidine, cells are harvested with a multiple-sample harvester and counted with a Wallac 1450 microbeta PLUS liquid scintillation counter (Perkin-Elmer, Waltham, Mass.). Using this approach, the ability of DC to stimulate T cell proliferation can be quantitated.

In certain embodiments of the present invention, naïve CD4 T cells are isolated by cell sorting. Naïve CD4 T cells are identified by the levels of expression of certain cell surface markers. Specifically, these cells are $CD62L^{high}$ $CD44^{low}$ $CD25^-$ cells that can be isolated by fluorescence activated cell sporting (FACS). The CD4 T cells are strained with fluorescently-conjugated antibodies specific for epitopes of CD62L, CD44, and CD25, and sorted based on their fluorescence properties to isolate the CD62L$^{high}$ CD44$^{low}$ CD25$^{-}$ population. This approach yields highly pure (>99%) populations of naïve CD4 T cells.

In certain embodiments, intestinal cell damage is induced using dextran sulfate sodium (DSS). DSS induces an inflammatory bowel disease-like colitis in animals. In addition to using DSS for the study of inflammation, numerous animal models exist for the study of colorectal and intestinal cancers in which mice are genetically manipulated or challenged with chemicals, such as DSS, to develop malignancies in the gastrointestinal tract. These models enable researchers to study the onset, progression of the disease, and understand in depth the molecular events that contribute to the development and spread of colorectal cancer. For example, human Inflammatory Bowel Disease (IBD) is a group of inflammatory conditions in the large and small intestine. It is well known that chronic inflammation in the colon can cause cancer. Genetic mouse models for IBD-associated colon cancer include a model in which IL-10 knock out mice develop invasive adenocarcinoma in the colon, a model in which mice that are mutant for IL-2 and beta microglobulin genes have ulcerative colitis-like phenotypes and develop adenocarcinomas in the colon, and a model in which a mouse mutant for N-cadherin suffers IBD conditions and adenomas but does not develop carcinomas.

Compositions and Methods for Inhibiting a $T_H$17 Response or Inducing Immune Tolerance In certain embodiments, the present invention relates to methods for inhibiting $T_H$17 responses, and in other embodiments, the invention relates to methods for inducing immune tolerance in a mammal. These methods can involve administering to the DC an apoptotic cell in the absence of TLR ligands (e.g., an uninfected apoptotic cell), or administering an agent that blocks immune recognition of an apoptotic cell, or an apoptotic cell-associated agent. In yet other embodiments, an agent that blocks immune recognition of a Toll-like receptor (TLR) ligand or adjuvant may be administered. The present invention also relates to compositions and pharmaceutical formulations including one ore more blocking reagents useful for inhibiting $T_H$17 responses and/or for inducing immune tolerance (i.e. Treg responses).

Examples of suitable blocking agents include, but are not limited to antibodies that block recognition of apoptotic cells, or agents associated with apoptotic cells, such as, e.g., phosphatidylserine, an antibodies that block recognition of TLR ligands. Specific inhibitors of TLR signaling include but are not limited to novel small molecule TLR4 antagonists such as TAK-242 [M. Ii, N. et al (2006) *Mol Pharmacol* 69: 1288], Eritoran (E-5564), an antagonistic version of the lipid A portion of LPS that binds TLR4 and acts as an antagonist (ref2), small molecule inhibitors of IKK2 (ref 3), NF-κB inhibitor pyrrolidine dithiocarbamate (PDTC) [M. Säemann et al (2004) *Am J Transplant* 4:1448], NF-κB oligodeoxyribonucleotide decoys or RNA for silencing the NF-κB genes [C. A. Bonham et al. (2002) J Immunol 169:3382; M. Li et. al., (2006) Am J Transplant (suppl), p. 311 WTC-Congress Boston, abstract #725], agents that block endosomal acidifications, such as chloroquine or hydroxychloroquine thereby blocking signaling by intracellular TLRs, vaccine virus derived proteins A46R and A52R, anti-inflammatory agents such as aspirin, salicylate and other non-steroidal anti-inflammatory drugs (NSAIDS), glucocorticoids which interfere with NF-κB-mediated gene transcription, natural products such as parthenolide that block IKK2, NEMO-binding peptides, PS-1145 a proteoasome inhibitor that blocks IκB degradation, IRAK-4 inhibitors, inhibitors of protein-protein interactions that might be used to inhibit TIR domain interactions (e.g., MyD88 recruitment to TLRs or IRAK-1/TRAF-6 interactions), and inhibition of TRAF-6 and TAK-1 ubiquitination. [reviewed in O'Neill LA. (2003) Curr Opin Pharmacol; 3:396-403].

Agents that block recognition of apoptotic cells include but are not limited to monoclonal antibodies (mAb) that serve to inhibit phosphatidylserine-dependent phagocytosis of apoptotic cells in vitro. one mAb, Kat 5-19, which is specific to the newly identified phosphatidylserine receptor, the T cell immunoglobulin mucin-4 (Tim-4), can do so in vitro and in vivo by specifically blocking spontaneous ingestion of apoptotic cells by macrophages [M. Miyanishi, et al (2007) Nature 450; 435-439]. Other neutralizing antibodies that block recognition of phsophatidylserine have also been described [Kobayashi N, et. al (2007) Immunity, 27: 927-940]. Recognition of phosphatidylserine is likely complex and possibly involves both thrombospondin (TSP) and GAS6 which might bridge apoptotic cell phosphatidylserine to phagocyte αv integrins and Mer kinase, respectively. Blocking the ability of these molecules to form a bridge between phosphatidylserine and the DC may be an effective means of blocking apoptotic cell recognition. Finally, milk fat globule epidermal growth factor 8 (MFG-E8) has also been identified as a bridging molecule between apoptotic cell phosphatidylserine and the DC αyintegrins, an interaction which may also be blocked to prevent recognition of apoptotic cell exposed phosphatidylserine [Reviewed in Savill and Gregory (2007) Immunity 2007 27:830-832].

In some aspects of the present invention, methods for the treatment of a $T_H$17-driven disease or condition are provided. Diseases or conditions that may benefit from the compositions and methods of the present invention include, but are not limited to, inflammatory bowel disease, Crohn's disease, colitis, systemic sclerosis (scleroderma), atopic dermatitis, psoriasis, rheumatoid arthritis, diabetes, cystic fibrosis, allergic airway disease, atopic asthma, allergic asthma, Sjogren's Syndrome, and systemic lupus erythematosus.

Vaccine Compositions

The vaccine compositions of the present invention may be used to induce $T_H$17 responses in a patient. Alternatively, the vaccine compositions of the present invention may be used to inhibit $T_H$17 responses and, optionally, to induce $T_{reg}$ cell responses.

In certain embodiments, the vaccine compositions of the present invention preferentially induce $T_H$17 responses based on the novel combination of adjuvants which they contain. Specifically, in certain embodiments, the vaccine compositions contain a TLR ligand-containing apoptotic cell or an apoptotic cell-associated agent preferably administered with a TLR ligand as a single entity or physical form. Conventionally, vaccine compositions contain adjuvants, such as cholera toxin, that stimulate the immune response. Many of the adjuvants that are safe for human use do not elicit effective immune responses, in part because they do not specifically elicit $T_H$17-driven responses in mucosal sites. Most vaccines are delivered to mucosal sites, either via the airways or orally, where $T_H$17 responses are thought to be preferred. Thus, the present invention provides vaccine compositions which preferentially induce $T_H$17 responses.

For the treatment of certain diseases, preferential induction of $T_H$17 responses by a vaccine composition is highly preferred. For example, as discussed, supra, certain cancers, such as epithelial or mixed epithelial carcinomas, are adversely effected by the presence of $T_{reg}$ cells, which may prevent successful immune responses against the tumor. In this case, the compositions and methods provided by the present invention, which preferentially induce a $T_H$17 response, thereby inhibiting the $T_{reg}$ response, are highly useful for the treatment of certain cancers. Similarly, infections with certain strains of bacteria that cause significant apoptosis and cell death in infected tissues may preferentially benefit from the induction of $T_H17$ responses. These may include but are not limited to infections with *Pseudomona aeruginosa, Klebsiella pneumoniae, Shigella dysenteriae,* and enteropathogenic or enterohemorrhagic *E. coli* (EPEC and EHEC, respectively).

In certain other embodiments, the vaccine compositions of the present invention inhibit $T_H17$ responses. This is achieved by the selective inhibition of $T_H17$ response by blocking recognition of either one or both of the TLR ligand and the apoptotic cell.

In certain other embodiments, the vaccine compositions of the present invention inhibits $T_H17$ responses and instead induced $T_{reg}$ responses. This is achieved by the selective inhibition of the $T_H17$ response by blocking the TLR stimulating component of the TLR ligand-containing apoptotic cell adjuvant discovered by the present invention. This results in activity of the apoptotic cell alone (without TLR ligand), a scenario that favors $T_{reg}$ responses and thus serves to modulate $T_H17$ responses to $T_{reg}$ responses.

Vaccine compositions which inhibit $T_H17$ responses are highly useful for the treatment of autoimmune diseases, such as inflammatory bowel disease, Crohn's disease, colitis, systemic sclerosis (scleroderma), atopic dermatitis, psoriasis, rheumatoid arthritis, diabetes, cystic fibrosis, allergic airway disease, atopic asthma, allergic asthma, Sjogren's Syndrome, and systemic lupus erythematosus. Such vaccine compositions provided by the present invention are also highly useful for the treatment of certain cancers, in which it is useful to inhibit $T_H17$ responses, and to increase the number of $T_{reg}$ cells. As discussed, supra, such cancers include, but are not limited to, Hodgkin lymphoma, follicular lymphoma, multiple myeloma, monoclonal gammopathy, and T cell leukemia/lymphoma, In certain embodiments of the invention, compositions and formulations of the invention, including vaccine compositions, contain DC along with the combination of a TLR adjuvant and an apoptotic cell component preferably administered as a single entity or in one physical form. The present invention discloses the surprising finding that loading DC, either during or before transfer to a patient, with the combination of a TLR agonist and an apoptotic cell or apoptotic cell-associated agent (as one entity, e.g., encapsulated in liposomes or physically linked or contained within a carrier), can generate a T17 response in vivo. "Loading" of a DC means that the DC is cultured en vivo or in vitro and pulsed with the cargo with which the DCs is to be "loaded". For example, in certain embodiments, the DC is pulsed with a microbe-infected apoptotic cell or an apoptotic cell that previously internalized as inactivated form of a microbe. Upon phagocytosis of the infected apoptotic cell, the DC concurrently recognizes the TLR ligands associated with the microbe infecting the cell and that the cell is apoptotic (e.g., through receptor-mediated binding of phosphatidylserine), and thus becomes primed to induce a $T_H17$ response upon transfer to the recipient (patient). Moreover, if the DC is also loaded with a suitable vaccine antigen, e.g., a tumor-associated antigen, the DC will present peptides of this antigen in the context of surface MHC class II molecules to CD4 T cells in the patient, thereby inducing an antigen-specific, $T_H17$-driven immune response.

Definitions

The following definitions are provided for the clarity of illustrative purposes only, and are not intended to limit the scope of the invention.

Expression Construct

By "expression construct" is meant a nucleic acid sequence comprising a target nucleic acid sequence or sequences whose expression is desired, operatively associated with expression control sequence elements which provide for the proper transcription and translation of the target nucleic acid sequence(s) within the chosen host cells. Such sequence elements may include a promoter and a polyadenylation signal. The "expression construct" may further comprise "vector sequences". By "vector sequences" is meant any of several nucleic acid sequences established in the art which have utility in the recombinant DNA technologies of the invention to facilitate the cloning and propagation of the expression constructs including (but not limited to) plasmids, cosmids, phage vectors, viral vectors, and yeast artificial chromosomes.

Expression constructs of the present invention may comprise vector sequences that facilitate the cloning and propagation of the expression constructs. A large number of vectors, including plasmid and fungal vectors, have been described for replication and/or expression in a variety of eukaryotic and prokaryotic host cells. Standard vectors useful in the current invention are well known in the art and include (but are not limited to) plasmids, cosmids, phage vectors, viral vectors, and yeast artificial chromosomes. The vector sequences may contain a replication origin for propagation in *Escherichia coli* (*E. coli*); the SV40 origin of replication; an ampicillin, neomycin, or puromycin resistance gene for selection in host cells; and/or genes (e.g., dihydrofolate reductase gene) that amplify the dominant selectable marker plus the gene of interest.

Express and Expression

The terms "express" and "expression" mean allowing or causing the information in a gene or DNA sequence to become manifest, for example producing a protein by activating the cellular functions involved in transcription and translation of a corresponding gene or DNA sequence. A DNA sequence is expressed in or by a cell to form an "expression product" such as a protein. The expression product itself, e.g., the resulting protein, may also be said to be "expressed" by the cell. An expression product can be characterized as intracellular, extracellular or secreted. The term "intracellular" means something that is inside a cell. The term "extracellular" means something that is outside a cell. A substance is "secreted" by a cell if it appears in significant measure outside the cell, from somewhere on or inside the cell.

Transfection

The term "transfection" means the introduction of a foreign nucleic acid into a cell. The term "transformation" means the introduction of a "foreign" (i.e. extrinsic or extracellular) gene. DNA or RNA sequence to a cell, so that the host cell will express the introduced gene or sequence to produce a desired substance, typically a protein or enzyme coded by the introduced gene or sequence. The introduced gene or sequence may also be called a "cloned" or "foreign" gene or sequence, may include regulatory or control sequences, such as start, stop, promoter, signal, secretion, or other sequences used by cells genetic machinery. The gene or sequence may include nonfunctional sequences or sequences with no known function. A host cell that receives and expresses introduced DNA or RNA has been "transformed" and is a "transformant" or a "clone". The DNA or RNA introduced to a host cell can come from any source, including cells of the same genes or species as the host cell, or cells of a different genus or species. In certain embodiments of the present invention, for example, MFB-F11 mouse fibroblast cells are stably transfected with a reporter plasmid consisting of TGF-β-responsive Smad-binding elements coupled to a secreted alkaline phosphatase reporter gene (SBE-SEAP).

Electroporation

"Electroporation", as used herein, is a significant increase in the electrical conductivity and permeability of the cell plasma membrane caused by an externally applied electrical field. It is usually used in molecular biology as a way of introducing some substance into a cell, such as loading it with a molecular probe, a drug that can change the cell's function, or a piece of coding DNA.

Expression System

The term "expression system" means a host cell and compatible vector under suitable conditions, e.g. for the expression of a protein coded for by foreign DNA carried by the vector and introduced to the host cell.

Gene or Structural Gene

The term "gene", also called a "structural gene" means a DNA sequence that codes for or corresponds to a particular sequence of amino acids which comprise all or part of one or more proteins or enzymes, and may or may not include regulatory DNA sequences, such as promoter sequences, which determine for example the conditions under which the gene is expressed. Some genes, which are not structural genes, may be transcribed from DNA to RNA, but are not translated into an amino acid sequence. Other genes may function as regulators of structural genes or as regulator of DNA transcription.

A coding sequence is "under the control of" or "operatively associated with" expression control sequences in a cell when RNA polymerase transcribes the coding sequence into RNA, particularly mRNA, which is then trans-RNA spliced (if it contains introns) and translated into the protein encoded by the coding sequence.

The term "expression control sequence" refers to a promoter and any enhancer or suppression elements that combine to regulate the transcription of a coding sequence. In a preferred embodiment, the element is an origin of replication.

Protein or Polypeptide

The definitions of protein and polypeptide are well-known in the art. The term "protein", as used herein, is synonymous with the term "polypeptide", and is understood to mean a chain of amino acids arranged linearly and joined together by peptide bonds between the carboxyl and amino groups of adjacent amino acid residues.

Heterologous

The term "heterologus" refers to a combination of elements not naturally occurring. For example, heterologous DNA refers to DNA not naturally located in the cell, or in a chromosomal site of the cell. Preferably, the heterologous DNA includes a gene foreign to the cell. For example, the present invention includes chimeric DNA molecules that comprise a DNA sequence and a heterologous DNA sequence which is not part of the DNA sequence. A heterologous expression regulatory element is such an element that is operatively associated with a different gene than the one it is operatively associated with in nature. In the context of the present invention, a gene encoding a protein of interest is heterologous to the vector DNA in which it is inserted for cloning or expression, and it is heterologous to a host cell containing such a vector, in which it is expressed.

Homologous

The term "homologous" as used in the art commonly refers to the relationship between nucleic acid molecules or proteins that possess a "common evolutionary origin," including nucleic acid molecules or proteins within superfamilies (e.g., the immunoglobulin superfamily) and nucleic acid molecules or proteins have sequence (Reeck et al., Cell 1987; 50: 667). Such nucleic acid molecules or proteins have sequence homology, as reflected by their sequence similarity, whether in terms of substantial percent similarity or the presence of specific residues or motifs at conserved positions.

Host Cell

The term "host cell" means any cell of any organism that is selected, modified, transformed, grown or used or manipulated in any way for the production of a substance by the cell. For example, a host cell may be one that is manipulated to express a particular gene, a DNA or RNA sequence, a protein or an enzyme. Host cells can further be used for screening or other assays that are described infra. Host cells may be cultured in vitro or one or more cells in a non-human animal (e.g., a transgenic animal or a transiently transfected animal). Suitable host cells include but are not limited to *Streptomyces* species and *E. coli.*

Microbe or Pathogen

The terms "microbe" and "microorganism" are understood to include, but are not limited to, bacteria, viruses, fungi, archaea, and protists. One of ordinary skill in the art will understand that the term "microbe" applies to any biological microscopic organism. A pathogen is typically defined as an organism or microbe, such as a bacterium or virus that can invade a host and cause harm to the host. Intracellular and extracellular parasites may also be pathogens. Usually, a pathogen will elicit an immune response in the infected host. Some microbes are not normally pathogenic, such as, e.g., the bacteria that line the gut or the surface of the epithelium (skin), however, even conventionally non-pathogenic bacteria may become pathogenic in certain circumstances, e.g., if they become overpopulated, or if they colonize sites of the body that they normally do not populate. The present invention identifies that bacteria which cause significant apoptosis and tissue damage at epithelial surfaces are most likely best suited to induce $T_H17$ immunity. Apoptosis is typically caused by special type III secretion systems that inject bacterial apoptosis effector proteins into the host cell.

Treating or Treatment (1) Preventing or delaying the appearance of clinical or sub-clinical symptoms of the state, disorder or condition developing in a mammal that may be afflicted with or predisposed to the state, disorder or condition but does not yet experience or display clinical or subclinical symptoms of the state, disorder or condition; or (2) inhibiting the state, disorder or condition, i.e., arresting, reducing or delaying the development of the disease or a relapse thereof (in case of maintenance treatment) or at lease one clinical sub-clinical symptom thereof; or (3) Relieving the disease, i.e., causing regression of the state, disorder or condition or at least one of its clinical or sub-clinical symptoms.

The benefit to a subject to be treated is either statistically significant or at least perceptible to the patient or to the physician.

Patient or Subject

"Patient" or "subject" refers to mammals and includes human and veterinary subjects.

Therapeutically Effective Amount

A "therapeutically effective amount" means the amount of a compound that, when administered to a mammal for treating a state, disorder or condition, is sufficient to effect such treatment. The "therapeutically effective amount" will vary depending on the compound, the disease and its severity and the age, weight, physical condition and responsiveness of the mammal to be treated.

Prophylactically Effective Amount

A "prophylactically effective amount" refers to an amount effective, at dosages and for periods of time necessary, to achieve the desired prophylactic result. Typically, since a prophylactic does is used in subjects prior to or at an earlier stage of disease, the prophylactically effective amount will be less than the therapeutically effective amount.

About or Approximately

The term "about" or "approximately" means within an acceptable range for the particular value as determined by one of ordinary skill in the art, which will depend in part on how the value is measured or determined, e.g., the limitations of the measurement system. For example, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value. Unless otherwise stated, the term 'about' means within an acceptable error range for the particular value.

Include or Comprise

As used herein, the terms "include" and "comprise" are used synonymously. It should be understood that the terms "a" and "an" as used herein refer to "one or more" of the enumerated components. The use of the alternative (e.g., "or") should be understood to mean either one, both, or any combination thereof of the alternatives.

Isolated

As used herein, the term "isolated" means that the referenced material is removed from the environment in which it is normally found. Thus, an isolated biological material can be free of cellular components, i.e., components of the cells in which the material is found or produced. Isolated nucleic acid molecules include, for example, a PCR product, an isolated mRNA, a cDNA, or a restriction fragment. Isolated nucleic acid molecules also include, for example, sequences inserted into plasmids, cosmids, artificial chromosomes, and the like. An isolated nucleic acid molecule is preferably excised from the genome in which it may be found, and more preferably is no longer joined to non-regulatory sequences, non-coding sequences, or to other genes located upstream or downstream of the nucleic acid molecule when found within the genome. An isolated protein may be associated with other proteins or nucleic acids, or both, with which it associates in the cell, or with cellular membranes if it is a membrane-associated protein.

Purified

The term "purified" as used herein refers to material that has been isolated under conditions that reduce or eliminate the presence of unrelated materials, i.e. contaminants, including native materials from which the material is obtained. The isolated material is preferably substantially free of cell or culture components, including tissue culture components, contaminants, and the like. As used herein, the term "substantially free" is used operationally, in the context of analytical testing of the material. Preferably, purified material substantially free of contaminants is at least 50% pure, more preferably, at least 90% pure, and more preferably still at least 99% pure. Purity can be evaluated by chromatography, gel electrophoresis, immunoassay, composition analysis, biological assay, and other methods known in the art.

Mutant

As used herein, the terms "mutant" and "mutation" refer to any detectable change in genetic material (e.g., DNA) or any process, mechanism, or result of such a change. This includes gene mutations, in which the structure (e.g., DNA sequence) of a gene is altered, any gene or DNA arising from any mutation process, and any expression product (e.g., protein or enzyme) expressed by a modified gene or DNA sequence. As used herein, the term "mutating" refers to a process of creating a mutant or mutation.

Nucleic Acid Molecule

A "nucleic acid molecule" or "oligonucleotide" refers to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine, "DNA molecules"), or any phophoester analogs thereof, such as phosphorothioates and thioesters, in either single stranded form, or a double-stranded helix. Double stranded DNA-DNA, DNA-RNA and RNA-RNA helices are possible. The term nucleic acid molecule, and in particular DNA or RNA molecule, refers only to the primary and secondary structure of the molecule, and does not limit it to any particular tertiary forms. Thus, this term includes double-stranded DNA found, inter alia, in linear (e.g., restriction fragments) or circular DNA molecules, plasmids, and chromosomes. In discussing the structure of particular double-stranded DNA molecules, sequences may be described herein according to the normal convention of giving only the sequence in the 5' to 3' direction along the non-transcribed strand of DNA (i.e., the strand having a sequence homologous to the mRNA). A "recombinant DNA molecule" is a DNA molecule that has undergone a molecular biological manipulation.

The nucleic acid molecules of sequences disclosed herein are written according to The International Union of Pure and Applied Chemistry (IUPAC) DNA codes. Specifically, "A" is Adenine, "C" is Cystosine, "G" is Guanine, "T" is Thymine, "U" is Uracil, "R" is any Purine (A or G), "Y" is any Pyrimidine (C, T, or U), "M" is C or A, "K" is T, U, or G, "W" is T, U, or A, "S" is C or G, "B" is C, T, U or G (not A), "D" is A, T, U, or G (not C), "H" is A, T, U, or C (not G), "V" is A, C, or G (not T, not U), and "N" is any base (A, C, G, T, or U).

Nucleic Acid Hybridization

The term "nucleic acid hybridization" refers to anti-parallel hydrogen bonding between two single-stranded nucleic acids, in which A pairs with T (or U if an RNA nucleic acid) and C pairs with G. Nucleic acid molecules are "hybridizable" to each other when at least one strand of one nucleic acid molecule can form hydrogen bonds with the complementary bases of another nucleic acid molecule under defined stringency conditions. Stringency of hybridization is determined, e.g., by (i) the temperature at which hybridization and/or washing is performed, and (ii) the ionic strength and (iii) concentration of denaturants such as formamide of the hybridization and washing solutions, as well as other parameters. Hybridization requires that the two strands contain substantially complementary sequences. Depending on the stringency of hybridization, however, some degree of mismatches may be tolerated. Under "low stringency" conditions, a greater perecentage of mismatches are tolerable (i.e., will not prevent formation of an anti-parallel hybrid.) See Molecular Biology of the Cell, Alberts et al., 3rd ed., New York and London: Garland Publ., 1994, Ch. 7.

Typically, hybridization of two strands at high stringency requires that the sequences exhibit a high degree of complementarity over an extended portion of their length. Examples of high stringency conditions include: hybridization to filter-bound DNA in 0.5 M $NaHPO_4$, 7% SDS, 1 mM EDTA at 65° C., followed by washing in 0.1x SSC/0.1% SDS at 68° C. (where 1x SSC is 0.15M NaCl, 0.15M Na citrate) or for oligonucleotide molecules washing in 6xSSC/0.5% sodium pyrophosphate at about 37° C. (for 14 nucleotide-long oligos), at about 48° C. (for about 17 nucleotide-long oligos), at about 55° C. (for 20 nucleotide-long oligos), and at about 60°

C. (for 23 nucleotide-long oligos)). Accordingly, the term "high stringency hybridization" refers to a combination of solvent and temperature where two strands will pair to form a "hybrid" helix only if their nucleotide sequences are almost perfectly complementary (see Molecular Biology of the Cell, Alberts et al., 3rd ed., New York and London: Garland Publ., 1994, Ch. 7).

Conditions of intermediate or moderate stringency (such as, for example, an aqueous solution of 2XSSC at 65° C., alternatively, for example, hybridization to filter-bound DNA in 0.5 M NaHPO4, 7% SDS, 1 mM EDTA at 65° C., and washing in 0.2×SSC/0.1% SDS at 42° C.) and low stringency (such as, for example, an aqueous solution of 2XSSC at 55° C.), require correspondingly less overall complementarity for hybridization to occur between two sequences. Specific temperature and salt conditions for any given stringency hybridization reaction depend on the concentration of the target DNA and length and base composition of the probe, and are normally determined empirically in preliminary experiments, which are routine (see Southern, J. Mol. Biol. 1975; 98: 503; Sambrook et al., Molecular Closing: A Laboratory Manual, 2nd ed., vol 2, ch. 9.50, CSH Laboratory Press, 1989; Ausubel et al (eds.), 1989, Current Protocols in Molecular Biology, Vol. I, Green Publishing Associates, Inc., and John Wiley & Sons, Inc., New York, at p. 2.10.3).

As used herein, the terms "standard hybridization conditions" refers to hybridization conditions that allow hybridization of sequences having at least 75% sequence identity. According to a specific embodiment, hybridization conditions of higher stringency may be used to allow hybridization of only sequences having at least 80% sequence identity, at least 90% sequence identity, at least 95% sequence identity, or at least 99% sequence identity.

Nucleic acid molecules that "hybridize" to any desired nucleic acids of the present invention may be of any length. In one embodiment, such nucleic acid molecules are at least 10, at least 15, at least 20, at least 30, at least 40, at least 50, and at least 70 nucleotides in length. In another embodiment, nucleic acid molecules that hybridize are of about the same length as the particular desired nucleic acid.

Techniques to isolate and modify specific nucleic acids and proteins are well known to those of skill in the art. In accordance with the present disclosure there may be employed conventional molecular biology, microbiology, and recombinant DNA techniques within the skill of the art. Such techniques are explained fully in the literature. See, e.g., Sambrook, Fritsch & Maniatis, Molecular Cloning: A Laboratory Manual, Second Edition. Cold Spring Harbor, N.Y.: Cold Spring Harbor Laboratory Press, 1989 (herein "Sambrook et al., 1989"); DNA Cloning: A Practical Approach, Volumes I and II (D. N. Glover ed. 1985); Oligonucleotide Synthesis (M. J. Gait ed. 1984); Nucleic Acid Hybridization [B. D. Hames & S. J. Higgins eds. (1985)]; Transcription and Translation [B. D. Hames & S. J. Higgins, eds. (1984)]; Animal Cell Culture [R. I. Freshney, ed. (1986)]; Immobolized Cells and Enzymes [IRL Press, (1986)]; B. Perbal, A Practical Guide to Molecular Cloning (1984); Ausubel, F. M. et al (eds.). Current Protocols in Molecular Biology. John Wiley & Sons, Inc., 1994. These techniques include site directed mutagenesis employing oligonucleotides with altered nucleotides for generating PCR products with mutations (e.g., the "Quickchange" kit manufactured by Stratagene).

Primers

The term "primer," as used herein, refers to an oligonucleotide capable of acting as a point of initiation of DNA synthesis under conditions in which synthesis of a primer extension product complementary to a nucleic acid strand is induced, i.e., either in the presence of four different nucleoside triphosphates and an agent for extension (e.g., a DNA polymerase or reverse transcriptase) in an appropriate buffer and at a suitable temperature. A primer is preferably a single-stranded DNA. The appropriate length of a primer depends on the intended use of the primer but typically ranges from 6 to 50 nucleotides, preferably from 15-35 nucleotides. Short primer molecules generally require cooler temperatures to form sufficiently stable hybrid complexes with the template. A primer need not reflect the exact sequence of the template nucleic acid, but must be sufficiently complementary to hybridize with the template. The design of suitable primers for the amplification of a given target sequence is well known in the art and described in the literature cited herein. As used herein, a "forward primer" is understood to mean a primer that is capable of hybridizing to a region of DNA along the 5' (coding) strand of DNA. A "reverse" primer is understood to mean a primer that is capable of hybridizing to a region of DNA along the 3' (non-coding) strand of DNA.

As used herein, a primer is "specific," for a target sequence if, when used in an amplification reaction under sufficiently stringent conditions, the primer hybridizes primarily only the target nucleic acid. Typically, a primer is specific for a target sequence if the primer-target duplex stability is greater than the stability of a duplex formed between the primer and any other sequence found in the sample. One of skill in the art will recognize that various factors, such as salt conditions as well as base composition of the primer and the location of the mismatches, will affect the specificity of the primer, and that routine experimental confirmation of the primer specificity will be need in most cases. Hybridization conditions can be chosen under which the primer can form stable duplexes only with a target sequence. Thus, the use of target-specific primers under suitably stringent amplification conditions enables the specific amplification of those target sequences which contain the target primer binding sites. The use of sequence-specific amplification conditions enables the specific amplification of those target sequences which contain the exactly complementary primer binding sites.

A "primer set" or "primer pair" refers to a specific combination of a forward primer and a reverse primer. The "primer set" or "primer pair" may be used in a PCR reaction to generate a specific PCR product or amplicon.

In certain embodiments, the term "primer" is also intended to encompass the oligonucleotides used in ligation-mediated amplification processes, in which one oligonucleotide is "extended" by ligation to a second oligonucleotide which hybridizes at an adjacent position. Thus, the term "primer extension", as used herein, refers to both the polymerization of individual nucleoside triphosphates using the primer as a point of initiation of DNA synthesis and to the ligation of two oligonucleotides to form an extended product.

Oligonucleotide Preparation

Oligonucleotides can be prepared by any suitable method, including direct chemical synthesis by a method such as the phosphotriester method of Narang et al., 1979, Meth. Enzymol. 68:90-99; the phosphodiester method of Brown et al., 1080, Meth. Enzymol. 68:109-151; the diethylphosphoramidite method of Beaucage et al., 1981, Tetrahedron Lett. 22:1859-1862; and the solid support method of U.S. Pat. No. 4,458,066, each incorporated herein by reference. A review of synthesis methods of conjugates of oligonucleotides and modified nucleotides is provided in Goodchild, 1990, Bioconjugate Chemistry 1(3): 165-187, incorporated herein by reference.

Complementary

As used herein, "complementary" refers to a nucleic acid molecule that can form hydrogen bond(s) with another nucleic acid molecule by either traditional Watson-Crick base pairing or other non-traditional types of pairing (e.g., Hoogsteen or reversed Hoogsteen hydrogen bonding) between complementary nucleosides or nucleotides.

Target Sequence, Region or Nucleic Acid

The terms target, "target sequence", "target region", and "target nucleic acid," as used herein, are synonymous and refer to a region or subsequence of a nucleic acid which is to be amplified or detected.

Amplification Reaction

The term "amplification reaction" refers to any chemical reaction, including an enzymatic reaction, which results in increased copies of a template nucleic acid sequence or results in transcription of a template nucleic acid. Amplification reactions include reverse transcription and the polymerase chain reaction (PCR), including Real Time PCR (see U.S. Pat. Nos. 4,683,195 and 4,683,202; PCR Protocols: A Guide to Methods and Applications (Innis et al., eds, 1990)). Exemplary "amplification reactions conditions" or "amplification conditions" typically comprise either two or three step cycles. Two step cycles have a denaturation step followed by a hybridization/elongation step. Three step cycles comprise a denaturation step followed by a hybridization step followed by a separate elongation step.

Polymerase Chain Reaction

Polymerase chain reaction (PCR) is a method that allows exponential amplification of short DNA sequences (usually 100 to 600 bases) within a longer double stranded DNA molecule. PCR entails the use of a pair of primers, each about 20 nucleotides in length, that are complementary to a defined sequence on each of the two strands of the DNA. These primers are extended by a DNA polymerase so that a copy is made of the designated sequence. After making this copy, the same primers can be used again, not only to make another copy of the input DNA strand but also of the short copy made in the first round of synthesis. This leads to logarithmic amplification. Since it is necessary to raise the temperature to separate the two strands of the double strand DNA in each round of the amplification process, a major step forward was the discovery of a thermo-stable DNA polymerase (Taq polymerase) that was isolated from *Thermus aquaticus*, a bacterium that grows in hot pools; as a result it is not necessary to add new polymerase in every round of amplification. After several (often about 40) rounds of amplification, the PCR product is analyzed on an agarose gel and is abundant enough to be detected with an ethidium bromide stain.

Real-Time or Quantitative Polymerase Chain Reaction

In other embodiments, real-time PCR, also called quantitative real time PCR, quantitative PCR (Q-PCR/qPCR), or kinetic polymerase chain reaction, is a laboratory technique based on PCR, which is used to amplify and simultaneously quantify a targeted DNA molecule. qPCRA enables both detection and quantification (as absolute number of copies of relative amount when normalized to DNA input or additional normalizing genes) of a specific sequence in a DNA sample. For example, in the embodiments disclosed herein, qPCR may be used to quantify the amount of fungal DNA in a patient sample. The procedure follows the general principle of PCR; its key feature is that the amplified DNA is quantified as it accumulates in the reaction in real time after each amplification cycle. Two common methods of quantification are the use of fluorescent dyes that intercalate with double-stranded DNA, and modified DNA oligonucleotide probes that fluoresce when hybridized with a complementary DNA. The qPCR results may be quantitated using the ΔΔCt method. This method involves calculating a ΔCt between the average target gene Ct and average housekeeping gene Ct for a given target in each treatment group. The ΔΔCt is used to calculate the "n-fold" change in gene expression between groups.

Polymerase

As used herein, a "polymerase" refers to an enzyme that catalyzes the polymerization of nucleotides. Generally, the enzyme will initiate synthesis at the 3'-end of the primer annealed to a nucleic acid template sequence. "DNA polymerase" catalyzes the polymerization of deoxyribonucleotides. Known DNA polymerases include, for example, *Pyrococcus furiosus* (Pfu) DNA polymerase (Lundberg et al., 1991, Gene 108:1), *E. coli* DNA polymerase I (Lecomte and Doubleday, 1983, Nucleic Acids Res. 11:7505), T7 DNA polymerase (Nordstrom et al., 1981, J. Biol. Chem. 256: 3112). *Thermus thermophilus* (Tth) DNA polymerase (Myers and Gelfand 1991, Biochemistry 30:7661), *Bacillus stearothermophilus* DNA polymerase (Stenesh and McGowan, 1977. Biochim Biophys Acta 475:32), *Thermococcus litoralis* (Tli) DNA polymerase (also referred to as Vent DNA polymerase, Cariello et al., 1991, Nucleic Acids Res, 19: 4193, *Thermotoga maritima* (Tma) DNA polymerase (Diaz and Sabino, 1998 Braz J. Med. Res, 31:1239), *Thermus aquaticus* (Taq) DNA polymerase (Chien et al., 1976, J. Bacteoriol, 127: 1550), *Pyrococcus kodakaraensis* KOD DNA polymerase (Takagi et al., 1997, Appl. Environ. Microbiol. 63:4504), JDF-3 DNA polymerase (Patent application WO 0132887), and *Pyrococcus* GB-D (PGB-D) DNA polymerase (Juncosa-Ginesta et al., 1994, Biotechniques, 16:820). The polymerase activity of any of the above enzymes can be determined by means well known in the art.

Reaction Mixture

The term "reaction mixture" as used herein, refers to a solution containing reagents necessary to carry out a given reaction. An "amplification reaction mixture", which refers to a solution containing reagents necessary to carry out an amplification reaction, typically contains oligonucleotide primers and a DNA polymerase or ligase in a suitable buffer. A "PCR reaction mixture" typically contains oligonucleotide primers, a DNA polymerase (most typically a thermostable DNA polymerase), dNTPs, and a divalent metal cation in a suitable buffer. A reaction mixture is referred to as complete if it contains all reagents necessary to enable the reaction, and incomplete if it contains only a subset of the necessary reagents. It will be understood by one of skill in the art that reaction components are routinely stored as separate solutions, each containing a subset of the total components, for reasons of convenience, storage stability, or to allow for application-dependent adjustment of the component concentrations, and that reaction components are combined prior to the reaction to create a complete reaction mixture. Furthermore, it will be understood by one of skill in the art that reaction components are packaged separately for commercialization and that useful commercial kits may contain any subset of the reaction components which includes the blocked primers of the disclosure.

Ligation and Ligase

The term "ligation" as used herein refers to the covalent joining of two polynucleotide ends. In various embodiments, ligation involves the covalent joining of a 3' end of a first polynucleotide (the acceptor) to a 5' end of a second polynucleotide (the donor). Ligation results in a phosphodiester bond being formed between the polynucleotide ends. In various embodiments, ligation may be mediated by any enzyme, chemical, or process that results in a covalent joining of the polynucleotide ends. In certain embodiments, ligation is mediated by a ligase enzyme.

As used herein, "ligase" refers to an enzyme that is capable of covalently linking the 3' hydroxyl group of neucleotide to the 5' phosphate group of a second nucleotide. Examples of ligases include *E. coli* DNA ligase, T4 DNA ligase, etc.

The litigation reaction can be employed in DNA amplification methods such as the "ligase chain reaction" (LCR), also referred to as the "ligase amplification reaction" (LAR), see Barany, Proc. Natl. Acad. Sci., 88:189 (1991); and Wu and Wallace, Genomics 4:560 (1989) incorporated herein by reference. In LCR, four oligonucleotides, two adjacent oligonucleotides which uniquely hybridize to one strand of the target DNA, and a complementary set of adjacent oligonucleotides, that hybridize to the opposite strand are mixed and DNA ligase is added to the mixture. Provided that there is complete complementarity at the junction, ligase will covalently link each set of hybridized molecules. Importantly, in LCR, two probes are ligated together only when they base-pair with sequences in the target sample, without gaps or mismatches. Repeated cycles of denaturation, hybridization and ligation amplify a short segment of DNA. LCR has also been used in combination with PCR to achieve enhanced detection of single-base changes. see Segev, PCT Public. No. WO9001069 A1 (1990).

Orthologs

As used herein, the term "orthologs" refers to genes in different species that apparently evolved from a common ancestral gene by speciation. Normally, orthologs retain the same function through the course of evolution. Identification of orthologs can provide reliable prediction of gene function in newly sequenced genomes. Sequence comparison algorithms that can be used to identify orthologs include without limitation BLAST, FASTA, DNA Strider, and the GCG pileup program. Orthologs often have high sequence similarity. The present invention encompasses all orthologs of the desired protein.

Operative Associated

By "operatively associated with" is meant that a target nucleic acid sequence and one or more expression control sequences (e.g., promoters) are physically linked so as to permit expression of the polypeptide encoded by the target nucleic acid sequence within a host cell.

Percent Sequence Similarity or Percent Sequence Identity

The terms "percent (%) sequence similarity", "percent (%) sequence identity", and the like, generally refer to the degree of identity or correspondence between different nucleotide sequences of nucleic acid molecules or amino acid sequences of proteins that may or may not share a common evolutionary origin (see Reeck et al., supra). Sequence identity can be determined using any of a number of publicly available sequence comparison algorithms, such as BLAST, FASTA, DNA Strider, GCG (Genetics Computer Group, Program Manual for the GCG Package, Version 7, Madison, Wis.), etc.

To determine the percent identity between two amino acid sequences or two nucleic acid molecules, the sequences are aligned for optimal comparison purposes. The percent identity between the two sequences is a function of the number of identical positions shared by the sequences (i.e., percent identity=number of identical positions/total number of positions (e.g., overlapping positions)×100). In one embodiment, the two sequences are, or are about, of the same length. The percent identity between two sequences can be determined using techniques similar to those described below, with or without allowing gaps. In calculating percent sequence identity, typically exact matches are counted.

The determination of percent identity between two sequences can be accomplished using a mathematical algorithm. A non-limiting example of a mathematical algorithm utilized for the comparison of two sequences is the algorithm of Karlin and Altschul, Proc. Natl. Acad. Sci. USA 1990, 87:2264, modified as in Karlin and Altschul, Proc. Natl. Acad. Sci. USA 1993, 90:5873-5877. Such an algorithm is incorporated into the NBLAST and XBLAST programs of Altschul et al., J. Mol. Biol. 1990; 215:403. BLAST nucleotide searches can be performed with the NBLAST program, score=100, wordlength=12, to obtain nucleotide sequences homologous to sequences of the invention. BLAST protein searches can be performed with the XBLAST program, score=50, wordlength=3, to obtain amino acid sequences homologous to protein sequences of the invention. To obtain gapped alignments for comparison purposes, Gapped BLAST can be utilized as described in Altschul et al., Nucleic Acids Res. 1997, 25:3389. Alternatively, PSI-Blast can be used to perform an iterated search that detects distant relationship between molecules. See Altschul et al. (1997) supra. When utilizing BLAST, Gapped BLAST, and PSI-Blast programs, the default parameters of the respective programs (e.g., XBLAST and NBLAST) can be used. See ncbi.nlm.nih.gov/BLAST/ on the WorldWideWeb. Another non-limiting example of a mathematical algorithm utilized for the comparison of sequences is the algorithm of Myers and Miller, CABIOS 1988; 4: 11-17. Such an algorithm is incorporated into the ALIGN program (version 2.0), which is part of the GCG sequence alignment software package. When utilizing the ALIGN program for comparing amino acid sequences, a PAM120 weight residue table, a gap length penalty of 12, and a gap penalty of 4 can be used.

In a preferred embodiment, the percent identity between two amino acid sequences is determined using the algorithm of Needleman and Wunsch (J. Mol. Biol. 1970, 48:444-453), which has been incorporated into the GAP program in the GCG software package Accelrys, Burlington, Mass.; available at accelrys.com on the WorldWideWeb), using either a Blossum 62 matrix or a PAM250 matrix, a gap weight of 16, 14, 12, 10, 8, 6, or 4, and a length weight of 1, 2, 3, 4, 5, or 6. In yet another preferred embodiment, the percent identity between two nucleotide sequences is determined using the GAP program in the GCG software package using a NWSgapdna.CMP matrix, a gap weight of 40, 50, 60, 70, or 80, and a length weight of 1, 2, 3, 4, 5, or 6. A particularly preferred set of parameters (and the one that can be used if the practitioner is uncertain about what parameters should be applied to determine if a molecule is a sequence identity or homology limitation of the invention) is using a Blossum 62 scoring matrix with a gap open penalty of 12, a gap extend penalty of 4, and a frameshift gap penalty of 5.

In addition to the cDNA sequences encoding various desired proteins, the present invention further provides polynucleotide molecules comprising nucleotide sequences having certain percentage sequence identities to any of the aforementioned sequences. Such sequences preferably hybridize under conditions of moderate or high stringency as described above, and may include species orthologs.

Variant

The term "variant" may also be used to indicate a modified or altered gene, DNA sequences, enzyme, cell, etc., i.e., any kind of mutant.

Immune Response

An "immune response" refers to the development in the host of a cellular and/or antibody-mediated immune response to a composition or vaccine of interest. Such a response usually consists of the subject producing antibodies, B cells, helper T cells, and/or cytotoxic T cells directed specifically to an antigen or antigens included in the composition or vaccine of interest. The immune response also may include regulatory T-cells, whose activity may suppress other immune or allergic responses. In certain embodiments, "immune response" or "innate immune response" may also refer to the initial response of immune cells to the presence of microbial organism or to the presence of "pathogen associated molecular patterns (PAMPs)", which are evolutionarily conserved amino acid or nucleic acid sequences recognized by pattern recognition receptors on immune cells. This initial response is characterized by the release of pro-inflammatory cytokines and other pro-immune mediators by the detecting immune cells and is usually necessary for the induction of the cellular and/or antibody-mediated "adaptive" immune responses discussed above. TLR ligands expressed by *E. coli* and *Citrobacter rodentium* include but are not limited to LPS (TLR4 ligand), PGN (TLR2 ligand), triacyl lipopetides (TLR2 ligand), lipoproteins (TLR2 ligand), unmethylated DNA (TLR9 ligand), and single stranded RNA (TLR7 and TLR8). Other preferred microbes for the present invention include bacterial strains selected for use as live attenuated vaccines. Examples of those include but are not limited to *Mycobacterium bovis* BCG vaccine against tuberculosis, *Salmonella typhi* Ty21a vaccine against typhoid fever, and *Vibrio cholerae* CVD 103-HgR vaccine against cholera. These microorganisms may additionally express the TLR5 ligand Flagellin in addition to the PAMPs shared by *E. coli* and *Citrobacter rodentium.*

Antigen and Immunogen

An "antigen" (from antibody-generating) or "immunogen" is a substance that prompts the generation of antibodies and can cause an immune response. For example, in the present invention, proteins associated with tumors may be used as antigens or immunogens to stimulate an immune response against a tumor. An "immunodominant antigen" is defined as an antigen for which a higher relative number of T cells will be specific during an immune response, compared to the numbers of T cells with T cell receptors that recognize other antigens.

Antibody

Antibodies (also knows an immunoglobulins (Ig)) are gamma globulin proteins that are found in blood or other bodily fluids of vertebrates, and are used by the immune system to identify and neutralize foreign objects, such as bacteria and viruses. They are typically made of basic structural units—each with two large heavy chains and two small light chains—to form, for example, monomers with one unit, dimers with two units or pentameters with five units. Antibodies are produced by B cells. There are several different types of antibody heavy changes, and several different kinds of antibodies, which are grouped into different isotypes based on which heavy chain they possess. Five different antibody isotypes are known in mammals, which perform different roles, and help direct the appropriate immune response for each different type of foreign object they encounter.

Although the general structure of all antibodies is very similar, a small region at the tip of the protein is extremely variable, allowing millions of antibodies with slightly different tip structures to exist. This region is known as the hypervariable region. Each of these variants can bind to a different target, known as an antigen. This huge diversity of antibodies allows the immune system to recognize an equally wide diversity of antigens. The unique part of the antigen recognized by an antibody is termed an "epitope." These epitopes bind with their antibody in a highly specific interaction, called induced fit, which allows antibodies to identify and bind only their unique antigen in the midst of the millions of different molecules that make up an organism. Recognition of an antigen by an antibody tags it for attack by other parts of the immune system. Antibodies can also neutralize targets directly by, for example, binding to a part of a pathogen that it needs to cause an infection. Production of antibodies is the main function of the humoral immune system.

Enzyme-Linked Immunoabsorbent Assay (ELISA)

Enzyme-Linked ImmunoSorbent Assay, also called ELISA, Enzyme ImmunoAssay or EIA, is a biochemical technique used to detect the presence of an antibody or an antigen in a sample. In ELISA, an unknown amount of antigen is affixed to a surface, and then a specific antibody is washed over the surface so that it can bind to the antigen. This antibody is linked to an enzyme, and in the final step a substance is added that the enzyme can convert to some detectable signal. Thus in the case of fluorescene ELISA, when light of the appropriate wavelength is shone upon the sample, any antigen/antibody complexes will fluoresce so that the amount of antigen in the sample can be inferred through the magnitude of the fluorescene. Performing an ELISA involves at least one antibody with specificity for a particular antigen. The sample with an unknown amount of antigen is immobilized on a solid support (usually a polystyrene microtiter plate) either non-specifically (via adsorption to the surface) or specifically (via capture by another antibody specific to the same antigen, in a "sandwich" ELISA). After the antigen is immobilized the detection antibody is added, forming a complex with the antigen. The detection antibody can be covalently linked to an enzyme, or can itself be detected by a secondary antibody which is linked to an enzyme through bioconjugation. Between each step the plate is typically washed with a mild detergent solution to remove any proteins or antibodies that are not specifically bound. After the final wash step the plate is developed by adding an enzymatic substrate to produce a visible signal, which indicates the quantity of antigen in the sample. Older ELISAs utilize chromogenic substrates, though never assays employ fluorogenic substrates enabling much higher sensitivity.

Transgenic Mouse

A transgenic mouse contains additional, artifically-introduced genetic material in every cell. This often confers a gain of function, for example the mouse may produce a new protein, but a loss of function may occur if the integrated DNA interrupts another gene. A transgenic mouse is a very useful system for studying mammalian gene function and regulator because analysis is carried out on the whole organism. Transgenic mice are also used to model human diseases that involve the overexpression or misexpression of a particular protein. There are two major methods. Methods for making transgenic mice include "pronuclear microinjection", in which the foreign DNA is introduced directly into the mouse egg just after fertilization. Using a fine needle, the DNA is injected into the large male pronucleus, which is derived from the sperm. The DNA tends to integrate as many tandemly arranged copies at a random position in the genome, often after one or two cell divisions have occurred. Therefore, the resulting mouse is only partially transgenic. If the transgenic cells contribute to the germ line, then some transgenic eggs or sperm will be produced and the next generation of mice will be fully transgenic. In another method, DNA is introduced into embryonic stem cells (ES cells). These are derived from the very early mouse embryo and can therefore differentiate into all types of cell when introduced into another embryo. DNA introduced into ES cells may integrate randomly, as in the case of pronuclear microinjection. However, if the introduced DNA is similar in sequence to part of the mouse genome, it may undergo "homologous recombination" and integrate as a single copy at a specific site. ES cells will colonize a host embryo and often contribute to the germ line, resulting in the production of some sperm carrying the extra DNA. When these transgenic sperm fertilize a normal egg, a transgenic mouse is produced with the same foreign DNA in every cell.

Knockout Mouse

A knockout mouse is a laboratory mouse in which researchers have inactivated, or "knocked out," an existing gene by replacing it or disrupting it with an artificial piece of DNA. The loss of gene activity often causes changes in a mouse's phenotype, which includes appearance, behavior and other observable physical and biochemical characteristics. Researchers begin by harvesting embryonic stem (ES) cells from early-stage mouse embryos four days after fertilization. ES cells are used because they are able to differentiate into nearly any type of adult cell, which means that if a gene is knocked out in an ES cell, the effects can be observed in any tissue in an adult mouse. In addition, ES cells grown in the lab can be used to make knockout mice as long as 10 years after they were harvested. To produce knockout mice, researchers use one of two methods to insert artificial DNA into the chromosomes contained in the nuclei of ES cells. Both methods are carried out in vitro that is in cultured cells grown in laboratory conditions. In the first strategy, called gene targeting or homologous recombination researchers specifically manipulate a gene in the nucleus of an ES cell. Typically, this is done by introducing an artificial piece of DNA that shares identical, or homologous, sequence to the gene. This homologous sequence flanks the existing gene's DNA sequence both upstream and downstream of the gene's location on the chromosome. The cell's own nuclear machinery automatically recognizes the identical stretches of sequence and swaps out the existing gene or portion of a gene with the artificial piece of DNA. Because the artificial DNA is inactive, bearing only a genetic tag, or "reporter gene," designed for use in tracking, the swap eliminates, or "knocks out," the function of the existing gene.

In the second strategy, called gene trapping, researchers again manipulate a gene in an ES cell. However, instead of directly targeting a gene of interest, a random process is used. A piece of artificial DNA containing a reporter gene is designed to insert randomly into any gene. The inserted piece of artificial DNA prevents the cell's RNA "splicing" machinery from working properly, thus preventing the existing gene from producing its designated protein and knocking out its function. As in the first strategy, researchers can track the activity of the artificial reporter gene to determine the existing gene's normal pattern of activity in mouse tissues. For both gene targeting and gene trapping, the vehicle used to ferry the artificial DNA into ES cells often consists of a modified viral vector or a linear fragment of bacterial DNA. After the artificial DNA is inserted, the genetically altered ES cells are grown in a lab dish for several days and injected into early-stage mouse embryos. The embryos are implanted into the uterus of a female mouse and allowed to develop into mouse pups. The resulting mouse pups have some tissues in which a gene has been knocked out—those derived from the altered ES cells. However, they also have some normal tissues derived from the non-altered embryos into which the altered ES cells were injected. Consequently, they are not complete knockout mice. It is necessary to crossbreed such mice to produce lines of mice in which both copies of the gene (one on each chromosome) are knocked out in all tissues. These mice are referred to as homozygous knockouts.

In certain embodiments, "double knockout" mice are used. Double knockout mice have two genes that have been deleted, as described above. Examples of knockout mice of the present invention include TLR4 knockout mice ($TLR4^{-/-}$), $IL6^{-/-}$, and $MyD88^{-/-}/TRIF^{-/-}$ double knockout mice.

Pharmaceutically Acceptable

When formulated in a pharmaceutical composition, a therapeutic compound of the present invention can be admixed with a pharmaceutically acceptable carrier or excipient. As used herein, the phrase "pharmaceutically acceptable" refers to molecular entities and compositions that are generally believed to be physiologically tolerable and do not typically produce an allergic or similar untoward reaction, such as gastric upset, dizziness and the like, when administered to a human.

Pharmaceutically Acceptable Derivative

The term "pharmaceutically acceptable derivative" as used herein means any pharmaceutically acceptable salt, solvate or prodrug, e.g. ester, of a compound of the invention, which upon administration to the recipient is capable of providing (directly or indirectly) a compound of the invention, or an active metabolite or residue thereof. Such derivatives are recognizable to those skilled in the art, without undue experimentation. Nevertheless, reference is made to the teaching of Burger's Medicinal Chemistry and Drug Discovery, 5th Edition, Vol 1: Principles and Practice, which is incorporated herein by reference to the extent of teaching such derivatives. Preferred pharmaceutically acceptable derivatives are salts, solvates, esters, carbamates, and phosphate esters. Particularly preferred pharmaceutically acceptable derivatives are salts, solvates, and esters. Most preferred pharmaceutically acceptable derivatives are salts and esters.

Pharmaceutical Compositions and Administration

While it is possible to use a composition provided by the present invention for therapy as is, it may be preferable to administer it in a pharmaceutical formulation, e.g., in admixture with a suitable pharmaceutical excipient, diluent, or carrier selected with regard to the intended route of administration and standard pharmaceutical practice. Accordingly, in one aspect, the present invention provides a pharmaceutical composition or formulation comprising at least one active composition, or a pharmaceutically acceptable derivative thereof, in association with a pharmaceutically acceptable excipient, diluent, and/or carrier. The excipient, diluent and/or carrier must be "acceptable" in the sense of being compatible with the other ingredients of the formulation and not deleterious to the recipient thereof.

The compositions of the invention can be formulated for administration in any convenient way for use in human or veterinary medicine.

Pharmaceutical Carrier

The term "carrier" refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions. Alternatively, the carrier can be a solid dosage form carrier, including but not limited to one or more of a binder (for compressed pills), a glidant, an encapsulating agent, a flavorant, and a colorant. Suitable pharmaceutical carriers are described in "Remington's Pharmaceutical Sciences" by E. W. Martin (1990, Mack Publishing Co., Easton, Pa. 18042).

In one embodiment, the pharmaceutical composition is conveniently administered as a liquid oral formulation. Although there are no physical limitations to delivery of the formulation, oral delivery is preferred because of its ease and convenience, and because oral formulations readily accommodate additional mixtures, such as milk, yogurt, and infant formula. Other oral dosage forms are well known in the art and include tablets, caplets, gelcaps, capsules, and medical foods. Tablets, for example, can be made by well-known compression techniques using wet, dry, or fluidized bed granulation methods.

Such oral formulations may be presented for use in a conventional manner with the aid of one or more suitable excipients, diluents, and carriers. Pharmaceutically acceptable excipients assist or make possible the formation of a dosage form for a bioactive material and include diluents, binding agents, lubricants, glidants, disintegrants, coloring agents, and other ingredients. Preservatives, stabilizers, dyes and even flavoring agents may be provided in the pharmaceutical composition. Examples of preservatives include sodium benzoate, ascorbic acid and esters of p-hydroxybenzoic acid. Antioxidants and suspending agents may be also used. An excipient is pharmaceutically acceptable if, in addition to performing its desired function, it is non-toxic, well tolerated upon ingestion, and does not interfere with absorption of bioactive materials.

Acceptable excipients, diluents, and carriers for therapeutic use are well known in the pharmaceutical art, and are described, for example, in Remington: The Science and Practice of Pharmacy. Lippincott Williams & Wilkins (A. R. Gennaro edit 2005). The choice of pharmaceutical excipient, diluent, and carrier can be selected with regard to the intended route of administration and standard pharmaceutical practice.

The invention also encompasses pharmaceutical compositions and vaccines. The pharmaceutical compositions and vaccine compositions of the invention include at least one of the compositions of the invention, a suitable antigen (for vaccines), and a pharmaceutically acceptable carrier or excipient. Methods of formulating pharmaceutical compositions and vaccines are well-known to those of ordinary skill in the art, as described in Remington's, supra.

Formulations

The compositions, vaccines and formulations of the present invention may comprise pharmaceutically acceptable diluents, preservatives, solubilizers, emulsifiers, adjuvants and/or carriers. Such compositions include diluents of various buffer content (e.g., Tris-HCl, acetate, phosphate), pH and ionic strength; additives such as detergents and solubilizing agents (e.g., Tween 80, Polysorbate 80), anti-oxidants (e.g., ascorbic acid, sodium metabisulfite), preservatives (e.g., Thimersol, benzyl alcohol) and bulking substances, (e.g., lactose, mannitol); incorporation of the material into particulate preparations of polymeric compounds such as polylactic acid, polyglycolic acid, etc. or into liposomes. Hylauronic acid may also be used. See, e.g., Remington's Pharmaceutical Sciences, 18th Ed. (1990, Mack Publishing Co., Easton, Pa. 18042) pages 1435 1712 which are herein incorporated by reference.

Contemplated for use herein are oral solid dosage forms, which are described generally in Remington's Pharmaceutical Sciences, 18th Ed. 1990 (Mack Publishing Co. Easton Pa. 18042) at Chapter 89, which is herein incorporated by reference. Solid dosage forms include tablets, capsules, pills, troches or lozenges, cachets, pellets, powders, or granules. Also, liposomal or proteinoid encapsulation may be used to formulate the present compositions (as, for example, proteinoid microspheres reported in U.S. Pat. No. 4,925,673). Liposomal encapsulation may be used and the liposomes may be derivatized with various polymers (e.g., U.S. Pat. No. 5,013, 556). A description of possible solid dosage forms for the therapeutic is given by Marshall, K. In: Modern Pharmaceutical Edited by G. S. Banker and C. T. Rhodes Chapter 10, 1979, herein incorporated by reference. In general, the formulation will include the therapeutic agent and inert ingredients which allow for protection against the stomach environment, and release of the biologically active material in the intestine.

Also contemplated for use herein are liquid dosage forms for oral administration, including pharmaceutically acceptable emulsions, solutions, suspensions, and syrups, which may contain other components including inert diluents, adjuvants, wetting agents, emulsifying and suspending agents, and sweetening flavoring, coloring, and perfuming agents.

For oral formulations, the location of release may be the stomach, the small intestine (the duodenum, the jejunem, or the ileum), or the large intestine. One skilled in the art has available formulations which will not dissolve in the stomach, yet will release the material in the duodenum or elsewhere in the intestine, e.g., by the use of an enteric coating. Examples of the more common inert ingredients that are used as enteric coatings are cellulose acetate trimellitate (CAT), hydroxypropylmethylcellulose phthalate (HPMCP), HPMCP 50, HPMCP 55, polyvinyl acetate phthalate (PVAP), Eudragit L30D, Aquateric, cellulose acetate phthalate (CAP), Eudragit L, Eudragit S, and Shellac. These coatings may be used as mixed films.

A coating or mixture of coatings can also be used on tablets, which are not intended for protection against the stomach. This can include sugar coatings, or coatings which make the tablet easier to swallow. Capsules may consist of a hard shell (such as gelatin) for delivery of dry therapeutic (i.e. powder), for liquid forms a soft gelatin shell may be used. The shell material of cachets could be thick starch or other edible paper. For pills, lozenges, molded tablets or tablet triturates, moist massing techniques can be used. The formulation of the material for capsule administration could also be as a powder, lightly compressed plugs, or even as tablets. These therapeutics could be prepared by compression.

One may dilute or increase the volume of the therapeutic agent with an inert material. These diluents could include carbohydrates, especially mannitol, lactose, anhydrous lactose, cellulose, sucrose, modified dextrans and starch. Certain inorganic salts may be also used as fillers including calcium triphosphate, magnesium carbonate and sodium chloride. Some commercially available diluents are Fast-Flo, Emdex, STA-Rx 1500, Emcompress and Avicell.

Disintegrants may be included in the formulation of the therapeutic agent into a solid dosage form. Materials used as disintegrates include but are not limited to starch, including the commercial disintegrant based on starch, Explotab, Sodium starch glycolate, Amberlite, sodium carboxymethylcellulose, ultramylopectin, sodium alginate, gelatin, orange peel, acid carboxymethyl cellulose, nature sponge and bentonite may all be used. The disintegrants may also be insoluble cationic exchange resins. Powdered gums may be used as disintegrants and as binders, and can include powdered gums such as agar, Karaya or tragacanth. Alginic acid and its sodium salt are also useful as disintegrants. Binders may be used to hold the therapeutic agent together to form a hard tablet and include materials from natural products such as acacia, tragacanth, starch and gelatin. Others include methyl cellulose (MC), ethyl cellulose (EC) and carboxymethyl cellulose (CMC). Polyvinyl pyrrolidone (PVP) and hydroxypropylmethyl cellulose (HPMC) could both be used in alcoholic solutions to granulate the peptide (or derivative).

An artifrictional agent may be included in the formulation to prevent sticking during the formulation process. Lubricants may be used as a layer between the peptide (or derivative) and the die wall, and these can include but are not limited to; stearic acid including its magnesium and calcium salts, polytetrafluoroethylene (PTFE), liquid paraffin, vegetable oils and waxes. Soluble lubricants may also be used such as sodium lauryl sulfate, magnesium lauryl sulfate, polyethylene glycol of various molecular weights, Carbowax 4000 and 6000.

Glidants that might improve the flow properties drug during formulation and to aid rearrangement during compression might be added. The glidants may include starch, talc, pyrogenic silica and hydrated silicoaluminate.

To aid dissolution of the therapeutic agent into the aqueous environment a surfactant might be added as a wetting agent. Surfactants may include anionic detergents such as sodium lauryl sulfate, dioctyl sodium sulfosuccinate and dioetyl sodium sulfonate. Cationic detergents might be used and could include benzalkonium chloride or benzethomium chloride. The list of potential nonionic detergents that could be included in the formulation as surfactants are lauromacrogol 400, polyoxyl 40 stearate, polyoxyethylene hydrogenated castor oil 10, 50, and 60, glycerol monostearate, polysorbate 40, 60, 65 and 80, sucrose fatty acid ester, methyl cellulose and carboxymethyl cellulose. These surfactants could be present in the formulation of the protein or derivative either alone or as a mixture in different ratios.

Controlled release oral formulations may be used in practicing the present invention. The therapeutic agent could be incorporated into an inert matrix which permits release by either diffusion or leaching mechanisms, e.g., gums. Slowly degenerating matrices may also be incorporated into the formulation. Some enteric coatings also have a delayed release effect. Another form of a controlled release is by a method based on the Oros therapeutic system (Alza Corp.), i.e. the therapeutic agent is enclosed in a semipermeable membrane which allows water to enter and push agent out through a single small opening due to osmotic effects.

Other coatings may be used for the formulation. These include a variety of sugars which could be applied in a coating pan. The therapeutic agent could also be given in a film coated tablet and the materials used in this instance are divided into 2 groups. The first are the nonenteric materials and include methyl cellulose, ethyl cellulose, hydroxyethyl cellulose, methylhydroxy-ethyl cellulose, hydroxypropyl cellulose, hydroxypropyl-methyl cellulose, sodium carboxy-methyl cellulose, providone and the polyethylene glycols. The second group consists of the enteric materials that are commonly esters of phthalic acid. A mix of materials might be used to provide the optimum film coating. Film coating may be carried out in a pan coater or in a fluidized bed or by compression coating.

Preparations according to this invention for parenteral administration include sterile aqueous or non-aqueous solutions, suspensions, or emulsions. Examples of non-aqueous solvents or vehicles are propylene glycol, polyethylene glycol, vegetable oils, such as olive oil and corn oil, gelatin, an injectable organic esters such as ethyl oleate. Such dosage forms may also contain adjuvants, preserving, wetting, emulsifying, and dispersing agents. The pharmaceutical compositions may be sterilizing agents into the compositions, by irradiating the compositions, or by heating the compositions. They can also be manufactured using sterile water, or some other injectable medium, immediately before use.

Vaccines

In the case of vaccines, it is often observed that a primary challenge with an antigen alone, in the absence of an adjuvant, will fail to elicit a humoral or cellular immune response. Therefore the vaccines of the invention may contain adjuvants including, but not limited to, cholera toxin, fragments and mutants or derivatives with adjuvants properties, *E. coli* heat-labile enterotoxin, fragments and mutants or derivatives with adjuvant properties, oil-in-water and water-in-oil emulsions, toll-like receptor ligands such as muramyl dipeptide, *E. coli* LPS, oiligonucleotides comprised of unmethylated DNA, poly I:C, lipoteichoic acid, peptidoglycan. Enterotoxins and their adjuvant active derivatives such as cholera toxin, heat-labile *E. coli* enterotoxin, pertussis toxin, shiga toxin and analogs. Other adjuvants can be used such as complete Freund's adjuvant, incomplete Freund's adjuvant, saponin, mineral gels such as aluminum hydroxide, surface active substances such as lysolecithin, pluronic polyols, polyanions, peptides, oil or hydrocarbon emulsions, keyhole limpet hemocyanins, and potentially useful human adjuvants such as N-acetyl-muramyl-L-threonyl-D-isoglutamine (thr-MDP), N-acetyl-nor-muramyl-L-alanyl-D-isoglutamine, N-acetyl-muramyl-L-alanyl-D-isoglutaminyl-L-alanine-2-(1'-2'-dipalmitoyl-sn -glycero-3-hydroxyphosphoryloxy)-ethylamine, BCG (bacille Calmette-Guerin) and *Corynebacterium parvum*. An adjuvant can serve as a tissue depot that slowly releases the antigen and also as a lymphoid system activator that non-specifically enhances the immune response (Hood et al., Immunology, Second Ed., 1984, Benjamin/Cummings: Menlo Park, Calif., p. 384). Where the vaccine is intended for use in human subjects, the adjuvant should be pharmaceutically acceptable.

Vaccine Administration

The pharmaceutical formulations and vaccines may be for administration by oral (solid or liquid), parenteral (intramuscular, intraperitoneal, intravenous (IV) or subcutaneous injection), transdermal (either passively or using ionophoresis or electroporation), transmucosal (nasal, vaginal, rectal, or sublingual), or inhalation routes of administration, or using bioerodible inserts and can be formulated in dosage forms appropriate for each route of administration.

In a preferred embodiment, the compositions or vaccines are administered by pulmonary delivery. The composition or vaccine is delivered to the lungs of a mammal while inhaling and traverses across the lung epithelial lining to the blood stream [see, e.g., Adjei, et al. Pharmaceutical Research 1990; 7:565 569; Adjei, et al. Int. J. Pharmaceutics 1990; 63:135 144 (leuprolide acetate); Braquet, et al. J. Cardiovascular Pharmacology 1989; 13(sup5):143 146 (endothelin-1); Hubbard, et al. (1989) Annals of Internal Medicine, Vol. III, pp. 206 212 ($\alpha$1 antitrypsin); Smith, et al. J. Clin. Invest. 1989; 84:1145-1146 ($\alpha$ 1-proteinase); Oswein, et al. "Aerosolization of Proteins". 1990; Proceedings of Symposium on Respiratory Drug Delivery II Keystone, Colo. (recombinant human growth hormone); Debs, et al. J. Immunol. 1988; 140:3482 3488 (interferon $\gamma$ and tumor necrosis factor $\alpha$); and U.S. Pat. No. 5,284,656 to Platz, et al. (granulocyte colony stimulating factor). A method and composition for pulmonary delivery of drugs for systemic effect is described in U.S. Pat. No. 5,451,569 to Wong, et al. See also U.S. Pat. No. 6,651,655 to Licalsi et al.

Contemplated for use in the practice of this invention are a wide range of mechanical devices designed for pulmonary delivery of therapeutic products, including but not limited to nebulizers, metered dose inhalers, and powder inhalers, all of which are familiar to those skilled in the art. Some specific examples of commercially available devices suitable for the practice of this invention are the Ultravent nebulizer (Mallinckrodt Inc., St. Louis, Mo.); the Acorn II nebulizer (Marquest Medical Products, Englewood, Colo.); the Ventolin metered dose inhaler (Glaxo Inc., Research Triangle Park, N.C.); and the Spinhaler powder inhaler (Fisons Corp., Bedford, Mass.). All such devices require the use of formulations suitable for the dispensing of the therapeutic agent. Typically, each formulation is specific to the type of device employed and may involve the use of an appropriate propellant material, in addition to the usual diluents, adjuvants, surfactants and/or carriers useful in therapy. Also, the use of lipsomes, microcapsules or microspheres, inclusion complexes, or other types of carriers is contemplated.

Formulations for use with a metered dose inhaler device will generally comprise a finely divided powder containing the therapeutic agent suspended in a propellant with the aid of a surfactant. The propellant may be any conventional material employed for this purpose, such as a chloroflurocarbon, a hydrochlorofluorocarbon, a hydrofluorocarbon, or a hydrocarbon, including trichlorofluoromethane, dichlorodifluoromethane, dichlorotetrafluoroethanol, and 1,1,1,2 tetrafluorethane, or combinations thereof. Suitable surfactants include sorbitan trioleate and soya lecithin. Oleic acid may also be useful as a surfactant.

Formulations for dispensing from a powder inhaler device will comprise a finely divided dry powder containing the therapeutic agent, and may also include a bulking agent, such as lactose, sorbitol, sucrose, or mannitol in amounts which facilitate dispersal of the powder from the device, e.g., 50 to 90% by weight of the formulation. The therapeutic agent should most advantageously be prepared in particulate form with an average particle size of less than 10 mm (or microns), most preferably 0.5 to 5 mm, for most effective delivery to the distal lung.

Nasal or other mucosal delivery of the therapeutic agent is also contemplated. Nasal delivery allows the passage to the blood stream directly after administering the composition to the nose, without the necessity for deposition of the product in the lung. Formulations for nasal delivery include those with dextran or cyclodextran and saponin as an adjuvant.

The composition of vaccine of the present invention may be administered in conjunction with one or more additional active ingredients, pharmaceutical compositions, or vaccines. The therapeutic agents of the present invention may be administered to an animal, preferably a mammal, most preferably a human.

Dosage

The dosage of the therapeutic formulation or vaccine of the present invention will vary widely, depending upon the nature of the disease, the patient's medical history, the frequency of administration, the manner of administration, the clearance of the agent from the host, and the like. The initial dose may be larger, followed by smaller maintenance doses. The dose may be administered as infrequently as weekly or biweekly, or fractionated into smaller doses and administered daily, semi-weekly, etc., to maintain an effective dosage level.

Following methodologies which are well-established in the art, effective doses and toxicity of the compounds, vaccines and compositions of the instant invention, which performed well in in vitro tests, are then determined in preclinical studies using small animal models (e.g., mice or rats) in which the tumor-associated antigens, dendritic cells, polypeptides, apoptotic cells, TLR adjuvants or agonists, apoptotic cell-associated agents, pharmaceutical, or vaccine compositions have been found to be therapeutically effective and in which these drugs can be administered by the same route proposed for the human clinical trials.

For any pharmaceutical composition or vaccine used in the methods of the invention, the therapeutically effective dose can be estimated initially from animal models. Dose-response curves derived from animal systems are then used to determine testing doses for the initial clinical studies in humans. In safety determination for each composition, the dose and frequency of administration should meet or exceed those anticipated for use in the clinical trial.

As disclosed herein, the dose of the components in the compositions, vaccines and formulations of the present invention is determined to ensure that the dose administered continuously or intermittently will not exceed an amount determined after consideration of the results in test animals and the individual conditions of a patient. A specific dose naturally varies depending on the dosage procedure, the conditions of a patient or a subject animal such as age, body weight, sex, sensitivity, food, dosage period, drugs used in combination, and seriousness of the disease. The appropriate dose and dosage times under certain conditions can be determined by the test based on the above-described indices but may be refined and ultimately decided according to the judgment of the practitioner and each patients circumstances, (age, general condition, severity of symptoms, sex, etc.) according to standard clinical techniques. DC are loaded with apoptotic cells or TLR-ligand carrying apoptotic cells or apoptotic cells carrying inactivated microbes at a ratio of 1 DC to 2 apoptotic cells. DC vaccines will be administered every 28 to 30 days at 1-12$\times10^6$ DCs/vaccination. As a safety measure, vaccination may be initialized at 1$\times10^6$ DC/vaccination for the first 4 vaccines. If no toxicity is observed, after completion of 4 vaccinations, doses may be increased to 4$\times10^6$ DC, and finally to a maximum of 12$\times10^6$ DC/vaccine. These are suggested guidelines based on DC vaccinations of patients with metastatic melanoma in the study by Palucka et al. (2006) J. Immunother; 29:545-57. Actual dosage and composition or pharmaceutical formulations of TLR ligands in combination with apoptotic cell-associated agents may be determined in pre-clinical and clinical trials by standard practices known in the art.

Toxicity and therapeutic efficacy of the compositions, vaccines, and formulations of the invention can be determined by standard pharmaceutical procedures in experimental animals, e.g., by determining the LD50 (the dose lethal to 50% of the population) and the ED50 (the dose therapeutically effective in 50% of the population). The dose ratio between therapeutic and toxic effects is the therapeutic index and it can be expressed as the ratio ED50/LD50. Compositions that exhibit large therapeutic indices are preferred.

The data obtained from animal studies can be used in formulating a range of doses for use in humans. The therapeutically effective doses of in humans lay preferably within a range of circulating concentrations that include the ED50 with little or no toxicity. The dosage can vary within this range depending upon the dosage form employed and the route of administration utilized. Ideally, a single dose of each drug should be used daily.

Kits

In one embodiment, the invention relates to a kit comprising any one of the compositions or formulations of the present invention. The compositions or formulations included in the kit may be useful for inducing $T_H17$ responses, or for inhibiting $T_H17$ responses, or for inducing $T_{reg}$ responses. In certain embodiments, the compositions or formulations included in the kit are useful for treating a disease or condition. The kit further comprises a means for detecting improvement in the disease or condition following treatment with an agent.

The abbreviations in the specification correspond to units of measure, techniques, properties or compounds as follows: "min" means minutes, "h" means hour(s), "μL" mean microliter(s), "mL" means milliliter(s), "mM" means millimolar, "M" means molar, "μl" means micriliter(s); "mmole" means millimole(s), "kb" means kilobase, "bp" means base pair(s), and "IU" means International Units. "Polymerase chain reaction" is abbreviated PCR; "Reverse transcriptase polymerase chain reaction" is abbreviated RT-PCR; "Estrogen receptor" is abbreviated ER; "DNA binding domain" is abbreviated DBD; "Untranslated region" is abbreviated UTR; "Sodium dodecyl sulfate" is abbreviated SDS; and "High Pressure Liquid Chromatography" is abbreviated HPLC; dendritic cell is abbreviated "DC"; bone-marrow-derived dentritic cell is abbreviated "BMDC"; and culture medium is abbreviated "CM".

EXAMPLES

The following example are included to demonstrate certain embodiments of the invention. These specific examples are described solely for purposes of illustration, and are not intended to limit the scope of the disclosure. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention. Although specific targets, terms, and values have been employed herein, such targets, terms, and values will likewise be understood as exemplary and non-limiting to the scope of this invention.

Example 1

Materials and Methods

The following describes the materials and methods employed in Examples 2-6. In all Examples, all cell culture plasticware, including culture dishes, Petri dishes, culture plates and tubes were obtained from Beckton Dickinson (BD) Falcon (Franklin Lakes, N.J.).

Description of Mice Used in Examples 2-6

The following mice were used in Examples, where described: C3H/HeOuJ mice (The Jackson Laboratory, Bar Harbor, Me.), C57BL/6J (The Jackson Laboratory, Bar Harbor, Me.), TLR4 knockout ($^{-/-}$) mice on the C57BL/6J background (from S. Akira, Japan), MyD88$^{-/-}$/Trif$^{-/-}$mice (from S. Akira, Japan), IL-6$^{-/-}$ mice (on the C57BL/6J background) (from R. Medzhitov, Yale University, New Haven, Conn.). All mice were females 6-8 weeks of age. [See, Akira S and Takeda K. (2004) *C R Biol.* 327:581-9].

Preparation of Conditioned Media (CM) From Bone Marrow Derived Dendritic Cells (BMDC)

Bone marrow (BM)-derived GM-CSF DC cultures were grown in RPMI supplemented with GM-CSF and 5% foetal bovine serum (FBS), plus 100 μg/mL penicillin, 100 μg/mL streptomycin, 2 mM L-glutamine, 10 mM HEPES, 1 nM sodium pyruvate, 1X MEM nonessential amino acids, and 2.5 μM β-mercaptoethanol (all from Sigma-Aldrich, St. Louis, Mo.), as previously described[1]. Semi-adherent cells were harvested on ice on day 5 and re-plated immediately in fresh GM-CSF medium at $1\times10^6$ cells/well in 24-well tissue culture-treated plates. Soluble or phagocytic stimuli were added right away to the plates in the same medium and the cells were centrifuged for 2 min at 2000 rpm. Supernatants (conditioned medium, CM) were collected after 18 hours. LPS (from *E. coli*, serotype 055:B5,L-2880) was purchased from Sigma-Aldrich. BMDC were treated with various doses of soluble LPS or 2:1 A20 LPS blasts:DC to titrate the LPS such that levels of IL-6 produced by DC in response to these stimuli was similar. Soluble LPS was used at a final concentration of 1 ng/ml. The A20 B-cell line was obtained from the ATCC (TIB-208), A20 LPS blasts were prepared by culturing A20 cells at $1\times10^6$ cells/mL, 3 mL/well in 6-well tissue culture plates for four days in RPMI medium supplemented with 10% FBS, with 100 μg/mL penicillin, 100 μg/mL streptomycin, 2 mM L-glutamine, 10 mM HEPES, 1 nM sodium pyruvate, plus 25 μg/mL LPS, as previously described in Blander, J. M. and Medzhitov, R. (2004) Science 304(5673):1014. Apoptosis of A20 cells and A20 LPS blasts was induced by culturing cells with 0.5 μg/mL anti-CD95 (clone Jo2; BD) for four hours. Necrotic A20 cells were prepared by submitting cells (resuspended at $2\times10^6$ cells/mL in PBS) to two cycles of freezing/thawing by successive incubations in dry ice/ethanol and water at 37° C. Neutrophils and neutrophils/*E. coli* were prepared as follows: C57BL/6J mice were injected intraperitoneally with either 1 mL thioglycollate (Fisher) or 1 mL thioglycollate spiked with $10^5$ live DH5 *E. coli* (*Escherichia coli* K12, ATCC 23716). After 14 hours, the mice were sacrificed and cells were collected from a peritoneal wash of the contents of the abdominal cavity. Cells were centrifuged, counted, and apoptosis was induced by UV irradiation at 350 mJ. After irradiation, neutrophils were incubated for four hours at 37° C. before use as phagocytic cargo for DC. Apoptosis of A20 B-cells and neutrophils were confirmed by staining cells with cell death Annexin-V-PE detection kit (Roche, Indianapolis, Ind.) and observing a majority of Annexin-V$^+$/7AAD$^-$ cells after four hours. Apoptotic cells were added to BMDC at a ration of 2:1.

In Vitro T-cell Differentiation

Naïve CD4 T cells were isolated first by sorting with MACS® CD4$^+$ beads (Miltenyi Biotech, Auburn, Calif.) according to manufacturer's instructions and then by fluorescence activated cell sorting (FACS) using MoFlo™, Vantage, or Influx™ cell sorter for CD25$^-$CD44$^{low}$CD62L$^{high}$ cells using allophycocyanin (APC)-conjugated anti-CD25 monoclonal antibody (mAb) (clone PC61.5), FITC-conjugated CD62L mAb (clone MEL-14), and PE-Cy5-conjugated CD44 mAb (clone IM7) (all from eBioscience™, San Diego, Calif.). Cells were grown in complete IMDM (Gibco, Carlsbad, Calif.) supplemented with 10% FBS, 100 μg/mL penicillin, 100 μg/mL streptomycin, 2 mM L-glutamine, 10 mM HEPES, and 1 nM sodium pyruvate, and activated on 48-well tissue-culture plates which had been coated with 4 μg anti-CD3 (clone 2C11) for 3 h at 37° C., then washed 3 times with PBS. Cultures were supplemented with 2 μg/mL anti-CD28 (clone 37-51, a kind gift from J. Allison, Sloan-Keterring Cancer Center) and anti-IL-4 ascites (clone 11B11, a kind gift from T. Moran, Mount Sinai School of Medicine, ATCC number HB188) at 1:500, mAbs 2C11 and 37-51 were purified from hybridoma supernatants by BioXCell Company (West Lebanon, N.H.). When cultured with conditioned medium (CM) from BMDC, T cells were grown in 1:1 CM:fresh complete IMDM. Cytokines and neutralizing antibodies were added at the following concentrations where indicated: IL-6 (Peprotech, Rocky Hill, N.J.) 50 ng/mL; TGF-β (Peprotech) 5 ng/mL; IL-12 (eBioscience™) 10 ng/mL; IL-23 (eBioscience™) 10 ng/mL; and-IFN-γ (clone XMG1.2, a kind gift from T. Moran) 5 μg/mL; anti-TGF-β (clone 1D11, R&D Systems, Minneapolos, Minn.) 1, 5, or 10 μg/mL; anti-IL-23p19 (clone G23-8, eBioscience™) 2, 5, 10 or 20 μg/mL; anti-IL-6 (clone MP5-20FS; eBioscience™) 1 or 5 μg/mL.

Isolation of Intraepithelial Lymphocytes (IEL) and Lamina Propria Lymphocytes (LPL)

The small intestines and colons of C57BL/6J or C3H/HeOuJ mice were harvested at the indicated times. Colons of mice of either strain that had been infected with *C. rodentium* wild-type or mutant strains showed inflammation grossly, with thickening of the intestinal walls and development of Peyer's patch-like tertiary lymphoid structures. To prepare IEL/LPL, small intestines and colons were flushed with HBSS medium without calcium or magnesium (Gibco). Intestines were cut longitudinally and washed twice briefly in HBSS, 2% FBS in 6-well plates and then placed in 15 mL ice-cold HBSS, 2% FBS in 50-mL conical tubes and vortexed at maximum setting for 15-20 seconds. Tissue was removed using long forceps into a new tube with 15 mL ice-cold HBSS, 2% FBS and vortexed again twice, for a total of three washes. The tissues were then placed in 50-mL conical tubes containing 25 mL HBSS, 5% FBS, and 1 mM DTT (Sigma-Aldrich). Tubes were incubated on a rocker at 37° C. for 20 minutes followed by vortexing extensively at maximum setting. For IEL, fractions were collected after two rounds of 20 minutes in HBSS/FBS/DTT. Tissues were then placed in fresh tubes containing 25 mL of PBS with 1.3 mM EDTA, incubated on a rocker for 60 minutes at 37° C. and vortexed. Tissues were then rinsed twice in RPMI, 2% FBS in 14 6-well plates, placed in new 6-well dishes with 5 mL (colons) or 7 mL (small intestines) of RPMI, 5% FBS, 1.6 mg/mL collagenase D (Roche), and cut into small pieces. Tissues were then incubated for one hour at 37° C. before homogenization using a 20 gauge syringe and filtered through a 70 μm cell strainer (BD) into a 50-mL conical tube. Wells and strainers were washed with RPMI, 5% FBS to reduce cell loss. Tubes were centrifuged to collect the cell pellet and cells were washed again in RPMI +5% FBS. Cell pellets were then resuspended in 8 mL 44% iso-osmotic Percoll™ (GE Healthcare) in RPMI and transferred to FBS-coated 15 mL polystyrene round-bottom tubes. 5 mL of 66% iso-osmotic Percoll™/RPMI was carefully layered underneath the cells layer using Pasteur pipets. Tubes were then centrifuged for 20 minutes at 2800 rpm, 4° C., with brakes in the lowest setting. After the spin, interface cells were collected using a plastic collection pipet, placed in 15-mL conical tubes, and washed twice with RPMI, 5% FBS. To restimulate the cells for measuring intracellular cytokine production, cells were then resuspended in complete IMDM with 0.1 μg/mL Phorbol 12-myristate 13-acetate (PMA, Sigma-Aldrich), 0.5 μg/mL ionomycin calcium salt, from *Streptomyces conglobatus* (Sigma-Aldrich), and 10 μg/mL Brefeldin A, from *Eupenicillium brefeldanium* (Sigma-Aldrich), and cultured for four hours at 37° C. before intracellular cytokine staining.

Preparation of Tissues and Immunostaining

Colons of C3H/HeOuJ mice were harvested on day 6 and flushed with PBS. Tissues were fresh-frozen in O.C.T. Compound (Sakura Finetek, Zoeterwoude, The Netherlands) and stored at −80° C. Sections of 6 μm were cut and fixed with either 4% paraformaldehyde or ice-cold acetone for 1 h, dried, and stored at −20° C. TUNEL staining was performed using the In Site Cell Death Detection Kit, TMR Red (Roche) according to manufacturer's instructions. For immunostaining, sections were blocked and incubated with primary antibodies in a humidified atmosphere for 1 hour at room temperature. After washing, conjugated secondary antibodies were added for 35 minutes. The slides were then washed and mounted with Fluoromount-G (Southern Biotech, Birmingham, Ala.). Tissues were stained with Alexa Flur® 594-conjugated Phalloidin (Invitrogen, Carlsbad Calif.), and *E. coli* O antigen, polyvalent 8, O152 (Denka Seiken, Accurate Chemical US distributers, Westbury, N.Y.) [Mundy, R. et al. (2204) Infect Immun 72 (4), 2288] followed by secondary Alexa Fluor® 488 anti-rabbit IgG (Molecular Probes, Eugene, Oreg.). Analyses were performed using 10X and 20X dry objectives on a Nikon Eclipse E-600 fluorescence microscope and Adobe® Photoshop® software (Adobe Systems, San Jose, Calif.).

*Citrobacter Rodentium* Inuculation

Wild-type (WT) *C. rodentium* as well as two mutants of *C. rodentium*, one with a mutation in EPEC-secreted protein F (ΔEspF) [McNamara, B. P. and Donnenberg, M. S. (1998) FEMS Microbiol Lett166 (1):71], and one with a mutation in the mitochondrial associated protein (ΔMap) [Kenny, B. et al. (2002) Mol Microbiol 44 (4):1095] were obtained from B. B. Finlay, University of British Columbia, WT, ΔEspF, and ΔMap mutant *C. rodentium* strains exhibit similar attachment to and effacement of a colonic cell line [Crane, J. K., et al. (2001) Cell Microbiol 3 (4):197; McNamara, B. P. et al. (2001) J Clin Invest 107 (5):621], and all three stains colonize the intestinal epithelium to similar levels as shown by staining intestinal epithelium sections of infected mice for *C. rodentium* O antigen 01522. In addition, WT, ΔEspF- and ΔMap-infected mice all have similar numbers of *C. rodentium* in shed stools, and similar levels of colonic hyperplasia demonstrated by increased colon weight [Mundy, R. et al., supra].

WT and mutant *C. rodentium* were prepared by incubation with shaking at 37° C. for 8 hours in LB broth medium. After 8 hours, the bacterial density was assessed at an optical density of 600 nm and confirmed by plating of serial dilutions. Inoculation of mice was by oral administration with $2.5\times10^8$ (for C3H/HeOuJ strain) or $2\times10^9$ (for C57BL/6J strain) colony forming units (CFU). Before inoculation, mice were deprived of food and water for 8-12 hours. Tissues were collected for immunostaining and/or flow cytometry at times indicated after inoculation. Mice treated with Q-VD-OPH pan-caspase inhibitor (SM Biochemicals)[7] received intraperitoneal injections of 0.4 mg in 15% DMSO/85% PBS at 90 minutes, 24 h, and 48 h after inoculation. C3H/HeOuJ mice also were treated on days 3 and 5 (total 5 doses) and C57BL/6J were treated on days 4, 6, and 8 (total 6 doses). Mice treated with dextran sulfate sodium (DSS) (Sigma-Aldrich) were given water containing 2.5 mg/mL DSS for seven days [Okayasu, I. et al. (1990) Gastroenterology 98 (3):694] at which point the DSS-water was removed and replaced with plain water for the reminder of the experiment. For anti-CD3-injected mice, mice were injected with 20 μg of anti-CD3 (clone 2C11) i.p. three times with an interval of two days and sacrificed four hours after the final injection [Kamanaka, M. et al. (2006) Immunity 25 (6):941]

Flow Cytometry

Figure 15:
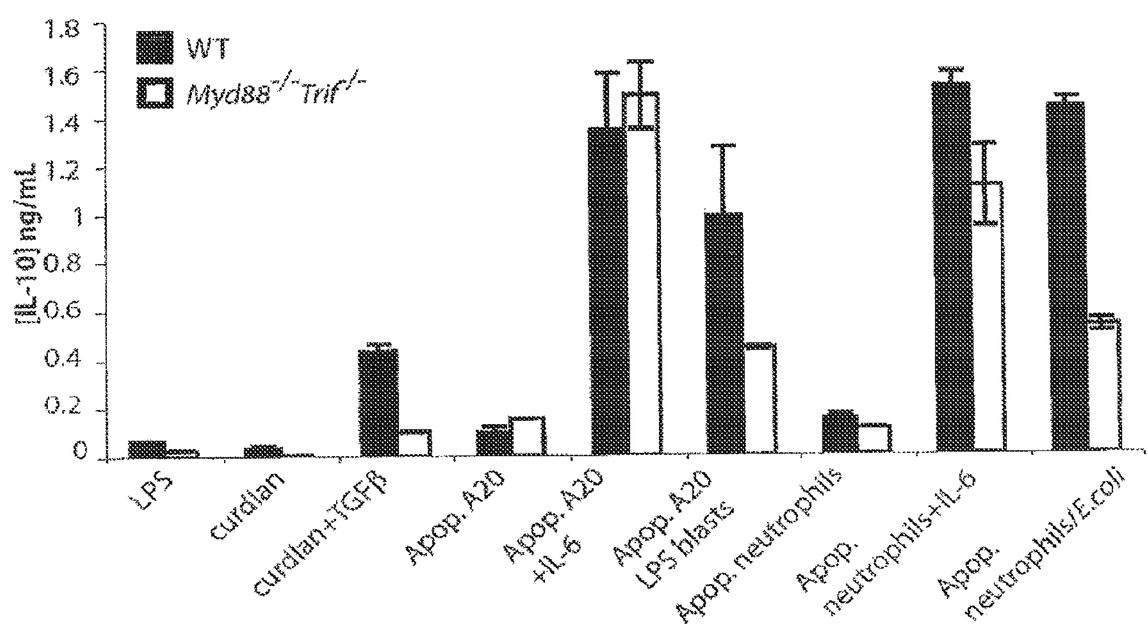
FIG. 15 shows the protein level of IL-10 in the culture supernatants of CD4 T cells following culture in the presence of LPS, curdlan, or curdlan+TGF-β, or following culture with conditioned media from C57BL/6J (WT) or MyD88$^{-/-}$ TRIF$^{-/-}$ dendritic cells that had phagocytosed the indicated stimuli.

T cells were stimulated for four hours with 0.1 μg/mL Phorbol 12-myristate 13-acetate (PMA, Sigma), 0.5 μg/mL, ionmycin calcium salt, from *Streptomyces conglobatus* (Sigma-Aldrich), and 10 μg/mL Brefeldin A, from *Eupenicillium brefeldanium* (Sigma-Aldrich). Cells were then pelleted and resuspended in cold FACS buffer (PBS containing 0.1% $NaN_3$ and 1% heat-inactivated FBS). Cells were surface stained for 20 minutes at 4° C. with either: 1) APC-conjugated anti-CD4 mAb (clone GK1.5), or 2) APC-conjugated anti-CD3 mAb (clone 17A2), PE-conjugated anti-CD4 mAb (clone GK1.5), and FITC-conjugated anti-CD8α mAb (clone 53-6.7) (all from eBioscience™), in FACS buffer. Cells were then fixed and permeabilized using the IC Staining kit (eBioscience™) according to manufacturer's instructions with minor modifications (washing four times with permeabilization buffer before incubation with intracellular cytokine antibody). For Foxp3 staining in FIGS. 8 and 15, eBioscience™

Foxp3 staining kit was used according to manufacturer's instructions. Fixed and permeabilized cells were stained intracellularly with PE-conjugated anti-IL-17 mAb (clone TC11-18H10, BD, Pharmingen) or PE-conjugated anti-Foxp3 mAb (clone FJK-16s, eBioscience™), and FITC-conjugated anti-IFN-γ mAb (clone XMG1.2, BD, Pharmingen) or FITC-conjugated anti-IL-10 mAb (clone JES5-16E3, BD, Pharmingen). Samples were required on FACSCalibur™ (BD Biosciences) flow cytometer, and data analyses were conducted using FlowJo software (Tree Star, Inc., Ashland, Oreg.).

TGF-β Bioassay

Analysis of bioactive TGF-β was performed as previously described in Tesseur, I. et al. (2006) BMC Cell Biol 7: 15. MFB-F11 mouse fibroblast cells stably transfected with a reporter plasmid consisting of TGF-β-responsive Smad-binding elements coupled to a secreted alkaline phosphatase reporter gene (SBE-SEAP) were seeded at $3\times10^4$ cells/well in 96-well flat bottom tissue culture plates and cultured overnight in DMEM supplemented with 10% FBS and penicillin/streptomycin (DMEM/P/S). Cells were washed twice with PBS and incubated in 50 μL serum-free DMEM for 2 hours. Conditioned medium from DC was diluted 1:5 in serum-free DMEM/P/S and 5 μL was added to the MFB-F11 cells. For detection of total TGF-β, diluted conditioned medium was activated by adding 1.5 μL 6M HCl to 150 μL of sample and incubating 10 minutes at room temperature. Neutralization was performed by adding 1.5 μL 6M NaOH. 10 μL of the cultured supernatant from MFB-F11 cells was collected after 24 hours. SEAP activity was measured using Great EscAPe™ SEAP Reporter System 3 (Clontech, Mountain View, Calif.) according to the manufacturer's protocol with 96-well white/flat bottom plates. Luciferase activity was measured with a FLUOStar Optima reader (BMG Labtech, Durham, N.C.). For each sample, the concentration of biologically active TGF-β was calculated as follows: (luciferase activity of bioactive TGF-β/luciferase activity for total TGF-β)×100.

T Cell Proliferation Assay

Day 5 WT C57BL/6J BMDC were left untreated or cultured for 6-8 hours with heat-killed *C. rodentium* at a multiplicity of infection (MOI) of 50. Mesenteric lymph nodes (MLN) were harvested from uninfected or infected mice that had been treated or not with Q-VD-OPH and MLN cells were isolated. These cells were incubated either with untreated BMDC in the presence or absence of 01 μg/mL anti-CD3 or with *C. rodentium*-exposed BMDC at two different DC:MLN cell ratios in triplicate in 96-well round-bottom plates. At 72 hours, 1 μCi of $^3$H-thymidine was added to each well. 18 hours after pulsing with $^3$H-thymidine, cells were harvested with a multiple-sample harvester and counted with a Wallac 1450 microbeta PLUS liquid scintillation counter (Perkin-Elmer, Waltham, Mass.).

RNA Isolation cDNA Synthesis and Quantitative Real-Time RT-PCR

T cells cultured for 48 hours under the indicated conditions were lysed and RNA isolated by TRIzol® extraction (Invitrogen) according to manufacturer's instructions. For restimulated T cells cultures, cells were collected after four days and plated on new plates coated with anti-CD3 in the presence or absence of 20 ng/mL recombinant (rm) IL-23 (eBioscience™) for six hours. RNA isolation was performed in the same manner as above. Quantitative real-time, reverse transcription polymerase chain reaction (qPCR) was conducted on an ABI Prism® 7900 instrument (Applied Biosystems, Foster City, Calif.) with primer pairs and probes as follows. All probe sequences are in the format: 5' FAM-sequence-BHQ-1 3':

(HPRT Probe, SEQ ID NO: 61)
TGTTGGATACAGGCCAGACTTTGTTGGAT (HPRT FW, SEQ ID NO: 62)
CTGGTGAAAAGGACCTCTCG (HPRT RV, SEQ ID NO: 63)
TGAAGTACTCATTATAGTCAAGGGCA (β-actin Probe, SEQ ID NO: 64)
AGCCACCCCCACTCCTAAGAGGAGG (β-actin FW, SEQ ID NO: 65)
GAAGTCCCTCACCCTCCCAA (β-actin RV, SEQ ID NO: 66)
GGCATGGACGCGACCA (IL-6 Probe, SEQ ID NO: 67)
TCTGCAAGAGACTTCCATCCAGTTGCCT (IL-6 FW, SEQ ID NO: 68)
CCAGAAACCGCTATGAAGTTCC (IL-6 RV, SEQ ID NO: 69)
TCACCAGCATCAGTCCCAAG (IL-17A Probe, SEQ ID NO: 70)
TCTGGGAAGCTCAGTGCCGCCACCAGC (IL-17A FW, SEQ ID NO: 71)
CTCCAGAAGGCCCTCAGACTAC (IL-17A RV, SEQ ID NO: 72)
AGCTTTCCCTCCGCATTGACACAG (Foxp3 Probe, SEQ ID NO: 73)
ATCCTACCCACTGCTGGCAAATGGAGTC (Foxp3 FW, SEQ ID NO: 74)
CCCAGGAAAGACAGCAACCTT (Foxp3 RV, SEQ ID NO: 75)
TTCTCACAACCAGGCCACTTG (RORγt Probe, SEQ ID NO: 76)
AAGGGCTTCTTCCGCCGCAGCCAGCAG (RORγt FW, SEQ ID NO: 77)
CCGCTGAGAGGGCTTCAC (RORγt RV, SEQ ID NO: 78)
TGCAGGAGTAGGCCACATTACA (Tbet Probe, SEQ ID NO: 79)
CCGGGAGAACTTTGAGTCCATGTACGC (Tbet FW, SEQ ID NO: 80)
CAACAACCCCTTTGCCAAAG (Tbet RV, SEQ ID NO: 81)
TCCCCCAAGCAGTTGACAGT (IL-22 Probe, SEQ ID NO: 82)
TGAGCACCTGCTTCATCAGGTAGCA (IL-22 FW, SEQ ID NO: 83)
TCCGAGGAGTCAGTGCTAAA (IL-22 RV, SEQ ID NO: 84)
AGAACGTCTTCCAGGGTGAA (IL-12p40 Probe, SEQ ID NO: 85)
TGCAGCAAGTGGGCATGTGTTCC (IL-12p40 FW, SEQ ID NO: 86)
CTCAGGATCGCTATTACAATTCCTC (IL-12p40 RV, SEQ ID NO: 87)
TTCCAACGTTGCATCCTAGGATC -continued

```
                    (IL-12p35 Probe, SEQ ID NO: 88)
TCTGGCCGTCTTCACCATGTCA

                    (IL-12p35 FW, SEQ ID NO: 89)
CTTAGCCAGTCCCGAAACCT

                    (IL-12p35 RV, SEQ ID NO: 90)
TTGGTCCCGTGTGATGTCT
```

The above primers and probe sets synthesized by Biosearch Technologies (Novato, Calif.). Applied Biosystems TaqMan® gene expression assay ID numbers Mm00518984_ml and Mm00770031_ml were used for the primers and probe sets for IL-23p19 and tumor necrosis factor (ligand) superfamily member 15 (TNFsf15), respectively. The sequences of these commercially-available primers are proprietary and are not disclosed by Applied Biosystems. All primers annealed in different exons and when possible, probes were designed to anneal across exon boundaries. Sequence references where the sequences are based on a previously published sequence are as follows: Rorγt and IL-17A [Ivanov, II et al. (2006) Cell 126 (6):1121], IL-6 [Wang, T. et al., (2004) Nat Med 10 (12):1366], IL-22 [Zheng, Y. et al. (2008) Nat Med 14 (3): 282], Foxp3 [Uhlig, H. H. et al (2006) J Immunol 177 (9): 5852].

Quantitative PCR was performed using TaqMan® quantitative PCR Master Mix at a concentrate of 1X (Applied Biosystems). Reactions were run in duplicates and samples were normalized to the internal controls β-actin and HPRT. "Fold inductions" were calculated using the ΔΔCt method relative to T cells activated under neutral conditions (No cytokines or CM).

Enzyme-Linked Immunoabsorbent Assays (ELISA)

Supernatant from cultured DC or T cells was collected at the times indicated. ELISA monoclonal Ab (mAb) pairs used were as noted below in Table 1. All mAbs were obtained from BD, Pharmingen except the IL-23p19 capture antibody, clone 5B2, from eBioscience™. All ELISA antibodies were used at 1.5 μg/mL capture and 1.5 μg/mL detection with the following exceptions: IL-23p19 capture mAb was used at 4 μb/mL, IL-10 capture and detection mAbs were used at 2 μg/mL.

TABLE 1

ELISA Antibody Pairs

| Cytokine | Capture Ab | Biotinylated Ab |
|---|---|---|
| TGF-β | A75.2 | A75.3 |
| IL-6 | MP5-20F3 | MP5-32C11 |
| IL-12p40/p70 | C15.6 | C17.8 |
| IL-23p19 | 5B2 | C17.8 |
| IL-17 | TC11-18H10 | TC11-BH4.1 |
| IL-10 | JES5-2A5 | SXC-1 |

Example 2

DC Cytokine Production Following Concomitant Exposure to LPS and Apoptotic Cells The following example demonstrates the cytokines produced by DC following exposure to various inflammatory stimuli and the ability of treated DC to stimulate $T_H17$ cell differentiation.

It was next determined which innate immune recognition events trigger simultaneous synthesis of IL-6 and TGF-β. Whereas phagocytosis of apoptotic cells induces TGF-β synthesis by macrophages[7]. IL-6 synthesis is strongly induced in innate immune cells when microbial structures activate pattern recognition receptors like Toll-like receptors (TLRs)[6, 14]. However, it was unknown whether concomitant litigation of TLRs during phagocytosis of infected apoptotic cells might constitute a scenario where IL-6 and TGF-β may be induced together.

In these experiments, either apoptotic neutrophils isolated from the peritoneal cavity of mice following injection of live *E. coli* (Apop./Neutrophils/*E. coli*), or apoptotic B-cells carrying the TLR4 ligand lipopolysaccharide (LPS) generated from LPS-treated B-cells (ApopA20/LPS-blasts)[15] were used. As controls for the requirement for a microbe or TLR adjuvant for $T_H17$ induction, either apoptotic neutrophils (Apop./Neutrophils) or apoptotic A20 B cells (Apop./A20) were used. Bone marrow DC were stimulated with LPS or phagocytic cargo as indicated in FIG. 1 and cytokine production was measured by ELISA in culture supernatants following 18 hours of culture. DC that phagocytosed apoptotic LPS-blasts secreted more TGF-β and IL-23 than DC treated with free LPS and similar amounts of IL-6 where the concentration of free LPS chosen approximated IL-6 levels induced by apoptotic LPS-blasts (FIG. 1). Importantly, phagocytosis of apoptotic cells and apoptotic LPS-blasts uniquely induced production of biologically active TGF-β whereas free LPS did not (FIG. 1). Notably, despite similar IL-6 levels, the level of IL-12 produced by DC following phagocytosis of apoptotic LPS B cell-blasts was consistently lower than that in response to free LPS (FIG. 1), which may also favor $T_H17$ over $T_H1$ development.

Figure 2:
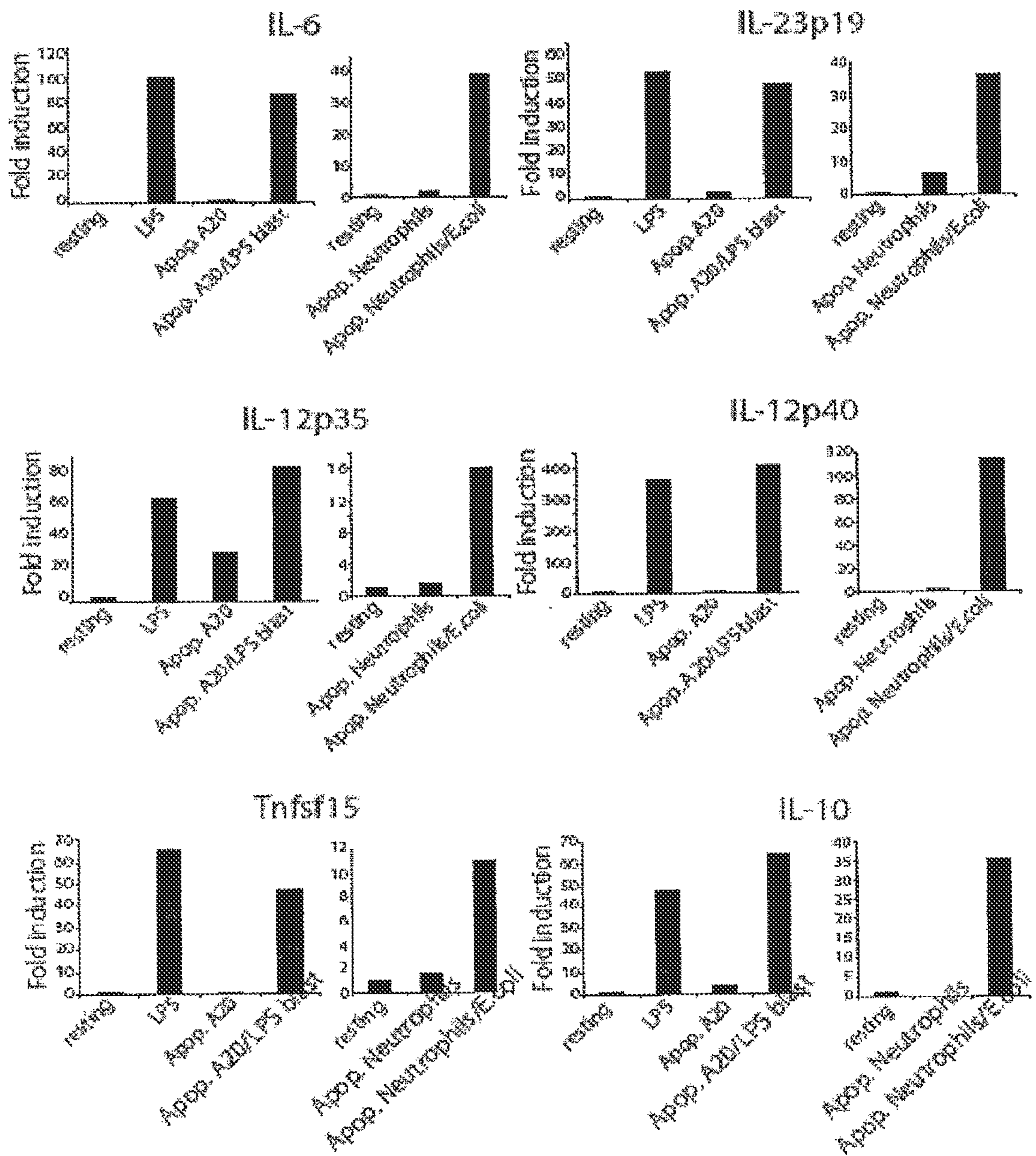
FIG. 2 shows mRNA levels of cytokines produced by bone marrow dendritic cells following in vitro stimulation with LPS, apoptotic A20/LPS blasts, or apoptotic neutrophils/*E. coli.*

The mRNA expression of DC stimulated in vitro by the stimuli indicated in FIG. 2 was determined by quantitative reverse transcription-polymerase chain reaction (qPCR) analyses. Analysis by qPCR of RNA from these DC further showed induction of IL-6, IL-23p19, IL-12p35, IL-12p40, IL-10, and TNF family member, TL1A (Tnfsfl5), which promotes $T_H17$ proliferation[16], in response to apoptotic LPS-blasts and apoptotic neutrophils/*E. coli*. For all cytokines tested, the levels of induction were similar to levels induced by free LPS (FIG. 2). These transcripts were also induced in DC in response to infected apoptotic neutrophils, but not to uninfected apoptotic B-cells or uninfected apoptotic neutrophils (FIG. 2). The raw data was normalized to β-actin and HPRT and expressed as fold-induction over unstimulated DC.

Example 3

$T_H17$ and $T_{reg}$ Cell Differentiation

The following example describes whether the cytokine milieu created by the conditions of DC activation described in Example 2, above, is conducive for $T_H17$ induction.

Figure 3:
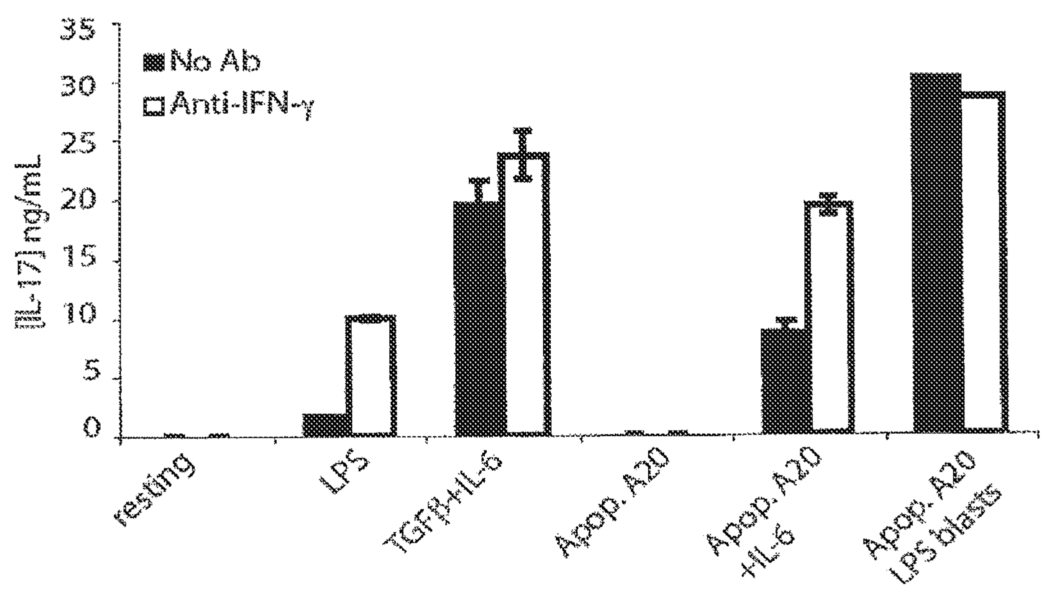
FIG. 3 shows protein levels of IL-17 produced by CD4 T cells following culture with LPS or TGF-β+IL-6, or following culture with conditioned media from dendritic cells that phagocytosed apoptotic B cells, apoptotic cells+IL-6, or apoptotic B cell LPS blasts.

Naïve ($CD25^-CD62L^{high}CD44^{low}$) CD4 T-cells, isolated from C57BL/6J mice and activated with 4 μg anti-CD3 and 2 μg/mL anti-CD28 plus anti-IL-4, were cultured for three days in conditioned media (CM) derived from DC that phagocytosed apoptotic LPS-blasts or apoptotic B cells (control) with or without IFN-γ neutralizing antibody. Following restimulation with PMA and ionocmycin, the CD4 T-cells cultured with DCCM-apoptotic LPS-blasts secreted IL-17, as determine by ELISA of the culture supernatants, strongly suggesting differentiation into the $T_H17$ lineage (FIG. 3, filled bars).

Standard in vitro protocols for generating $T_H17$ require neutralizing the antagonistic effects of the cytokine interferon-γ (IFN-γ)[1, 10, 11], and TLR ligands are classically considered to induce $T_H1$ cells producing IFN-γ[6]. Neutralization of this cytokine allowed some induction of IL-17 secreting (IL-17) CD4 T-cells by CM from DC treated with free LPS (FIG. 3, open bars). In contrast, anti-IFN-γ was not required for IL-17 production by T-cells activated in DCCM-apoptotic LPS-blasts (FIG. 3, open bars), indicating that DC stimulation by TLR ligands within the context of apoptotic cells creates particularly efficient conditions, which more closely mimic physiological settings, for the generation of IL-17$^+$ CD4 T-cells. No IL-17 was detected when naïve CD4 T-cells were cultured in the presence of CM from DC that phagocytosed apoptotic B-cells not carrying TLR ligands (DCCM-apoptotic B-cells), and supplementation of this CM with IL-6 restored IL-17 production, indicating the presence of TGF-β and reinforcing the contribution of TLRs to IL-6 production (FIG. 3, filled bars). Here, anti-IFN-γ consistently increased the levels of IL-17 (FIG. 3, open bars).

Figure 4:
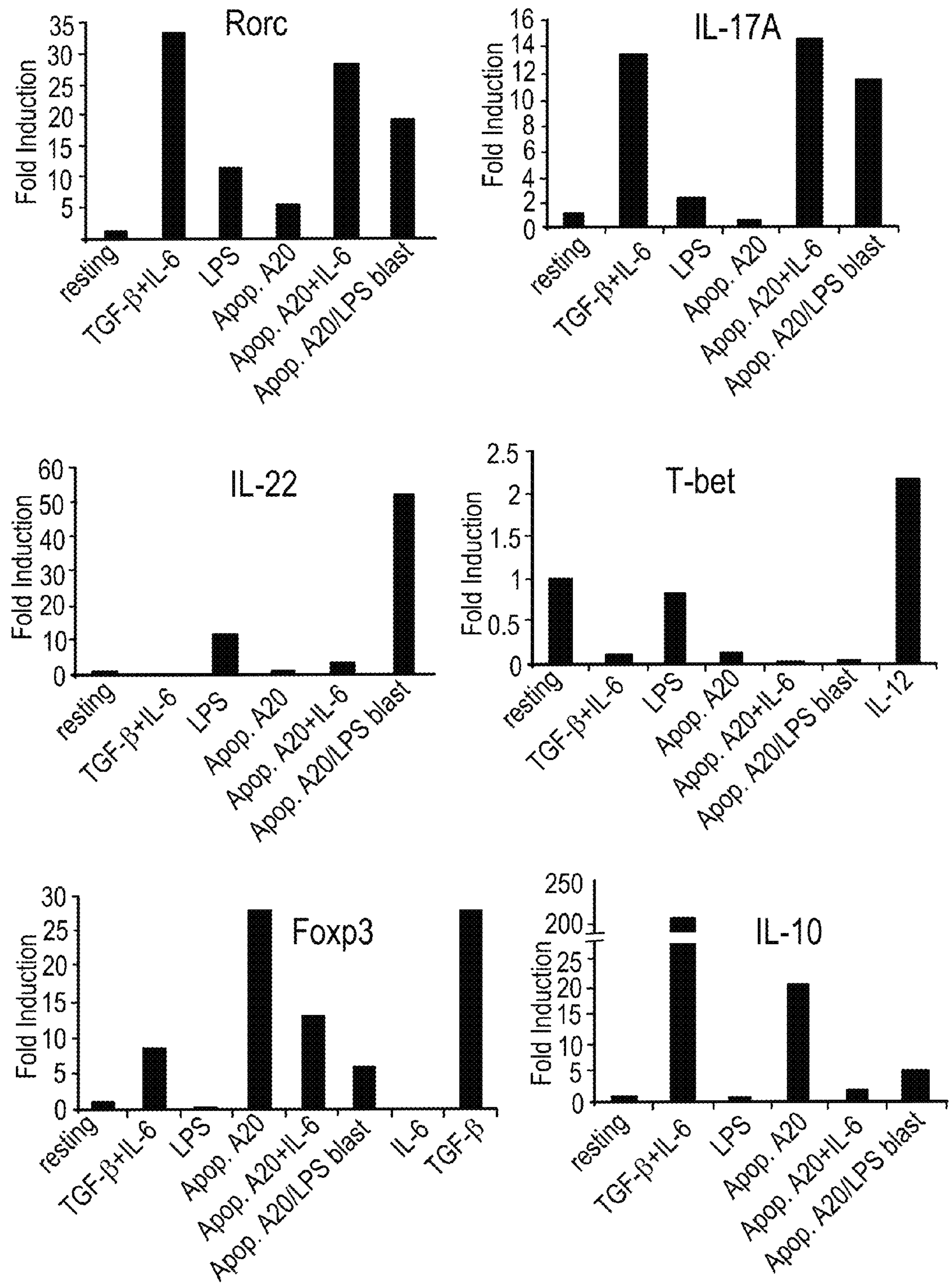
FIG. 4 shows mRNA expression levels of Rorγt (Rorc), IL-17A, IL-22, T-bet, Foxp3, and IL-10 in CD4 T cells following culture with LPS or TGF-β+IL-6, or following culture with conditioned media from dendritic cells that phagocytosed apoptotic B cells, apoptotic cells+IL-6, or apoptotic B cell LPS blasts.

Moreover, qPCR performed with RNA from sorted naïve CD4 T-cells after 48 hours of culture with DCCM from the indicated groups. qPCR analysis showed high induction of the $T_H17$ lineage specific transcription factor RORγt[4] (Rorc) and IL-17A when these cells were activated in the presence of DCCM-apoptotic LPS-blasts, and DCCM-apoptotic B-cells supplemented with IL-6 (FIG. 4). Notably, induction of the IL-10 family cytokine, IL-22, synthesis of which is induced by IL-23[17], was greatest in response to DCCM-apoptotic LPS-blasts (FIG. 4), consistent with the ability of apoptotic LPS-blasts, but not apoptotic cells, to induce IL-23 cytokine synthesis (FIG. 1). IL-22 was not induced upon stimulation with TGF-β plus IL-6, likely due to the absence of IL-23 under these conditions (FIG. 4). As expected, none of the T-cells, except the ones activated in the presence of IL-12, expressed the $T_H1$ lineage-specific transcription factor T-bet[18] (FIG. 4). Collectively, these results confirmed that IL-17[30] CD4 T-cells generated in response to phagocytosis of TLR ligand-containing apoptotic cells were bona fide $T_H17$ cells.

Figure 5:
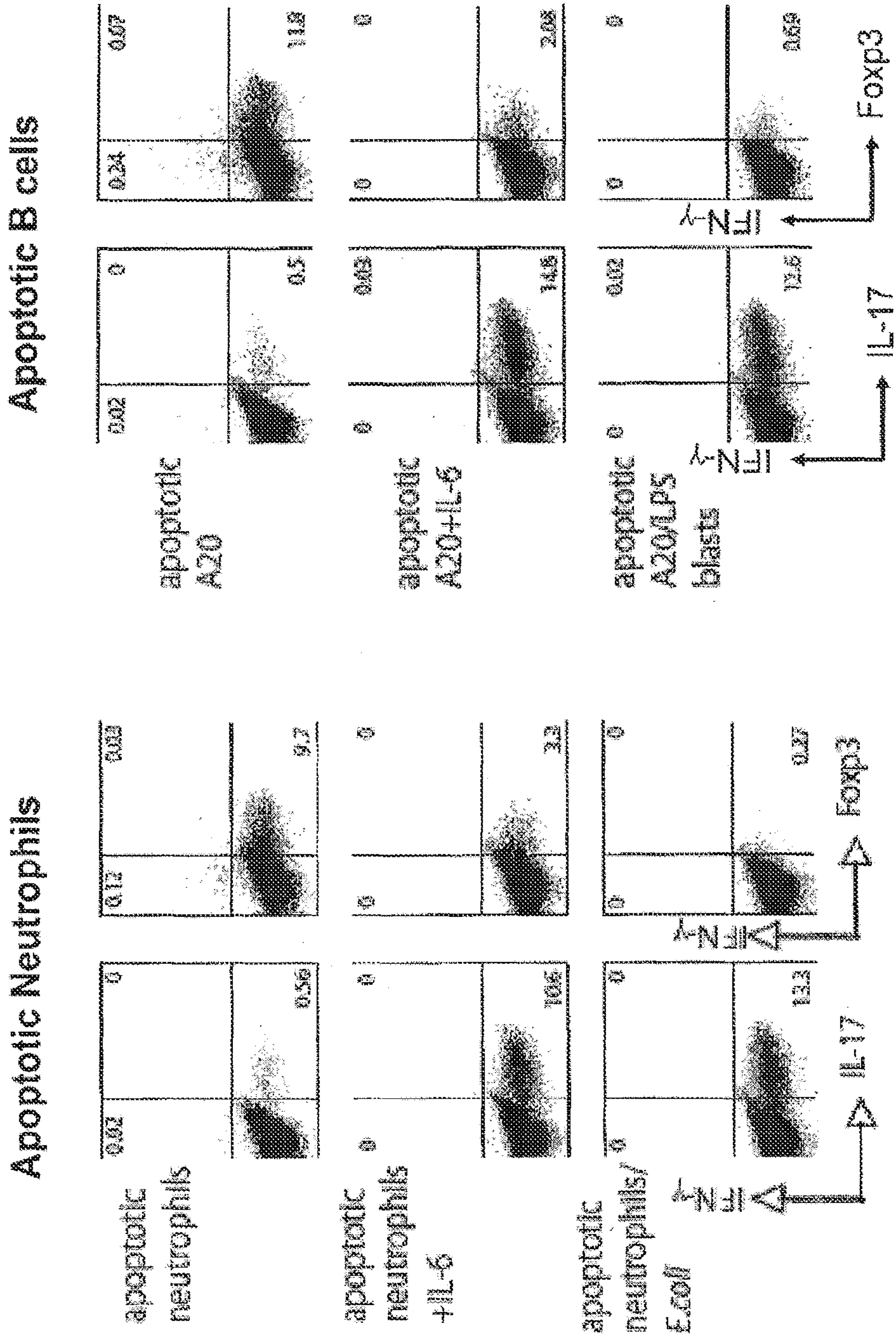
FIG. 5 shows FACS plots of intracellular cytokine staining of Foxp3, IL-17, and IFN-γ in CD4 T cells following culture with conditioned media from dendritic cells that phagocytosed the indicated stimuli.

Because development of $T_{reg}$ cells is reciprocally related to $T_H17$ cells[10] expression of Foxp3, a transcription factor unique to $T_{reg}$ cells[19] was examined. After 3 days of culture with DCCM from the indicated groups, T cells were restimulated with PMA and ionmycin for 4 hours with Brefeldin A before intracellular cytokine staining for IL-17 and IFN-γ was performed, and expression of these cytokines was determined by FACS. In FIG. 5, FACS plots are gated on CD4$^+$ cells and quadrant percentiles of cells staining positive for the indicate cytokines are shown.

IL-17$^+$ CD4 T-cells developed in DCCM-apoptotic LPS-blasts and DCCM-apoptotic neutrophils/*E. coli* and, as expressed, did not express Foxp3 (FIG. 5). In contrast, Foxp3-expressing cells were generated in response to DCCM-apoptotic B-cells or DCCM-apoptotic neutrophils. No IL-17 producing cells were obtained under these conditions, indicating preferential $T_{reg}$ development (FIG. 5). Addition of IL-6 to DCCM-apoptotic B-cells or to DCCM-apoptotic neutrophils restored IL-17 production and markedly impaired Foxp3 expression (FIG. 5). Quantitative RT-PCR showed Foxp3 induction inversely mirrored RORγt, with highest induction when T-cells were activated in the presence of DCCM-apoptotic B-cells or TGF-β (FIG. 4). Foxp3 induction was impaired when IL-6 was added consistent with the ability of IL-6 to inhibit Foxp3 induction[10], and when T-cells were activated in the presence of DCCM-apoptotic LPS-blasts (FIG. 4), which contains IL-6 (FIG. 1). Although Foxp3 induction was not completely abrogated under the latter two conditions, this had no negative impact on $T_H17$ development (FIGS. 3 and 5) perhaps owing to the high levels of RORγt induced under these two conditions (FIG. 4, RORc panel). Persistence of Foxp3 transcripts in the TGF-β plus IL-6 conditions (unlike previous reports[10, 20]) may be a consequence of the comparatively high levels of TGF-β (5 ng/ml) that were used. This concentration was chosen as it approximates the average concentrations of TGF-β present within DCCM-apoptotic B-cells, or DCCM-apoptotic LPS-blasts (FIG. 1). These data collectively demonstrate that phagocytosis of apoptotic cells by DC instructed development of Foxp3 expressing $T_{reg}$ cells and phagocytosis of infected apoptotic cells (which have TLR ligands) instructed development of $T_H17$ cells.

Figure 6:
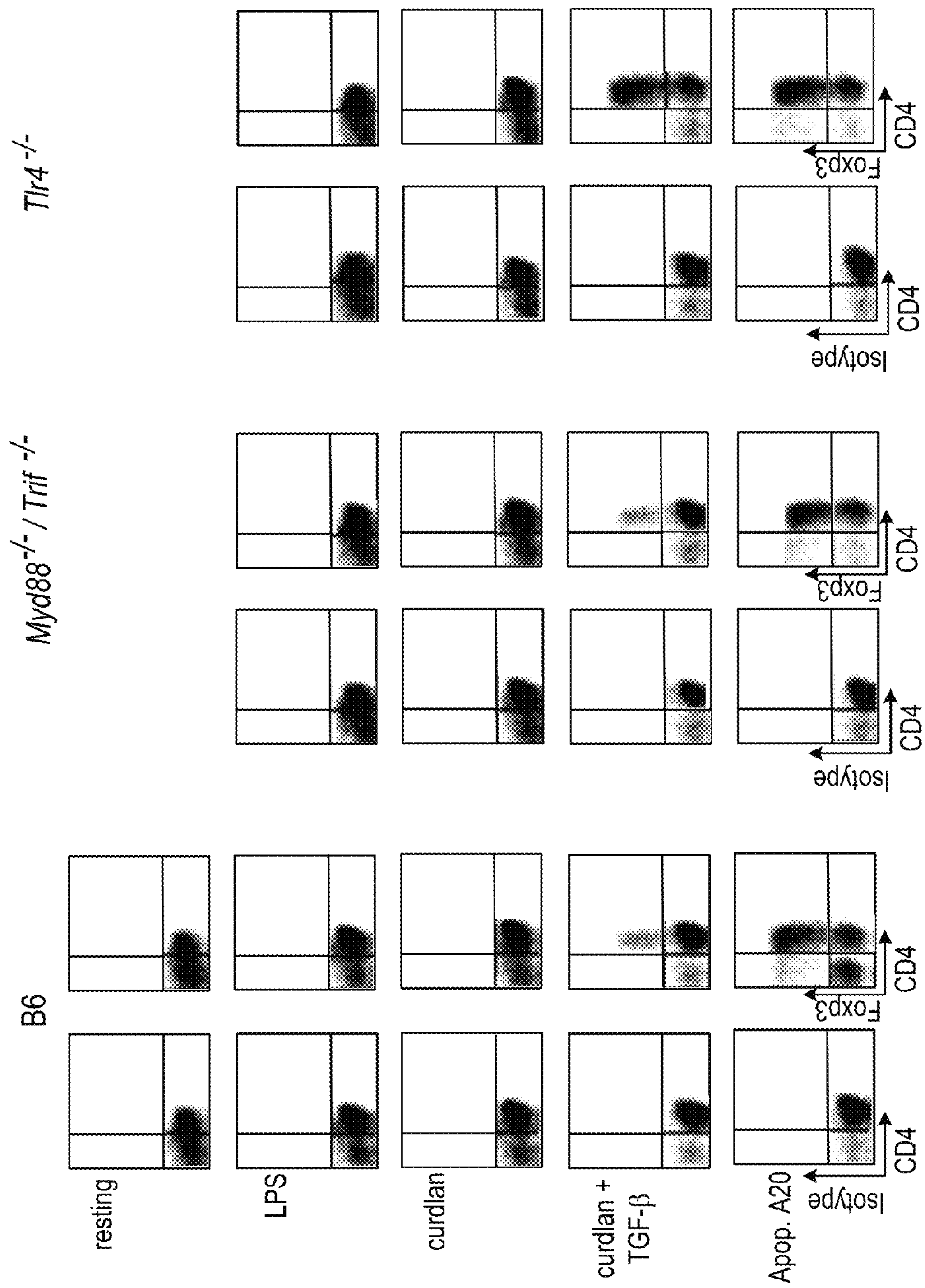
FIG. 6 shows FACS plots of intracellular cytokine staining of CD4 and Foxp3 or antibody isotype control in CD4 T cells following culture with conditioned media from dendritic cells isolated from C57BL/6J (B6), $MyD88^{-/-}/TRIF^{-/-}$, or $TLR4^{-/-}$ mice, that had phagocytosed the indicated stimuli.
Figure 6:
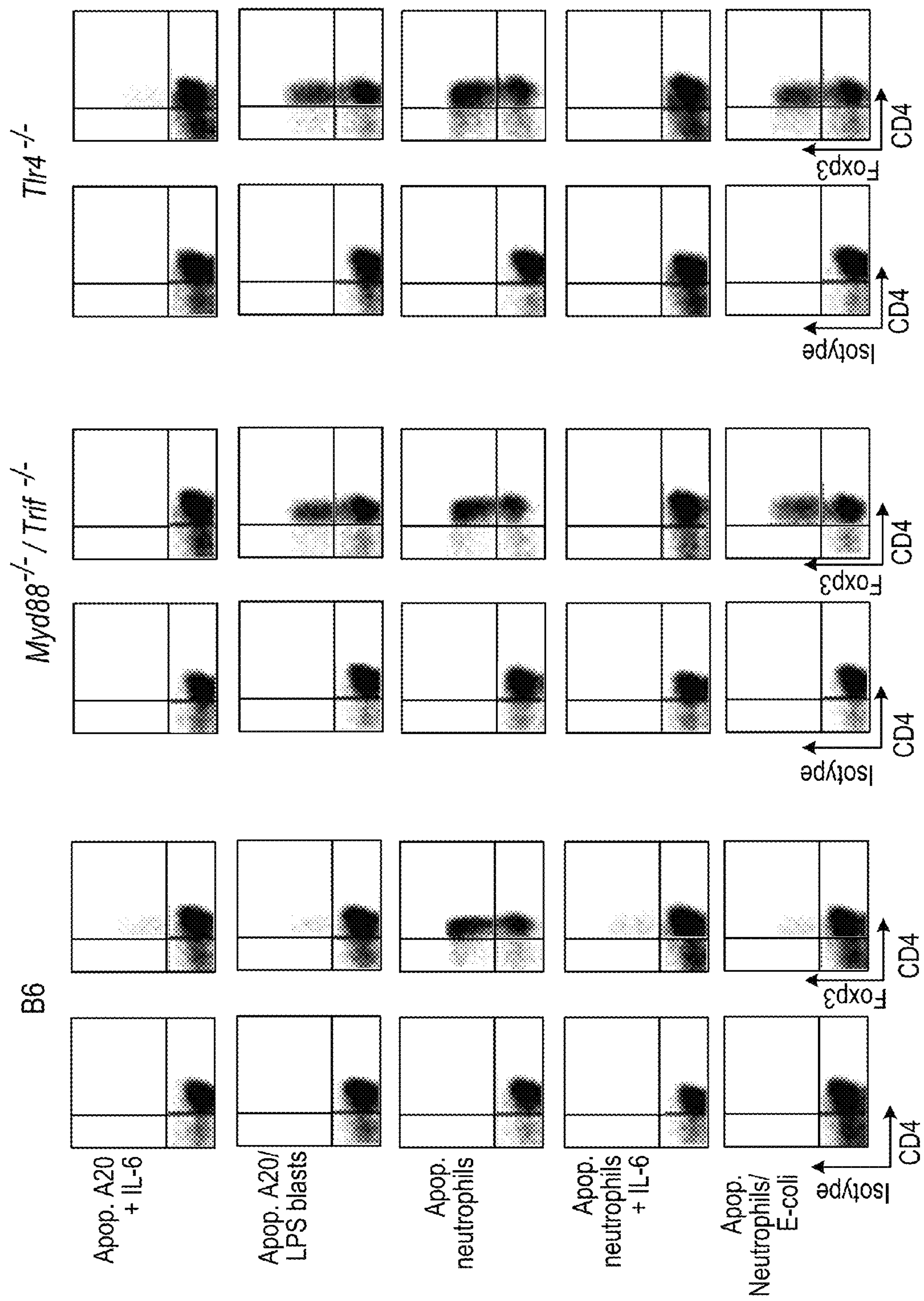

FIG. 6 shows that the absence of TLR signaling in DC impairs $T_H17$ cell development in response to phagocytosis of infected apoptotic cells, and support $T_{reg}$ development instead. Naïve CD4 T cells were isolated from C57BL/6J mice and activated with 4 μg anti-CD3 and 2 μg/mL anti-CD28 plus anti-IL-4 with conditioned medium from wild-type C57BL/6J, Myd88$^{-/-}$/Trif$^{-/-}$, or Tlr4$^{-/-}$ BMDC under the indicated conditions. IL-6 and TGF-β cytokines were added to T cell—DC conditioned medium cultures. Cells were recovered after three days and surface staining for CD4 and intracellular cytokine staining for Foxp3 were performed. Cells were analyzed for flow cytometry and in the plots shown in FIG. 6, plots are gated on CD4$^+$ cells and quadrant percentiles of cells staining positively for the indicated cytokines or markers are shown. Under these conditions, CM from DC derived from Myd88$^{-/-}$ Trif$^{-/-}$ mice (FIG. 6, where absence of the signaling adaptors MyD88 and Trif abrogates responses through all TLRs[14]) or Tlr4$^{-/-}$ mice (FIG. 6, where absence of TLR4 abrogates responses to LPS[14]) did not support $T_H17$ development, but rather supported development of Foxp3 express $T_{reg}$ cells.

Figure 7:
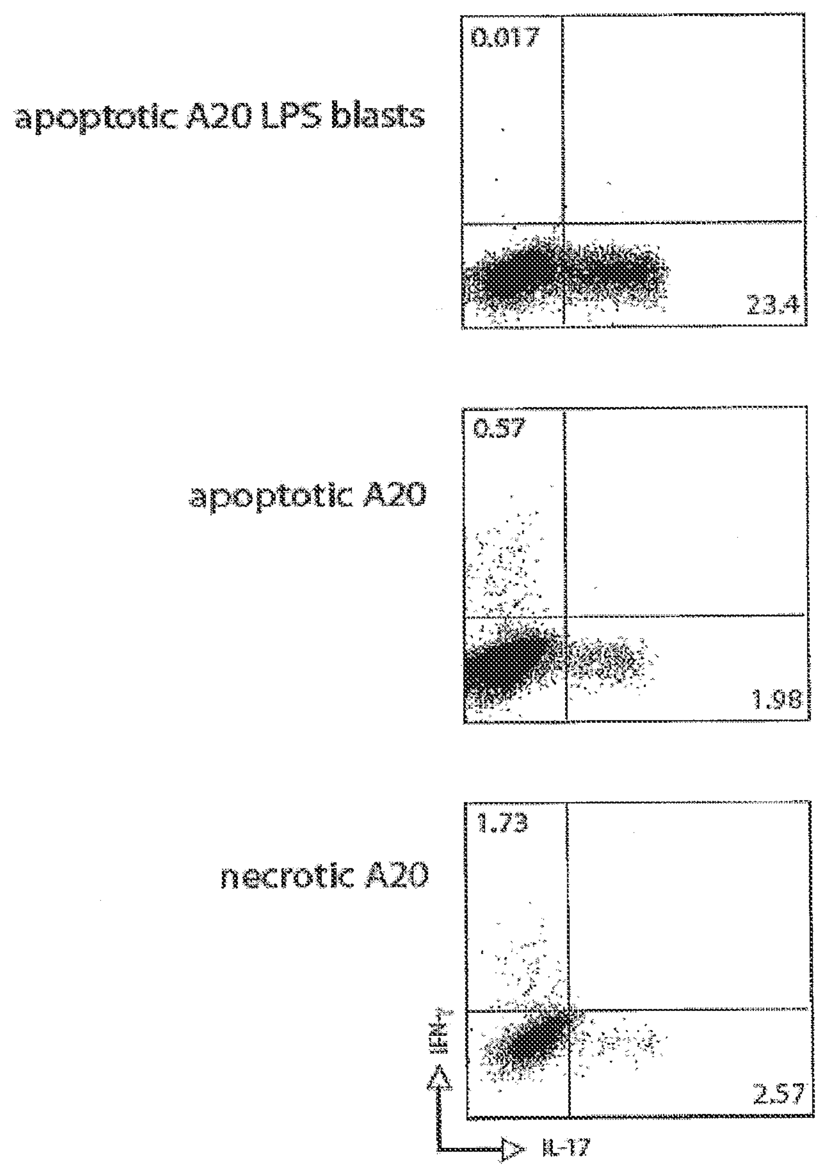
FIG. 7 shows FACS plots of intracellular cytokine staining of IFN-γ and IL-17 in CD4 T cells following culture with conditioned media from dendritic cells that had phagocytosed the indicate stimuli.

FIG. 7 demonstrates that phagocytosis of necrotic cells by BMDC does not induce $T_H17$ differentiation. Naïve CD4 T cells were isolated from C57BL/6J mice and activated with 4 μg anti-CD3 and 2 μg/mL anti-CD28 plus anti-IL-4 with conditioned medium from C57BL/6J BMDC that phagocytosed either apoptotic A20 LPS blasts, apoptotic A20 cells, or necrotic A20 cells. Cells were recovered after three days and restimulated with PMA plus ionomycin with Brefeldin A before intracellular cytokine staining for IL-17 and IFN-γ, and analysis by flow cytometry. Plots were gated on CD4+ cells and quadrant percentiles of cells staining positively for the indicated cytokines are shown.

The TLR ligand and apoptotic cell cannot be administered as separate entities as this combination does as such does not lend to the induction of $T_H17$ responses. The TLR ligand must be physically incorporated and present within the apoptotic cell in order to effectively mimic an infected apoptotic cell and induce a $T_H17$ response. See Example 5 and FIG. 25 below.

Figure 8:
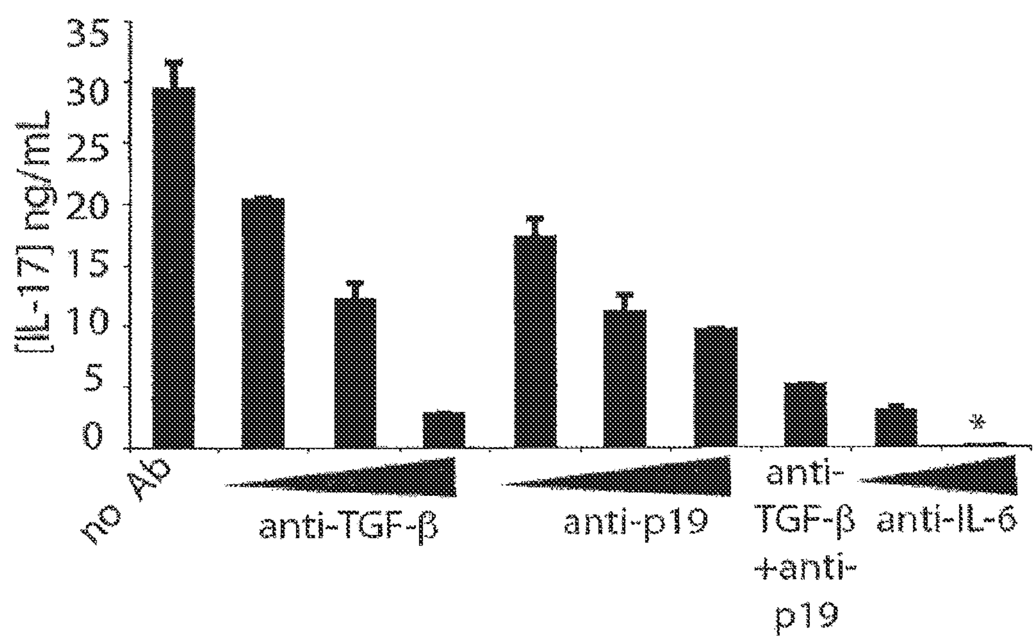
FIG. 8 shows protein levels of IL-17 in the culture supernatants of CD4 T cells following culture with conditioned media from dendritic cells that had phagocytosed apoptotic LPS blasts and in the presence of absence of the indicated TGF-β, p19, or IL-6 neutralizing antibodies.
Figure 9:
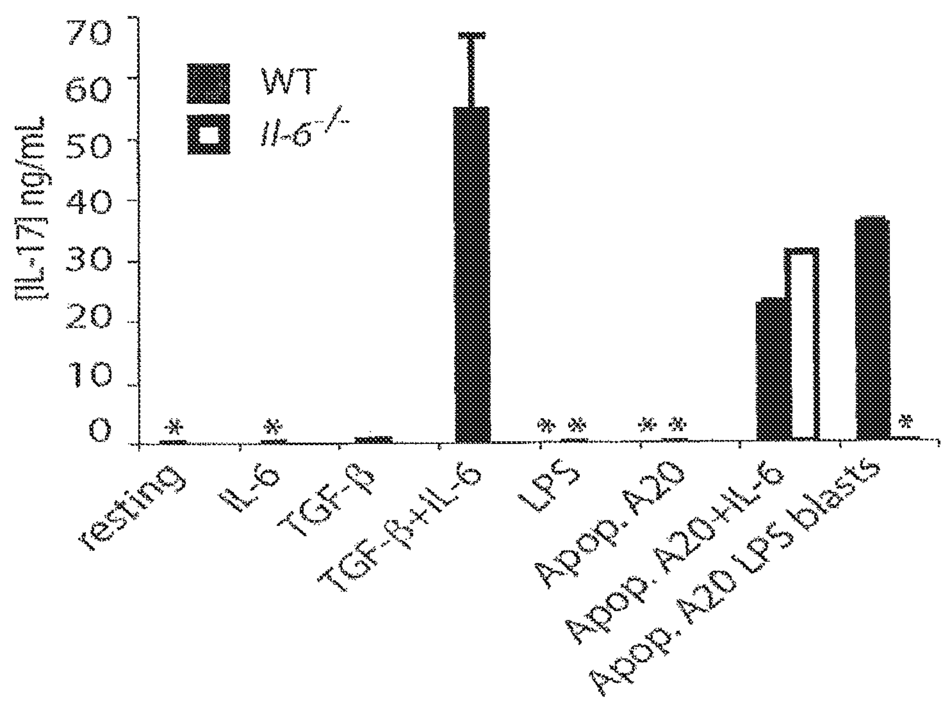
FIG. 9 shows protein levels of IL-17 in the culture supernatants of CD4 T cells following culture with the indicated cytokines only, or following culture with conditioned media from C57BL/6J (WT) or $IL\text{-}6^{-/-}$ dendritic cells that had phagocytosed the indicated stimuli.
Figure 10:
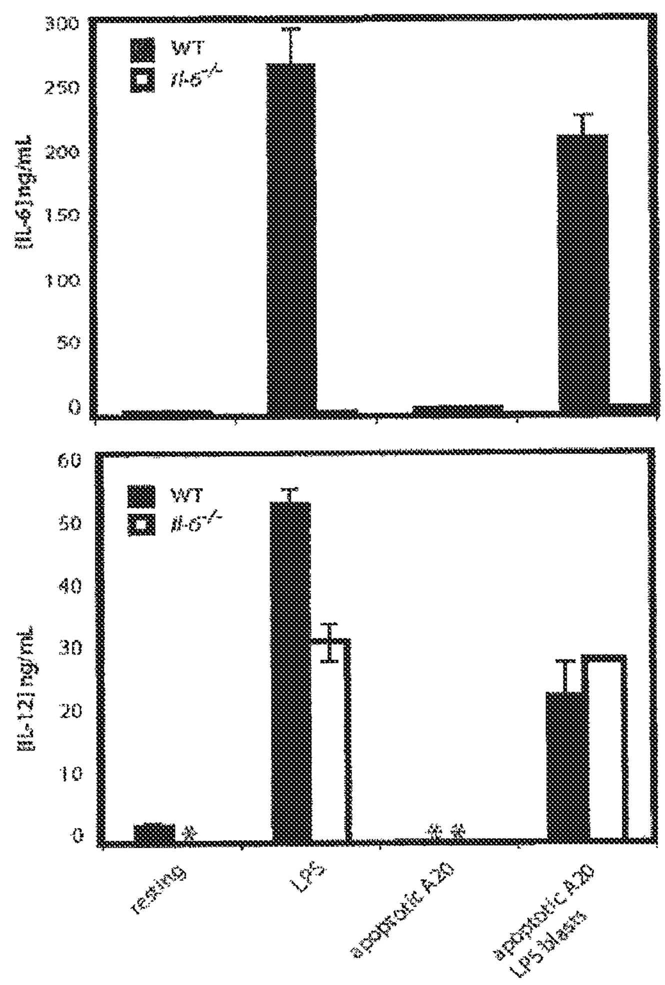
FIG. 10 shows protein levels of IL-6 and IL-12 in the culture supernatants of CD4 cells following culture with conditioned media from C57BL/6J (WT) or $IL\text{-}6^{-/-}$ dendritic cells that had been treated with LPS or that had phagocytosed the indicated stimuli.

Next, naïve CD4 T-cells were isolated from C57BL/6J mice and activated with 4 μg anti-CD3 and 2 μg/ML anti-CD28 plus anti-IL-4 with CM from C57BL/6J (WT) BMDC that had phagocytosed apoptotic LPS B cell-blasts. Neutralizing mAbs were added (or not) as indicated (anti-TGF-β 1 μg/mL, 5 μg/mL, 10 μg/mL; anti-IL-23p19 5 μg/mL, 10 μg/mL, 20 μg/mL; anti-IL-6 1 μg/mL, 5 μg/mL). After four days, cells were re-plated on anti-CD3-coated plates for 48 h. Cytokines were quantified in supernatants by ELISA. As shown in FIG. 8, development of $T_H17$ cells in the presence of DCCM-apoptotic LPS-blasts were severely compromised in a dose dependent manner in the presence of neutralizing antibody to TGF-β, with no further synergistic inhibition with a neutralizing antibody to the p19 polypetide of IL-23 (FIG. 8). Neutralization of p19 alone still permitted the existence of a fraction of $T_H17$ cells, consistent with the role of IL-23 in expanding but not initiating development of these cells (FIG. 8). Neutralization of IL-6 also strongly inhibited IL-17 secretion (FIG. 8). Its requirement was further documented by the fact that IL-$6^{-/-}$DCCM-apoptotic LPS-blasts failed to support development of $T_H17$ cells (FIG. 9). Addition of exogenous IL-6 to DCCM-apoptotic B-cells from both WT and IL-$6^{-/-}$DC, led to similar levels of IL-17 production from activated naïve CD4 T-cells (FIG. 9). FIG. 10 shows the levels of IL-6 and IL-12 produced by CD4 T cells following culture with DCCM treated with the conditions shown (resting, LPS, apoptotic B cells, or LPS blasts) in WT or IL-$6^{-/-}$ mice. IL-$6^{-/-}$ failed to produce IL-6, but produced similar levels of IL-12 following exposure to LPS or apoptotic A20 LPS blasts. Collectively, these data suggest that DC phagocytosis of infected apoptotic cells results in production of cytokines strongly conducive for $T_H17$ differentiation.

Example 4

Role of Toll-like Receptor Signaling in $T_H17$ Development

The following example describes whether development of IL-$17^+$ CD4 T-cells required TLR signaling within DC upon phagocytosis of infected apoptotic neutrophils or apoptotic LPS-blasts.

Figure 11:
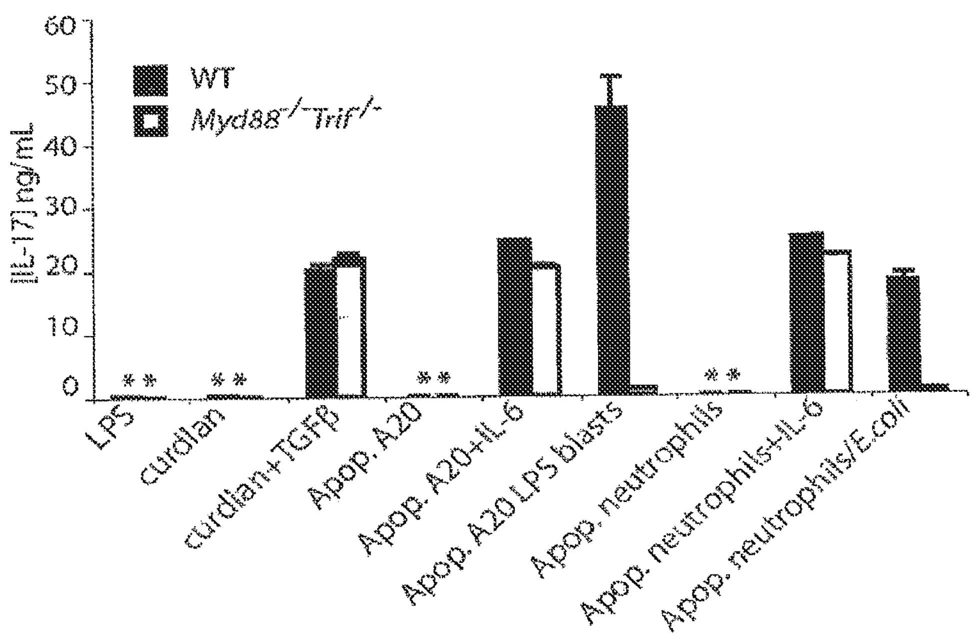
FIG. 11 shows protein levels of IL-17 in the culture supernatants of CD4 T cells following culture in the presence of LPS, curdlan, or curdlan+TGF-β, or following culture with conditioned media from C57BL/6J (WT) or $MyD88^{-/-}$ $TRIF^{-/-}$ dendritic cells that had phagocytosed the indicated stimuli.
Figure 12:
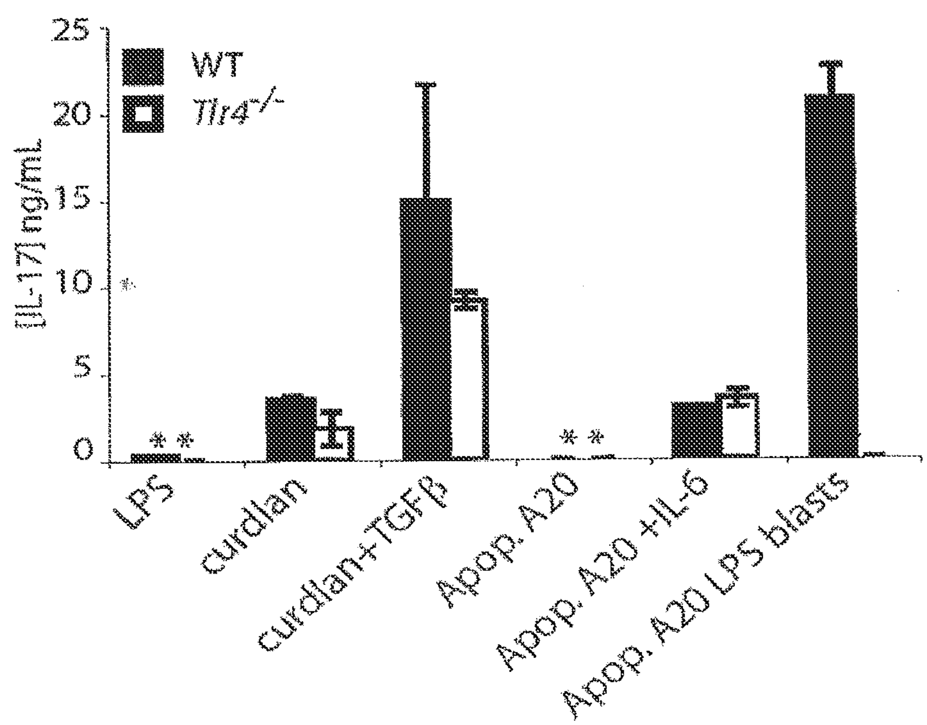
FIG. 12 shows protein levels of IL-17 in the culture supernatants of CD4 T cells following culture in the presence of LPS, curdlan, or curdlan+TGF-β, or following culture with conditioned media from C57BL/6J (WT) or $TLR4^{-/--}$ dendritic cells that had phagocytosed the indicated stimuli.

Under the same conditions as in Example 3, CM from DC derived from Myd$88^{-/-}$Trif$^{-/-}$ mice (FIG. 11, where absence of the signaling adaptors MyD88 and Trif abrogates responses through all TLRs[14]) or Tlr$4^{-/-}$ mice (FIG. 12, where absence of TLR4 abrogates responses to LPS[14]) did not support $T_H17$ development. However, consistent with the lack of involvement of TLRs in recognition of apoptotic cells per se, generation of $T_H17$ cells was unaffected by the absence of TLR signaling under conditions when DCCM-apoptotic B-cells or DCCM-apoptotic neutrophils were supplemented with Il-6 (FIGS. 11 and 12). Furthermore, DC derived from MyD$88^{-/-}$Trif$^{-/-}$and Tlr$4^{-/-}$ mice were able to direct induction of IL-$17^+$ CD4 T-cells when stimulated with curdlan, a fungal β-glucan that activates DC independently of TLR4, Trif or MyD88, and induces $T_H17$ development when TGF-β is concomitantly present[21].

Example 5

Induction of IL-10 Regulatory Component

The following example describes the ability of TLR ligands and apoptotic cells to induce IL-10 secreting, "regulatory" T cells in addition to $T_H17$ cells.

Given the reported implications of $T_H17$ cells in autoimmunity, and the present finding that infected apoptotic cells can drive $T_H17$ development, it was next asked whether this process is accompanied by the induction of a regulatory component that might curb the pathogenic potential of these T-cells. Naïve CD4 T-cells were isolated from C57BL/6J mice and activated with 4 μg anti-CD3 and 2 μg/mL and anti-CD28 plus anti-IL-4 with CM from C57BL/6J, Myd$88^{-/-}$Trif$^{-/-}$ or Tlr$4^{-/-}$ BMDC under the indicated conditions. For the data shown in FIGS. 13, 17 and 24, after three days, cells were restimulated with PMA and ionmycin for four hours with Brefeldin A before intracellular cytokine staining for IL-17 and IFN-γ, or IL-17 and IL-10, and analyzed by flow cytometry. Plots were gated on $CD4^+$ cells and quadrant percentiles of cells staining positively for the indicated cytokines are shown.

Figure 13:
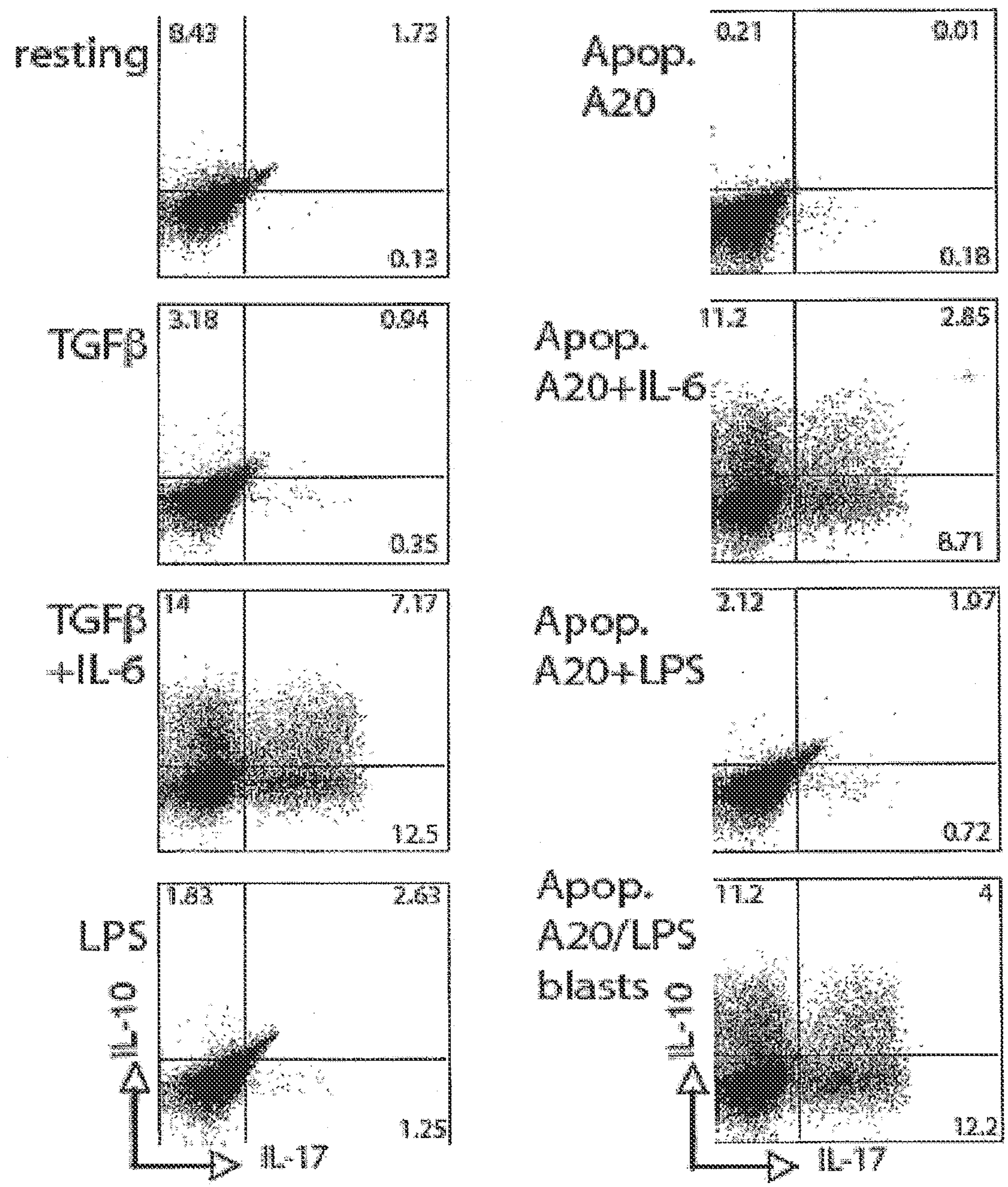
FIG. 13 shows FACS plots of intracellular cytokine staining of IL-17 and IL-10 in CD4 T cells culture with TGF-β, TGF-β+IL-6, or LPS, or following culture with conditioned media from dendritic cells that had phagocytosed the indicated stimuli.
Figure 24:
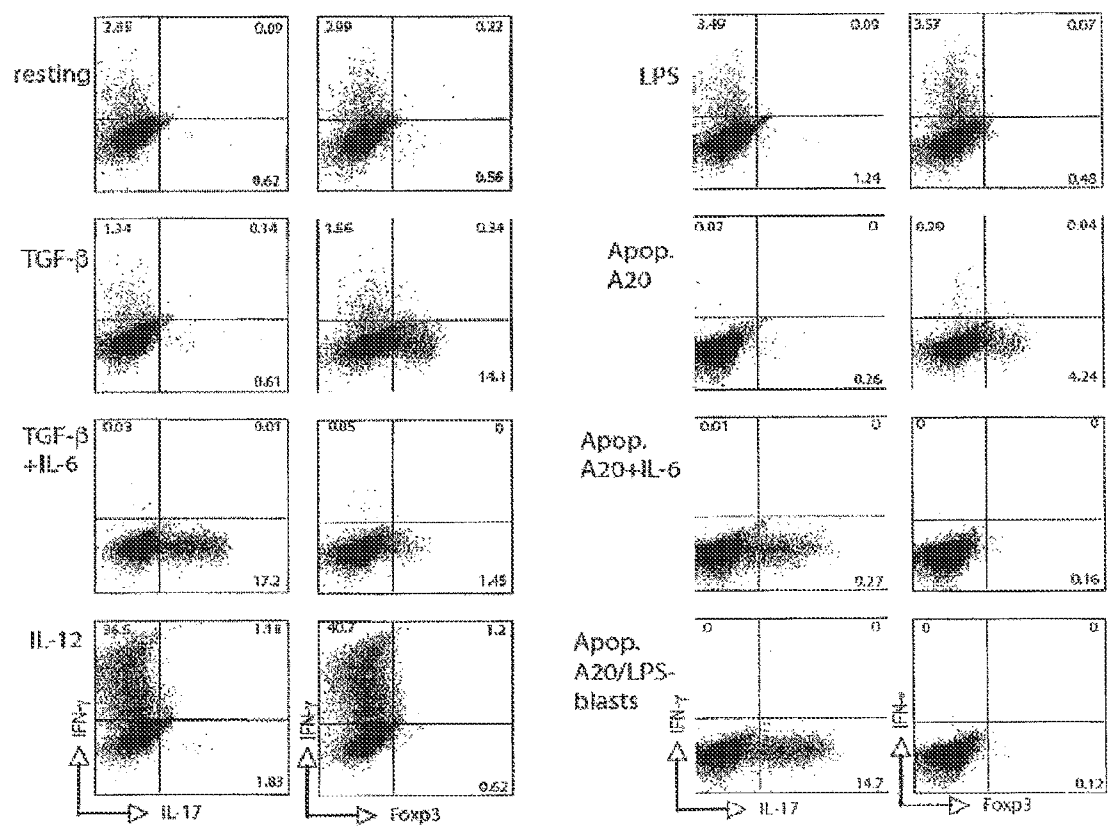
FIG. 24 shows FACS plots of intracellular cytokine staining in CD4 T cells following culture with condition medium.

It was found that 25% of the IL-17[30] CD4 T-cells induced by DCCM-apoptotic LPS-blasts, also secreted IL-10, a potent anti-inflammatory cytokine[22] (FIG. 13) (for IFN-γ, IL-17 and Foxp3 profiles, see FIG. 24). Notably, a distinct IL-10 secreting (IL-$10^+$) CD4 T-cell population that did not secrete IL-17 was also induced. Similar 'IL-$10^+$ only' cells and 'dual IL-$10^+$ and IL-$17^{+}$' cells were induced in response to DCCM-apoptotic B-cells supplemented with IL-6 (FIG. 13). It was found that induction of IL-10 transcripts in response to DCCM-apoptotic B-cells, although by staining IL-$10^+$ CD4 T-cells could not be detected in response to apoptotic cells alone, perhaps due to differences in the kinetics of expression (FIG. 13). Consistent with previous reports[23,24], TGF-β plus IL-6 also induced three distinct populations: 'IL-$17^+$ only', 'IL-$10^{+}$' only, and 'dual IL-$10^+$ and IL-$17^{+}$' CD4 T cells (FIG. 13).

Figure 14:
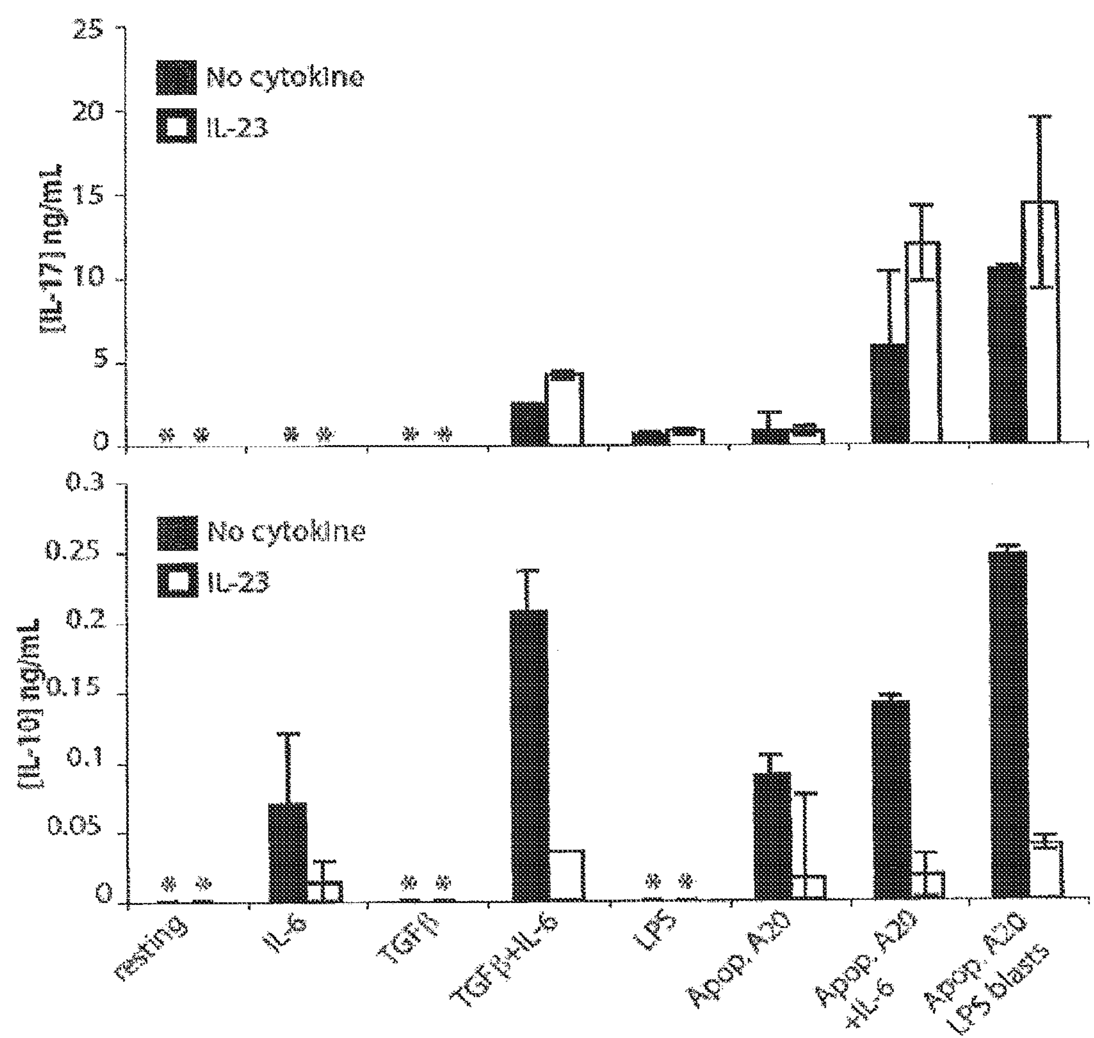
FIG. 14 shows the protein levels of IL-17 and IL-10 in the culture supernatants of CD4 T cells cultured in the presence or absence of IL-23, that had also been cultured with IL-6, TGF-β, TGF-β+IL-6, or LPS, or with conditioned media from dendritic cells that had phagocytosed the indicated stimuli.
Figure 16:
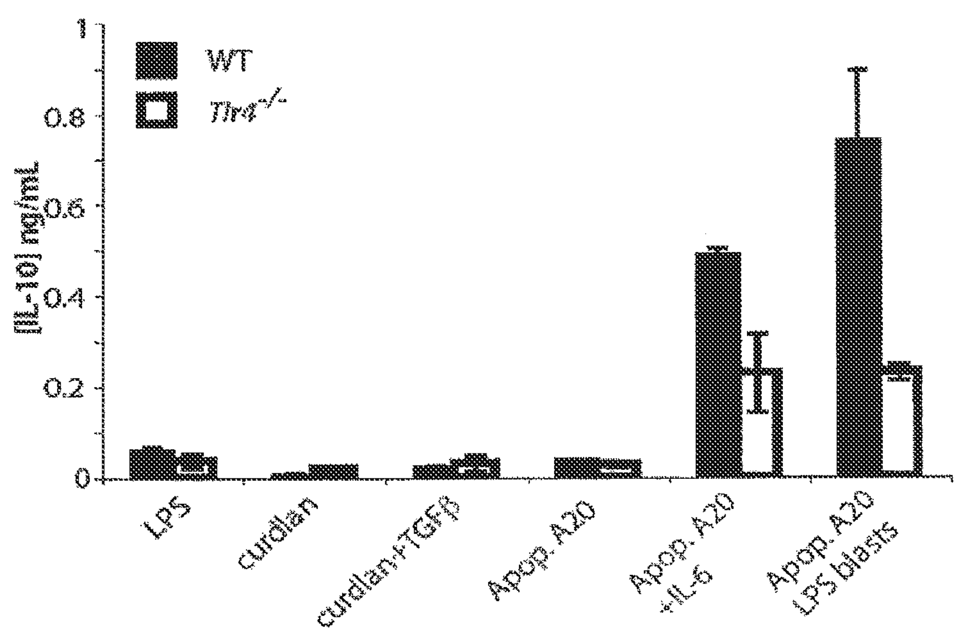
FIG. 16 shows the protein level of IL-10 in the culture supernatants of CD4 T cells following culture in the presence of LPS, curdlan, or curdlan+TFGF-β, or following culture with conditioned media from C57BL/6J (WT or TLR4$^{-/-}$ dendritic cells that had phagocytosed the indicated stimuli.
Figure 17:
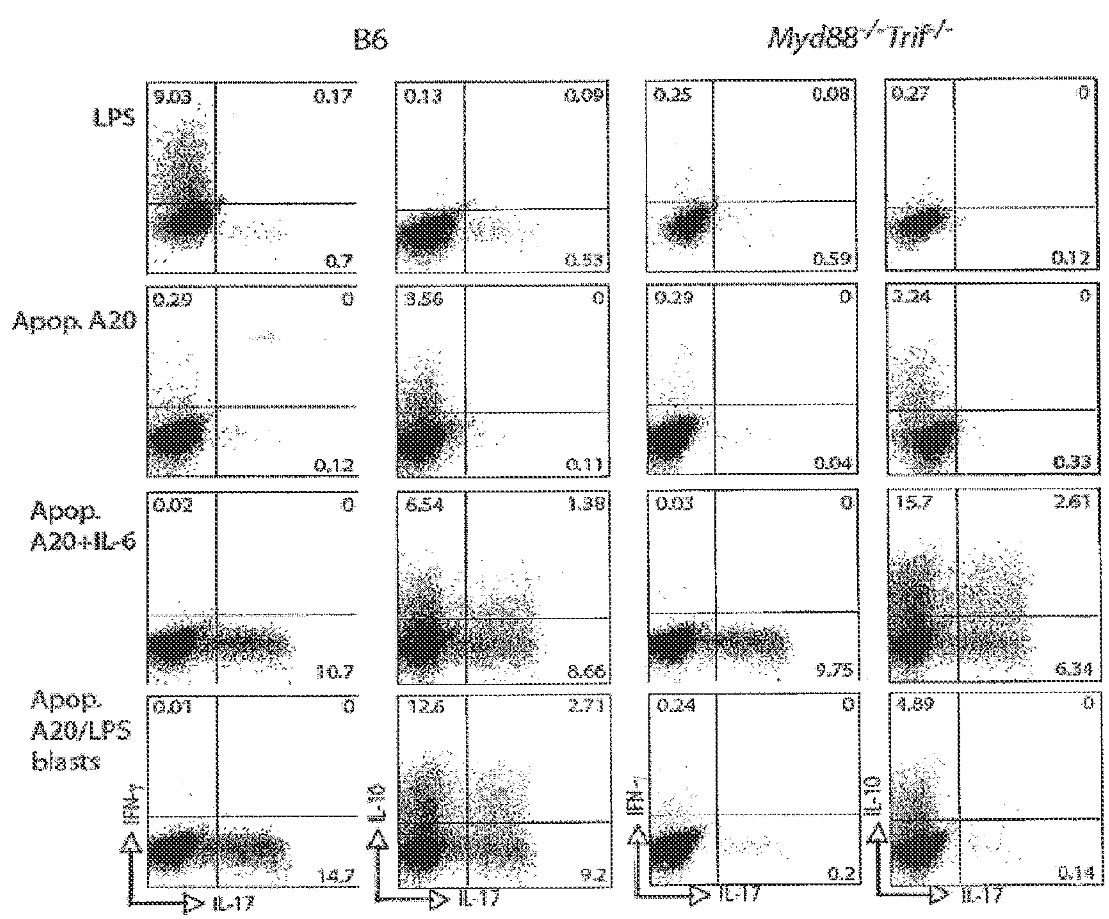
FIG. 17 shows FACS plots of intracellular cytokine staining of IL-10, IL-17, and IFN-γ in CD4 T cells following culture with conditioned media from C57BL/6J (B6) or MyD88$^{-/-}$ TRIF$^{-/-}$ dendritic cells that had been treated with LPS or that had phaocytosed the indicated stimuli.

In some experiments, after four days, cells were re-plated on anti-CD3-coated plates for 48 h in the presence or absence of 10 ng/mL IL-23. Re-stimulation of these cultured CD4 T-cells in the presence of IL-23 only slightly increased the levels of IL-17 produced, consistent with IL-23's primary role in expanding $T_H17$ cells[10-12] (FIG. 14, top panel). However, the total levels of IL-10 produced were markedly impaired, as previously reported[23], when IL-23 was present upon re-stimulation (FIG. 14, bottom panel). In contrast to IL-17, 30-45% of IL-10 secretion remained in response to DCCM-apoptotic LPS-blasts or DCCM-neutrophils/*E. coli* when TLR signaling was absent in the phagocytic DC (FIGS. 15 and 16), and was confined to the 'IL-$10^+$ only' cells (FIG. 17). As expected, all three populations were intact in response to MyD$88^{-/-}$Trif$^{-/-}$DCCM-apoptotic+IL-6 compared to WT DCCM-apoptotic+IL-6 (FIG. 17). These data collectively suggest that the initial development of IL-17 secreting cells in response to apoptosis of infected cells is accompanied by concomitant induction of IL-10 secreting populations. IL-10 production may serve to limit excessive inflammatory responses mediated by those cells during infections[22]. Moreover, the inflammatory cytokines prevailing upon reactivation of these cells may directly impact their IL-10-mediated rather than IL-17mediated effector functions.

Figure 25:
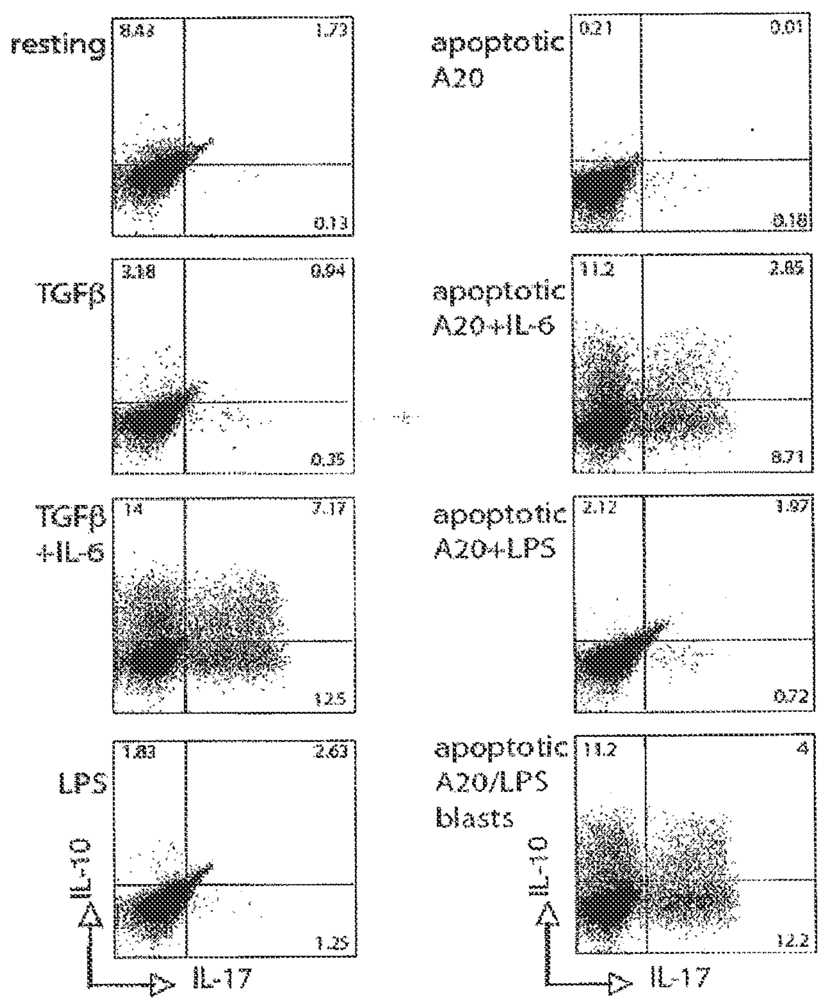
FIG. 25 shows FACS plots of intracellular cytokine staining of CD4 T cells following culture with conditioned medium from DC that were given apoptotic cells and soluble LPS separately (Apoptotic A20+LPS) or from DC that were given apoptotic cells with the TLR ligand physically integrated (Apoptotic A20/LPS blasts).

In one set of experiments, the results of which are shown in FIG. 25, naive CD4 T cells were isolated from C57BL/6J mice and activated with 4 μg anti-CD3 and 2 μg/mL anti-CD28 plus anti-IL-4 with CM from wild-type C57BL/6J BMDC under various conditions, as indicated in the Figure. When apoptotic cells and LPS were co-administered, but as separate entities (Apoptotic A20+LPS), a surprising result was found. CM derived from DC stimulated with LPS during phagocystosis of apoptotic cells induced neither IL-17 nor IL-10 secreting cells despite the expectation that LPS would induce DC production of IL-6 (FIG. 25). However, when DC were stimulated with apoptotic A20/LPS blasts (where the apoptotic cell and TLR ligand are physically associated). CM derived from these cultures induced IL-17 and IL-10 secreting CD4 T cells (FIG. 25). These results demonstrated that the TLR ligand and apoptotic cell should be delivered to DC as one entity (which allows them to be internalized together by a DC. These results also strengthened the discovery of the present invention that an infected apoptotic cell is uniquely capable of inducing $T_H17$ responses and that TLR ligands must be physically present within the apoptotic cell to accurately mimic an infected apoptotic cell. These results also demonstrated that the $T_H17$-inducing effects of A20/LPS blasts were not due to contaminating free LPS. Furthermore, CM from cultures of DC stimulated with apoptotic A20 cells and IL-6 (Apoptotic A20+IL-6) stimulated IL-17 and IL-10 secreting CD4 T cells, indicating that addition of IL-6 can overcome the need for the presence of a TLR ligand (or adjuvant) associated as a single entity with an apoptotic cells for the induction of a $T_H17$-inducing DC.

Example 6

Blockade of Apoptosis

The following example describes whether blockade of apoptosis impairs development of $T_H17$ cells in vitro during bacterial infections known to trigger $T_H17$ responses.

*Citrobacter rodentium* is a rodent pathogen that serves as a model for human infections with the attaching and effacing enteropathogenic and enterohemorrhagic *E. coli*[9]. C3H/HeOuJ mice were infected orogastrically with *C. rodentium* wild-type (WT), *C. rodentium* ΔEspF, or *C. rodentium* ΔMap, and/or treated with 20 mg/kg caspase inhibitor Q-VD-OPH intraperitoneally on days 0, 1, 2, 3, and 5. Mice were sacrificed on day 6 and colons were harvested and frozen for tissue sectioning and TUNEL analysis.

Figure 18:
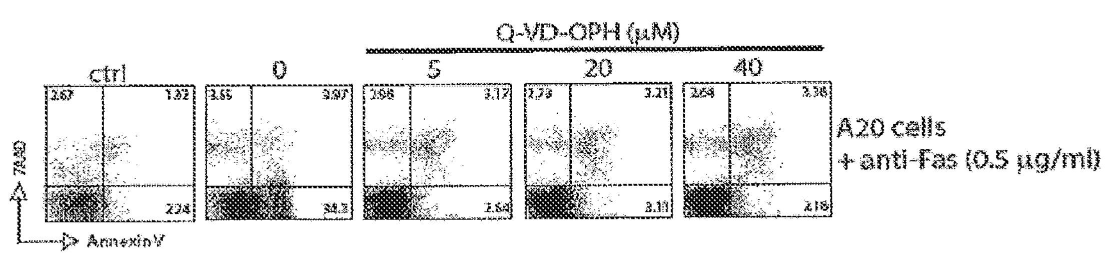
FIG. 18 is a FACS plot of 7AAD- and Annexin V-stained apoptotic A20 B cells (treated with anti-Fas) showing that Q-VD-OPH inhibits apoptosis.

FIG. 18 shows the inhibition of apoptosis by pan-caspase inhibitor Q-VD-OPH. A20 cells were incubated in the presence or absence of anti-Fas (anti-CD95) to induce apoptosis with or without the indicated concentrations of Q-VD-OPH for four hours before staining for Annexin-V and 7-AAD and analysis by flow cytometry. When A10 LPS blasts were incubated with Q-VD-OPH during Fas treatment, they were protected from undergoing Fas-induced apoptosis as shown by Annexin V/7AAD staining. In the absence of Q-VD-OPH treatment, 100% of the cells become apoptotic at later time points.

Figure 19:
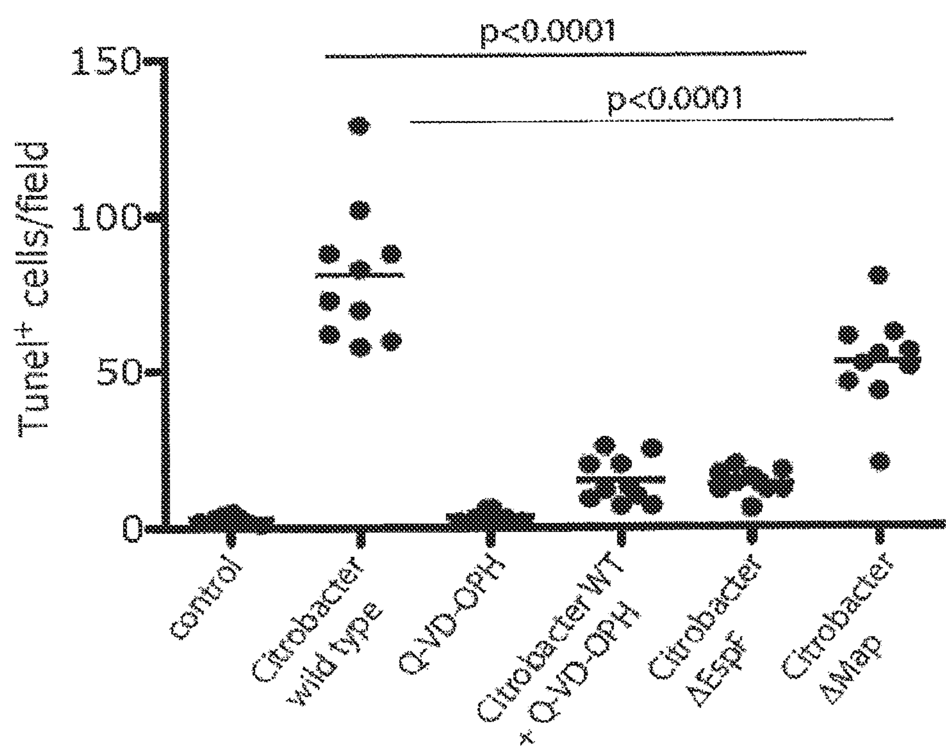
FIG. 19 is a graph quantifying the amount of TUNEL staining in sections of colonic epithelial cells taken from the colons of mice infected with the indicated bacteria in the presence or absence of the caspase inhibitor Q-VD-OPH.
Figure 23:
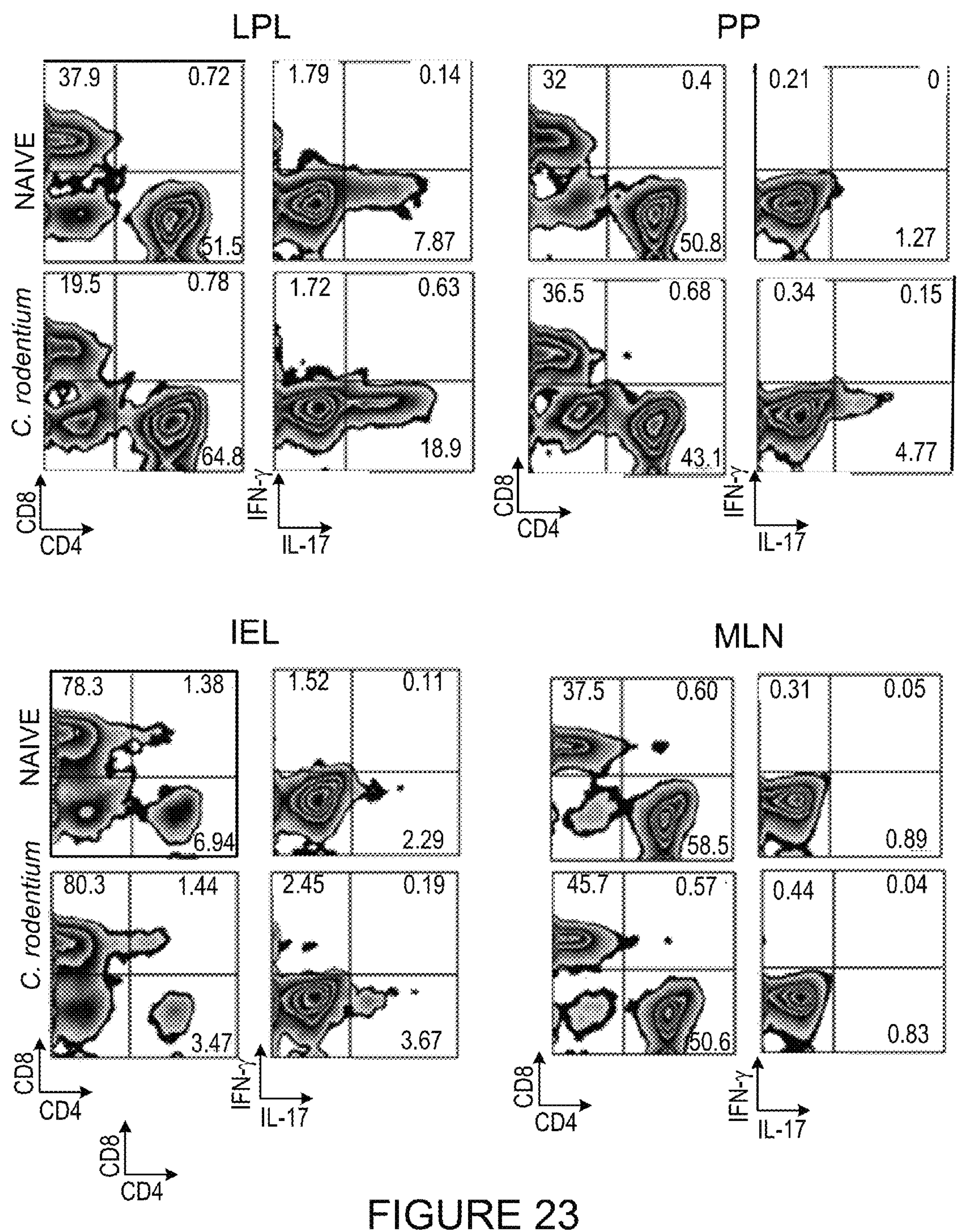
FIG. 23 shows FACS plots of intracellular cytokine staining of CD4, CD8α, IFN-γ, and IL-17 in cells isolated from the indicated tissues from mice infected with *Citrobacter rodentium.*

Importantly, orogastric infection with this pathogen resulted in massive apoptosis in intestinal epithelial cell[25, 26], as measured by TUNEL staining and quantified in the graph in FIG. 19. Moreover, IL-17$^+$ CD4 T-cells were increased in number and predominate within the lamina propria[11, 17] (LP) of *C. rodentium* infected mice (shown in FIG. 20), to a lesser degree in intraepithelial lymphocytes and Peyer's patches, and not detectable in the mesenteric lymph nodes (FIG. 23) and spleen. Such infection also led to increased numbers of IL-17$^+$ CD4 T-cells in the small intestinal and colonic LP of the more susceptible C3H/HeOuJ mice[26] (FIG. 21).

Figure 20:
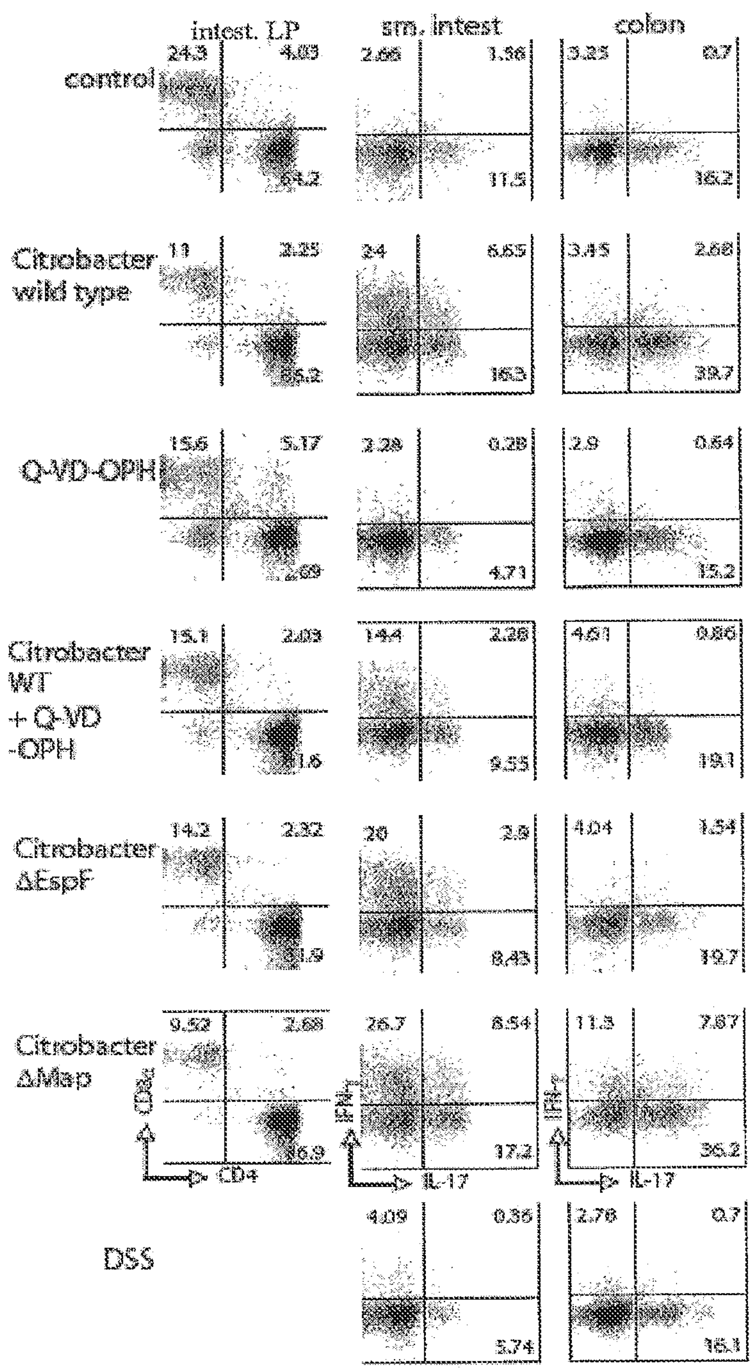
FIG. 20 shows FACS plots of intracellular cytokine staining of CD4, CD8α, IFN-γ, and IL-17 in cells isolated from the indicated tissues from mice infected with the indicated bacteria or treated with DSS.
Figure 21:
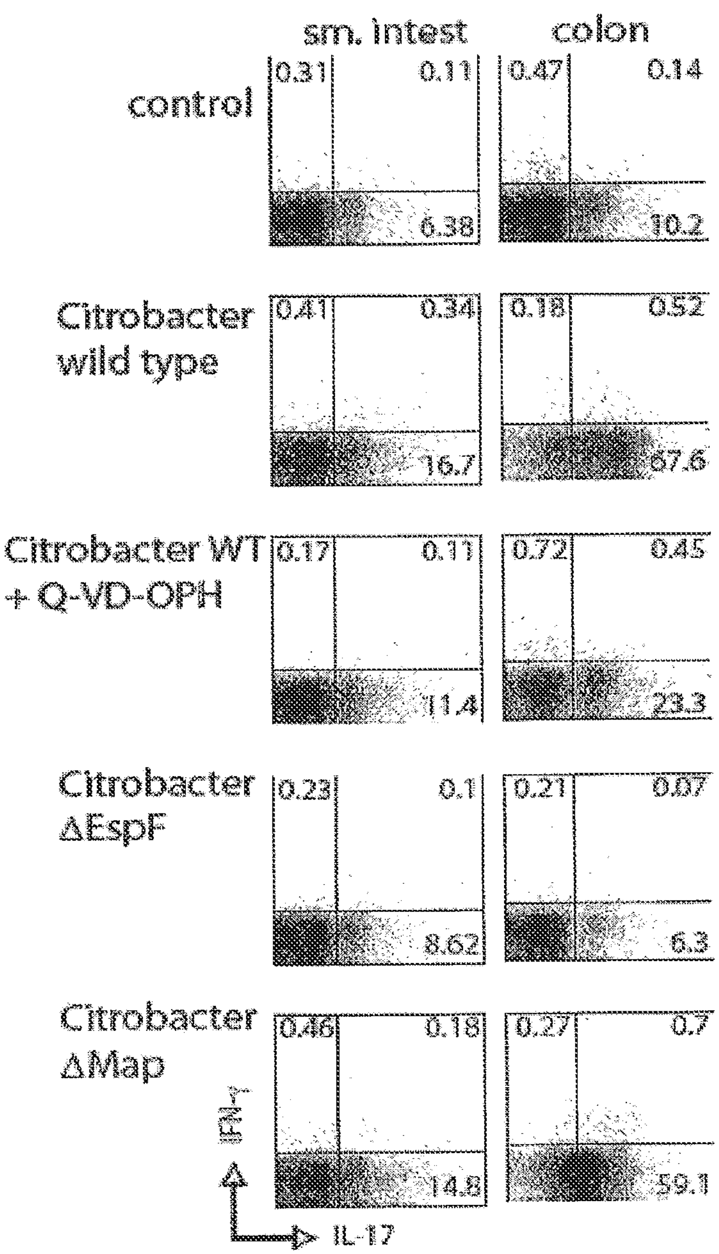
FIG. 21 shows FACS plots of intracellular cytokine staining of IFN-γ and IL-17 in cells isolated from the indicated tissues from mice infected with the indicated bacteria.

Treatment of *C. rodentium* infected mice with the pan-caspase inhibitor Q-VD-OPH resulted in decreased numbers of TUNEL cells (FIG. 19) and also profoundly diminished the number of IL-17$^+$ CD4 T-cells in both strains of infected mice, and in C57BL/6J mice to levels similar to those found in uninfected mice (FIGS. 20 and 21). Thus, caspase inhibition results in blockade of epithelial cell apoptosis in a relevant infection model in vivo, and profoundly interferes with the generation of a $T_H17$ response.

Given that Q-VD-OPH is a broad-spectrum caspase inhibitor, it likely affects processes independent of apoptosis, like activation of the inflammasome, which is important for generation of immune responses[27]. Secretion of cytokines such as IL-1 and IL-18 may thus be perturbed by Q-VD-OPH. Therefore, the requirements for apoptosis in $T_H17$ induction was tested by a fundamentally different approach, based on the usage of a *C. rodentium* mutant incapable of inducing apoptosis. EspF (EPEC-secreted protein F) and Map (mitochondrial associated protein) are effectors encoded by the locus of enterocyte effacement (LEE) pathogenicity island[28]. Despite similar colonization (FIG. 19), shedding in the stool, and colonic hyperplasia, only WT and ΔMap induce apoptosis and tight junction disruption in vitro and in vivo, while ΔEspF mutants fail to do so[25, 26, 29, 30]. This is indicated by the increased numbers of apoptotic TUNEL$^+$ cells in the distal colon of WT- and ΔMap-infected mice, but not ΔEspF-infected compared to uninfected mice (FIG. 19). Thus, development of $T_H17$ cells in the intestinal LP in response to infection with these strains of *C. rodentium* was assessed. Equivalent numbers of CD4 and CD8 T-cells were present in the LP of all WT-, ΔEspF- and ΔMap-infected C57BL/6J (FIG. 20, leftmost panels) and C3H/HeOuJ mice. Compared to uninfected mice, modest increases were observed in IL-17$^+$ CD4 T-cells in the small intestinal LP in response to WT and ΔMap infection, and not in response to ΔEspF infection (FIG. 20 and 21, small intestine panels). WT and ΔMap infection induced larger increases in the IL-17[30] CD4 T-cells in the colonic LP, but notably the numbers of IL-17$^+$ CD4 T-cells in ΔEspF-infected mice were similar to those in uninfected controls (FIGS 20 and 21, colon panels). In contrast to IL-17, similar levels of IFN-γ CD4 T-cells were found in the small intestinal LP of C57BL/6J mice infected with WT, ΔEspF, and ΔMap *C. rodentium* (FIG. 20, small intestine panels) consistent with intact expression of the bacterial outer membrane protein, intimin, reported to drive $T_H1$ responses in *C. rodentium* infections[9, 11].

Figure 22:
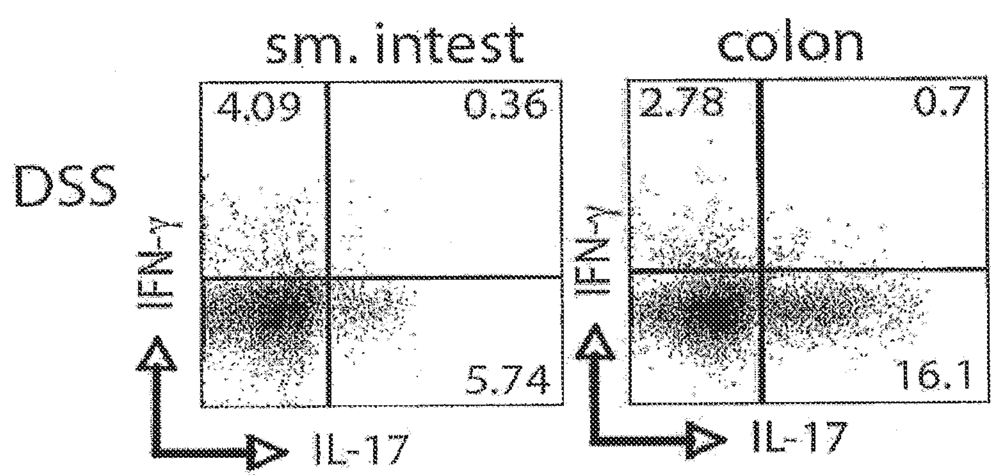
FIG. 22 shows FACS plots of intracellular cytokine staining if IFN-γ and IL-17 in cells isolated from the indicated tissues from mice treated with DSS.

Because ΔEspF can neither induce apoptosis nor disrupt tight junctions, it remained possible that tight junction disruption per se could drive the observed $T_H17$ response. However, tight junction disruption should not be affected in Q-VD-OPH treated WT *C. rodentium* infected mice as Q-VD-OPH despite reducing apoptosis, has no effects on infection induced barrier function[30]. Furthermore, dextran sulfate sodium (DSS)-induced damage of the intestinal epithelium did not increase IL-17$^+$ CD4 T-cells over uninfected controls (FIG. 22). For DSS experiments, C57BL/6 mice treated with DSS and sacrificed on day 9. Lamina propria lymphocytes (LPL) were isolated from small intestines (sm. Intest) and colons. LPL were the restimulated with PMA and ionomycin for 4 hours with Brefeldin A before surface staining for CD4 and intracellular cytokine staining for IL-17 and IFN-γ, and analysis by flow cytometry. Plots were gated on CD4$^+$ cells and quadrant percentiles of cells staining positively for the indicated cytokines are shown. These results argue against a role for disruption of intestinal epithelium integrity as a stimulus for $T_H17$ development.

Example 7

TLR Ligand-carrying or Infected Apoptotic Cell Engineered to Express an Exogenous Immune Antigen Generation of TLR ligand-carrying or infected apoptotic cell engineered to express an exogenous immune antigen derived of microbial or host origin is desirable for inducing a $T_H17$ immune response directed against a tumor-associated immune antigen as a form of tumor immunotherapy, or for inducing a $T_H17$ immune response directed against a particular immunodominant antigen expressed by a given bacterium. Such apoptotic cells may be prepared, by way of non-limiting example, by the following method.

A 1) A cell line is transfected with the exogenous immune antigen of interest (e.g., a tumor-associated antigen, an immunodominant antigen associated with an autoimmune disease or chronic inflammatory disease). This cell line can be a phagocytic cell line, such as one of monocytic or macrophage origin. The antigen may be a tumor-associated antigen, for example where $T_H17$ immune responses are desired against a given tumor, or an immunodominant antigen derived from a bacterium. This antigen can be expressed from a recombinant mammalian expression vector or viral vector engineered to encode the game sequence for the antigen. This gene sequence can either be the full gene or a portion of it encompassing immunodominant regions, if these are known. Clones derived from this transfected cell line are then propagated where they stably express the exogenous immune antigen at high levels. Alternatively, a tumor cell line is chosen that represents the tumor in the mammal. This tumor cell line would naturally express the tumor-associated antigen.

2) TLR ligands are introduced into the cell line. For non-phagocytic cell lines, a TLR ligand such as CpG or Poly (I:C) may be electroporated into the cell line. For phagocytic cell lines (e.g., a macrophage or monocytic cell line), an innoocuous microbe such as *E. coli* K12 may be given to the cells at a ratio of 10 microbes to one cell. Alternatively, attenuated *Mycobacterium bovis* BCG strain may be used, for example. For safety, the innocuous microbe is further inactivated by exposure to heat, UV, or fixative. Viable microbes are not necessary to induce the desired $T_H17$ response. The microbe here serves only to provide a source of mixed TLR ligands.

A variation of the above method is to choose a phagocytic cell line to which an inactivated form of the infecting microbe is given. In this variation, step 1 above is eliminated. For example, if $T_H17$ responses against a respiratory infection with *Klebsiella pneumoniae* are desired, a phagocytic monocytic cell line is given heat-inactivated *K. pneumonia* at a ratio of 10 bacteria to one cell for a period of 30-45 minutes. The cells would then internalize the inactivated *K. pneumonia* thus in effect carry not only the TLR ligands derived from *K. pneumonia*, but all the exogenous antigens derived from *K. pneumonia* as well. The cells are then washed to remove excess extracellular *K. pneumonia* that may not have been internalized.

3) Apoptosis is induced in the transfected cell line or tumor cell line now carrying TLR ligands. Alternatively, apoptosis is induced in the phagocytic cell line following its internalization of the desired microbe. The trigger chosen to induce apoptosis depends on the cell type. This trigger can be UV irradiation at a dose sufficient to induce Annexin-$V^+$ 7-$ADD^-$ at early time points (4 hours). High doses of UV should be avoided as these induce necrosis (which does not induce $T_H17$ responses) measured by the appearance of Annexin-$V^+$ 7-$AAD^-$ as early as 2 hours after UV irradiation. Other triggers might be anti-Fas antibody or treatment with Staurosporine. Staurosporine (antibiotic AM-2282 or STS) is a natural product originally isolated from bacterium *Streptomyces staurosporeus* [Omura S, et al. (1977) J. Antibiot. 30 (4): 275-282].

Example 8

Apoptotic Cell Engineered to Express an Exogenous Immune Antigen

Generation of an apoptotic cell engineered to express an exogenous immune antigen is desirable for inducing a $T_{reg}$ immune response. This immune response may be directed against a tumor-associated immune antigen as a form of tumor immunotherapy, or for inhibiting $T_H17$ immune responses directed against an exogenous antigen of microbial origin. Such apoptotic cells may be prepared, for example, as follows:

1) A cell line is transfected with the exogenous immune antigen of interest. For example, the antigen may be a tumor-associated antigen where $T_H17$ immune responses are desired against a given tumor or an immunodominant antigen derived from a bacterium or other source. This antigen can be expressed from a recombinant mammalian expression vector or viral vector engineered to encode the gene sequence for the antigen. This gene sequence can either be the full gene or a portion of it encompassing immunodominant regions if these are known. Clones derived from this transfected cell line are then propagated where they stably express the exogenous immune antigen at high levels. Alternatively, a tumor cell line is chosen that represents the tumor in the mammal. This tumor cell line would naturally express the tumor-associated antigen.

2) Apoptosis is induced in the transfected cell line or tumor cell line. The trigger chosen to induce apoptosis depends on the cell type. A skilled artisan will be able to determine the appropriate method for inducing apoptosis in a given cell line. This trigger can be UV irradiation at a dose sufficient to induce Annexin-$V^+$ 7-$AAD^-$ at early time points (4 hours). High doses of UV should be avoided as these induce necrosis (which does not induce $T_H17$ responses) measured by the appearance of Annexin-$V^+$ 7-$AAD^+$ as early as 2 hours after UV irradiation. Other triggers might be anti-Fas antibody or treatment with Staurosporine.

Example 9

Induction of a $T_H17$ Response In vivo by Transfer of $T_H17$-Inducing DC

Immunization with $T_H17$-inducing DC would be useful for inducing antigen-specific $T_H17$ responses in vivo. An example of this approach is provided for the mouse, but may be modified for immunization of humans, an example of which is also provided below. $T_H17$-inducing DC may be generated, for example, by the following steps:

1) Derivation of murine DC: Bone marrow (BM)-derived GM-CSF DC cultures are grown in RPMI medium supplemented with GM-CSF and 5% foetal bovine serum (FBS), plus 100 μg/mL penicillin, 100 μg/mL streptomycin, 2 mM L-glutamine, 10 mM HEPES, 1 nM sodium pyruvate, 1X MEM nonessential amino acids, and 2.5 μM β-mercaptoethanol (all from Sigma-Aldrich, St. Louis, Mo.), as previously described [Blander, J. M. & Medzhitov, R. (2006) Nature 440, 880-12].

2) Preparation of TLR-ligand carrying apoptotic cells expressing an exogenous immune antigen. The B cell line A20 stably expressing the exogenous immune antigen chicken ovalbumin (A20OVA) is stimulated with 25 μg/ml of the TLR ligand LPS for 4 days to generate A20OVA LPS blasts. Apoptosis of A20-OVA LPS blasts is induced by culturing cells with 0.5 μg/mL anti-CD95 (clone Jo2; BD) for four hours. Cells are then washed and counted.

3) Semi-adherent dendritic cells are harvested on ice on day 5 of GM-CSF DC cultures, and re-plated immediately in fresh GM-CSF medium at $1\times10^6$ cells/well in 24-well tissue culture-treated plates. Apoptotic A20-OVA LPS blasts are added right away to the plates in the same medium and the cells were centrifuged for 2 min at 2000 rpm. DC are incubated with the phagocytic cells for a period of 4-6 hours then harvested and washed. These cells now provide the $T_H17$-inducing DC.

4) Mice are injected intravenously with $10^7$ OVA-specific T cell receptor transgenic $CD4^+$ T cells called OT-II (available from the Jackson Laboratory). These OT-II T cells are introduced into the mouse as a readout for the activation of OVA-specific $T_H17$ $CD4^+$ T cells. $T_H17$-inducing DC are injected intravenously into the tail veins of these mice 6 hours later.

5) Immunized mice are sacrificed on day 6. Single cell suspension are prepared from the spleens and lymph nodes of these mice. These suspensions are enriched for $CD4^+$ T cells by sorting with MACS® $CD4^+$ beads (Miltenyi Biotech, Auburn, Calif.) according to manufacturer's instructions. A feeder layer of irradiated syngeneic splenocytes is added to these $CD4^+$ T cells, and co-cultures are immediately pulsed with various doses of OVA-derived peptide (0.1, 1, and 10 μg/ml). The peptide sequence is ISQAVHAAHAEINEAGR (SEQ ID NO: 91) and represents the immunodominant peptide derived from OVA encompassing residues 323-339 and presented by the major histocompatibility complex (MHC) class II molecule, I-$A^b$. Culture supernatants are harvested at 48 hours and the levels of $T_H$17 cytokine IL-17 are measured by ELISA. Supernatants are also tested for the production of IFN-γ and IL-4 as markers of $T_H$1 and $T_H$2 responses, respectively. Production of IL-17 by these CD4 T cells will indicate the induction of an antigen-specific $T_H$17 immune response.

6) Protective immunity against tumor may be measured for example. Mice are immunized with the $T_H$17 inducing DC as in steps 1, 2, 3 and 4 above (without adoptive transfer of OT-II $CD4^{30}$ T cells). One week and 21 days later, mice are challenged with a small number ($5\times10^4$-$10^5$) of tumor cells expressing OVA. These tumor cells may be an EL4 thymoma cell line engineered to express the exogenous antigen OVA, or the B cell lymphoma A20 engineered to express OVA. Tumor cells are injected subcutaneously and tumor development is monitored by measuring tumor size every 2 days over a period of 30 days. Tumor size will be measured on two perpendicular axes using a vernier caliper as described [Helmich, B. K. & Dutton, R. W. (2001) J Immunol 166, 6500-8; Taetle, R., et al. (1987) *Cancer Treat Rep* 71, 297-304], and tumor size will be approximated by multiplying the measured widths and lengths [Taetle, R., et al, supra ]. Mean tumor volume and standard errors of the mean will be averaged from 8-10 identically treated mice per group. Tumor development is compared between groups of immunized and unimmunized mice (8-10 mice per group, sex and age matched).

Modification for Humans:

Peripheral blood mononuclear cells (PBMCs) are enriched from apheresis by Ficoll gradient centrifugation, frozen, and stored at −180° C. as described [Palucka, A. K. et. al. (2006) *J. Immunotherapy*. 29:545-557]. The $T_H$17-inducing DC vaccine is generated under cGMP conditions by culturing monocytes, enriched from thawed PBMCs by 2 hours adherence, for 6 days in X-VIVO15 (BioWhittaker. Walkersville, Md.) supplemented with 1% autologous serum, GM-CSF (200 ng/mL, Leukine, Berlex Inc. (Bayer HealthCare), Montville, N.J.) and IL-4 (50 ng/mL, R&D systems) as described [Palucka et al, supra]. A third of the vaccine is loaded with control antigen keyhole limpet hemocyanin (KLH) (Biosyn Corp., Carlsbad, Calif.), and two-thrids are loaded with apoptotic TLR-ligand carrying or microbe-infected cells expressing an exogenous immune antigen. The TLR-ligand carrying or microbe-infected apoptotic cells are prepared as described in Example 7, above. The exogenous antigen may be a known immunodominant antigen derived from a bacterium, or other source, for example. Alternatively, if an immunodominant antigen is not defined, an inactivated form of, e.g., a bacterium is given to a phagocytic cell line, which is then induced to undergo apoptosis by UV irradiation (see Example 7). Following the loading procedure, DC are activated by adding tumor necrosis factor (TNF) (20 ng/mL) and soluble CD40 ligand (200 ng/mL, both from R&D Systems) in the last 30 hours of culture as described [Paleuka et al, supra]. DC are defined by CD11c surface expression, high levels of HLA-DR, CD83, and the costimulatory molecule CD80. The expression of the costimulatory molecule CD80 serves as a phenotype consistent with the activation and maturation of the $T_H$17-inducing DC.

An example of clinical monitoring can be the form of intracellular cytokine analysis for IFN-γ, IL-4 and IL-17. Frozen/thawed PBMCs are resuspended in $2\times10^6$ cells/mL and $2\times10^6$ PBMCs are stimulated with either the immunodominant microbial derived peptide (10 μM), the control KLH, or heat inactivated bacteria at a dose of 2-5 bacteria to 1 cell. The mAbs anti-CD28/CD49d are also added (BD bioscience) as described [Palucka et al, supra]. At 2 hours of stimulation, cells are harvested, and stained with anti-CD3 PerCP and/or anti-CD4 APC mAbs before fixation and permeabilization with BD Cytofix/Cytoperm solution (BD Pharmingen or eBioscience). The cells are then stained with anti-IFN-γ-FITC and anti-IL-17-PE (BD Pharmingen or eBioscience). PBMCs should respond to KLH as this serves as a positive control. Staining for IL-17 will indicate priming (induction) of a $T_H$17 CD4 T cell response against the exogenous immune antigen.

SUMMARY

The results described herein demonstrate that sensing by DC of infected apoptotic cells during infections triggers instructive signals critical for $T_H$17 development. They also explain the puzzling observations that some but not all microbial pathogens induce $T_H$17 cells, and indicate the importance of examining the induction of apoptosis by pathogens inducing $T_H$17 cells. Thus, $T_H$17 cells can be induced not only by the dectin-1 pathway in case of fungal infections[21], but also by the TLR pathway in case of infected apoptotic cells. The findings of the present invention additionally show a novel role for apoptosis in host-pathogen interactions along epithelial surfaces. Thus, these data highly suggest that $T_H$17 cells are critial in mediating effector functions during bacterial infections associated with significant apoptosis and tissue damage. In addition to neutrophil and macrophage recruitment, tissue repair processes uniquely associated with the effector functions of $T_H$17 cells [3, 17] would aid host response against these pathogens. Since $T_H$17 cells have been correlated with autoimmune diseases[1-5], investigation of the pathways of innate recognition of infected apoptotic cells might lead to improved understanding of the causative defects in autoimmunity.

Moreover, the present invention describes invention described a previously unappreciated role of apoptosis on host-pathogen interactions across the intestinal epithelium. The association of $T_H$17 cells with autoimmune diseases, combined with a previously unrecognized apoptotic cell component for instructing $T_H$17 development in conjunction with TLR signaling, suggest breakdown in critical regulatory pathways that direct $T_H$17 specificities to microbial components rather than to self. This novel understanding will be critical for design of the next generation of therapeutic agents and vaccines aimed at treating or preventing autoimmune diseases.

REFERENCES

1. Weaver, C. T., Hatton, R. D., Mangan, P. R. & Harrington, L. E. IL-17 family cytokines and the expanding diversity of effector T cell lineages. *Annu Rev Immunol* 25, 821-52 (2007).
2. Bettelli, E., Korn, T., Oukka, M. & Kuchroo, V. K. Induction and effector functions of T(H)17 cells. *Nature* 453, 1051-7 (2008).
3. Dong, C. TH17 cells in development: an updated view of their molecular identity and genetic programming. *Nat Rev Immunol* 8, 337-48 (2008).
4. Ivanov, II, Zhou, L. & Littman, D. R. Transcriptional regulation of TH17 cell differentiation. *Semin Immunol* 19, 409-17 (2007).
5. Stockinger, B. & Veldhoen, M. Differentiation and function of TH17 T cells. *Curr Opin Immunol* 19, 281-6 (2007).

6. Iwasaki, A. & Medzhitov, R. Toll-like receptor control of the adaptive immune responses. *Nat Immunol* 5, 987-95 (2004).
7. Serhan, C. N. & Savill, J. Resolution of inflammation: the beginning programs the end. *Nat Immunol* 6, 1191-7 (2005).
8. Sakaguchi, S. Naturally arising $CD4^+$ regulatory T cells for immunologic self-tolerance and negative control of immune responses. *Annu Rev Immunol* 22, 531-62 (2004).
9. Kaper, J. B., Nataro, J. P. & Mobley, H. L. Pathogenic *E. coli*. *Nat Rev Microbial* 2, 123-40 (2004).
10. Bettelli, E. et al. Reciprocal developmental pathways for the generation of pathogenic effector $T_H17$ and regulatory T cells. *Nature* 441, 235-8 (2006).
11. Mangan, P. R. et al. Transforming growth factor-beta induces development of the T(H)17 lineage. *Nature* 441, 231-4 (2006).
12. Veldhoen, M., Hocking, R. J., Atkins, C. J., Locksley, R. M. & Stockinger, B. TGFbeta in the context of an inflammatory cytokine milieu supports de nova differentiation of IL-17- producing T cells. *Immunity* 24, 179-89 (2006).
13. O'Garra, A., Stockinger, B. & Veldhoen, M. Differentiation of human T(H)-17 cells does require TGF-beta! *Nat Immunol* 9, 558-90 (2008).
14. Kawai, T. & Akira, S. TLR signaling. *Semin Immunol* 19, 24-32 (2007).
15. Blander, J. M. & Medzhitov, R. Toll-dependent selection of microbial antigens for presentation by dendritic cells. *Nature* 440, 808-12 (2006).
16. Pappu, B. P. et al. TLIA-DR3 interaction regulates TH17 cell function and TH17- mediated autoimmune disease. *J Exp Med* 205, 1049-62 (2008).
17. Cheng, Y. et al. Interleukin-22 mediates early host defense against attaching and effacing bacterial pathogens. *Nat Med* 14, 282-9 (2008).
18. Szabo, S. J. et al. A novel transcription factor, T-bet, directs Th1 lineage commitment. *Cell* 100, 655-69 (2000).
19. Zheng, Y. & Rudensky, A. Y. Foxp3 in control of the regulatory T cell lineage. *Nat Immunol* 8, 457-62 (2007).
20. Nurieva, R. at al. Essential autocrine regulation by IL-21 in the generation of inflammatory T cells. *Nature* 488, 480-3 (2007).
21. LeibundGut-Landmann, S. et al. Syk- and CARD9-dependent coupling of innate immunity to the induction of T helper cells that produce interleukin 17. *Nat Immunol* 8, 630-8 (2007).
22. Couper, K. N., Blount, D. G. & Riley, E. M. IL-10: the master regulator of immunity to infection. *J Immunol* 180, 5771-7 (2008).
23. McGeachy, M. J. et al. TGF-beta and IL-6 drive the production of IL-17 and IL-10 by T cells and restrain T(H)-17 cell-mediated pathology. *Nat Immunol* 8, 1390-7 (2007).
24. Stumhofer, J. S. et al. Interleukins 27 and 6 induce STAT3-mediated T cell production of interleukin 10. *Nat Immunol* 8, 1363-71 (2007).
25. Nagai, T., Abe, A. & Sasakawa, C. Targeting of enteropathogenic *E. coli* EspF to host mitochondria is essential for bacterial pathogenesis: critical role of the 16th leucine residue in EspF. *J Biol Chem* 280, 2998-3011 (2005).
26. Vallance, B. A., Deng, W., Jacobson, K. & Finlay, B. B. Host susceptibility to the attaching and effacing bacterial pathogen *Citrobacter rodentium*. *Infect Immun* 71, 3443-53 (2003).
27. Martinon, F. & Tschopp, J. Inflammatory caspases: linking an intracellular innate immune system to autoinflammatory diseases. *Cell* 117, 561-74 (2004).
28. Deng, W. et al. Dissecting virulence: systematic and functional analyses of a pathogenicity island. *Proc Natl Acad Sci U S A* 101, 3597-602 (2004).
29. Nougayrede, J. P. & Donnenberg, M. S. Enteropathogenic *E. coli* EspF is targeted to mitochondria and is required to initiate the mitochondrial death pathway. *Cell Microbiol* 6, 1097-111 (2004).
30. Viswanathan, V. K., Weflen, A., Koutsouris, A., Roxas, J. L. & Hecht, G. Enteropathogenic *E. coli*-induced barrier function alteration is not a consequence of host cell apoptosis. *Am J Physiol Gastrointest Liver Physiol* 294, G1165-70 (2008).
31. U.S. Patent Application 2006/0147456 to Lebecque et al.
32. U.S. Patent Application 2006/0147427 to Penninger et al.
33. U.S. Pat. No. 7,074,413 to Dietzschold et al.
34. U.S. Pat. No. 5,972,899 to Zychlinsky et al.

What is claimed:

1. A method for generating a $T_H$17-inducing dendritic cell (DC) that secretes interleukin-6 (IL-6) and transforming growth factor beta (TGF-β), wherein the combined amount of IL-6 and TGF-β secreted by the $T_H$17-inducing DC is effective for inducing a $T_H$17 response when the $T_H$17-inducing DC is administered to a subject, the method comprising administering to a DC in vitro a Toll-like receptor (TLR) agonist and an apoptotic cell-associated agent in a combined amount effective for generating the $T_H$17-inducing DC.

2. The method of claim 1, wherein the TLR agonist and the apoptotic cell-associated agent are either in direct physical association or are combined in a manner that allows internalization as a single entity by the DC in vitro.

3. The method according to claim 1, wherein the apoptotic cell-associated agent comprises any one of the agents selected from the group consisting of an apoptotic cell, an apoptotic cell mimic, phosphatidylserine, a microbe-infected apoptotic cell, a phosphatidylserine mimic, a mimic of cell surface calreticulin translocation, and a polypeptide that is a marker of apoptosis.

4. The method according to claim 1, wherein the TLR agonist comprises any one of the agents selected from the group consisting of a TLR ligand, a TLR ligand mimic, a synthetic or chemical TLR ligand, a cell or particle comprising a pathogen-associated molecular pattern, a microbial pathogen, a bacterium, a virus, and a viral particle.

5. A method for generating a $T_H$17-inducing dendritic cell (DC) that secretes interleukin-6 (IL-6) and transforming growth factor beta (TGF-β), wherein the combined amount of IL-6 and TGF-β secreted by the $T_H$17-inducing DC is effective for inducing a $T_H$17 response when the $T_H$17-inducing DC is administered to a subject, the method comprising administering to a DC in vitro (i) and (ii), as a single entity or in a combined form, wherein (i) is at least one member selected from the group consisting of a Toll-like receptor (TLR) ligand, a TLR ligand mimic, a synthetic or chemical TLR ligand, a cell or particle comprising a pathogen-associated molecular pattern, a microbial pathogen, a TLR agonist, a bacterium, and a virus or viral-like particle, and wherein (ii) is at least one member selected from the group consisting of an apoptotic cell, a microbe-infected apoptotic cell, an apoptotic cell mimic, phosphatidylserine, a phosphatidylserine mimic, an apoptotic cell-associated agent, a mimic of cell surface calreticulin translocation, and a polypeptide that is a marker of apoptosis; wherein the combined amount of (i) and (ii) is effective for generating the $T_H$17-inducing DC.

6. An immunogenic composition comprising a) a $T_H$17-inducing DC that secretes IL-6 and TGF-β, b) an immune antigen, and c) a pharmaceutically acceptable carrier or diluent, wherein a combined amount of the IL-6 and the TGF-β secreted by the $T_H$17-inducing DC and the immune antigen is effective for eliciting a $T_H$17 response to the immune antigen in a subject which is administered the immunogenic composition.

7. The immunogenic composition of claim 6, wherein the $T_H$17-inducing DC is generated by a method comprising pre-treating a DC in vitro with a TLR agonist and an apoptotic cell-associated agent in a combined amount effective for generating the $T_H$17-inducing DC.

8. The immunogenic composition of claim 7, wherein the TLR agonist and the apoptotic cell-associated agent are combined in a manner that allows internalization as a single entity by the DC in vitro.

9. The immunogenic composition of claim 6, wherein the $T_H17$-inducing DC is pre-treated in vitro with the immune antigen or with a peptide fragment derived from the immune antigen.

10. A method for inducing in a patient an antigen-specific $T_H17$-driven immune response, which comprises administering to a patient in need thereof the immunogenic composition according to claim 6 in an effective amount for inducing the antigen-specific $T_H17$-driven immune response.

11. The method according to claim 10, wherein the antigen-specific $T_H17$-driven immune response comprises a mucosal immune response.

12. The method according to claim 10, wherein the patient is a human.

13. A method for treating cancer in a mammal, which comprises administering to a mammal in need thereof the immunogenic composition according to claim 6 in an effective amount for treating cancer, wherein the immune antigen in the immunogenic composition is a tumor-specific antigen.

14. The method of claim 13, wherein the cancer is an epithelial or mixed epithelial carcinoma.

15. The method of claim 14, wherein the epithelial or mixed epithelial carcinoma is a member selected from the group consisting of ovarian cancer, breast cancer, pancreatic cancer, lung carcinoma, laryngeal carcinoma, adenoid cystic carcinoma, epithelial carcinomas of the upper aerodigestive tract, hepatocellular carcinoma, colorectal carcinoma, lymphoepithelial carcinoma, squamous cell carcinoma, renal cell carcinoma, mixed epithelial and stromal tumors of the kidney, and renal angiomyoadenomatous tumors.

16. The method according to claim 13, wherein the immunogenic composition is administered to the mammal by an oral or mucosal route.

* * * * *

SEQUENCE LISTING

```
<160> NUMBER OF SEQ ID NOS: 93

<210> SEQ ID NO 1
<211> LENGTH: 1131
<212> TYPE: DNA
<213> ORGANISM: Homo sapiens

<400> SEQUENCE: 1

cattctgccc tcgagcccac cgggaacgaa agagaagctc tatctcccct ccaggagccc      60

agctatgaac tccttctcca caagcgcctt cggtccagtt gccttctccc tggggctgct     120

cctggtgttg cctgctgcct tccctgcccc agtaccccca ggagaagatt ccaaagatgt     180

agccgcccca cacagacagc cactcacctc ttcagaacga attgacaaac aaattcggta     240

catcctcgac ggcatctcag ccctgagaaa ggagacatgt aacaagagta acatgtgtga     300

aagcagcaaa gaggcactgg cagaaaacaa cctgaacctt ccaaagatgg ctgaaaaaga     360

tggatgcttc caatctggat tcaatgagga gacttgcctg gtgaaaatca tcactggtct     420

tttggagttt gaggtatacc tagagtacct ccagaacaga tttgagagta gtgaggaaca     480
```

```
agccagagct gtgcagatga gtacaaaagt cctgatccag ttcctgcaga aaaaggcaaa    540

gaatctagat gcaataacca cccctgaccc aaccacaaat gccagcctgc tgacgaagct    600

gcaggcacag aaccagtggc tgcaggacat gacaactcat ctcattctgc gcagctttaa    660

ggagttcctg cagtccagcc tgagggctct tcggcaaatg tagcatgggc acctcagatt    720

gttgttgtta atgggcattc cttcttctgg tcagaaacct gtccactggg cacagaactt    780

atgttgttct ctatggagaa ctaaaagtat gagcgttagg acactatttt aattattttt    840

aatttattaa tatttaaata tgtgaagctg agttaattta tgtaagtcat atttatattt    900

ttaagaagta ccacttgaaa cattttatgt attagttttg aaataataat ggaaagtggc    960

tatgcagttt gaatatcctt tgtttcagag ccagatcatt tcttggaaag tgtaggctta   1020

cctcaaataa atggctaact tatacatatt tttaaagaaa tatttatatt gtatttatat   1080

aatgtataaa tggtttttat accaataaat ggcattttaa aaaattcagc a            1131
```

<210> SEQ ID NO 2
<211> LENGTH: 1087
<212> TYPE: DNA
<213> ORGANISM: Murine sp.

<400> SEQUENCE: 2

```
ccaagaacga tagtcaattc cagaaaccgc tatgaagttc ctctctgcaa gagacttcca     60

tccagttgcc ttcttgggac tgatgctggt gacaaccacg gccttcccta cttcacaagt    120

ccggagagga gacttcacag aggataccac tcccaacaga cctgtctata ccacttcaca    180

agtcggaggc ttaattacac atgttctctg ggaaatcgtg gaaatgagaa aagagttgtg    240

caatggcaat tctgattgta tgaacaacga tgatgcactt gcagaaaaca atctgaaact    300

tccagagata caaagaaatg atggatgcta ccaaactgga tataatcagg aaatttgcct    360

attgaaaatt tcctctggtc ttctggagta ccatagctac ctggagtaca tgaagaacaa    420

cttaaaagat aacaagaaag acaaagccag agtccttcag agagatacag aaactctaat    480

tcatatcttc aaccaagagg taaaagattt acataaaata gtccttccta ccccaatttc    540

caatgctctc ctaacagata agctggagtc acagaaggag tggctaagga ccaagaccat    600

ccaattcatc ttgaaatcac ttgaagaatt tctaaaagtc actttgagat ctactcggca    660

aacctagtgc gttatgccta agcatatcag tttgtggaca ttcctcactg tggtcagaaa    720

atatatcctg ttgtcaggta tctgacttat gttgttctct acgaagaact gacaatatga    780

atgttgggac actattttaa ttatttttaa tttattgata atttaaataa gtaaacttta    840

agttaattta tgattgatat ttattatttt tatgaagtgt cacttgaaat gttatatgtt    900

atagttttga aatgataacc taaaaatcta tttgatataa atattctgtt acctagccag    960

atggtttctt ggaatgtata agtttacctc aatgaattgc taatttaaat atgtttttaa   1020

agaaatcttt gtgatgtatt tttataatgt ttagactgtc ttcaaacaaa taaattatat   1080

tatattt                                                             1087
```

<210> SEQ ID NO 3
<211> LENGTH: 1629
<212> TYPE: DNA
<213> ORGANISM: Homo sapiens

<400> SEQUENCE: 3

```
acacatcagg ggcttgctct tgcaaaacca aaccacaaga cagacttgca aaagaaggca     60

tgcacagctc agcactgctc tgttgcctgg tcctcctgac tggggtgagg gccagcccag    120
```

```
gccagggcac ccagtctgag aacagctgca cccacttccc aggcaacctg cctaacatgc    180
ttcgagatct ccgagatgcc ttcagcagag tgaagacttt ctttcaaatg aaggatcagc    240
tggacaactt gttgttaaag gagtccttgc tggaggactt taagggttac ctgggttgcc    300
aagccttgtc tgagatgatc cagttttacc tggaggaggt gatgccccaa gctgagaacc    360
aagacccaga catcaaggcg catgtgaact ccctgggga gaacctgaag accctcaggc     420
tgaggctacg gcgctgtcat cgatttcttc cctgtgaaaa caagagcaag gccgtggagc    480
aggtgaagaa tgcctttaat aagctccaag agaaaggcat ctacaaagcc atgagtgagt    540
ttgacatctt catcaactac atagaagcct acatgacaat gaagatacga aactgagaca    600
tcagggtggc gactctatag actctaggac ataaattaga ggtctccaaa atcggatctg    660
gggctctggg atagctgacc cagccccttg agaaacctta ttgtacctct cttatagaat    720
atttattacc tctgatacct caaccccat ttctatttat ttactgagct tctctgtgaa     780
cgatttagaa agaagcccaa tattataatt tttttcaata tttattattt tcacctgttt    840
ttaagctgtt tccatagggt gacacactat ggtatttgag tgttttaaga taaattataa    900
gttacataag ggaggaaaaa aaatgttctt tggggagcca acagaagctt ccattccaag    960
cctgaccacg ctttctagct gttgagctgt tttccctgac ctccctctaa tttatcttgt   1020
ctctgggctt ggggcttcct aactgctaca aatactctta ggaagagaaa ccagggagcc   1080
cctttgatga ttaattcacc ttccagtgtc tcggagggat tcccctaacc tcattcccca   1140
accacttcat tcttgaaagc tgtggccagc ttgttattta taacaaccta aatttggttc   1200
taggccgggc gcggtggctc acgcctgtaa tcccagcact ttgggaggct gaggcgggtg   1260
gatcacttga ggtcaggagt tcctaaccag cctggtcaac atggtgaaac cccgtctcta   1320
ctaaaaatac aaaaattagc cggggcatggt ggcgcgcacc tgtaatccca gctacttggg  1380
aggctgaggc aagagaattg cttgaaccca ggagatggaa gttgcagtga gctgatatca   1440
tgcccctgta ctccagcctg ggtgacagag caagactctg tctcaaaaaa taaaaaataaa  1500
aataaatttg gttctaatag aactcagttt taactagaat ttattcaatt cctctgggaa   1560
tgttacattg tttgtctgtc ttcatagcag attttaattt tgaataaata aatgtatctt   1620
attcacatc                                                           1629
```

```
<210> SEQ ID NO 4
<211> LENGTH: 1314
<212> TYPE: DNA
<213> ORGANISM: Murine sp.

<400> SEQUENCE: 4

gggggggggg atttagagac ttgctcttgc actaccaaag ccacaaagca gccttgcaga     60
aaagagagct ccatcatgcc tggctcagca ctgctatgct gcctgctctt actgactggc    120
atgaggatca gcaggggcca gtacagccgg gaagacaata actgcaccca cttcccagtc    180
ggccagagcc acatgctcct agagctgcgg actgccttca gccaggtgaa gactttcttt    240
caaacaaagg accagctgga caacatactg ctaaccgact ccttaatgca ggactttaag    300
ggttacttgg gttgccaagc cttatcggaa atgatccagt tttacctggt agaagtgatg    360
ccccaggcag agaagcatgg cccagaaatc aaggagcatt tgaattccct gggtgagaag    420
ctgaagaccc tcaggatgcg gctgaggcgc tgtcatcgat ttctcccctg tgaaaataag    480
agcaaggcag tggagcaggt gaagagtgat tttaataagc tccaagacca aggtgtctac    540
```

```
aaggccatga atgaatttga catcttcatc aactgcatag aagcatacat gatgatcaaa    600

atgaaaagct aaaacacctg cagtgtgtat tgagtctgct ggactccagg acctagacag    660

agctctctaa atctgatcca gggatcttag ctaacggaaa caactccttg gaaaacctcg    720

tttgtacctc tctccgaaat atttattacc tctgatacct cagttcccat tctatttatt    780

cactgagctt ctctgtgaac tatttagaaa gaagcccaat attataattt tacagtattt    840

attattttta acctgtgttt aagctgtttc cattggggac actttatagt atttaaaggg    900

agattatatt atatgatggg aggggttctt ccttgggaag caattgaagc ttctattcta    960

aggctggcca cacttgagag ctgcagggcc ctttgctatg gtgtcctttc aattgctctc   1020

atccctgagt tcagagctcc taagagagtt gtgaagaaac tcatgggtct tgggaagaga   1080

aaccagggag atcctttgat gatcattcct gcagcagctc agagggttcc cctactgtca   1140

tcccccagcc gcttcatccc tgaaaactgt ggccagtttg ttatttataa ccacctaaaa   1200

ttagttctaa tagaactcat ttttaactag aagtaatgca attcctctgg gaatggtgta   1260

ttgtttgtct gcctttgtag cagcatctaa ttttgaataa atggatctta ttcg         1314
```

<210> SEQ ID NO 5
<211> LENGTH: 1444
<212> TYPE: DNA
<213> ORGANISM: Homo sapiens

<400> SEQUENCE: 5

```
tttcattttg ggccgagctg gaggcggcgg ggccgtcccg gaacggctgc ggccgggcac     60

cccgggagtt aatccgaaag cgccgcaagc cccgcgggcc ggccgcaccg cacgtgtcac    120

cgagaagctg atgtagagag agacacagaa ggagacagaa agcaagagac cagagtcccg    180

ggaaagtcct gccgcgcctc gggacaatta taaaaatgtg gccccctggg tcagcctccc    240

agccaccgcc ctcacctgcc gcggccacag gtctgcatcc agcggctcgc cctgtgtccc    300

tgcagtgccg gctcagcatg tgtccagcgc gcagcctcct ccttgtggct accctggtcc    360

tcctggacca cctcagtttg gccagaaacc tccccgtggc cactccagac ccaggaatgt    420

tcccatgcct tcaccactcc caaaacctgc tgagggccgt cagcaacatg ctccagaagg    480

ccagacaaac tctagaattt tacccttgca cttctgaaga gattgatcat gaagatatca    540

caaaagataa aaccagcaca gtggaggcct gtttaccatt ggaattaacc aagaatgaga    600

gttgcctaaa ttccagagag acctctttca taactaatgg gagttgcctg gcctccagaa    660

agacctcttt tatgatggcc ctgtgcctta gtagtattta tgaagacttg aagatgtacc    720

aggtggagtt caagaccatg aatgcaaagc ttctgatgga tcctaagagg cagatctttc    780

tagatcaaaa catgctggca gttattgatg agctgatgca ggccctgaat ttcaacagtg    840

agactgtgcc acaaaaatcc tcccttgaag aaccggattt ttataaaact aaaatcaagc    900

tctgcatact tcttcatgct ttcagaattc gggcagtgac tattgataga gtgatgagct    960

atctgaatgc ttcctaaaaa gcgaggtccc tccaaaccgt tgtcattttt ataaaacttt   1020

gaaatgagga aactttgata ggatgtggat taagaactag ggagggggaa agaaggatgg   1080

gactattaca tccacatgat acctctgatc aagtattttt gacatttact gtggataaat   1140

tgtttttaag ttttcatgaa tgaattgcta agaagggaaa atatccatcc tgaaggtgtt   1200

tttcattcac tttaatagaa gggcaaatat ttataagcta tttctgtacc aaagtgtttg   1260

tggaaacaaa catgtaagca taacttattt taaaatattt atttatataa cttggtaatc   1320

atgaaagcat ctgagctaac ttatatttat ttatgttata tttattaaat tatttatcaa   1380
```

```
gtgtatttga aaaatatttt taagtgttct aaaaataaaa gtattgaatt aaagtgaaaa   1440

aaaa                                                                1444


<210> SEQ ID NO 6
<211> LENGTH: 2347
<212> TYPE: DNA
<213> ORGANISM: Homo sapiens

<400> SEQUENCE: 6

ctgtttcagg gccattggac tctccgtcct gcccagagca agatgtgtca ccagcagttg     60

gtcatctctt ggttttccct ggtttttctg gcatctcccc tcgtggccat atgggaactg    120

aagaaagatg tttatgtcgt agaattggat tggtatccgg atgcccctgg agaaatggtg    180

gtcctcacct gtgacacccc tgaagaagat ggtatcacct ggaccttgga ccagagcagt    240

gaggtcttag gctctggcaa aaccctgacc atccaagtca aagagtttgg agatgctggc    300

cagtacacct gtcacaaagg aggcgaggtt ctaagccatt cgctcctgct gcttcacaaa    360

aaggaagatg gaatttggtc cactgatatt ttaaaggacc agaaagaacc caaaaataag    420

acctttctaa gatgcgaggc caagaattat tctggacgtt tcacctgctg gtggctgacg    480

acaatcagta ctgatttgac attcagtgtc aaaagcagca gaggctcttc tgacccccaa    540

ggggtgacgt gcggagctgc tacactctct gcagagagag tcagagggga caacaaggag    600

tatgagtact cagtggagtg ccaggaggac agtgcctgcc cagctgctga ggagagtctg    660

cccattgagg tcatggtgga tgccgttcac aagctcaagt atgaaaacta caccagcagc    720

ttcttcatca gggacatcat caaacctgac ccacccaaga acttgcagct gaagccatta    780

aagaattctc ggcaggtgga ggtcagctgg gagtaccctg acacctggag tactccacat    840

tcctacttct ccctgacatt ctgcgttcag gtccagggca agagcaagag agaaaagaaa    900

gatagagtct tcacggacaa gacctcagcc acggtcatct gccgcaaaaa tgccagcatt    960

agcgtgcggg cccaggaccg ctactatagc tcatcttgga gcgaatgggc atctgtgccc   1020

tgcagttagg ttctgatcca ggatgaaaat ttggaggaaa agtggaagat attaagcaaa   1080

atgtttaaag acacaacgga atagacccaa aaagataatt tctatctgat ttgctttaaa   1140

acgttttttt aggatcacaa tgatatcttt gctgtatttg tatagttaga tgctaaatgc   1200

tcattgaaac aatcagctaa tttatgtata gattttccag ctctcaagtt gccatgggcc   1260

ttcatgctat ttaaatattt aagtaattta tgtatttatt agtatattac tgttatttaa   1320

cgtttgtctg ccaggatgta tggaatgttt catactctta tgacctgatc catcaggatc   1380

agtccctatt atgcaaaatg tgaatttaat tttatttgta ctgacaactt ttcaagcaag   1440

gctgcaagta catcagtttt atgacaatca ggaagaatgc agtgttctga taccagtgcc   1500

atcatacact tgtgatggat gggaacgcaa gagatactta catggaaacc tgacaatgca   1560

aacctgttga gaagatccag gagaacaaga tgctagttcc catgtctgtg aagacttcct   1620

ggagatggtg ttgataaagc aatttagggc cacttacact tctaagcaag tttaatcttt   1680

ggatgcctga attttaaaag ggctagaaaa aaatgattga ccagcctggg aaacataaca   1740

agaccccgtc tctacaaaaa aaatttaaaa ttagccaggc gtggtggctc atgcttgtgg   1800

tcccagctgt tcaggaggat gaggcaggag gatctcttga gcccaggagg tcaaggctat   1860

ggtgagccgt gattgtgcca ctgcatacca gcctaggtga cagaatgaga ccctgtctca   1920

aaaaaaaaaa tgattgaaat taaaattcag ctttagcttc catggcagtc ctcacccca   1980
```

```
cctctctaaa agacacagga ggatgacaca gaaacaccgt aagtgtctgg aaggcaaaaa   2040

gatcttaaga ttcaagagag aggacaagta gttatggcta aggacatgaa attgtcagaa   2100

tggcaggtgg cttcttaaca gccctgtgag aagcagacag atgcaaagaa aatctggaat   2160

ccctttctca ttagcatgaa tgaacctgat acacaattat gaccagaaaa tatggctcca   2220

tgaaggtgct acttttaagt aatgtatgtg cgctctgtaa agtgattaca tttgtttcct   2280

gtttgtttat ttatttattt atttttgcat tctgaggctg aactaataaa aactcttctt   2340

tgtaatc                                                             2347
```

<210> SEQ ID NO 7
<211> LENGTH: 1281
<212> TYPE: DNA
<213> ORGANISM: Murine sp.

<400> SEQUENCE: 7

```
tgccacctac tcccttggat ctgagctgga cccttgcatc tggcgtctac actgctgctg     60

aaatcttctc accgtgcaca tccaaggata tctctatggt cagcgttcca acagcctcac    120

cctcggcatc cagcagctcc tctcagtgcc ggtccagcat gtgtcaatca cgctacctcc    180

tctttttggc cacccttgcc ctcctaaacc acctcagttt ggccagggtc attccagtct    240

ctggacctgc caggtgtctt agccagtccc gaaacctgct gaagaccaca gatgacatgg    300

tgaagacggc cagagaaaaa ctgaaacatt attcctgcac tgctgaagac atcgatcatg    360

aagacatcac acgggaccaa accagcacat tgaagacctg tttaccactg gaactacaca    420

agaacgagag ttgcctggct actagagaga cttcttccac aacaagaggg agctgcctgc    480

ccccacagaa gacgtctttg atgatgaccc tgtgccttgg tagcatctat gaggacttga    540

agatgtacca gacagagttc caggccatca acgcagcact tcagaatcac aaccatcagc    600

agatcattct agacaagggc atgctggtgg ccatcgatga gctgatgcag tctctgaatc    660

ataatggcga gactctgcgc cagaaacctc ctgtgggaga agcagaccct tacagagtga    720

aaatgaagct ctgcatcctg cttcacgcct tcagcacccg cgtcgtgacc atcaacaggg    780

tgatgggcta tctgagctcc gcctgaaagg ctcaaggccc tctgccacag cgccctcctc    840

acacagatag gaaacaaaga aagattcata agagtcaggt ggtcttggcc tggtgggcct    900

taagctcctt caggaatctg ttctcccatc acatctcatc tccccaaagg tggcacagct    960

acctcagcat ggtcccctcc atcgcttctc tcatattcac tatacaagtt gtttgtaagt   1020

tttcatcaaa atattgttaa ggggcgaaga cgtcctcccc tcaatgtgtt agcagaagag   1080

caagaactga taagctattg tttttgtgcc aaagtgttta tgaaaacact cagtcacccc   1140

ttatttaaaa atatttattg ctatatttta tactcatgaa agtacatgag cctatttata   1200

tttatttatt ttctatttat tataatattt cttatcagat gaatttgaaa catttttgaaa  1260

cataccttat tttgtggttc t                                             1281
```

<210> SEQ ID NO 8
<211> LENGTH: 1951
<212> TYPE: DNA
<213> ORGANISM: Murine sp.

<400> SEQUENCE: 8

```
agaaggaaca gtgggtgtcc aggcacatca gaccaggcag ctcgcagcaa agcaaggtaa     60

gttctctcct cttccctgtc gctaactccc tgcatctaga ggctgtccag attcagactc    120

caggggacag gctacccctg aaccaggcag cgtgggagtg ggatgtgtcc tcagaagcta    180
```

```
accatctcct ggtttgccat cgttttgctg gtgtctccac tcatggccat gtgggagctg    240
gagaaagacg tttatgttgt agaggtggac tggactcccg atgcccctgg agaaacagtg    300
aacctcacct gtgacacgcc tgaagaagat gacatcacct ggacctcaga ccagagacat    360
ggagtcatag gctctggaaa gaccctgacc atcactgtca aagagtttct agatgctggc    420
cagtacacct gccacaaagg aggcgagact ctgagccact cacatctgct gctccacaag    480
aaggaaaatg gaatttggtc cactgaaatt ttaaaaaatt tcaaaaacaa gactttcctg    540
aagtgtgaag caccaaatta ctccggacgg ttcacgtgct catggctggt gcaaagaaac    600
atggacttga agttcaacat caagagcagt agcagttccc ctgactctcg ggcagtgaca    660
tgtggaatgg cgtctctgtc tgcagagaag gtcacactgg accaaaggga ctatgagaag    720
tattcagtgt cctgccagga ggatgtcacc tgcccaactg ccgaggagac cctgcccatt    780
gaactggcgt tggaagcacg gcagcagaat aaatatgaga actacagcac cagcttcttc    840
atcagggaca tcatcaaacc agacccgccc aagaacttgc agatgaagcc tttgaagaac    900
tcacaggtgg aggtcagctg ggagtaccct gactcctgga gcactcccca ttcctacttc    960
tccctcaagt tctttgttcg aatccagcgc aagaaagaaa agatgaagga gacagaggag   1020
gggtgtaacc agaaaggtgc gttcctcgta gagaagacat ctaccgaagt ccaatgcaaa   1080
ggcgggaatg tctgcgtgca agctcaggat cgctattaca attcctcatg cagcaagtgg   1140
gcatgtgttc cctgcagggt ccgatcctag gatgcaacgt tggaaaggaa agaaaagtgg   1200
aagacattaa ggaagaaaaa tttaaactca ggatggaaga gtcccccaaa agctgtcttc   1260
tgcttggttg gctttttcca gttttcctaa gttcatcatg acacctttgc tgatttctac   1320
atgtaaatgt taaatgcccg cagagccagg gagctaatgt atgcatagat attctagcat   1380
tccacttggc cttatgctgt tgaaatattt aagtaattta tgtatttatt aatttatttc   1440
tgcatttcac atttgtatac caagatgtat tgaatatttc atgtgctcgt ggcctgatcc   1500
actgggacca ggccctatta tgcaaattgt gagcttgtta tcttcttcaa cagctcttca   1560
atcagggctg cgtaggtaca ttagcttttg tgacaaccaa taagaacata atattctgac   1620
acaagcagtg ttacatattt gtgaccagta aagacatagg tggtatttgg agacatgaag   1680
aagctgtaaa gttgactctg aagagtttag cactagtttc aacaccaaga aagacttttt   1740
agaagtgata ttgataagaa accagggcct tctttagaag ggtacctaaa tttaaaagaa   1800
ttttgaaagg ctgggtatcg gtggtatatg cttttaattc cagcactcag gagaccaagg   1860
caggcagatc tctgtgagtt tgaggacagc ctggtgtaca gagggagttc cagcacagcc   1920
agtgccacac agaaattctg tctcaaaaac a                                  1951
```

<210> SEQ ID NO 9
<211> LENGTH: 1147
<212> TYPE: DNA
<213> ORGANISM: Homo sapiens

<400> SEQUENCE: 9

```
cgaccaggtt ctccttcccc agtcaccagt tgctcgagtt agaattgtct gcaatggccg     60
ccctgcagaa atctgtgagc tctttcctta tggggaccct ggccaccagc tgcctccttc    120
tcttggccct cttggtacag ggaggagcag ctgcgcccat cagctcccac tgcaggcttg    180
acaagtccaa cttccagcag ccctatatca ccaaccgcac cttcatgctg gctaaggagg    240
ctagcttggc tgataacaac acagacgttc gtctcattgg ggagaaactg ttccacggag    300
```

```
tcagtatgag tgagcgctgc tatctgatga agcaggtgct gaacttcacc cttgaagaag    360

tgctgttccc tcaatctgat aggttccagc cttatatgca ggaggtggtg cccttcctgg    420

ccaggctcag caacaggcta agcacatgtc atattgaagg tgatgacctg catatccaga    480

ggaatgtgca aaagctgaag gacacagtga aaaagcttgg agagagtgga gagatcaaag    540

caattggaga actggatttg ctgtttatgt ctctgagaaa tgcctgcatt tgaccagagc    600

aaagctgaaa aatgaataac taaccccctt tccctgctag aaataacaat tagatgcccc    660

aaagcgattt tttttaacca aaaggaagat gggaagccaa actccatcat gatgggtgga    720

ttccaaatga acccctgcgt tagttacaaa ggaaaccaat gccacttttg tttataagac    780

cagaaggtag actttctaag catagatatt tattgataac atttcattgt aactggtgtt    840

ctatacacag aaaacaattt attttttaaa taattgtctt tttccataaa aaagattact    900

ttccattcct ttaggggaaa aaacccctaa atagcttcat gtttccataa tcagtacttt    960

atatttataa atgtatttat tattattata agactgcatt ttatttatat cattttatta   1020

atatggattt atttatagaa acatcattcg atattgctac ttgagtgtaa ggctaatatt   1080

gatatttatg acaataatta tagagctata acatgtttat ttgacctcaa taaacacttg   1140

gatatcc                                                             1147
```

<210> SEQ ID NO 10
<211> LENGTH: 1121
<212> TYPE: DNA
<213> ORGANISM: Murine sp.

<400> SEQUENCE: 10

```
cctaaacagg ctctcctctc acttatcaac tgttgacact tgtgcgatct ctgatggctg     60

tcctgcagaa atctatgagt tttccctta tggggacttt ggccgccagc tgcctgcttc    120

tcattgccct gtgggcccag gaggcaaatg cgctgcccgt caacacccgg tgcaagcttg    180

aggtgtccaa cttccagcag ccgtacatcg tcaaccgcac ctttatgctg gccaaggagg    240

ccagccttgc agataacaac acagacgtcc ggctcatcgg ggagaaactg ttccgaggag    300

tcagtgctaa agatcagtgc tacctgatga agcaggtgct caacttcacc ctggaagacg    360

ttctgctccc ccagtcagac aggttccagc cctacatgca ggaggtggta cctttcctga    420

ccaaactcag caatcagctc agctcctgtc acatcagcgg tgacgaccag aacatccaga    480

agaatgtcag aaggctgaag gagacagtga aaaagcttgg agagagtgga gagatcaagg    540

cgattgggga actggacctg ctgtttatgt ctctgagaaa tgcttgcgtc tgagcgagaa    600

gaagctagaa aacgaagaac tgctccttcc tgccttctaa aaagaacaat aagatccctg    660

aatggacttt tttactaaag gaaagtgaga agctaacgtc catcatcatt agaagatttc    720

acatgaaacc tggctcagtt gaaaaagaaa atagtgtcaa gttgtccatg agaccagagg    780

tagacttgat aaccacaaag attcattgac aatattttat tgtcactgat gatacaacag    840

aaaaataatg tactttaaaa aattgtttga aaggaggtta cctctcattc ctttagaaaa    900

aaagcttatg taacttcatt tccatatcca atattttata tatgtaagtt tatttattat    960

aagtatacat tttatttatg tcagtttatt aatatggatt tatttataga aacattatct   1020

gctattgata tttagtataa ggcaaataat atttatgaca ataactatgg aaacaagata   1080

tcttaggctt taataaacac atggatatca taaaaaaaaa a                       1121
```

<210> SEQ ID NO 11
<211> LENGTH: 1049

<212> TYPE: DNA
<213> ORGANISM: Homo sapiens

<400> SEQUENCE: 11

```
aaaacaacag gaagcagctt acaaactcgg tgaacaactg agggaaccaa accagagacg     60
cgctgaacag agagaatcag gctcaaagca agtggaagtg ggcagagatt ccaccaggac    120
tggtgcaagg cgcagagcca gccagatttg agaagaaggc aaaaagatgc tggggagcag    180
agctgtaatg ctgctgttgc tgctgccctg gacagctcag ggcagagctg tgcctggggg    240
cagcagccct gcctggactc agtgccagca gctttcacag aagctctgca cactggcctg    300
gagtgcacat ccactagtgg gacacatgga tctaagagaa gagggagatg aagagactac    360
aaatgatgtt ccccatatcc agtgtggaga tggctgtgac ccccaaggac tcagggacaa    420
cagtcagttc tgcttgcaaa ggatccacca gggtctgatt ttttatgaga agctgctagg    480
atcggatatt ttcacagggg agccttctct gctccctgat agccctgtgg gccagcttca    540
tgcctcccta ctgggcctca gccaactcct gcagcctgag ggtcaccact gggagactca    600
gcagattcca agcctcagtc ccagccagcc atggcagcgt ctccttctcc gcttcaaaat    660
ccttcgcagc ctccaggcct ttgtggctgt agccgcccgg gtctttgccc atggagcagc    720
aaccctgagt ccctaaaggc agcagctcaa ggatggcact cagatctcca tggcccagca    780
aggccaagat aaatctacca ccccaggcac ctgtgagcca acaggttaat tagtccatta    840
attttagtgg gacctgcata tgttgaaaat taccaatact gactgacatg tgatgctgac    900
ctatgataag gttgagtatt tattagatgg gaagggaaat ttggggatta tttatcctcc    960
tggggacagt ttggggagga ttatttattg tatttatatt gaattatgta ctttttttcaa   1020
taaagtctta tttttgtggc taaaaaaaa                                    1049
```

<210> SEQ ID NO 12
<211> LENGTH: 1359
<212> TYPE: DNA
<213> ORGANISM: Murine sp.

<400> SEQUENCE: 12

```
cgcttagaag tcggactaca gagttagact cagaaccaaa ggaggtggat agggggtcca     60
caggcctggt gcagatcaca gagccagcca gatctgagaa gcagggaaca agatgctgga    120
ttgcagagca gtaataatgc tatggctgtt gccctgggtc actcagggcc tggctgtgcc    180
taggagtagc agtcctgact gggctcagtg ccagcagctc tctcggaatc tctgcatgct    240
agcctggaac gcacatgcac cagcgggaca tatgaatcta ctaagagaag aagaggatga    300
agagactaaa aataatgtgc cccgtatcca gtgtgaagat ggttgtgacc cacaaggact    360
caaggacaac agccagttct gcttgcaaag gatccgccaa ggtctggctt tttataagca    420
cctgcttgac tctgacatct tcaaagggga gcctgctcta ctccctgata gccccatgga    480
gcaacttcac acctccctac taggactcag ccaactcctc cagccagagg atcacccccg    540
ggagacccaa cagatgccca gcctgagttc tagtcagcag tggcagcgcc cccttctccg    600
ttccaagatc cttcgaagcc tccaggcctt tttggccata gctgcccggg tctttgccca    660
cggagcagca actctgactg agcccttagt gccaacagct taaggatgcc caggttccca    720
tggctaccat gataagacta atctatcagc ccagacatct accagttaat taacccatta    780
ggacttgtgc tgttcttgtt ttgtttgttt tgcgtgaagg gcaaggacac cattattaaa    840
gagaaaagaa acaaacccca gagcaggcag ctggctagag aaaggagctg gagaagaaga    900
```

```
ataaagtctc gagcccttgg ccttggaagc gggcaagcag ctgcgtggcc tgaggggaag     960

ggggcggtgg catcgagaaa ctgtgagaaa acccagagca tcagaaaaag tgagcccagg    1020

ctttggccat tatctgtaag aaaaacaaga aaaggggaac attatacttt cctgggtggc    1080

tcagggaaat gtgcagatgc acagtactcc agacagcagc tctgtacctg cctgctctgt    1140

ccctcagttc taacagaatc tagtcactaa gaactaacag gactaccaat acgaactgac    1200

aaatactacc actatgacct gtgacaaagc tgcatattta ttaagtggga agggaacttt    1260

tgatattatt tatccttgta acagtataga tgatggttat ttattctatt tataaggaat    1320

tatgtatttt ttttttcaat aaagatttat ttatgtggc                           1359
```

<210> SEQ ID NO 13
<211> LENGTH: 2346
<212> TYPE: DNA
<213> ORGANISM: Homo sapiens

<400> SEQUENCE: 13

```
ccttcgcgcc ctgggccatc tccctcccac ctccctccgc ggagcagcca gacagcgagg      60

gccccggccg ggggcagggg ggacgccccg tccggggcac ccccccggct ctgagccgcc     120

cgcggggccg gcctcggccc ggagcggagg aaggagtcgc cgaggagcag cctgaggccc     180

cagagtctga gacgagccgc cgccgccccc gccactgcgg ggaggagggg gaggaggagc     240

gggaggaggg acgagctggt cgggagaaga ggaaaaaaac ttttgagact tttccgttgc     300

cgctgggagc cggaggcgcg gggacctctt ggcgcgacgc tgccccgcga ggaggcagga     360

cttggggacc ccagaccgcc tccctttgcc gccggggacg cttgctccct ccctgccccc     420

tacacggcgt ccctcaggcg cccccattcc ggaccagccc tcgggagtcg ccgacccggc     480

ctcccgcaaa gacttttccc cagacctcgg gcgcaccccc tgcacgccgc cttcatcccc     540

ggcctgtctc ctgagccccc gcgcatccta gaccctttct cctccaggag acggatctct     600

ctccgacctg ccacagatcc cctattcaag accacccacc ttctggtacc agatcgcgcc     660

catctaggtt atttccgtgg gatactgaga cacccccggt ccaagcctcc cctccaccac     720

tgcgcccttc tccctgagga cctcagcttt ccctcgaggc cctcctacct tttgccggga     780

gacccccagc ccctgcaggg gcggggcctc cccaccacac cagccctgtt cgcgctctcg     840

gcagtgccgg ggggcgccgc ctcccccatg ccgccctccg ggctgcggct gctgccgctg     900

ctgctaccgc tgctgtggct actggtgctg acgcctggcc ggccggccgc gggactatcc     960

acctgcaaga ctatcgacat ggagctggtg aagcggaagc gcatcgaggc catccgcggc    1020

cagatcctgt ccaagctgcg gctcgccagc cccccgagcc agggggaggt gccgcccggc    1080

ccgctgcccg aggccgtgct cgccctgtac aacagcaccc gcgaccgggt ggccggggag    1140

agtgcagaac cggagcccga gcctgaggcc gactactacg ccaaggaggt cacccgcgtg    1200

ctaatggtgg aaacccacaa cgaaatctat gacaagttca agcagagtac acacagcata    1260

tatatgttct tcaacacatc agagctccga gaagcggtac ctgaacccgt gttgctctcc    1320

cgggcagagc tgcgtctgct gaggctcaag ttaaaagtgg agcagcacgt ggagctgtac    1380

cagaaataca gcaacaattc ctggcgatac ctcagcaacc ggctgctggc acccagcgac    1440

tcgccagagt ggttatcttt tgatgtcacc ggagttgtgc ggcagtggtt gagccgtgga    1500

ggggaaattg agggctttcg ccttagcgcc cactgctcct gtgacagcag ggataacaca    1560

ctgcaagtgg acatcaacgg gttcactacc ggccgccgag gtgacctggc caccattcat    1620

ggcatgaacc ggcctttcct gcttctcatg gccaccccgc tggagagggc ccagcatctg    1680
```

```
caaagctccc ggcaccgccg agccctggac accaactatt gcttcagctc cacggagaag   1740
aactgctgcg tgcggcagct gtacattgac ttccgcaagg acctcggctg gaagtggatc   1800
cacgagccca agggctacca tgccaacttc tgcctcgggc cctgccccta catttggagc   1860
ctggacacgc agtacagcaa ggtcctggcc ctgtacaacc agcataaccc gggcgcctcg   1920
gcggcgccgt gctgcgtgcc gcaggcgctg gagccgctgc ccatcgtgta ctacgtgggc   1980
cgcaagccca aggtggagca gctgtccaac atgatcgtgc gctcctgcaa gtgcagctga   2040
ggtcccgccc cgccccgccc cgccccggca ggcccggccc caccccgccc cgccccccgct   2100
gccttgccca tgggggctgt atttaaggac acccgtgccc caagcccacc tggggcccca   2160
ttaaagatgg agagaggact gcggatctct gtgtcattgg gcgcctgcct ggggtctcca   2220
tccctgacgt tcccccactc ccactccctc tctctccctc tctgcctcct cctgcctgtc   2280
tgcactattc ctttgcccgg catcaaggca caggggacca gtggggaaca ctactgtagt   2340
tagatc                                                              2346
```

<210> SEQ ID NO 14
<211> LENGTH: 2094
<212> TYPE: DNA
<213> ORGANISM: Murine sp.

<400> SEQUENCE: 14

```
cgccgccgcc gccgcccttc gcgccccagg ccgtccccct cctcctcccg ccgcggatcc     60
tccagacagc caggcccccg gccggggcag gggggacgcc ccttcggggc acccccggct    120
ctgagccgca ctcggagtcg gcctccgctg ggagccggca aaggagcagc cgaggagccg    180
tccgaggccc cagagtctga gaccagccgc cgccgcaggg aggaggggga ggaggagtgg    240
gaggagggac gagctggttg agagaagagg aaaaaagttt tgagactttt ccgctgctac    300
tgcaagtcag agacgtgggg acttcttggc actgcgctgt ctcgcaagga ggcaggacct    360
gaggactcca gacagccctg ctcaccgtcg tggacactcg atcgctaccc ggcgttcctc    420
agacgcccct attccggacc agccctcggg agccacaaac ccgcctcccc gcgaagactt    480
caccccaaag ctggggcgca ccccttgcac gccgccctcc ccccagcctg cctcttgagt    540
ccctcgcatc ccaggaccct ctctcccccg agaggcagat ctccctcgga cctgctggca    600
gtagctcccc tatttaagaa cacccacttt tggatctcag agagcgctca tctcgatttt    660
taccctggtg gtatactgag acaccttggt gtcagagcct caccgcgact cctgctgctt    720
tctccctcaa cctcaaatta ttcaggacta tcacctacct ttccttggga gaccccaccc    780
cacaagccct gcaggggcgg ggcctccgca tcccaccttt gccgagggtt cccgctctcc    840
gaagtgccgt ggggcgccgc ctcccccatg ccgccctcgg ggctgcggct actgccgctt    900
ctgctcccac tcccgtggct tctagtgctg acgcccggga ggccagccgc gggactctcc    960
acctgcaaga ccatcgacat ggagctggtg aaacggaagc gcatcgaagc catccgtggc   1020
cagatcctgt ccaaactaag gctcgccagt cccccaagcc agggggaggt accgcccggc   1080
ccgctgcccg aggcggtgct cgctttgtac aacagcaccc gcgaccgggt ggcaggcgag   1140
agcgccgacc cagagccgga gcccgaagcg gactactatg ctaaagaggt cacccgcgtg   1200
ctaatggtgg accgcaacaa cgccatctat gagaaaacca aagacatctc acacagtata   1260
tatatgttct tcaatacgtc agacattcgg gaagcagtgc ccgaaccccc attgctgtcc   1320
cgtgcagagc tgcgcttgca gagattaaaa tcaagtgtgg agcaacatgt ggaactctac   1380
```

```
cagaaatata gcaacaattc ctggcgttac cttggtaacc ggctgctgac ccccactgat   1440
acgcctgagt ggctgtcttt tgacgtcact ggagttgtac ggcagtggct gaaccaagga   1500
gacggaatac agggctttcg attcagcgct cactgctctt gtgacagcaa agataacaaa   1560
ctccacgtgg aaatcaacgg gatcagcccc aaacgtcggg gcgacctggg caccatccat   1620
gacatgaacc ggcccttcct gctcctcatg gccacccccc tggaaagggc ccagcacctg   1680
cacagctcac ggcaccggag agccctggat accaactatt gcttcagctc cacagagaag   1740
aactgctgtg tgcggcagct gtacattgac tttaggaagg acctgggttg gaagtggatc   1800
cacgagccca agggctacca tgccaacttc tgtctgggac cctgccccta tatttggagc   1860
ctggacacac agtacagcaa ggtccttgcc ctctacaacc aacacaaccc gggcgcttcg   1920
gcgtcaccgt gctgcgtgcc gcaggctttg gagccactgc ccatcgtcta ctacgtgggt   1980
cgcaagccca aggtggagca gttgtccaac atgattgtgc gctcctgcaa gtgcagctga   2040
agccccgccc cgccccgccc ctcccggcag gcccggcccc gcccccgccc cgcc         2094
```

<210> SEQ ID NO 15
<211> LENGTH: 2397
<212> TYPE: DNA
<213> ORGANISM: Homo sapiens

<400> SEQUENCE: 15

```
gcacacactc atcgaaaaaa atttggatta ttagaagaga gaggtctgcg gcttccacac     60
cgtacagcgt ggtttttctt ctcggtataa aagcaaagtt gtttttgata cgtgacagtt    120
tcccacaagc caggctgatc cttttctgtc agtccacttc accaagcctg cccttggaca    180
aggacccgat gcccaacccc aggcctggca agccctcggc cccttccttg gcccttggcc    240
catccccagg agcctcgccc agctggaggg ctgcacccaa agcctcagac ctgctggggg    300
cccggggccc agggggaacc ttccagggcc gagatcttcg aggcggggcc catgcctcct    360
cttcttcctt gaaccccatg ccaccatcgc agctgcagct gcccacactg cccctagtca    420
tggtggcacc ctccggggca cggctgggcc ccttgcccca cttacaggca ctcctccagg    480
acaggccaca tttcatgcac cagctctcaa cggtggatgc ccacgcccgg acccctgtgc    540
tgcaggtgca ccccctggag agcccagcca tgatcagcct cacaccaccc accaccgcca    600
ctggggtctt ctccctcaag gcccggcctg gcctcccacc tgggatcaac gtggccagcc    660
tggaatgggt gtccagggag ccggcactgc tctgcacctt cccaaatccc agtgcaccca    720
ggaaggacag caccctttcg gctgtgcccc agagctccta cccactgctg gcaaatggtg    780
tctgcaagtg gcccggatgt gagaaggtct tcgaagagcc agaggacttc ctcaagcact    840
gccaggcgga ccatcttctg gatgagaagg gcagggcaca atgtctcctc cagagagaga    900
tggtacagtc tctggagcag cagctggtgc tggagaagga gaagctgagt gccatgcagg    960
cccacctggc tgggaaaatg gcactgacca aggcttcatc tgtggcatca tccgacaagg   1020
gctcctgctg catcgtagct gctggcagcc aaggccctgt cgtcccagcc tggtctggcc   1080
cccgggaggc ccctgacagc ctgtttgctg tccggaggca cctgtggggt agccatggaa   1140
acagcacatt cccagagttc ctccacaaca tggactactt caagttccac aacatgcgac   1200
cccctttcac ctacgccacg ctcatccgct gggccatcct ggaggctcca gagaagcagc   1260
ggacactcaa tgagatctac cactggttca cacgcatgtt tgccttcttc agaaaccatc   1320
ctgccacctg gaagaacgcc atccgccaca acctgagtct gcacaagtgc tttgtgcggg   1380
tggagagcga gaagggggct gtgtggaccg tggatgagct ggagttccgc aagaaacgga   1440
```

```
gccagaggcc cagcaggtgt tccaacccta cacctggccc ctgacctcaa gatcaaggaa   1500

aggaggatgg acgaacaggg gccaaactgg tgggaggcag aggtggtggg ggcagggatg   1560

ataggccctg gatgtgccca cagggaccaa gaagtgaggt ttccactgtc ttgcctgcca   1620

gggcccctgt tcccccgctg gcagccaccc cctcccccat catatccttt gccccaaggc   1680

tgctcagagg ggcccccggtc ctggccccag cccccacctc cgccccagac acaccccccca   1740

gtcgagccct gcagccaaac agagccttca caaccagcca cacagagcct gcctcagctg   1800

ctcgcacaga ttacttcagg gctggaaaag tcacacagac acacaaaatg tcacaatcct   1860

gtccctcact caacacaaac cccaaaacac agagagcctg cctcagtaca ctcaaacaac   1920

ctcaaagctg catcatcaca caatcacaca caagcacagc cctgacaacc cacacacccc   1980

aaggcacgca cccacagcca gcctcagggc ccacaggggc actgtcaaca caggggtgtg   2040

cccagaggcc tacacagaag cagcgtcagt accctcagga tctgaggtcc caacacgtgc   2100

tcgctcacac acacggcctg ttagaattca cctgtgtatc tcacgcatat gcacacgcac   2160

agccccccag tgggtctctt gagtcccgtg cagacacaca cagccacaca cactgccttg   2220

ccaaaaatac cccgtgtctc ccctgccact cacctcactc ccattccctg agccctgatc   2280

catgcctcag cttagactgc agaggaacta ctcatttatt tgggatccaa ggcccccaac   2340

ccacagtacc gtccccaata aactgcagcc gagctcccca caaaaaaaaa aaaaaaa      2397
```

<210> SEQ ID NO 16
<211> LENGTH: 3739
<212> TYPE: DNA
<213> ORGANISM: Murine sp.

<400> SEQUENCE: 16

```
gctgatcccc ctctagcagt ccacttcacc aaggtgagcg agtgtccctg ctctccccca     60

ccagacacag ctctgctggc gaaagtggca gagaggtatt gagggtgggt gtcaggagcc    120

caccagtaca gctggaaaca cccagccact ccagctcccg gcaacttctc ctgactctgc    180

cttcagacga gacttggaag acagtcacat ctcagcagct cctctgccgt tatccagcct    240

gcctctgaca agaacccaat gcccaaccct aggccagcca agcctatggc tccttccttg    300

gcccttggcc catccccagg agtcttgcca agctggaaga ctgcacccaa gggctcagaa    360

cttctaggga ccaggggctc tgggggaccc ttccaaggtc gggacctgcg aagtggggcc    420

cacacctctt cttccttgaa ccccctgcca ccatcccagc tgcagctgcc tacagtgccc    480

ctagtcatgg tggcaccgtc tggggcccga ctaggtccct caccccacct acaggccctt    540

ctccaggaca gaccacactt catgcatcag ctctccactg tggatgccca tgcccagacc    600

cctgtgctcc aagtgcgtcc actggacaac ccagccatga tcagcctccc accaccttct    660

gctgccactg ggtcttctc cctcaaggcc cggcctggcc tgccacctgg gatcaatgtg    720

gccagtctgg aatgggtgtc cagggagcca gctctactct gcaccttccc acgctcgggt    780

acacccagga aagacagcaa ccttttggct gcaccccaag gatcctaccc actgctggca    840

aatggagtct gcaagtggcc tggttgtgag aaggtcttcg aggagccaga agagtttctc    900

aagcactgcc aagcagatca tctcctggat gagaaaggca aggcccagtg cctcctccag    960

agagaagtgg tgcagtctct ggagcagcag ctggagctgg aaaaggagaa gctgggagct   1020

atgcaggccc acctggctgg gaagatggcg ctggccaagg ctccatctgt ggcctcaatg   1080

gacaagagct cttgctgcat cgtagccacc agtactcagg gcagtgtgct cccggcctgg   1140
```

-continued

```
tctgctcctc gggaggctcc agacggcggc ctgtttgcag tgcggaggca cctctgggga   1200
agccatggca atagttcctt cccagagttc ttccacaaca tggactactt caagtaccac   1260
aatatgcgac ccccttcac ctatgccacc cttatccgat gggccatcct ggaagccccg   1320
gagaggcaga ggacactcaa tgaaatctac cattggttta ctcgcatgtt cgcctacttc   1380
agaaaccacc ccgccacctg gaagaatgcc atccgccaca acctgagcct gcacaagtgc   1440
tttgtgcgag tggagagcga gaagggagca gtgtggaccg tagatgaatt tgagtttcgc   1500
aagaagagga gccaacgccc caacaagtgc tccaatccct gcccttgacc tcaaaaccaa   1560
gaaaaggtgg gcgggggagg gggccaaaac catgagactg aggctgtggg ggcaaggagg   1620
caagtcctac gtgtacctat ggaaaccggg cgatgatgtg cctgctatca gggcctctgc   1680
tccctatcta gctgccctcc tagatcatat catctgcctt acagctgaga ggggtgccaa   1740
tcccagccta gcccctagtt ccaacctagc cccaagatga actttccagt caaagagccc   1800
tcacaaccag ctatacatat ctgccttggc cactgccaag cagaaagatg acagacacca   1860
tcctaatatt tactcaaccc aaaccctaaa acatgaagag cctgccttgg tacattcgtg   1920
aactttcaaa gttagtcatg cagtcacaca tgactgcagt cctactgact cacaccccaa   1980
agcactcacc cacaacatct ggaaccacgg gcactatcac acataggtgt atatacagac   2040
ccttacacag caacagcact ggaaccttca caattacatc cccccaaacc acacaggcat   2100
aactgatcat acgcagcctc aagcaatgcc caaaatacaa gtcagacaca gcttgtcaga   2160
acacgctcgt gtgcacgtac acacatgcag cccctccact ctatctcctg agttccatga   2220
atacacaccg actctccaag atgtacccca cgtctcactt gccactgacc ccagttccct   2280
acccacaagc cccaatccat gcctaagcgt ggcccacaga agaacttctc ttttatttgg   2340
gatccaaggc ccctggcccc cagtgcccat ccaataaact gtggtcagct ggacaatcac   2400
cctgatcaga tatgggaaca tataagcaga cagctgggtt taagatccca gcaggagaaa   2460
gcggatacca aatgaaagag agtgctagaa caggtgcctc agcactgtct ccagcacccc   2520
aaattcctgc ctgtggttag gagacatcca tcagggctct aggcctctcg gacccggccc   2580
aagaggccag cattctcctg gcgaagggct cggtagtcct cacagatctt ctccaggttg   2640
ctcaaagtct tcttgcccat ctctgtctca atctaagaaa acaggatgca cacttcttca   2700
gcccctgcag gctgcccctc tactgaactc ctccctgctc ctcctattcc cgtaacagca   2760
gcctgttcct tcccatcact gggcttctgg gtatgtcctt ccctccactc cacctaaagc   2820
agcaacttct gccatgggct ctgggaggca ttaggagccg caagctaaaa gccagggctc   2880
agagtaggct actggctagc ttcaggtccc aggcacagtg ggcacgaagg caaagcctct   2940
agctgttagt tgtctggttt caaagactct cagcgcaaaa caaggaacta tcccctggcc   3000
tgtctccatt cccttacca gtcccaggtc tcacctgctc ctcaagatct cgaacttccc   3060
tcatgatagt gcctgtgtcc tcaatggtct ggatgagctg actgcaattc tggagacagc   3120
aagaatacaa ggcttgcacc tatgctggcc ctctccagcc aacccaccag gcacatggct   3180
cccctcacct catgcagggc agctaggtac ttgtaggctt tccgaacagc atcatccttc   3240
ttagcatcct gataagacaa aggggatctc cgagatatca gcaagccatt ccccctttc   3300
cactactcta tgcccctata agaccaccct ttactagtac tttgccttca tcctccacag   3360
agcaaagcta ggccccaagc aacagtgcac ctaaaggact cacagagggg caggcaacaa   3420
ctcagtcccg cctccaccct cccggaggcc agcctgctcc ataccttgaa cacaagctca   3480
tcagtcactg caaatgtccg gtcgagcttc ccagagagag agttgatttc cttctgcagt   3540
```

```
tcctttgtgt ccgacaagat ctggtagaaa ccagggtaac tatcagtgca catcttgggc   3600

aaggtagctg atcagtgata acactcacgt gcctatactt acatccagtc agggcccatg   3660

tcgctgtgtt ggggtgacta ttatgtgttg gagtgtgcct gaacagctct gcctagtagt   3720

gagcataaag tccctgtgt                                                3739


<210> SEQ ID NO 17
<211> LENGTH: 2011
<212> TYPE: DNA
<213> ORGANISM: Homo sapiens

<400> SEQUENCE: 17

ggaaaaggga aggaggagac tgagtgatta agtcacccac tgtgagagct ggtcttctat     60

ttaatggggg ctctctctgc ccaggagtca gaggtgcctc caggagcagc aggagcatgg    120

ccgaggatct gggactgagc tttggggaaa cagccagtgt ggaaatgctg ccagagcacg    180

gcagctgcag gcccaaggcc aggagcagca gcgcacgctg ggctctcacc tgctgcctgg    240

tgttgctccc cttccttgca ggactcacca catacctgct tgtcagccag ctccgggccc    300

agggagaggc ctgtgtgcag ttccaggctc taaaaggaca ggagtttgca ccttcacatc    360

agcaagttta tgcacctctt agagcagacg gagataagcc aagggcacac ctgacagttg    420

tgagacaaac tcccacacag cactttaaaa atcagttccc agctctgcac tgggaacatg    480

aactaggcct ggccttcacc aagaaccgaa tgaactatac caacaaattc ctgctgatcc    540

cagagtcggg agactacttc atttactccc aggtcacatt ccgtgggatg acctctgagt    600

gcagtgaaat cagacaagca ggccgaccaa acaagccaga ctccatcact gtggtcatca    660

ccaaggtaac agacagctac cctgagccaa cccagctcct catggggacc aagtctgtat    720

gcgaagtagg tagcaactgg ttccagccca tctacctcgg agccatgttc tccttgcaag    780

aaggggacaa gctaatggtg aacgtcagtg acatctcttt ggtggattac acaaaagaag    840

ataaaacctt ctttggagcc ttcttactat aggaggagag caaatatcat tatatgaaag    900

tcctctgcca ccgagttcct aattttcttt gttcaaatgt aattataacc aggggttttc    960

ttggggccgg gagtaggggg cattccacag ggacaacggt ttagctatga aatttggggc   1020

ccaaaatttc acacttcatg tgccttactg atgagagtac taactggaaa aaggctgaag   1080

agagcaaata tattattaag atgggttgga ggattggcga gtttctaaat attaagacac   1140

tgatcactaa atgaatggat gatctactcg ggtcaggatt gaaagagaaa tatttcaaca   1200

ccttcctgct atacaatggt caccagtggt ccagttattg ttcaatttga tcataaattt   1260

gcttcaattc aggagctttg aaggaagtcc aaggaaagct ctagaaaaca gtataaactt   1320

tcagaggcaa aatccttcac caatttttcc acatactttc atgccttgcc taaaaaaaat   1380

gaaaagagag ttggtatgtc tcatgaatgt tcacacagaa ggagttggtt ttcatgtcat   1440

ctacagcata tgagaaaagc tacctttctt ttgattatgt acacagatat ctaaataagg   1500

aagtatgagt ttcacatgta tatcaaaaat acaacagttg cttgtattca gtagagtttt   1560

cttgcccacc tattttgtgc tgggttctac cttaacccag aagacactat gaaaaacaag   1620

acagactcca ctcaaaattt atatgaacac cactagatac ttcctgatca aacatcagtc   1680

aacatactct aaagaataac tccaagtctt ggccaggcgc agtggctcac acctgtaatc   1740

ccaacacttt gggaggccaa ggtgggtgga tcatctaagg ccgggagttc aagaccagcc   1800

tgaccaacgt ggagaaaccc catctctact aaaaatacaa aattagccgg gcgtggtagc   1860
```

```
gcatggctgt aatcctggct actcaggagg ccgaggcaga agaattgctt gaactgggga   1920

ggcagaggtt gcggtgagcc cagatcgcgc cattgcactc cagcctgggt aacaagagca   1980

aaactctgtc caaaaaaaaa aaaaaaaaaa a                                  2011


<210> SEQ ID NO 18
<211> LENGTH: 3319
<212> TYPE: DNA
<213> ORGANISM: Murine sp.

<400> SEQUENCE: 18

ttaatggggg gctctctggt cagaagggat cagaagtctc tccaagacag cagaaggatg     60

gcagaggagc tggggttggg cttcggagaa ggagtcccag tggaagtgct gccggaaggc    120

tgtagacaca ggccagaggc cagggccggg ctagctgcca ggagcaaagc ctgcctggct    180

ctcacctgct gcctgttgtc atttcccatc ctcgcaggac ttagcaccct cctaatggct    240

ggccagctcc gggtccccgg aaaagactgt atgcttcggg ccataacaga agagagatct    300

gagccttcac cacagcaagt ttactcacct cccagaggca agccgagagc acacctgaca    360

attaagaaac aaaccccagc accacatctg aaaaatcagc tctctgctct acactgggaa    420

catgacctag ggatggcctt caccaagaac gggatgaagt acatcaacaa atccctggtg    480

atcccagagt caggagacta tttcatctac tcccagatca cattccgagg gaccacatct    540

gtgtgtggtg acatcagtcg gggggagacga ccaaacaagc cagactccat caccatggtt    600

atcaccaagg tagcagacag ctaccctgag cctgcccgcc tactaacagg gtccaagtct    660

gtgtgtgaaa taagcaacaa ctggttccag tccctctacc ttggggccac gttctccttg    720

gaagaaggag acagactaat ggtaaacgtc agtgacatct ccttggtgga ttacacaaaa    780

gaagataaaa ctttctttgg agctttcttg ctataaggag gagaaaacca tcattccaag    840

gggctcccct gcctcctact ttccaatttc cttttctcat atggatctat aaacaggggc    900

tttagaggga tcagggaagg ggacagtggt ttagctatat aatttaggaa cccaatattg    960

atccgtatat gccttatgga ctaaaatagt aaatggaaaa cccagtacag ctcatgtttg   1020

atagagacct gctgggtttt aaaaattgaa acacgcctca tccaatggca caatctactg   1080

atttcaggac agaacctttc cacagtgccc tctgtccaag tcctttctga attcagcagt   1140

tcagttagag ctgaattcga caatgaactt actccagatc aagagctaaa gacagaatcc   1200

aaagaaagac tgagaaaatg atgttatttc tccaagaggc aatgcatttc cacattcttt   1260

tgtgcctaac ctaaaaaata agaaagaaga aaggaaggaa ggaaggaagg aaggaaggaa   1320

ggaaggaagg aaggaaggaa ggaaggaagg aaggaaggga caagaaaaga caagacaaga   1380

caagaaaaaa gaaaaaatgg tatttctcgt gaatattccc taaaaggaat tggttttctg   1440

ctgtgaagga gaaacctcac ctttcttctg attgcatcct ttagtatcca aacatacaag   1500

tgggaattcc aaatgcacat ggaacataga acacttttat tattgtgaga acatgtttat   1560

tgagtaccta ctatgctctg ggcactcagc ccacaggacc atgaagagaa agtcaaattt   1620

tcttaaaaac taaatgaatc ctcaatacat acttcctgat caactaccac tcaaaatgta   1680

taacttccaa agtataactt caagtcagcc atctaggtgg tttcttgggt aaaggtgctt   1740

gtcattaagc ctgacacctg ggtttgacct cccagaaccc aaaagctgga aggagagaat   1800

tggttcccac aaattatcct caaacccccca tacaaatgat gtggcatgca cacatgtaac   1860

taaataaata agtgtaaaac aaaaacaaaa acaaaatttt aaagaaaaat ttcaagtcct   1920

gaaagacagc attcctgaga atgttgtctc catcgttgtc cagtataggc taaccagctg   1980
```

```
atagagacac tgaaggaatt taaagacaga catcaagtga aatggagcac tgtagaaaca   2040

cttgattcat gccaggagtc aatgtactat gaagaccaac aacaaagtgt cagtcatcaa   2100

atccagaggt gtttatctag atctgctttc aagtttggtt tgcagccttt atatagtctc   2160

tattacaaat gctcgtgtca tggtagatgc cacaaggagt caggggggtaa acttagcccc   2220

aaaccactgc tgagccatct tctaggaaac cttcgaagca gagctgggca gcgtgactcc   2280

cacacaatga ctgggaaagt agtagctgat caaaatttgt tgagtaataa tttgttagaa   2340

aattcatctc cactgcctac taaacctaag ttgtatacta tctagcttct gctaagccaa   2400

cttacattgg ccactttttc tgtcttcaac ttcttgaagt atcacaggtc tcagtgagaa   2460

cacagggaaa ggtgaggtcg ccttcccctg gttcttcata ggggaaacca cacctgaaag   2520

aagatgagca gcctgaggtg acctggagga agggctgtct cagaagaagg acttattttt   2580

tggcttaggt ctaaaacctt gagagtaatg ctcactggtc aattgaggat gctttatcaa   2640

tgactccagt ctgactccaa ggtcagaaag gagagtgaga tgctctctct gcctgcatat   2700

atcttcatgg aacatgagaa tattgagcaa catagactta taggaaaaca cttgcccaaa   2760

agtagccaga gtaacctggt catcccctct actaaaccca agctttgtgt caagggcctt   2820

caaagctgcc cagaagtgat ctggatggct tgggaattta tccaagacag gaatttcctg   2880

acagccaaag atgcttgagt ccttgtgcct gacatgcatt tattttgccc ctgtttattg   2940

aagactgtaa ctgttgattt gtgggtatac atacatacat acatacatac atacatacat   3000

acatacatat gctgtcatga aggcagcatc aaacattact aattggactc aaaccagcat   3060

ttctgtttcc aagatactaa gtattcccat gcaaacagga gcatgctatt tttctaaagc   3120

aaaatgaaaa aaatagtttt gaaagtatat atatgatgga gtcaagtgta atggcataca   3180

tctgtaaacc cagcacatgg gatgctgagc caggaggatc gccgtgagtt tgaggagaac   3240

aggggctaaa tagtaatttt caggaaagcc ttgcctatat aacaagacct tgtctcaaat   3300

gaaaaaaaaa aaaaaaaaa                                                3319
```

<210> SEQ ID NO 19
<211> LENGTH: 1859
<212> TYPE: DNA
<213> ORGANISM: Homo sapiens

<400> SEQUENCE: 19

```
gcaggcacaa actcatccat ccccagttga ttggaagaaa caacgatgac tcctgggaag     60

acctcattgg tgtcactgct actgctgctg agcctggagg ccatagtgaa ggcaggaatc    120

acaatcccac gaaatccagg atgcccaaat tctgaggaca agaacttccc ccggactgtg    180

atggtcaacc tgaacatcca taaccggaat accaatacca atcccaaaag gtcctcagat    240

tactacaacc gatccacctc accttggaat ctccaccgca atgaggaccc tgagagatat    300

ccctctgtga tctgggaggc aaagtgccgc cacttgggct gcatcaacgc tgatgggaac    360

gtggactacc acatgaactc tgtccccatc cagcaagaga tcctggtcct gcgcagggag    420

cctccacact gccccaactc cttccggctg gagaagatac tggtgtccgt gggctgcacc    480

tgtgtcaccc cgattgtcca ccatgtggcc taagagctct ggggagccca cactccccaa    540

agcagttaga ctatggagag ccgacccagc ccctcaggaa ccctcatcct tcaaagacag    600

cctcatttcg gactaaactc attagagttc ttaaggcagt ttgtccaatt aaagcttcag    660

aggtaacact tggccaagat atgagatctg aattaccttt ccctctttcc aagaaggaag    720
```

```
gtttgactga gtaccaattt gcttcttgtt tacttttttta agggctttaa gttatttatg    780
tatttaatat gccctgagat aactttgggg tataagattc cattttaatg aattacctac    840
tttattttgt ttgtcttttt aaagaagata agattctggg cttgggaatt ttattattta    900
aaaggtaaaa cctgtattta tttgagctat ttaaggatct atttatgttt aagtatttag    960
aaaaaggtga aaaagcacta ttatcagttc tgcctaggta aatgtaagat agaattaaat   1020
ggcagtgcaa aatttctgag tctttacaac atacggatat agtatttcct cctctttgtt   1080
tttaaaagtt ataacatggc tgaaaagaaa gattaaacct actttcatat gtattaattt   1140
aaattttgca atttgttgag gttttacaag agatacagca agtctaactc tctgttccat   1200
taaaccctta taataaaatc cttctgtaat aataaagttt caaaagaaaa tgtttatttg   1260
ttctcattaa atgtatttta gcaaactcag ctcttcccta ttgggaagag ttatgcaaat   1320
tctcctataa gcaaaacaaa gcatgtcttt gagtaacaat gacctggaaa tacccaaaat   1380
tccaagttct cgatttcaca tgccttcaag actgaacacc gactaaggtt ttcatactat   1440
tagccaatgc tgtagacaga agcattttga taggaataga gcaaataaga taatggccct   1500
gaggaatggc atgtcattat taaagatcat atggggaaaa tgaaaccctc cccaaaatac   1560
aagaagttct gggaggagac attgtcttca gactacaatg tccagtttct cccctagact   1620
caggcttcct ttggagatta aggcccctca gagatcaaca gaccaacatt tttctcttcc   1680
tcaagcaaca ctcctagggc ctggcttctg tctgatcaag gcaccacaca acccagaaag   1740
gagctgatgg ggcagaacga actttaagta tgagaaaagt tcagcccaag taaaataaaa   1800
actcaatcac attcaattcc agagtagttt caagtttcac atcgtaacca ttttcgccc    1859
```

<210> SEQ ID NO 20
<211> LENGTH: 1171
<212> TYPE: DNA
<213> ORGANISM: Murine sp.

<400> SEQUENCE: 20

```
atccacctca cacgaggcac aagtgcaccc agcaccagct gatcaggacg cgcaaacatg     60
agtccaggga gagcttcatc tgtgtctctg atgctgttgc tgctgctgag cctggcggct    120
acagtgaagg cagcagcgat catccctcaa agctcagcgt gtccaaacac tgaggccaag    180
gacttcctcc agaatgtgaa ggtcaacctc aaagtcttta actcccttgg cgcaaaagtg    240
agctccagaa ggccctcaga ctacctcaac cgttccacgt caccctggac tctccaccgc    300
aatgaagacc ctgatagata tccctctgtg atctgggaag ctcagtgccg ccaccagcgc    360
tgtgtcaatg cggagggaaa gctggaccac cacatgaatt ctgttctcat ccagcaagag    420
atcctggtcc tgaagaggga gcctgagagc tgccccttca ctttcagggt cgagaagatg    480
ctggtgggtg tgggctgcac ctgcgtggcc tcgattgtcc gccaggcagc ctaaacagag    540
acccgcggct gaccccctaag aaacccccac gtttctcagc aaacttactt gcatttttaa    600
aacagttcgt gctattgatt ttcagcaagg aatgtggatt cagaggcaga ttcagaattg    660
tctgccctcc acaatgaaaa gaaggtgtaa aggggtccca aactgcttcg tgtttgtttt    720
tctgtggact ttaaattatt tgtgtattta caatatccca agatagcttt gaagcgtaac    780
ttattttaat gaagtatcta cattattatt atgtttcttt ctgaagaaga caaaattcaa    840
gactcagaaa ttttattatt taaaaggtaa agcctatatt tatatgagct atttatgaat    900
ctatttattt ttcttcagta tttgaagtat taagaacatg attttcagat ctacctaggg    960
aagtcctaag taagattaaa tattaatgga aatttcagct ttactatttg tttatttaag   1020
```

```
gttctctcct ctgaatgggg tgaaaaccaa acttagtttt atgtttaata actttttaaa   1080

ttattgaaga ttcaaaaaat tggataattt agctccctac tctgttttaa aaaaaaattg   1140

taacaatatc actgtaataa taaagttttg g                                  1171
```

<210> SEQ ID NO 21
<211> LENGTH: 711
<212> TYPE: DNA
<213> ORGANISM: Homo sapiens

<400> SEQUENCE: 21

```
tggggttcca ggcgggcagc agctgcaggc tgaccttgca gcttggcgga atggactggc     60

ctcacaacct gctgtttctt cttaccattt ccatcttcct ggggctgggc cagcccagga    120

gccccaaaag caagaggaag ggcaagggc ggcctgggcc cctggcccct ggccctcacc    180

aggtgccact ggacctggtg tcacggatga aaccgtatgc ccgcatggag gagtatgaga    240

ggaacatcga ggagatggtg gcccagctga ggaacagctc agagctggcc cagagaaagt    300

gtgaggtcaa cttgcagctg tggatgtcca acaagaggag cctgtctccc tggggctaca    360

gcatcaacca cgaccccagc cgtatccccg tggacctgcc ggaggcacgg tgcctgtgtc    420

tgggctgtgt gaaccccttc accatgcagg aggaccgcag catggtgagc gtgccggtgt    480

tcagccaggt tcctgtgcgc cgccgcctct gcccgccacc gccccgcaca gggccttgcc    540

gccagcgcgc agtcatggag accatcgctg tgggctgcac ctgcatcttc tgaatcacct    600

ggcccagaag ccaggccagc agcccgagac catcctcctt gcacctttgt gccaagaaag    660

gcctatgaaa agtaaacact gacttttgaa agcaaaaaaa aaaaaaaaaa a             711
```

<210> SEQ ID NO 22
<211> LENGTH: 692
<212> TYPE: DNA
<213> ORGANISM: Murine sp.

<400> SEQUENCE: 22

```
ggggttcctg gcgggtggca gctgcgggcc tgccgcctga cttggtggga tggactggcc     60

gcacagcctg ctcttcctcc tggccatctc catcttcctg gcgccaagcc acccccggaa    120

caccaaaggc aaaagaaaag ggcaagggag gcccagtccc ttggcccctg ggcctcatca    180

ggtgccgctg gacctggtgt ctcgagtaaa gccctacgct cgaatggaag agtatgagcg    240

gaaccttggg gagatggtgg cccagctgag gaacagctcc gagccagcca agaagaaatg    300

tgaagtcaat ctacagctgt ggttgtccaa caagaggagc ctgtccccat ggggctacag    360

catcaaccac gaccccagcc gcatccctgc ggacttgccc gaggcgcggt gcctatgttt    420

gggttgcgtg aatcccttca ccatgcagga ggaccgtagc atggtgagcg tgccagtgtt    480

cagccaggtg ccggtgcgcc gccgcctctg tcctcaacct cctcgccctg ggccctgccg    540

ccagcgtgtc gtcatggaga ccatcgctgt gggttgcacc tgcatcttct gagccaacca    600

ccaacccggt ggcctctgca acaaccctcc ctccctgcac ccactgtgac cctcaaggct    660

gataaacagt aaacgctgtt ctttgtaaag ga                                 692
```

<210> SEQ ID NO 23
<211> LENGTH: 808
<212> TYPE: DNA
<213> ORGANISM: Homo sapiens

<400> SEQUENCE: 23

```
gaacacaggc atacacagga agatacattc acagaaagag cttcctgcac aaagtaagcc      60

accagcgcaa catgacagtg aagaccctgc atggcccagc catggtcaag tacttgctgc     120

tgtcgatatt ggggcttgcc tttctgagtg aggcggcagc tcggaaaatc cccaaagtag     180

gacatacttt tttccaaaag cctgagagtt gcccgcctgt gccaggaggt agtatgaagc     240

ttgacattgg catcatcaat gaaaaccagc gcgtttccat gtcacgtaac atcgagagcc     300

gctccacctc cccctggaat tacactgtca cttgggaccc caaccggtac ccctcggaag     360

ttgtacaggc ccagtgtagg aacttgggct gcatcaatgc tcaaggaaag gaagacatct     420

ccatgaattc cgttcccatc cagcaagaga ccctggtcgt ccggaggaag caccaaggct     480

gctctgtttc tttccagttg gagaaggtgc tggtgactgt tggctgcacc tgcgtcaccc     540

ctgtcatcca ccatgtgcag taagaggtgc atatccactc agctgaagaa gctgtagaaa     600

tgccactcct tacccagtgc tctgcaacaa gtcctgtctg acccccaatt ccctccactt     660

cacaggactc ttaataagac ctgcacggat ggaaacagaa aatattcaca atgtatgtgt     720

gtatgtacta cactttatat ttgatatcta aaatgttagg agaaaaatta atatattcag     780

tgctaatata ataaagtatt aataattt                                        808
```

<210> SEQ ID NO 24
<211> LENGTH: 1178
<212> TYPE: DNA
<213> ORGANISM: Murine sp.

<400> SEQUENCE: 24

```
gacataccca ggaagacata cttagaagaa agtacttcct gagggaagaa gcagccattg      60

gagaaaccag catgaagtgc acccgtgaaa cagccatggt caagtctttg ctactgttga     120

tgttgggact tgccattctg agggaggtag cagctcggaa gaaccccaaa gcaggggttc     180

ctgccttgca gaaggctggg aactgtcctc ccctggagga taacactgtg agagttgaca     240

ttcgaatctt caaccaaaac cagggcattt ctgtcccacg tgaattccag aaccgctcca     300

gttccccatg ggattacaac atcactcgag acccccaccg gttcccctca gagatcgctg     360

aggcccagtg cagacactca ggctgcatca atgcccaggg tcaggaagac agcaccatga     420

actccgtcgc cattcagcaa gaaatcctgg tccttcggag ggagccccag ggctgttcta     480

attccttcag gttggagaag atgctcctaa aagttggctg cacctgtgtc aagcccattg     540

tccaccaagc ggcctgacaa cgctgcatac aaaaatcagt tgaagacttc cactgagaaa     600

aagcctcctt ttatccagag ctctgtgtga agcccgatct ccaagtcttt atgctttcta     660

ggactctcag taaggtgtgc atggcattct tgcagctctg cagtagatat agcttgaact     720

ttctggcttg ctttagaatt gttaccagtc ctggtgtgtt cccaatgcct cacttaaact     780

cctaaaaaca aaggtaaatg aaggcaccct tggcccagtc tctttgtgtt agatgatgac     840

cacagttctt gtctgtcaag actgtcactt tgatgcagta ccattcttgt agagttcaat     900

gaaatgctca tatttgtgat ggaaagaaaa caaacataat cagaatgcat gggaggaggc     960

ctgtgtagca ggggctggac tggcaaggaa gaagcacaca tggtatgtgt gtttttagag    1020

aaaaatttgg taaatataaa tgaagttggc ataaactatt atatatttat gttggtaggg    1080

gaactataca tatatttatg acctattgat tatatatcaa tttagtagaa aattaatata    1140

tccattaatt atataataaa atatttttaa ttcaaaaa                            1178
```

<210> SEQ ID NO 25
<211> LENGTH: 2589

<212> TYPE: DNA
<213> ORGANISM: Homo sapiens

<400> SEQUENCE: 25

```
cggcccgctg gagaggaagc ccgagagctg ccgcgcgcct gccggacgag ggcgtagaag     60
ccaggcgtca gagcccgggc tccggtgggg tcccccaccc ggccctcggg tcccccgccc    120
cctgctccct gcccatccca gcccacgcga ccctctcgcg cgcggagggg cgggtcctcg    180
acggctacgg gaaggtgcca gcccgccccg gatgggcatc gtggagccgg gttgcggaga    240
catgctgacg ggcaccgagc cgatgccggg gagcgacgag ggccgggcgc ctggcgccga    300
cccgcagcac cgctacttct acccggagcc gggcgcgcag gacgcggacg agcgtcgcgg    360
gggcggcagc ctggggtctc cctacccggg gggcgccttg gtgcccgccc cgccgagccg    420
cttccttgga gcctacgcct acccgccgcg accccaggcg gccggcttcc ccggcgcggg    480
cgagtccttc ccgccgcccg cggacgccga gggctaccag ccgggcgagg gctacgccgc    540
cccggacccg cgcgccgggc tctacccggg gccgcgtgag gactacgcgc tacccgcggg    600
actggaggtg tcggggaaac tgagggtcgc gctcaacaac cacctgttgt ggtccaagtt    660
taatcagcac cagacagaga tgatcatcac caagcaggga cggcggatgt tcccattcct    720
gtcatttact gtggccgggc tggagcccac cagccactac aggatgtttg tggacgtggt    780
cttggtggac cagcaccact ggcggtacca gagcggcaag tgggtgcagt gtggaaaggc    840
cgagggcagc atgccaggaa accgcctgta cgtccacccg gactccccca acacaggagc    900
gcactggatg cgccaggaag tttcatttgg gaaactaaag ctcacaaaca acaagggggc    960
gtccaacaat gtgacccaga tgattgtgct ccagtccctc cataagtacc agccccggct   1020
gcatatcgtt gaggtgaacg acggagagcc agaggcagcc tgcaacgctt ccaacacgca   1080
tatctttact ttccaagaaa cccagttcat tgccgtgact gcctaccaga atgccgagat   1140
tactcagctg aaaattgata ataacccctt tgccaaagga ttccgggaga actttgagtc   1200
catgtacaca tctgttgaca ccagcatccc ctccccgcct ggacccaact gtcaattcct   1260
tgggggagat cactactctc ctctcctacc caaccagtat cctgttccca gccgcttcta   1320
ccccgacctt cctggccagg cgaaggatgt ggttccccag gcttactggc tgggggcccc   1380
ccgggaccac agctatgagg ctgagtttcg agcagtcagc atgaagcctg cattcttgcc   1440
ctctgcccct gggcccacca tgtcctacta ccgaggccag gaggtcctgg cacctggagc   1500
tggctggcct gtggcacccc agtaccctcc caagatgggc ccggccagct ggttccgccc   1560
tatgcggact ctgcccatgg aacccggccc tggaggctca gagggacggg gaccagagga   1620
ccagggtccc cccttggtgt ggactgagat tgcccccatc cggccggaat ccagtgattc   1680
aggactgggc gaaggagact ctaagaggag gcgcgtgtcc ccctatcctt ccagtggtga   1740
cagctcctcc cctgctgggg ccccttctcc ttttgataag gaagctgaag gacagtttta   1800
taactatttt cccaactgag cagatgacat gatgaaagga acagaaacag tgttattagg   1860
ttggaggaca ccgactaatt tgggaaacgg atgaaggact gagaaggccc ccgctccctc   1920
tggcccttct ctgtttagta gttggttggg gaagtggggc tcaagaagga ttttggggtt   1980
caccagatgc ttcctggccc acgatgaaac ctgagagggg tgtccccttg ccccatcctc   2040
tgccctaact acagtcgttt acctggtgct gcgtcttgct tttggtttcc agctggagaa   2100
aagaagacaa gaaagtcttg ggcatgaagg agctttttgc atctagtggg tgggaggggt   2160
caggtgtggg acatgggagc aggagactcc actttcttcc tttgtacagt aactttcaac   2220
```

```
cttttcgttg gcatgtgtgt taatccctga tccaaaaaga acaaatacac gtatgttata   2280
accatcagcc cgccagggtc agggaaagga ctcacctgac tttggacagc tggcctgggc   2340
tccccctgct caaacacagt ggggatcaga gaaaaggggc tggaaagggg ggaatggccc   2400
acatctcaag aagcaagata ttgtttgtgg tggttgtgtg tgggtgtgtg ttttttcttt   2460
ttctttcttt ttattttttt tgaatggggg aggctattta ttgtactgag agtggtgtct   2520
ggatatattc cttttgtctt catcactttc tgaaaataaa cataaaactg ttaaaaaaaa   2580
aaaaaaaaa                                                           2589
```

<210> SEQ ID NO 26
<211> LENGTH: 2482
<212> TYPE: DNA
<213> ORGANISM: Murine sp.

<400> SEQUENCE: 26

```
gcggccgcgt cgaccgcgcg ctcaggagcc aagcgtccca gctcccgctc cagtgaagtt     60
tcattggtct tcggacgccg cccccgtcgc cccagcccta aggaccctcg ggtctcttcg    120
acggctgctg gaaggcgccc agcccgcctc ggatgggcat cgtggagccg ggctgcggag    180
acatgctgac cggcaccgag ccgatgccga gtgacgaggg ccgggggccc ggagcggacc    240
aacagcatcg tttcttctat cccgagccgg gcgcacagga cccgaccgat cgccgcgcag    300
gtagcagcct ggggacgccc tactctgggg gcgccctggt gcctgccgcg ccgggtcgct    360
tccttggatc cttcgcctac ccgcccccggg ctcaggtggc tggctttccc gggcctggcg    420
agttcttccc gccgcccgcg ggtgcggagg gctacccgcc cgtggatggc taccctgccc    480
ctgacccgcg cgcggggctc tacccagggc cgcgcgagga ctacgcattg cccgcggggt    540
tggaggtgtc tgggaagctg agagtcgcgc tcagcaacca cctgttgtgg tccaagttca    600
accagcacca gacagagatg atcatcacta agcaaggacg gcgaatgttc ccattcctgt    660
ccttcaccgt ggctgggctg gagcccacaa gccattacag gatgtttgtg gatgtggtct    720
tggtggacca gcaccactgg cggtaccaga gcggcaagtg ggtgcagtgt ggaaaggcag    780
aaggcagcat gccagggaac cgcttatatg tccacccaga ctcccccaac accggagccc    840
actggatgcg ccaggaagtt tcatttggga agctaaagct caccaacaac aagggggctt    900
ccaacaatgt gacccagatg atcgtcctgc agtctctcca caagtaccag ccccggctgc    960
acatcgtgga ggtgaatgat ggagagccag aggctgcctg cagtgcttct aacacacacg   1020
tctttacttt ccaagagacc cagttcattg cagtgactgc ctaccagaac gcagagatca   1080
ctcagctgaa aatcgacaac aaccccttttg ccaaaggatt ccgggagaac tttgagtcca   1140
tgtacgcatc tgttgatacg agtgtcccct cgccacctgg acccaactgt caactgcttg   1200
ggggagaccc cttctcacct cttctatcca accagtatcc tgttcccagc cgtttctacc   1260
ccgaccttcc aggccagccc aaggatatga tctcacagcc ttactggctg gggacacctc   1320
gggaacacag ttatgaagcg gagttccgag ctgtgagcat gaagcccaca ctcctaccct   1380
ctgccccggg gcccactgtg ccctactacc ggggccaaga cgtcctggcg cctggagctg   1440
gttggcccgt ggcccctcaa tacccgccca agatgagccc agctggctgg ttccggccca   1500
tgcgaactct gcccatggac ccgggcctgg gatcctcaga ggaacagggc tcctccccct   1560
cgctgtggcc tgaggtcacc tccctccagc cggagtccag cgactcagga ctaggcgaag   1620
gagacactaa gaggaggagg atatccccct atccttccag tggcgacagc tcctctcccg   1680
ctggggcccc ttctcctttt gataaggaaa ccgaaggcca gttttataat tattttccca   1740
```

```
actgagaaaa tgccgctgaa ttggaaggtg cccactaact tagaaaacag acgcggggct   1800

gagagccccg agctcttccc catcccttcc ctgtatagtg attggttgga gaggaagcgg   1860

ggcaagaagg attctggggt ttacttcttg tttcctggcc cacaaggaaa tacgacagga   1920

gtgtcccctg cccctttctc tgcccgaact acagtcacga acctggtgct gcttctgacc   1980

ccatggttcc atggagaacg gagaatggac tccagagagt tttggaccca gagggacttc   2040

atggctttct gcgaggtgga ggggtcgggg tggggagtcc aggagagctg ctctcttccc   2100

ctgtccagtc agtaactttc aactgttggt ctgacacctg tgttaatctc tgacctgaaa   2160

gtgaagatac acgcattttt acaacagcca gccaaacaga gaagactcag gtgactgcgg   2220

gcggactggg ccacctgcga ggagacaaga gagggtgggt gcagaggaag ggtttgaagg   2280

gtgcacattt caccaggcga ggtcactttg aaccggtgtg tacacacacg ggtgtctctt   2340

ttttatttct tcgggagggg ggaggctatt tattgtagag agtggtgtct ggatgtattt   2400

cttctgtttt gcatcacttt ctggaaataa acatggacct ggtaaaaaaa aaaaaaaaaa   2460

aaaaaaaaaa aaaaaaaaaa aa                                            2482
```

<210> SEQ ID NO 27
<211> LENGTH: 3084
<212> TYPE: DNA
<213> ORGANISM: Homo sapiens

<400> SEQUENCE: 27

```
gccaggtgct cccgccttcc accctccgcc ctcctccctc ccctgggccc tgctccctgc     60

cctcctgggc agccagggca gccaggacgg caccaaggga gctgccccat ggacagggcc    120

ccacagagac agcaccgagc ctcacgggag ctgctggctg caaagaagac ccacacctca    180

caaattgaag tgatcccttg caaaatctgt ggggacaagt cgtctgggat ccactacggg    240

gttatcacct gtgaggggtg caagggcttc ttccgccgga gccagcgctg taacgcggcc    300

tactcctgca cccgtcagca gaactgcccc atcgaccgca ccagccgaaa ccgatgccag    360

cactgccgcc tgcagaaatg cctggcgctg ggcatgtccc gagatgctgt caagttcggc    420

cgcatgtcca agaagcagag ggacagcctg catgcagaag tgcagaaaca gctgcagcag    480

cggcaacagc agcaacagga accagtggtc aagacccctc cagcaggggc ccaaggagca    540

gataccctca cctacacctt ggggctccca gacgggcagc tgcccctggg ctcctcgcct    600

gacctgcctg aggcttctgc ctgtccccct ggcctcctga aagcctcagg ctctgggccc    660

tcatattcca acaacttggc caaggcaggg ctcaatgggg cctcatgcca ccttgaatac    720

agccctgagc ggggcaaggc tgagggcaga gagagcttct atagcacagg cagccagctg    780

acccctgacc gatgtggact tcgttttgag gaacacaggc atcctgggct tggggaactg    840

ggacagggcc cagacagcta cggcagcccc agtttccgca gcacaccgga ggcaccctat    900

gcctccctga cagagataga gcacctggtg cagagcgtct gcaagtccta cagggagaca    960

tgccagctgc ggctggagga cctgctgcgg cagcgctcca acatcttctc ccgggaggaa   1020

gtgactggct accagaggaa gtccatgtgg gagatgtggg aacggtgtgc ccaccacctc   1080

accgaggcca ttcagtacgt ggtggagttc gccaagaggc tctcaggctt tatggagctc   1140

tgccagaatg accagattgt gcttctcaaa gcaggagcaa tggaagtggt gctggttagg   1200

atgtgccggg cctacaatgc tgacaaccgc acggtctttt ttgaaggcaa atacggtggc   1260

atggagctgt tccgagcctt gggctgcagc gagctcatca gctccatctt tgacttctcc   1320
```

```
cactccctaa gtgccttgca cttttccgag gatgagattg ccctctacac agcccttgtt   1380

ctcatcaatg cccatcggcc agggctccaa gagaaaagga aagtagaaca gctgcagtac   1440

aatctggagc tggcctttca tcatcatctc tgcaagactc atcgccaaag catcctggca   1500

aagctgccac ccaaggggaa gcttcggagc ctgtgtagcc agcatgtgga aaggctgcag   1560

atcttccagc acctccaccc catcgtggtc caagccgctt tccctccact ctacaaggag   1620

ctcttcagca ctgaaaccga gtcacctgtg ggctgtccca agtgacctgg aagagggact   1680

ccttgcctct ccctatggcc tgctggccca cctccctgga ccccgttcca ccctcaccct   1740

tttcctttcc catgaaccct ggagggtggt ccccaccagc tctttggaag tgagcagatg   1800

ctgcggctgg ctttctgtca gcaggccggc ctggcagtgg gacaatcgcc agagggtggg   1860

gctggcagaa caccatctcc agcctcagct ttgacctgtc tcatttccca tattccttca   1920

cacccagctt ctggaaggca tggggtggct gggatttaag gacttctggg ggaccaagac   1980

atcctcaaga aaacaggggc atccagggct ccctggatga atagaatgca attcattcag   2040

aagctcagaa gctaagaata agcctttgaa atacctcatt gcatttccct ttgggcttcg   2100

gcttggggag atggatcaag ctcagagact ggcagtgaga gcccagaagg acctgtataa   2160

aatgaatctg gagctttaca ttttctgcct ctgccttcct cccagctcag caaggaagta   2220

tttgggcacc ctaccctta cctggggtct aaccaaaaat ggatgggatg aggatgagag   2280

gctggagata attgttttat gggatttggg tgtgggacta gggtacaatg aaggccaaga   2340

gcatctcaga catagagtta aaactcaaac ctcttatgtg cactttaaag atagacttta   2400

ggggctggca caaatctgat cagagacaca tatccataca caggtgaaac acatacagac   2460

tcaacagcaa tcatgcagtt ccagagacac atgaacctga cacaatctct cttatccttg   2520

aggccacagc ttggaggagc ctagaggcct caggggaaag tcccaatcct gagggaccct   2580

cccaaacatt tccatggtgc tccagtccac tgatcttggg tctggggtga tccaaatacc   2640

accccagctc cagctgtctt ctaccactag aagacccaag agaagcagaa gtcgctcgca   2700

ctggtcagtc ggaaggcaag atcagatcct ggaggacttt cctggcctgc ccgccagccc   2760

tgctcttgtt gtggagaagg aagcagatgt gatcacatca ccccgtcatt gggcaccgct   2820

gactccagca tggaggacac cagggagcag ggcctgggcc tgtttcccca gctgtgatct   2880

tgcccagaac ctctcttggc ttcataaaca gctgtgaacc ctcccctgag ggattaacag   2940

caatgatggg cagtcgtgga gttggggggg ttgggggtgg gattgtgtcc tctaagggga   3000

cgggttcatc tgagtaaaca taaaccccaa cttgtgccat tctttataaa atgattttaa   3060

aggcaaaaaa aaaaaaaaaa aaaa                                          3084
```

<210> SEQ ID NO 28
<211> LENGTH: 2503
<212> TYPE: DNA
<213> ORGANISM: Murine sp.

<400> SEQUENCE: 28

```
ttgggccctg ctccctgccc tcctgggcag ccagggcagc aaggacggca ccaagggagc     60

taccccatgg acagggcccc acagagacac caccggacat ctcgggagct gctggctgca    120

aagaagaccc acacctcaca aattgaagtg atcccttgca agatctgtgg ggacaagtca    180

tctgggatcc actacggggt tatcacctgt gaggggtgca agggcttctt ccgccgcagc    240

cagcagtgta atgtggccta ctcctgcacg cgtcagcaga actgccccat tgaccgaacc    300

agccgcaacc gatgccagca ttgccgcctg cagaagtgcc tggctctggg catgtcccga    360
```

```
gatgctgtca agtttggccg aatgtccaag aagcagaggg acagtctaca tgcagaagtg    420
cagaaacaac tgcaacagca gcagcaacag gaacaagtgg ccaagactcc tccagctggg    480
agccgcggag cagacacact tacatacact ttagggctct cagatgggca gctaccactg    540
ggcgcctcac ctgacctacc cgaggcctct gcttgtcccc ctggcctcct gagagcctca    600
ggctctggcc caccatattc caataccttg gccaaaacag aggtccaggg ggcctcctgc    660
caccttgagt atagtccaga acgaggcaaa gctgaaggca gagacagcat ctatagcact    720
gacggccaac ttactcttgg aagatgtgga cttcgttttg aggaaaccag gcatcctgaa    780
cttggggaac cagaacaggg tccagacagc cactgcattc ccagtttctg cagtgcccca    840
gaggtaccat atgcctctct gacagacata gagtacctgg tacagaatgt ctgcaagtcc    900
ttccgagaga catgccagct gcgactggag gaccttctac ggcagcgcac caacctcttt    960
tcacgggagg aggtgaccag ctaccagagg aagtcaatgt gggagatgtg ggagcgctgt   1020
gcccaccacc tcactgaggc cattcagtat gtggtggagt ttgccaagcg gctttcaggc   1080
ttcatggagc tctgccagaa tgaccagatc atactactga aagcaggagc aatggaagtc   1140
gtcctagtca gaatgtgcag ggcctacaat gccaacaacc acacagtctt ttttgaaggc   1200
aaatacggtg gtgtggagct gtttcgagcc ttgggctgca gcgagctcat cagctccata   1260
tttgactttt cccacttcct cagcgccctg tgtttttctg aggatgagat tgccctctac   1320
acggccctgg ttctcatcaa tgccaaccgt cctgggctcc aagagaagag gagagtggaa   1380
catctgcaat acaatttgga actggctttc catcatcatc tctgcaagac tcatcgacaa   1440
ggcctcctag ccaagctgcc acccaaagga aaactccgga gcctgtgcag ccaacatgtg   1500
gaaaagctgc agatcttcca gcacctccac cccatcgtgg tccaagccgc cttccctcca   1560
ctctataagg aactcttcag cactgatgtt gaatcccctg aggggctgtc aaagtgatct   1620
ggaggaagga caactttcta tttccttcag ccctctgacc cgtctccctg gactcccttc   1680
acccagcctt tccctttctg cactctatga agggtggtat ccctaggagt aagcaaatcc   1740
taagactgat tttctgcccc taggcttgcc ttgtaggaca acagcagcaa gtgatggaga   1800
aaaggcttgt tatgtttgat ttcccataag ttccaccctg gcttctggaa gctgtggggt   1860
agatgggata gagataggat gaccaagtca aataaaaaac agactgacaa tcagcaggga   1920
taaatccagg tacctgggat aaggagaact caaatctagg cttgaaagct aataacagtc   1980
ctttcaatac ctcattgtat ttccccatgg gtcctcctgg ggggacatgg atctagctca   2040
gagactggtg gcaagccccc agaaggacct gtatataata agaatataga ttcctgagac   2100
ttttctgcct ttcttcttcc tagttaagaa atgttgttga ccccctctgc ctgttttctg   2160
ggacctaaaa tgcctggatg tgtaaagaat gagggtgggg tggagataag gtcccaagat   2220
aactgtttta tggggtttgg gtatgaagaa aaacatcact ggaaaaatta gaatggaaac   2280
ctctttgcac actttaaaag tgtcagattc gttagcagtc taatcagaga cacacatcca   2340
cacaggtgga gcacacagag gctctgcccc cagtgacacc attctgtaga ctttccctct   2400
ggcacacaat ctcttccttg aggttgcagc tctgagaagc ctgaggttct aattcataca   2460
ggacaccaga attcatccca gctccagctg tcctctgtcc cta                     2503
```

<210> SEQ ID NO 29
<211> LENGTH: 1435
<212> TYPE: DNA
<213> ORGANISM: Homo sapiens

<400> SEQUENCE: 29

```
ggcggggcct gcttctcctc agcttcaggc ggctgcgacg agccctcagg cgaacctctc     60
ggctttcccg cgcggcgccg cctcttgctg cgcctccgcc tcctcctctg ctccgccacc    120
ggcttcctcc tcctgagcag tcagcccgcg cgccggccgg ctccgttatg gcgacccgca    180
gccctggcgt cgtgattagt gatgatgaac caggttatga ccttgattta ttttgcatac    240
ctaatcatta tgctgaggat ttggaaaggg tgtttattcc tcatggacta attatggaca    300
ggactgaacg tcttgctcga gatgtgatga aggagatggg aggccatcac attgtagccc    360
tctgtgtgct caagggggc tataaattct ttgctgacct gctggattac atcaaagcac    420
tgaatagaaa tagtgataga tccattccta tgactgtaga ttttatcaga ctgaagagct    480
attgtaatga ccagtcaaca ggggacataa aagtaattgg tggagatgat ctctcaactt    540
taactggaaa gaatgtcttg attgtggaag atataattga cactggcaaa acaatgcaga    600
ctttgctttc cttggtcagg cagtataatc caaagatggt caaggtcgca agcttgctgg    660
tgaaaaggac cccacgaagt gttggatata agccagactt tgttggattt gaaattccag    720
acaagtttgt tgtaggatat gcccttgact ataatgaata cttcagggat ttgaatcatg    780
tttgtgtcat tagtgaaact ggaaaagcaa aatacaaagc ctaagatgag agttcaagtt    840
gagtttggaa acatctggag tcctattgac atcgccagta aaattatcaa tgttctagtt    900
ctgtggccat ctgcttagta gagctttttg catgtatctt ctaagaattt tatctgtttt    960
gtactttaga aatgtcagtt gctgcattcc taaactgttt atttgcacta tgagcctata   1020
gactatcagt tccctttggg cggattgttg tttaacttgt aaatgaaaaa attctcttaa   1080
accacagcac tattgagtga aacattgaac tcatatctgt aagaaataaa gagaagatat   1140
attagttttt taattggtat tttaattttt atatatgcag gaaagaatag aagtgattga   1200
atattgttaa ttataccacc gtgtgttaga aaagtaagaa gcagtcaatt ttcacatcaa   1260
agacagcatc taagaagttt tgttctgtcc tggaattatt ttagtagtgt ttcagtaatg   1320
ttgactgtat tttccaactt gttcaaatta ttaccagtga atctttgtca gcagttccct   1380
tttaaatgca aatcaataaa ttcccaaaaa tttaaaaaaa aaaaaaaaaa aaaaa        1435
```

<210> SEQ ID NO 30
<211> LENGTH: 1349
<212> TYPE: DNA
<213> ORGANISM: Murine sp.

<400> SEQUENCE: 30

```
ggagcctggc cggcagcgtt tctgagccat tgctgaggcg gcgagggaga gcgttgggct     60
tacctcactg ctttccggag cggtagcacc tcctccgccg gcttcctcct cagaccgctt    120
tttgccgcga gccgaccggt cccgtcatgc cgacccgcag tcccagcgtc gtgattagcg    180
atgatgaacc aggttatgac ctagatttgt tttgtatacc taatcattat gccgaggatt    240
tggaaaaagt gtttattcct catggactga ttatggacag gactgaaaga cttgctcgag    300
atgtcatgaa ggagatggga ggccatcaca ttgtggccct ctgtgtgctc aaggggggct    360
ataagttctt tgctgacctg ctggattaca ttaaagcact gaatagaaat agtgatagat    420
ccattcctat gactgtagat tttatcagac tgaagagcta ctgtaatgat cagtcaacgg    480
gggacataaa agttattggt ggagatgatc tctcaacttt aactggaaag aatgtcttga    540
ttgttgaaga tataattgac actggtaaaa caatgcaaac tttgctttcc ctggttaagc    600
agtacagccc caaaatggtt aaggttgcaa gcttgctggt gaaaaggacc tctcgaagtg    660
```

```
ttggatacag gccagacttt gttggatttg aaattccaga caagtttgtt gttggatatg    720
cccttgacta taatgagtac ttcagggatt tgaatcacgt ttgtgtcatt agtgaaactg    780
gaaaagccaa atacaaagcc taagatgagc gcaagttgaa tctgcaaata cgaggagtcc    840
tgttgatgtt gccagtaaaa ttagcaggtg ttctagtcct gtggccatct gcctagtaaa    900
gctttttgca tgaaccttct atgaatgtta ctgttttatt tttagaaatg tcagttgctg    960
cgtccccaga cttttgattt gcactatgag cctataggcc agcctaccct ctggtagatt   1020
gtcgcttatc ttgtaagaaa aacaaatctc ttaaattacc acttttaaat aataatactg   1080
agattgtatc tgtaagaagg atttaaagag aagctatatt agttttttaa ttggtatttt   1140
aatttttata tattcaggag agaaagatgt gattgatatt gttaatttag acgagtctga   1200
agctctcgat ttcctatcag taacagcatc taagaggttt tgctcagtgg aataaacatg   1260
tttcagcagt gttggctgta ttttcccact ttcagtaaat cgttgtcaac agttcctttt   1320
aaatgcaaat aaataaattc taaaaattc                                    1349
```

<210> SEQ ID NO 31
<211> LENGTH: 1852
<212> TYPE: DNA
<213> ORGANISM: Homo sapiens

<400> SEQUENCE: 31

```
accgccgaga ccgcgtccgc cccgcgagca cagagcctcg cctttgccga tccgccgccc     60
gtccacaccc gccgccagct caccatggat gatgatatcg ccgcgctcgt cgtcgacaac    120
ggctccggca tgtgcaaggc cggcttcgcg ggcgacgatg ccccccgggc cgtcttcccc    180
tccatcgtgg ggcgccccag gcaccagggc gtgatggtgg gcatgggtca gaaggattcc    240
tatgtgggcg acgaggccca gagcaagaga ggcatcctca ccctgaagta ccccatcgag    300
cacggcatcg tcaccaactg ggacgacatg gagaaaatct ggcaccacac cttctacaat    360
gagctgcgtg tggctcccga ggagcacccc gtgctgctga ccgaggcccc cctgaacccc    420
aaggccaacc gcgagaagat gacccagatc atgtttgaga ccttcaacac cccagccatg    480
tacgttgcta tccaggctgt gctatccctg tacgcctctg gccgtaccac tggcatcgtg    540
atggactccg gtgacggggt cacccacact gtgcccatct acgaggggta tgccctcccc    600
catgccatcc tgcgtctgga cctggctggc cgggacctga ctgactacct catgaagatc    660
ctcaccgagc gcggctacag cttcaccacc acggccgagc gggaaatcgt gcgtgacatt    720
aaggagaagc tgtgctacgt cgccctggac ttcgagcaag agatggccac ggctgcttcc    780
agctcctccc tggagaagag ctacgagctg cctgacggcc aggtcatcac cattggcaat    840
gagcggttcc gctgccctga ggcactcttc cagccttcct tcctgggcat ggagtcctgt    900
ggcatccacg aaactacctt caactccatc atgaagtgtg acgtggacat ccgcaaagac    960
ctgtacgcca acacagtgct gtctggcggc accaccatgt accctggcat tgccgacagg   1020
atgcagaagg agatcactgc cctggcaccc agcacaatga agatcaagat cattgctcct   1080
cctgagcgca agtactccgt gtggatcggc ggctccatcc tggcctcgct gtccaccttc   1140
cagcagatgt ggatcagcaa gcaggagtat gacgagtccg gcccctccat cgtccaccgc   1200
aaatgcttct aggcggacta tgacttagtt gcgttacacc ctttcttgac aaaacctaac   1260
ttgcgcagaa aacaagatga gattggcatg gctttatttg ttttttttgt tttgttttgg   1320
ttttttttt ttttttggct tgactcagga tttaaaaact ggaacggtga aggtgacagc   1380
```

```
agtcggttgg agcgagcatc ccccaaagtt cacaatgtgg ccgaggactt tgattgcaca   1440

ttgttgtttt tttaatagtc attccaaata tgagatgcgt tgttacagga agtcccttgc   1500

catcctaaaa gccaccccac ttctctctaa ggagaatggc ccagtcctct cccaagtcca   1560

cacaggggag gtgatagcat tgctttcgtg taaattatgt aatgcaaaat ttttttaatc   1620

ttcgccttaa tactttttta ttttgtttta ttttgaatga tgagccttcg tgcccccccct  1680

tccccctttt ttgtccccca acttgagatg tatgaaggct tttggtctcc ctgggagtgg   1740

gtggaggcag ccagggctta cctgtacact gacttgagac cagttgaata aaagtgcaca   1800

ccttaaaaat gaaaaaaaaa aaaaaaaaaa aaaaaaaaaa aaaaaaaaaa aa           1852
```

```
<210> SEQ ID NO 32
<211> LENGTH: 1889
<212> TYPE: DNA
<213> ORGANISM: Murine sp.

<400> SEQUENCE: 32

ctgtcgagtc gcgtccaccc gcgagcacag cttctttgca gctccttcgt tgccggtcca     60

cacccgccac cagttcgcca tggatgacga tatcgctgcg ctggtcgtcg acaacggctc    120

cggcatgtgc aaagccggct tcgcgggcga cgatgctccc cgggctgtat tcccctccat    180

cgtgggccgc cctaggcacc agggtgtgat ggtgggaatg ggtcagaagg actcctatgt    240

gggtgacgag gcccagagca agagaggtat cctgaccctg aagtacccca ttgaacatgg    300

cattgttacc aactgggacg acatggagaa gatctggcac cacaccttct acaatgagct    360

gcgtgtggcc cctgaggagc accctgtgct gctcaccgag gccccccctga accctaaggc   420

caaccgtgaa aagatgaccc agatcatgtt tgagaccttc aacaccccag ccatgtacgt    480

agccatccag gctgtgctgt ccctgtatgc ctctggtcgt accacaggca ttgtgatgga    540

ctccggagac ggggtcaccc acactgtgcc catctacgag ggctatgctc tccctcacgc    600

catcctgcgt ctggacctgg ctggccggga cctgacagac tacctcatga agatcctgac    660

cgagcgtggc tacagcttca ccaccacagc tgagagggaa atcgtgcgtg acatcaaaga    720

gaagctgtgc tatgttgctc tagacttcga gcaggagatg gccactgccg catcctcttc    780

ctccctggag aagagctatg agctgcctga cggccaggtc atcactattg gcaacgagcg    840

gttccgatgc cctgaggctc ttttccagcc ttccttcttg ggtatggaat cctgtggcat    900

ccatgaaact acattcaatt ccatcatgaa gtgtgacgtt gacatccgta aagacctcta    960

tgccaacaca gtgctgtctg gtggtaccac catgtaccca ggcattgctg acaggatgca   1020

gaaggagatt actgctctgg ctcctagcac catgaagatc aagatcattg ctcctcctga   1080

gcgcaagtac tctgtgtgga tcggtggctc catcctggcc tcactgtcca ccttccagca   1140

gatgtggatc agcaagcagg agtacgatga gtccggcccc tccatcgtgc accgcaagtg   1200

cttctaggcg gactgttact gagctgcgtt ttacaccctt tctttgacaa aacctaactt   1260

gcgcagaaaa aaaaaaaata agagacaaca ttggcatggc tttgtttttt taaatttttt   1320

ttaaagtttt tttttttttt tttttttttt tttttaagtt tttttgtttt gttttggcgc   1380

ttttgactca ggatttaaaa actggaacgg tgaaggcgac agcagttggt tggagcaaac   1440

atcccccaaa gttctacaaa tgtggctgag gactttgtac attgttttgt tttttttttt   1500

ttttggtttt gtcttttttt aatagtcatt ccaagtatcc atgaaataag tggttacagg   1560

aagtccctca ccctcccaaa agccaccccc actcctaaga ggaggatggt cgcgtccatg   1620

ccctgagtcc accccgggga aggtgacagc attgcttctg tgtaaattat gtactgcaaa   1680
```

```
aatttttta aatcttccgc cttaatactt catttttgtt tttaatttct gaatggccca   1740

ggtctgaggc ctccctttt tttgtccccc caacttgatg tatgaaggct ttggtctccc   1800

tgggaggggg ttgaggtgtt gaggcagcca gggctggcct gtacactgac ttgagaccaa   1860

taaaagtgca caccttacct tacacaaac                                    1889


<210> SEQ ID NO 33
<211> LENGTH: 212
<212> TYPE: PRT
<213> ORGANISM: Homo sapiens

<400> SEQUENCE: 33

Met Asn Ser Phe Ser Thr Ser Ala Phe Gly Pro Val Ala Phe Ser Leu
1               5                   10                  15

Gly Leu Leu Leu Val Leu Pro Ala Ala Phe Pro Ala Pro Val Pro Pro
            20                  25                  30

Gly Glu Asp Ser Lys Asp Val Ala Ala Pro His Arg Gln Pro Leu Thr
        35                  40                  45

Ser Ser Glu Arg Ile Asp Lys Gln Ile Arg Tyr Ile Leu Asp Gly Ile
    50                  55                  60

Ser Ala Leu Arg Lys Glu Thr Cys Asn Lys Ser Asn Met Cys Glu Ser
65                  70                  75                  80

Ser Lys Glu Ala Leu Ala Glu Asn Asn Leu Asn Leu Pro Lys Met Ala
                85                  90                  95

Glu Lys Asp Gly Cys Phe Gln Ser Gly Phe Asn Glu Glu Thr Cys Leu
            100                 105                 110

Val Lys Ile Ile Thr Gly Leu Leu Glu Phe Glu Val Tyr Leu Glu Tyr
        115                 120                 125

Leu Gln Asn Arg Phe Glu Ser Ser Glu Glu Gln Ala Arg Ala Val Gln
    130                 135                 140

Met Ser Thr Lys Val Leu Ile Gln Phe Leu Gln Lys Lys Ala Lys Asn
145                 150                 155                 160

Leu Asp Ala Ile Thr Thr Pro Asp Pro Thr Thr Asn Ala Ser Leu Leu
                165                 170                 175

Thr Lys Leu Gln Ala Gln Asn Gln Trp Leu Gln Asp Met Thr Thr His
            180                 185                 190

Leu Ile Leu Arg Ser Phe Lys Glu Phe Leu Gln Ser Ser Leu Arg Ala
        195                 200                 205

Leu Arg Gln Met
    210


<210> SEQ ID NO 34
<211> LENGTH: 211
<212> TYPE: PRT
<213> ORGANISM: Murine sp.

<400> SEQUENCE: 34

Met Lys Phe Leu Ser Ala Arg Asp Phe His Pro Val Ala Phe Leu Gly
1               5                   10                  15

Leu Met Leu Val Thr Thr Thr Ala Phe Pro Thr Ser Gln Val Arg Arg
            20                  25                  30

Gly Asp Phe Thr Glu Asp Thr Thr Pro Asn Arg Pro Val Tyr Thr Thr
        35                  40                  45

Ser Gln Val Gly Gly Leu Ile Thr His Val Leu Trp Glu Ile Val Glu
    50                  55                  60
```

```
Met Arg Lys Glu Leu Cys Asn Gly Asn Ser Asp Cys Met Asn Asn Asp
65                  70                  75                  80

Asp Ala Leu Ala Glu Asn Asn Leu Lys Leu Pro Glu Ile Gln Arg Asn
                85                  90                  95

Asp Gly Cys Tyr Gln Thr Gly Tyr Asn Gln Glu Ile Cys Leu Leu Lys
            100                 105                 110

Ile Ser Ser Gly Leu Leu Glu Tyr His Ser Tyr Leu Glu Tyr Met Lys
        115                 120                 125

Asn Asn Leu Lys Asp Asn Lys Lys Asp Lys Ala Arg Val Leu Gln Arg
    130                 135                 140

Asp Thr Glu Thr Leu Ile His Ile Phe Asn Gln Glu Val Lys Asp Leu
145                 150                 155                 160

His Lys Ile Val Leu Pro Thr Pro Ile Ser Asn Ala Leu Leu Thr Asp
                165                 170                 175

Lys Leu Glu Ser Gln Lys Glu Trp Leu Arg Thr Lys Thr Ile Gln Phe
            180                 185                 190

Ile Leu Lys Ser Leu Glu Glu Phe Leu Lys Val Thr Leu Arg Ser Thr
        195                 200                 205

Arg Gln Thr
    210


<210> SEQ ID NO 35
<211> LENGTH: 178
<212> TYPE: PRT
<213> ORGANISM: Homo sapiens

<400> SEQUENCE: 35

Met His Ser Ser Ala Leu Leu Cys Cys Leu Val Leu Leu Thr Gly Val
1               5                   10                  15

Arg Ala Ser Pro Gly Gln Gly Thr Gln Ser Glu Asn Ser Cys Thr His
            20                  25                  30

Phe Pro Gly Asn Leu Pro Asn Met Leu Arg Asp Leu Arg Asp Ala Phe
        35                  40                  45

Ser Arg Val Lys Thr Phe Phe Gln Met Lys Asp Gln Leu Asp Asn Leu
    50                  55                  60

Leu Leu Lys Glu Ser Leu Leu Glu Asp Phe Lys Gly Tyr Leu Gly Cys
65                  70                  75                  80

Gln Ala Leu Ser Glu Met Ile Gln Phe Tyr Leu Glu Glu Val Met Pro
                85                  90                  95

Gln Ala Glu Asn Gln Asp Pro Asp Ile Lys Ala His Val Asn Ser Leu
            100                 105                 110

Gly Glu Asn Leu Lys Thr Leu Arg Leu Arg Leu Arg Arg Cys His Arg
        115                 120                 125

Phe Leu Pro Cys Glu Asn Lys Ser Lys Ala Val Glu Gln Val Lys Asn
    130                 135                 140

Ala Phe Asn Lys Leu Gln Glu Lys Gly Ile Tyr Lys Ala Met Ser Glu
145                 150                 155                 160

Phe Asp Ile Phe Ile Asn Tyr Ile Glu Ala Tyr Met Thr Met Lys Ile
                165                 170                 175

Arg Asn


<210> SEQ ID NO 36
<211> LENGTH: 178
<212> TYPE: PRT
<213> ORGANISM: Murine sp.
```

<400> SEQUENCE: 36

```
Met Pro Gly Ser Ala Leu Leu Cys Cys Leu Leu Leu Leu Thr Gly Met
1               5                   10                  15

Arg Ile Ser Arg Gly Gln Tyr Ser Arg Glu Asp Asn Asn Cys Thr His
            20                  25                  30

Phe Pro Val Gly Gln Ser His Met Leu Leu Glu Leu Arg Thr Ala Phe
        35                  40                  45

Ser Gln Val Lys Thr Phe Phe Gln Thr Lys Asp Gln Leu Asp Asn Ile
    50                  55                  60

Leu Leu Thr Asp Ser Leu Met Gln Asp Phe Lys Gly Tyr Leu Gly Cys
65                  70                  75                  80

Gln Ala Leu Ser Glu Met Ile Gln Phe Tyr Leu Val Glu Val Met Pro
                85                  90                  95

Gln Ala Glu Lys His Gly Pro Glu Ile Lys Glu His Leu Asn Ser Leu
            100                 105                 110

Gly Glu Lys Leu Lys Thr Leu Arg Met Arg Leu Arg Arg Cys His Arg
        115                 120                 125

Phe Leu Pro Cys Glu Asn Lys Ser Lys Ala Val Glu Gln Val Lys Ser
    130                 135                 140

Asp Phe Asn Lys Leu Gln Asp Gln Gly Val Tyr Lys Ala Met Asn Glu
145                 150                 155                 160

Phe Asp Ile Phe Ile Asn Cys Ile Glu Ala Tyr Met Met Ile Lys Met
                165                 170                 175

Lys Ser
```

<210> SEQ ID NO 37
<211> LENGTH: 253
<212> TYPE: PRT
<213> ORGANISM: Homo sapiens

<400> SEQUENCE: 37

```
Met Trp Pro Pro Gly Ser Ala Ser Gln Pro Pro Pro Ser Pro Ala Ala
1               5                   10                  15

Ala Thr Gly Leu His Pro Ala Ala Arg Pro Val Ser Leu Gln Cys Arg
            20                  25                  30

Leu Ser Met Cys Pro Ala Arg Ser Leu Leu Leu Val Ala Thr Leu Val
        35                  40                  45

Leu Leu Asp His Leu Ser Leu Ala Arg Asn Leu Pro Val Ala Thr Pro
    50                  55                  60

Asp Pro Gly Met Phe Pro Cys Leu His His Ser Gln Asn Leu Leu Arg
65                  70                  75                  80

Ala Val Ser Asn Met Leu Gln Lys Ala Arg Gln Thr Leu Glu Phe Tyr
                85                  90                  95

Pro Cys Thr Ser Glu Glu Ile Asp His Glu Asp Ile Thr Lys Asp Lys
            100                 105                 110

Thr Ser Thr Val Glu Ala Cys Leu Pro Leu Glu Leu Thr Lys Asn Glu
        115                 120                 125

Ser Cys Leu Asn Ser Arg Glu Thr Ser Phe Ile Thr Asn Gly Ser Cys
    130                 135                 140

Leu Ala Ser Arg Lys Thr Ser Phe Met Met Ala Leu Cys Leu Ser Ser
145                 150                 155                 160

Ile Tyr Glu Asp Leu Lys Met Tyr Gln Val Glu Phe Lys Thr Met Asn
                165                 170                 175

Ala Lys Leu Leu Met Asp Pro Lys Arg Gln Ile Phe Leu Asp Gln Asn
```

```
            180                 185                 190

Met Leu Ala Val Ile Asp Glu Leu Met Gln Ala Leu Asn Phe Asn Ser
        195                 200                 205

Glu Thr Val Pro Gln Lys Ser Ser Leu Glu Glu Pro Asp Phe Tyr Lys
    210                 215                 220

Thr Lys Ile Lys Leu Cys Ile Leu Leu His Ala Phe Arg Ile Arg Ala
225                 230                 235                 240

Val Thr Ile Asp Arg Val Met Ser Tyr Leu Asn Ala Ser
                245                 250


<210> SEQ ID NO 38
<211> LENGTH: 328
<212> TYPE: PRT
<213> ORGANISM: Homo sapiens

<400> SEQUENCE: 38

Met Cys His Gln Gln Leu Val Ile Ser Trp Phe Ser Leu Val Phe Leu
1               5                   10                  15

Ala Ser Pro Leu Val Ala Ile Trp Glu Leu Lys Lys Asp Val Tyr Val
            20                  25                  30

Val Glu Leu Asp Trp Tyr Pro Asp Ala Pro Gly Glu Met Val Val Leu
        35                  40                  45

Thr Cys Asp Thr Pro Glu Glu Asp Gly Ile Thr Trp Thr Leu Asp Gln
    50                  55                  60

Ser Ser Glu Val Leu Gly Ser Gly Lys Thr Leu Thr Ile Gln Val Lys
65                  70                  75                  80

Glu Phe Gly Asp Ala Gly Gln Tyr Thr Cys His Lys Gly Gly Glu Val
                85                  90                  95

Leu Ser His Ser Leu Leu Leu Leu His Lys Lys Glu Asp Gly Ile Trp
            100                 105                 110

Ser Thr Asp Ile Leu Lys Asp Gln Lys Glu Pro Lys Asn Lys Thr Phe
        115                 120                 125

Leu Arg Cys Glu Ala Lys Asn Tyr Ser Gly Arg Phe Thr Cys Trp Trp
    130                 135                 140

Leu Thr Thr Ile Ser Thr Asp Leu Thr Phe Ser Val Lys Ser Ser Arg
145                 150                 155                 160

Gly Ser Ser Asp Pro Gln Gly Val Thr Cys Gly Ala Ala Thr Leu Ser
                165                 170                 175

Ala Glu Arg Val Arg Gly Asp Asn Lys Glu Tyr Glu Tyr Ser Val Glu
            180                 185                 190

Cys Gln Glu Asp Ser Ala Cys Pro Ala Ala Glu Glu Ser Leu Pro Ile
        195                 200                 205

Glu Val Met Val Asp Ala Val His Lys Leu Lys Tyr Glu Asn Tyr Thr
    210                 215                 220

Ser Ser Phe Phe Ile Arg Asp Ile Ile Lys Pro Asp Pro Pro Lys Asn
225                 230                 235                 240

Leu Gln Leu Lys Pro Leu Lys Asn Ser Arg Gln Val Glu Val Ser Trp
                245                 250                 255

Glu Tyr Pro Asp Thr Trp Ser Thr Pro His Ser Tyr Phe Ser Leu Thr
            260                 265                 270

Phe Cys Val Gln Val Gln Gly Lys Ser Lys Arg Glu Lys Lys Asp Arg
        275                 280                 285

Val Phe Thr Asp Lys Thr Ser Ala Thr Val Ile Cys Arg Lys Asn Ala
    290                 295                 300
```

```
Ser Ile Ser Val Arg Ala Gln Asp Arg Tyr Tyr Ser Ser Ser Trp Ser
305                 310                 315                 320

Glu Trp Ala Ser Val Pro Cys Ser
                325


<210> SEQ ID NO 39
<211> LENGTH: 215
<212> TYPE: PRT
<213> ORGANISM: Murine sp.

<400> SEQUENCE: 39

Met Cys Gln Ser Arg Tyr Leu Leu Phe Leu Ala Thr Leu Ala Leu Leu
1               5                   10                  15

Asn His Leu Ser Leu Ala Arg Val Ile Pro Val Ser Gly Pro Ala Arg
            20                  25                  30

Cys Leu Ser Gln Ser Arg Asn Leu Leu Lys Thr Thr Asp Asp Met Val
        35                  40                  45

Lys Thr Ala Arg Glu Lys Leu Lys His Tyr Ser Cys Thr Ala Glu Asp
    50                  55                  60

Ile Asp His Glu Asp Ile Thr Arg Asp Gln Thr Ser Thr Leu Lys Thr
65                  70                  75                  80

Cys Leu Pro Leu Glu Leu His Lys Asn Glu Ser Cys Leu Ala Thr Arg
                85                  90                  95

Glu Thr Ser Ser Thr Thr Arg Gly Ser Cys Leu Pro Pro Gln Lys Thr
            100                 105                 110

Ser Leu Met Met Thr Leu Cys Leu Gly Ser Ile Tyr Glu Asp Leu Lys
        115                 120                 125

Met Tyr Gln Thr Glu Phe Gln Ala Ile Asn Ala Ala Leu Gln Asn His
    130                 135                 140

Asn His Gln Gln Ile Ile Leu Asp Lys Gly Met Leu Val Ala Ile Asp
145                 150                 155                 160

Glu Leu Met Gln Ser Leu Asn His Asn Gly Glu Thr Leu Arg Gln Lys
                165                 170                 175

Pro Pro Val Gly Glu Ala Asp Pro Tyr Arg Val Lys Met Lys Leu Cys
            180                 185                 190

Ile Leu Leu His Ala Phe Ser Thr Arg Val Val Thr Ile Asn Arg Val
        195                 200                 205

Met Gly Tyr Leu Ser Ser Ala
    210                 215


<210> SEQ ID NO 40
<211> LENGTH: 335
<212> TYPE: PRT
<213> ORGANISM: Murine sp.

<400> SEQUENCE: 40

Met Cys Pro Gln Lys Leu Thr Ile Ser Trp Phe Ala Ile Val Leu Leu
1               5                   10                  15

Val Ser Pro Leu Met Ala Met Trp Glu Leu Glu Lys Asp Val Tyr Val
            20                  25                  30

Val Glu Val Asp Trp Thr Pro Asp Ala Pro Gly Glu Thr Val Asn Leu
        35                  40                  45

Thr Cys Asp Thr Pro Glu Glu Asp Asp Ile Thr Trp Thr Ser Asp Gln
    50                  55                  60

Arg His Gly Val Ile Gly Ser Gly Lys Thr Leu Thr Ile Thr Val Lys
65                  70                  75                  80
```

```
Glu Phe Leu Asp Ala Gly Gln Tyr Thr Cys His Lys Gly Gly Glu Thr
                85                  90                  95

Leu Ser His Ser His Leu Leu Leu His Lys Lys Glu Asn Gly Ile Trp
            100                 105                 110

Ser Thr Glu Ile Leu Lys Asn Phe Lys Asn Lys Thr Phe Leu Lys Cys
        115                 120                 125

Glu Ala Pro Asn Tyr Ser Gly Arg Phe Thr Cys Ser Trp Leu Val Gln
    130                 135                 140

Arg Asn Met Asp Leu Lys Phe Asn Ile Lys Ser Ser Ser Ser Ser Pro
145                 150                 155                 160

Asp Ser Arg Ala Val Thr Cys Gly Met Ala Ser Leu Ser Ala Glu Lys
                165                 170                 175

Val Thr Leu Asp Gln Arg Asp Tyr Glu Lys Tyr Ser Val Ser Cys Gln
            180                 185                 190

Glu Asp Val Thr Cys Pro Thr Ala Glu Glu Thr Leu Pro Ile Glu Leu
        195                 200                 205

Ala Leu Glu Ala Arg Gln Gln Asn Lys Tyr Glu Asn Tyr Ser Thr Ser
    210                 215                 220

Phe Phe Ile Arg Asp Ile Ile Lys Pro Asp Pro Pro Lys Asn Leu Gln
225                 230                 235                 240

Met Lys Pro Leu Lys Asn Ser Gln Val Glu Val Ser Trp Glu Tyr Pro
                245                 250                 255

Asp Ser Trp Ser Thr Pro His Ser Tyr Phe Ser Leu Lys Phe Phe Val
            260                 265                 270

Arg Ile Gln Arg Lys Lys Glu Lys Met Lys Glu Thr Glu Glu Gly Cys
        275                 280                 285

Asn Gln Lys Gly Ala Phe Leu Val Glu Lys Thr Ser Thr Glu Val Gln
    290                 295                 300

Cys Lys Gly Gly Asn Val Cys Val Gln Ala Gln Asp Arg Tyr Tyr Asn
305                 310                 315                 320

Ser Ser Cys Ser Lys Trp Ala Cys Val Pro Cys Arg Val Arg Ser
                325                 330                 335
```

<210> SEQ ID NO 41
<211> LENGTH: 179
<212> TYPE: PRT
<213> ORGANISM: Homo sapiens

<400> SEQUENCE: 41

```
Met Ala Ala Leu Gln Lys Ser Val Ser Ser Phe Leu Met Gly Thr Leu
1               5                   10                  15

Ala Thr Ser Cys Leu Leu Leu Leu Ala Leu Leu Val Gln Gly Gly Ala
            20                  25                  30

Ala Ala Pro Ile Ser Ser His Cys Arg Leu Asp Lys Ser Asn Phe Gln
        35                  40                  45

Gln Pro Tyr Ile Thr Asn Arg Thr Phe Met Leu Ala Lys Glu Ala Ser
    50                  55                  60

Leu Ala Asp Asn Asn Thr Asp Val Arg Leu Ile Gly Glu Lys Leu Phe
65                  70                  75                  80

His Gly Val Ser Met Ser Glu Arg Cys Tyr Leu Met Lys Gln Val Leu
                85                  90                  95

Asn Phe Thr Leu Glu Glu Val Leu Phe Pro Gln Ser Asp Arg Phe Gln
            100                 105                 110

Pro Tyr Met Gln Glu Val Val Pro Phe Leu Ala Arg Leu Ser Asn Arg
        115                 120                 125
```

Leu Ser Thr Cys His Ile Glu Gly Asp Asp Leu His Ile Gln Arg Asn
130 135 140

Val Gln Lys Leu Lys Asp Thr Val Lys Lys Leu Gly Glu Ser Gly Glu
145 150 155 160

Ile Lys Ala Ile Gly Glu Leu Asp Leu Leu Phe Met Ser Leu Arg Asn
165 170 175

Ala Cys Ile

<210> SEQ ID NO 42
<211> LENGTH: 179
<212> TYPE: PRT
<213> ORGANISM: Murine sp.

<400> SEQUENCE: 42

Met Ala Val Leu Gln Lys Ser Met Ser Phe Ser Leu Met Gly Thr Leu
1 5 10 15

Ala Ala Ser Cys Leu Leu Leu Ile Ala Leu Trp Ala Gln Glu Ala Asn
20 25 30

Ala Leu Pro Val Asn Thr Arg Cys Lys Leu Glu Val Ser Asn Phe Gln
35 40 45

Gln Pro Tyr Ile Val Asn Arg Thr Phe Met Leu Ala Lys Glu Ala Ser
50 55 60

Leu Ala Asp Asn Asn Thr Asp Val Arg Leu Ile Gly Glu Lys Leu Phe
65 70 75 80

Arg Gly Val Ser Ala Lys Asp Gln Cys Tyr Leu Met Lys Gln Val Leu
85 90 95

Asn Phe Thr Leu Glu Asp Val Leu Leu Pro Gln Ser Asp Arg Phe Gln
100 105 110

Pro Tyr Met Gln Glu Val Val Pro Phe Leu Thr Lys Leu Ser Asn Gln
115 120 125

Leu Ser Ser Cys His Ile Ser Gly Asp Asp Gln Asn Ile Gln Lys Asn
130 135 140

Val Arg Arg Leu Lys Glu Thr Val Lys Lys Leu Gly Glu Ser Gly Glu
145 150 155 160

Ile Lys Ala Ile Gly Glu Leu Asp Leu Leu Phe Met Ser Leu Arg Asn
165 170 175

Ala Cys Val

<210> SEQ ID NO 43
<211> LENGTH: 390
<212> TYPE: PRT
<213> ORGANISM: Homo sapiens

<400> SEQUENCE: 43

Met Pro Pro Ser Gly Leu Arg Leu Leu Pro Leu Leu Leu Pro Leu Leu
1 5 10 15

Trp Leu Leu Val Leu Thr Pro Gly Arg Pro Ala Ala Gly Leu Ser Thr
20 25 30

Cys Lys Thr Ile Asp Met Glu Leu Val Lys Arg Lys Arg Ile Glu Ala
35 40 45

Ile Arg Gly Gln Ile Leu Ser Lys Leu Arg Leu Ala Ser Pro Pro Ser
50 55 60

Gln Gly Glu Val Pro Pro Gly Pro Leu Pro Glu Ala Val Leu Ala Leu
65 70 75 80

Tyr Asn Ser Thr Arg Asp Arg Val Ala Gly Glu Ser Ala Glu Pro Glu

```
                85                  90                  95

Pro Glu Pro Glu Ala Asp Tyr Tyr Ala Lys Glu Val Thr Arg Val Leu
            100                 105                 110

Met Val Glu Thr His Asn Glu Ile Tyr Asp Lys Phe Lys Gln Ser Thr
        115                 120                 125

His Ser Ile Tyr Met Phe Phe Asn Thr Ser Glu Leu Arg Glu Ala Val
    130                 135                 140

Pro Glu Pro Val Leu Leu Ser Arg Ala Glu Leu Arg Leu Leu Arg Leu
145                 150                 155                 160

Lys Leu Lys Val Glu Gln His Val Glu Leu Tyr Gln Lys Tyr Ser Asn
                165                 170                 175

Asn Ser Trp Arg Tyr Leu Ser Asn Arg Leu Leu Ala Pro Ser Asp Ser
            180                 185                 190

Pro Glu Trp Leu Ser Phe Asp Val Thr Gly Val Val Arg Gln Trp Leu
        195                 200                 205

Ser Arg Gly Gly Glu Ile Glu Gly Phe Arg Leu Ser Ala His Cys Ser
    210                 215                 220

Cys Asp Ser Arg Asp Asn Thr Leu Gln Val Asp Ile Asn Gly Phe Thr
225                 230                 235                 240

Thr Gly Arg Arg Gly Asp Leu Ala Thr Ile His Gly Met Asn Arg Pro
                245                 250                 255

Phe Leu Leu Leu Met Ala Thr Pro Leu Glu Arg Ala Gln His Leu Gln
            260                 265                 270

Ser Ser Arg His Arg Arg Ala Leu Asp Thr Asn Tyr Cys Phe Ser Ser
        275                 280                 285

Thr Glu Lys Asn Cys Cys Val Arg Gln Leu Tyr Ile Asp Phe Arg Lys
    290                 295                 300

Asp Leu Gly Trp Lys Trp Ile His Glu Pro Lys Gly Tyr His Ala Asn
305                 310                 315                 320

Phe Cys Leu Gly Pro Cys Pro Tyr Ile Trp Ser Leu Asp Thr Gln Tyr
                325                 330                 335

Ser Lys Val Leu Ala Leu Tyr Asn Gln His Asn Pro Gly Ala Ser Ala
            340                 345                 350

Ala Pro Cys Cys Val Pro Gln Ala Leu Glu Pro Leu Pro Ile Val Tyr
        355                 360                 365

Tyr Val Gly Arg Lys Pro Lys Val Glu Gln Leu Ser Asn Met Ile Val
    370                 375                 380

Arg Ser Cys Lys Cys Ser
385                 390


<210> SEQ ID NO 44
<211> LENGTH: 390
<212> TYPE: PRT
<213> ORGANISM: Murine sp.

<400> SEQUENCE: 44

Met Pro Pro Ser Gly Leu Arg Leu Leu Pro Leu Leu Leu Pro Leu Pro
1               5                   10                  15

Trp Leu Leu Val Leu Thr Pro Gly Arg Pro Ala Ala Gly Leu Ser Thr
            20                  25                  30

Cys Lys Thr Ile Asp Met Glu Leu Val Lys Arg Lys Arg Ile Glu Ala
        35                  40                  45

Ile Arg Gly Gln Ile Leu Ser Lys Leu Arg Leu Ala Ser Pro Pro Ser
    50                  55                  60
```

```
Gln Gly Glu Val Pro Pro Gly Pro Leu Pro Glu Ala Val Leu Ala Leu
65                  70                  75                  80

Tyr Asn Ser Thr Arg Asp Arg Val Ala Gly Glu Ser Ala Asp Pro Glu
                85                  90                  95

Pro Glu Pro Glu Ala Asp Tyr Tyr Ala Lys Glu Val Thr Arg Val Leu
            100                 105                 110

Met Val Asp Arg Asn Asn Ala Ile Tyr Glu Lys Thr Lys Asp Ile Ser
        115                 120                 125

His Ser Ile Tyr Met Phe Phe Asn Thr Ser Asp Ile Arg Glu Ala Val
    130                 135                 140

Pro Glu Pro Pro Leu Leu Ser Arg Ala Glu Leu Arg Leu Gln Arg Leu
145                 150                 155                 160

Lys Ser Ser Val Glu Gln His Val Glu Leu Tyr Gln Lys Tyr Ser Asn
                165                 170                 175

Asn Ser Trp Arg Tyr Leu Gly Asn Arg Leu Leu Thr Pro Thr Asp Thr
            180                 185                 190

Pro Glu Trp Leu Ser Phe Asp Val Thr Gly Val Val Arg Gln Trp Leu
        195                 200                 205

Asn Gln Gly Asp Gly Ile Gln Gly Phe Arg Phe Ser Ala His Cys Ser
    210                 215                 220

Cys Asp Ser Lys Asp Asn Lys Leu His Val Glu Ile Asn Gly Ile Ser
225                 230                 235                 240

Pro Lys Arg Arg Gly Asp Leu Gly Thr Ile His Asp Met Asn Arg Pro
                245                 250                 255

Phe Leu Leu Leu Met Ala Thr Pro Leu Glu Arg Ala Gln His Leu His
            260                 265                 270

Ser Ser Arg His Arg Arg Ala Leu Asp Thr Asn Tyr Cys Phe Ser Ser
        275                 280                 285

Thr Glu Lys Asn Cys Cys Val Arg Gln Leu Tyr Ile Asp Phe Arg Lys
    290                 295                 300

Asp Leu Gly Trp Lys Trp Ile His Glu Pro Lys Gly Tyr His Ala Asn
305                 310                 315                 320

Phe Cys Leu Gly Pro Cys Pro Tyr Ile Trp Ser Leu Asp Thr Gln Tyr
                325                 330                 335

Ser Lys Val Leu Ala Leu Tyr Asn Gln His Asn Pro Gly Ala Ser Ala
            340                 345                 350

Ser Pro Cys Cys Val Pro Gln Ala Leu Glu Pro Leu Pro Ile Val Tyr
        355                 360                 365

Tyr Val Gly Arg Lys Pro Lys Val Glu Gln Leu Ser Asn Met Ile Val
    370                 375                 380

Arg Ser Cys Lys Cys Ser
385                 390


<210> SEQ ID NO 45
<211> LENGTH: 431
<212> TYPE: PRT
<213> ORGANISM: Homo sapiens

<400> SEQUENCE: 45

Met Pro Asn Pro Arg Pro Gly Lys Pro Ser Ala Pro Ser Leu Ala Leu
1               5                   10                  15

Gly Pro Ser Pro Gly Ala Ser Pro Ser Trp Arg Ala Ala Pro Lys Ala
            20                  25                  30

Ser Asp Leu Leu Gly Ala Arg Gly Pro Gly Gly Thr Phe Gln Gly Arg
        35                  40                  45
```

```
Asp Leu Arg Gly Gly Ala His Ala Ser Ser Ser Ser Leu Asn Pro Met
    50                  55                  60

Pro Pro Ser Gln Leu Gln Leu Pro Thr Leu Pro Leu Val Met Val Ala
65                  70                  75                  80

Pro Ser Gly Ala Arg Leu Gly Pro Leu Pro His Leu Gln Ala Leu Leu
                85                  90                  95

Gln Asp Arg Pro His Phe Met His Gln Leu Ser Thr Val Asp Ala His
            100                 105                 110

Ala Arg Thr Pro Val Leu Gln Val His Pro Leu Glu Ser Pro Ala Met
        115                 120                 125

Ile Ser Leu Thr Pro Pro Thr Thr Ala Thr Gly Val Phe Ser Leu Lys
    130                 135                 140

Ala Arg Pro Gly Leu Pro Pro Gly Ile Asn Val Ala Ser Leu Glu Trp
145                 150                 155                 160

Val Ser Arg Glu Pro Ala Leu Leu Cys Thr Phe Pro Asn Pro Ser Ala
                165                 170                 175

Pro Arg Lys Asp Ser Thr Leu Ser Ala Val Pro Gln Ser Ser Tyr Pro
            180                 185                 190

Leu Leu Ala Asn Gly Val Cys Lys Trp Pro Gly Cys Glu Lys Val Phe
        195                 200                 205

Glu Glu Pro Glu Asp Phe Leu Lys His Cys Gln Ala Asp His Leu Leu
    210                 215                 220

Asp Glu Lys Gly Arg Ala Gln Cys Leu Leu Gln Arg Glu Met Val Gln
225                 230                 235                 240

Ser Leu Glu Gln Gln Leu Val Leu Glu Lys Glu Lys Leu Ser Ala Met
                245                 250                 255

Gln Ala His Leu Ala Gly Lys Met Ala Leu Thr Lys Ala Ser Ser Val
            260                 265                 270

Ala Ser Ser Asp Lys Gly Ser Cys Cys Ile Val Ala Ala Gly Ser Gln
        275                 280                 285

Gly Pro Val Val Pro Ala Trp Ser Gly Pro Arg Glu Ala Pro Asp Ser
    290                 295                 300

Leu Phe Ala Val Arg Arg His Leu Trp Gly Ser His Gly Asn Ser Thr
305                 310                 315                 320

Phe Pro Glu Phe Leu His Asn Met Asp Tyr Phe Lys Phe His Asn Met
                325                 330                 335

Arg Pro Pro Phe Thr Tyr Ala Thr Leu Ile Arg Trp Ala Ile Leu Glu
            340                 345                 350

Ala Pro Glu Lys Gln Arg Thr Leu Asn Glu Ile Tyr His Trp Phe Thr
        355                 360                 365

Arg Met Phe Ala Phe Phe Arg Asn His Pro Ala Thr Trp Lys Asn Ala
    370                 375                 380

Ile Arg His Asn Leu Ser Leu His Lys Cys Phe Val Arg Val Glu Ser
385                 390                 395                 400

Glu Lys Gly Ala Val Trp Thr Val Asp Glu Leu Glu Phe Arg Lys Lys
                405                 410                 415

Arg Ser Gln Arg Pro Ser Arg Cys Ser Asn Pro Thr Pro Gly Pro
            420                 425                 430
```

<210> SEQ ID NO 46
<211> LENGTH: 429
<212> TYPE: PRT
<213> ORGANISM: Murine sp.

<400> SEQUENCE: 46

```
Met Pro Asn Pro Arg Pro Ala Lys Pro Met Ala Pro Ser Leu Ala Leu
1               5                   10                  15

Gly Pro Ser Pro Gly Val Leu Pro Ser Trp Lys Thr Ala Pro Lys Gly
            20                  25                  30

Ser Glu Leu Leu Gly Thr Arg Gly Ser Gly Gly Pro Phe Gln Gly Arg
        35                  40                  45

Asp Leu Arg Ser Gly Ala His Thr Ser Ser Ser Leu Asn Pro Leu Pro
    50                  55                  60

Pro Ser Gln Leu Gln Leu Pro Thr Val Pro Leu Val Met Val Ala Pro
65                  70                  75                  80

Ser Gly Ala Arg Leu Gly Pro Ser Pro His Leu Gln Ala Leu Leu Gln
                85                  90                  95

Asp Arg Pro His Phe Met His Gln Leu Ser Thr Val Asp Ala His Ala
            100                 105                 110

Gln Thr Pro Val Leu Gln Val Arg Pro Leu Asp Asn Pro Ala Met Ile
        115                 120                 125

Ser Leu Pro Pro Pro Ser Ala Ala Thr Gly Val Phe Ser Leu Lys Ala
    130                 135                 140

Arg Pro Gly Leu Pro Pro Gly Ile Asn Val Ala Ser Leu Glu Trp Val
145                 150                 155                 160

Ser Arg Glu Pro Ala Leu Leu Cys Thr Phe Pro Arg Ser Gly Thr Pro
                165                 170                 175

Arg Lys Asp Ser Asn Leu Leu Ala Ala Pro Gln Gly Ser Tyr Pro Leu
            180                 185                 190

Leu Ala Asn Gly Val Cys Lys Trp Pro Gly Cys Glu Lys Val Phe Glu
        195                 200                 205

Glu Pro Glu Glu Phe Leu Lys His Cys Gln Ala Asp His Leu Leu Asp
    210                 215                 220

Glu Lys Gly Lys Ala Gln Cys Leu Leu Gln Arg Glu Val Val Gln Ser
225                 230                 235                 240

Leu Glu Gln Gln Leu Glu Leu Glu Lys Glu Lys Leu Gly Ala Met Gln
                245                 250                 255

Ala His Leu Ala Gly Lys Met Ala Leu Ala Lys Ala Pro Ser Val Ala
            260                 265                 270

Ser Met Asp Lys Ser Ser Cys Cys Ile Val Ala Thr Ser Thr Gln Gly
        275                 280                 285

Ser Val Leu Pro Ala Trp Ser Ala Pro Arg Glu Ala Pro Asp Gly Gly
    290                 295                 300

Leu Phe Ala Val Arg Arg His Leu Trp Gly Ser His Gly Asn Ser Ser
305                 310                 315                 320

Phe Pro Glu Phe Phe His Asn Met Asp Tyr Phe Lys Tyr His Asn Met
                325                 330                 335

Arg Pro Pro Phe Thr Tyr Ala Thr Leu Ile Arg Trp Ala Ile Leu Glu
            340                 345                 350

Ala Pro Glu Arg Gln Arg Thr Leu Asn Glu Ile Tyr His Trp Phe Thr
        355                 360                 365

Arg Met Phe Ala Tyr Phe Arg Asn His Pro Ala Thr Trp Lys Asn Ala
    370                 375                 380

Ile Arg His Asn Leu Ser Leu His Lys Cys Phe Val Arg Val Glu Ser
385                 390                 395                 400

Glu Lys Gly Ala Val Trp Thr Val Asp Glu Phe Glu Phe Arg Lys Lys
                405                 410                 415
```

```
Arg Ser Gln Arg Pro Asn Lys Cys Ser Asn Pro Cys Pro
            420                 425
```

<210> SEQ ID NO 47
<211> LENGTH: 251
<212> TYPE: PRT
<213> ORGANISM: Homo sapiens

<400> SEQUENCE: 47

```
Met Ala Glu Asp Leu Gly Leu Ser Phe Gly Glu Thr Ala Ser Val Glu
1               5                   10                  15

Met Leu Pro Glu His Gly Ser Cys Arg Pro Lys Ala Arg Ser Ser Ser
            20                  25                  30

Ala Arg Trp Ala Leu Thr Cys Cys Leu Val Leu Leu Pro Phe Leu Ala
        35                  40                  45

Gly Leu Thr Thr Tyr Leu Leu Val Ser Gln Leu Arg Ala Gln Gly Glu
    50                  55                  60

Ala Cys Val Gln Phe Gln Ala Leu Lys Gly Gln Glu Phe Ala Pro Ser
65                  70                  75                  80

His Gln Gln Val Tyr Ala Pro Leu Arg Ala Asp Gly Asp Lys Pro Arg
                85                  90                  95

Ala His Leu Thr Val Val Arg Gln Thr Pro Thr Gln His Phe Lys Asn
            100                 105                 110

Gln Phe Pro Ala Leu His Trp Glu His Glu Leu Gly Leu Ala Phe Thr
        115                 120                 125

Lys Asn Arg Met Asn Tyr Thr Asn Lys Phe Leu Leu Ile Pro Glu Ser
    130                 135                 140

Gly Asp Tyr Phe Ile Tyr Ser Gln Val Thr Phe Arg Gly Met Thr Ser
145                 150                 155                 160

Glu Cys Ser Glu Ile Arg Gln Ala Gly Arg Pro Asn Lys Pro Asp Ser
                165                 170                 175

Ile Thr Val Val Ile Thr Lys Val Thr Asp Ser Tyr Pro Glu Pro Thr
            180                 185                 190

Gln Leu Leu Met Gly Thr Lys Ser Val Cys Glu Val Gly Ser Asn Trp
        195                 200                 205

Phe Gln Pro Ile Tyr Leu Gly Ala Met Phe Ser Leu Gln Glu Gly Asp
    210                 215                 220

Lys Leu Met Val Asn Val Ser Asp Ile Ser Leu Val Asp Tyr Thr Lys
225                 230                 235                 240

Glu Asp Lys Thr Phe Phe Gly Ala Phe Leu Leu
                245                 250
```

<210> SEQ ID NO 48
<211> LENGTH: 252
<212> TYPE: PRT
<213> ORGANISM: Murine sp.

<400> SEQUENCE: 48

```
Met Ala Glu Glu Leu Gly Leu Gly Phe Gly Glu Gly Val Pro Val Glu
1               5                   10                  15

Val Leu Pro Glu Gly Cys Arg His Arg Pro Glu Ala Arg Ala Gly Leu
            20                  25                  30

Ala Ala Arg Ser Lys Ala Cys Leu Ala Leu Thr Cys Cys Leu Leu Ser
        35                  40                  45

Phe Pro Ile Leu Ala Gly Leu Ser Thr Leu Leu Met Ala Gly Gln Leu
    50                  55                  60
```

```
Arg Val Pro Gly Lys Asp Cys Met Leu Arg Ala Ile Thr Glu Glu Arg
65                  70                  75                  80

Ser Glu Pro Ser Pro Gln Gln Val Tyr Ser Pro Pro Arg Gly Lys Pro
                85                  90                  95

Arg Ala His Leu Thr Ile Lys Lys Gln Thr Pro Ala Pro His Leu Lys
            100                 105                 110

Asn Gln Leu Ser Ala Leu His Trp Glu His Asp Leu Gly Met Ala Phe
        115                 120                 125

Thr Lys Asn Gly Met Lys Tyr Ile Asn Lys Ser Leu Val Ile Pro Glu
    130                 135                 140

Ser Gly Asp Tyr Phe Ile Tyr Ser Gln Ile Thr Phe Arg Gly Thr Thr
145                 150                 155                 160

Ser Val Cys Gly Asp Ile Ser Arg Gly Arg Arg Pro Asn Lys Pro Asp
                165                 170                 175

Ser Ile Thr Met Val Ile Thr Lys Val Ala Asp Ser Tyr Pro Glu Pro
            180                 185                 190

Ala Arg Leu Leu Thr Gly Ser Lys Ser Val Cys Glu Ile Ser Asn Asn
        195                 200                 205

Trp Phe Gln Ser Leu Tyr Leu Gly Ala Thr Phe Ser Leu Glu Glu Gly
    210                 215                 220

Asp Arg Leu Met Val Asn Val Ser Asp Ile Ser Leu Val Asp Tyr Thr
225                 230                 235                 240

Lys Glu Asp Lys Thr Phe Phe Gly Ala Phe Leu Leu
                245                 250


<210> SEQ ID NO 49
<211> LENGTH: 155
<212> TYPE: PRT
<213> ORGANISM: Homo sapiens

<400> SEQUENCE: 49

Met Thr Pro Gly Lys Thr Ser Leu Val Ser Leu Leu Leu Leu Leu Ser
1               5                   10                  15

Leu Glu Ala Ile Val Lys Ala Gly Ile Thr Ile Pro Arg Asn Pro Gly
            20                  25                  30

Cys Pro Asn Ser Glu Asp Lys Asn Phe Pro Arg Thr Val Met Val Asn
        35                  40                  45

Leu Asn Ile His Asn Arg Asn Thr Asn Thr Asn Pro Lys Arg Ser Ser
    50                  55                  60

Asp Tyr Tyr Asn Arg Ser Thr Ser Pro Trp Asn Leu His Arg Asn Glu
65                  70                  75                  80

Asp Pro Glu Arg Tyr Pro Ser Val Ile Trp Glu Ala Lys Cys Arg His
                85                  90                  95

Leu Gly Cys Ile Asn Ala Asp Gly Asn Val Asp Tyr His Met Asn Ser
            100                 105                 110

Val Pro Ile Gln Gln Glu Ile Leu Val Leu Arg Arg Glu Pro Pro His
        115                 120                 125

Cys Pro Asn Ser Phe Arg Leu Glu Lys Ile Leu Val Ser Val Gly Cys
    130                 135                 140

Thr Cys Val Thr Pro Ile Val His His Val Ala
145                 150                 155


<210> SEQ ID NO 50
<211> LENGTH: 158
<212> TYPE: PRT
```

<213> ORGANISM: Murine sp.

<400> SEQUENCE: 50

```
Met Ser Pro Gly Arg Ala Ser Ser Val Ser Leu Met Leu Leu Leu Leu
1               5                   10                  15

Leu Ser Leu Ala Ala Thr Val Lys Ala Ala Ala Ile Ile Pro Gln Ser
            20                  25                  30

Ser Ala Cys Pro Asn Thr Glu Ala Lys Asp Phe Leu Gln Asn Val Lys
        35                  40                  45

Val Asn Leu Lys Val Phe Asn Ser Leu Gly Ala Lys Val Ser Ser Arg
    50                  55                  60

Arg Pro Ser Asp Tyr Leu Asn Arg Ser Thr Ser Pro Trp Thr Leu His
65                  70                  75                  80

Arg Asn Glu Asp Pro Asp Arg Tyr Pro Ser Val Ile Trp Glu Ala Gln
                85                  90                  95

Cys Arg His Gln Arg Cys Val Asn Ala Glu Gly Lys Leu Asp His His
            100                 105                 110

Met Asn Ser Val Leu Ile Gln Gln Glu Ile Leu Val Leu Lys Arg Glu
        115                 120                 125

Pro Glu Ser Cys Pro Phe Thr Phe Arg Val Glu Lys Met Leu Val Gly
    130                 135                 140

Val Gly Cys Thr Cys Val Ala Ser Ile Val Arg Gln Ala Ala
145                 150                 155
```

<210> SEQ ID NO 51
<211> LENGTH: 163
<212> TYPE: PRT
<213> ORGANISM: Homo sapiens

<400> SEQUENCE: 51

```
Met Thr Val Lys Thr Leu His Gly Pro Ala Met Val Lys Tyr Leu Leu
1               5                   10                  15

Leu Ser Ile Leu Gly Leu Ala Phe Leu Ser Glu Ala Ala Ala Arg Lys
            20                  25                  30

Ile Pro Lys Val Gly His Thr Phe Phe Gln Lys Pro Glu Ser Cys Pro
        35                  40                  45

Pro Val Pro Gly Gly Ser Met Lys Leu Asp Ile Gly Ile Ile Asn Glu
    50                  55                  60

Asn Gln Arg Val Ser Met Ser Arg Asn Ile Glu Ser Arg Ser Thr Ser
65                  70                  75                  80

Pro Trp Asn Tyr Thr Val Thr Trp Asp Pro Asn Arg Tyr Pro Ser Glu
                85                  90                  95

Val Val Gln Ala Gln Cys Arg Asn Leu Gly Cys Ile Asn Ala Gln Gly
            100                 105                 110

Lys Glu Asp Ile Ser Met Asn Ser Val Pro Ile Gln Gln Glu Thr Leu
        115                 120                 125

Val Val Arg Arg Lys His Gln Gly Cys Ser Val Ser Phe Gln Leu Glu
    130                 135                 140

Lys Val Leu Val Thr Val Gly Cys Thr Cys Val Thr Pro Val Ile His
145                 150                 155                 160

His Val Gln
```

<210> SEQ ID NO 52
<211> LENGTH: 161
<212> TYPE: PRT
<213> ORGANISM: Murine sp.

<400> SEQUENCE: 52

```
Met Lys Cys Thr Arg Glu Thr Ala Met Val Lys Ser Leu Leu Leu Leu
1               5                   10                  15

Met Leu Gly Leu Ala Ile Leu Arg Glu Val Ala Ala Arg Lys Asn Pro
            20                  25                  30

Lys Ala Gly Val Pro Ala Leu Gln Lys Ala Gly Asn Cys Pro Pro Leu
        35                  40                  45

Glu Asp Asn Thr Val Arg Val Asp Ile Arg Ile Phe Asn Gln Asn Gln
    50                  55                  60

Gly Ile Ser Val Pro Arg Glu Phe Gln Asn Arg Ser Ser Ser Pro Trp
65                  70                  75                  80

Asp Tyr Asn Ile Thr Arg Asp Pro His Arg Phe Pro Ser Glu Ile Ala
                85                  90                  95

Glu Ala Gln Cys Arg His Ser Gly Cys Ile Asn Ala Gln Gly Gln Glu
            100                 105                 110

Asp Ser Thr Met Asn Ser Val Ala Ile Gln Gln Glu Ile Leu Val Leu
        115                 120                 125

Arg Arg Glu Pro Gln Gly Cys Ser Asn Ser Phe Arg Leu Glu Lys Met
    130                 135                 140

Leu Leu Lys Val Gly Cys Thr Cys Val Lys Pro Ile Val His Gln Ala
145                 150                 155                 160

Ala
```

<210> SEQ ID NO 53
<211> LENGTH: 535
<212> TYPE: PRT
<213> ORGANISM: Homo sapiens

<400> SEQUENCE: 53

```
Met Gly Ile Val Glu Pro Gly Cys Gly Asp Met Leu Thr Gly Thr Glu
1               5                   10                  15

Pro Met Pro Gly Ser Asp Glu Gly Arg Ala Pro Gly Ala Asp Pro Gln
            20                  25                  30

His Arg Tyr Phe Tyr Pro Glu Pro Gly Ala Gln Asp Ala Asp Glu Arg
        35                  40                  45

Arg Gly Gly Gly Ser Leu Gly Ser Pro Tyr Pro Gly Gly Ala Leu Val
    50                  55                  60

Pro Ala Pro Pro Ser Arg Phe Leu Gly Ala Tyr Ala Tyr Pro Pro Arg
65                  70                  75                  80

Pro Gln Ala Ala Gly Phe Pro Gly Ala Gly Glu Ser Phe Pro Pro Pro
                85                  90                  95

Ala Asp Ala Glu Gly Tyr Gln Pro Gly Glu Gly Tyr Ala Ala Pro Asp
            100                 105                 110

Pro Arg Ala Gly Leu Tyr Pro Gly Pro Arg Glu Asp Tyr Ala Leu Pro
        115                 120                 125

Ala Gly Leu Glu Val Ser Gly Lys Leu Arg Val Ala Leu Asn Asn His
    130                 135                 140

Leu Leu Trp Ser Lys Phe Asn Gln His Gln Thr Glu Met Ile Ile Thr
145                 150                 155                 160

Lys Gln Gly Arg Arg Met Phe Pro Phe Leu Ser Phe Thr Val Ala Gly
                165                 170                 175

Leu Glu Pro Thr Ser His Tyr Arg Met Phe Val Asp Val Val Leu Val
            180                 185                 190
```

```
Asp Gln His His Trp Arg Tyr Gln Ser Gly Lys Trp Val Gln Cys Gly
        195                 200                 205

Lys Ala Glu Gly Ser Met Pro Gly Asn Arg Leu Tyr Val His Pro Asp
    210                 215                 220

Ser Pro Asn Thr Gly Ala His Trp Met Arg Gln Glu Val Ser Phe Gly
225                 230                 235                 240

Lys Leu Lys Leu Thr Asn Asn Lys Gly Ala Ser Asn Asn Val Thr Gln
                245                 250                 255

Met Ile Val Leu Gln Ser Leu His Lys Tyr Gln Pro Arg Leu His Ile
            260                 265                 270

Val Glu Val Asn Asp Gly Glu Pro Glu Ala Ala Cys Asn Ala Ser Asn
        275                 280                 285

Thr His Ile Phe Thr Phe Gln Glu Thr Gln Phe Ile Ala Val Thr Ala
    290                 295                 300

Tyr Gln Asn Ala Glu Ile Thr Gln Leu Lys Ile Asp Asn Asn Pro Phe
305                 310                 315                 320

Ala Lys Gly Phe Arg Glu Asn Phe Glu Ser Met Tyr Thr Ser Val Asp
                325                 330                 335

Thr Ser Ile Pro Ser Pro Pro Gly Pro Asn Cys Gln Phe Leu Gly Gly
            340                 345                 350

Asp His Tyr Ser Pro Leu Leu Pro Asn Gln Tyr Pro Val Pro Ser Arg
        355                 360                 365

Phe Tyr Pro Asp Leu Pro Gly Gln Ala Lys Asp Val Val Pro Gln Ala
    370                 375                 380

Tyr Trp Leu Gly Ala Pro Arg Asp His Ser Tyr Glu Ala Glu Phe Arg
385                 390                 395                 400

Ala Val Ser Met Lys Pro Ala Phe Leu Pro Ser Ala Pro Gly Pro Thr
                405                 410                 415

Met Ser Tyr Tyr Arg Gly Gln Glu Val Leu Ala Pro Gly Ala Gly Trp
            420                 425                 430

Pro Val Ala Pro Gln Tyr Pro Pro Lys Met Gly Pro Ala Ser Trp Phe
        435                 440                 445

Arg Pro Met Arg Thr Leu Pro Met Glu Pro Gly Pro Gly Gly Ser Glu
    450                 455                 460

Gly Arg Gly Pro Glu Asp Gln Gly Pro Pro Leu Val Trp Thr Glu Ile
465                 470                 475                 480

Ala Pro Ile Arg Pro Glu Ser Ser Asp Ser Gly Leu Gly Glu Gly Asp
                485                 490                 495

Ser Lys Arg Arg Arg Val Ser Pro Tyr Pro Ser Ser Gly Asp Ser Ser
            500                 505                 510

Ser Pro Ala Gly Ala Pro Ser Pro Phe Asp Lys Glu Ala Glu Gly Gln
        515                 520                 525

Phe Tyr Asn Tyr Phe Pro Asn
    530                 535


<210> SEQ ID NO 54
<211> LENGTH: 530
<212> TYPE: PRT
<213> ORGANISM: Murine sp.

<400> SEQUENCE: 54

Met Gly Ile Val Glu Pro Gly Cys Gly Asp Met Leu Thr Gly Thr Glu
1               5                   10                  15

Pro Met Pro Ser Asp Glu Gly Arg Gly Pro Gly Ala Asp Gln Gln His
            20                  25                  30
```

```
Arg Phe Phe Tyr Pro Glu Pro Gly Ala Gln Asp Pro Thr Asp Arg Arg
        35                  40                  45

Ala Gly Ser Ser Leu Gly Thr Pro Tyr Ser Gly Gly Ala Leu Val Pro
    50                  55                  60

Ala Ala Pro Gly Arg Phe Leu Gly Ser Phe Ala Tyr Pro Pro Arg Ala
65                  70                  75                  80

Gln Val Ala Gly Phe Pro Gly Pro Gly Glu Phe Phe Pro Pro Pro Ala
                85                  90                  95

Gly Ala Glu Gly Tyr Pro Pro Val Asp Gly Tyr Pro Ala Pro Asp Pro
            100                 105                 110

Arg Ala Gly Leu Tyr Pro Gly Pro Arg Glu Asp Tyr Ala Leu Pro Ala
        115                 120                 125

Gly Leu Glu Val Ser Gly Lys Leu Arg Val Ala Leu Ser Asn His Leu
    130                 135                 140

Leu Trp Ser Lys Phe Asn Gln His Gln Thr Glu Met Ile Ile Thr Lys
145                 150                 155                 160

Gln Gly Arg Arg Met Phe Pro Phe Leu Ser Phe Thr Val Ala Gly Leu
                165                 170                 175

Glu Pro Thr Ser His Tyr Arg Met Phe Val Asp Val Val Leu Val Asp
            180                 185                 190

Gln His His Trp Arg Tyr Gln Ser Gly Lys Trp Val Gln Cys Gly Lys
        195                 200                 205

Ala Glu Gly Ser Met Pro Gly Asn Arg Leu Tyr Val His Pro Asp Ser
    210                 215                 220

Pro Asn Thr Gly Ala His Trp Met Arg Gln Glu Val Ser Phe Gly Lys
225                 230                 235                 240

Leu Lys Leu Thr Asn Asn Lys Gly Ala Ser Asn Asn Val Thr Gln Met
                245                 250                 255

Ile Val Leu Gln Ser Leu His Lys Tyr Gln Pro Arg Leu His Ile Val
            260                 265                 270

Glu Val Asn Asp Gly Glu Pro Glu Ala Ala Cys Ser Ala Ser Asn Thr
        275                 280                 285

His Val Phe Thr Phe Gln Glu Thr Gln Phe Ile Ala Val Thr Ala Tyr
    290                 295                 300

Gln Asn Ala Glu Ile Thr Gln Leu Lys Ile Asp Asn Asn Pro Phe Ala
305                 310                 315                 320

Lys Gly Phe Arg Glu Asn Phe Glu Ser Met Tyr Ala Ser Val Asp Thr
                325                 330                 335

Ser Val Pro Ser Pro Pro Gly Pro Asn Cys Gln Leu Leu Gly Gly Asp
            340                 345                 350

Pro Phe Ser Pro Leu Leu Ser Asn Gln Tyr Pro Val Pro Ser Arg Phe
        355                 360                 365

Tyr Pro Asp Leu Pro Gly Gln Pro Lys Asp Met Ile Ser Gln Pro Tyr
    370                 375                 380

Trp Leu Gly Thr Pro Arg Glu His Ser Tyr Glu Ala Glu Phe Arg Ala
385                 390                 395                 400

Val Ser Met Lys Pro Thr Leu Leu Pro Ser Ala Pro Gly Pro Thr Val
                405                 410                 415

Pro Tyr Tyr Arg Gly Gln Asp Val Leu Ala Pro Gly Ala Gly Trp Pro
            420                 425                 430

Val Ala Pro Gln Tyr Pro Pro Lys Met Ser Pro Ala Gly Trp Phe Arg
        435                 440                 445
```

```
Pro Met Arg Thr Leu Pro Met Asp Pro Gly Leu Gly Ser Ser Glu Glu
    450                 455                 460

Gln Gly Ser Ser Pro Ser Leu Trp Pro Glu Val Thr Ser Leu Gln Pro
465                 470                 475                 480

Glu Ser Ser Asp Ser Gly Leu Gly Glu Gly Asp Thr Lys Arg Arg Arg
                485                 490                 495

Ile Ser Pro Tyr Pro Ser Ser Gly Asp Ser Ser Ser Pro Ala Gly Ala
            500                 505                 510

Pro Ser Pro Phe Asp Lys Glu Thr Glu Gly Gln Phe Tyr Asn Tyr Phe
        515                 520                 525

Pro Asn
    530


<210> SEQ ID NO 55
<211> LENGTH: 518
<212> TYPE: PRT
<213> ORGANISM: Homo sapiens

<400> SEQUENCE: 55

Met Asp Arg Ala Pro Gln Arg Gln His Arg Ala Ser Arg Glu Leu Leu
1               5                   10                  15

Ala Ala Lys Lys Thr His Thr Ser Gln Ile Glu Val Ile Pro Cys Lys
            20                  25                  30

Ile Cys Gly Asp Lys Ser Ser Gly Ile His Tyr Gly Val Ile Thr Cys
        35                  40                  45

Glu Gly Cys Lys Gly Phe Phe Arg Arg Ser Gln Arg Cys Asn Ala Ala
    50                  55                  60

Tyr Ser Cys Thr Arg Gln Gln Asn Cys Pro Ile Asp Arg Thr Ser Arg
65                  70                  75                  80

Asn Arg Cys Gln His Cys Arg Leu Gln Lys Cys Leu Ala Leu Gly Met
                85                  90                  95

Ser Arg Asp Ala Val Lys Phe Gly Arg Met Ser Lys Lys Gln Arg Asp
            100                 105                 110

Ser Leu His Ala Glu Val Gln Lys Gln Leu Gln Gln Arg Gln Gln Gln
        115                 120                 125

Gln Gln Glu Pro Val Val Lys Thr Pro Pro Ala Gly Ala Gln Gly Ala
    130                 135                 140

Asp Thr Leu Thr Tyr Thr Leu Gly Leu Pro Asp Gly Gln Leu Pro Leu
145                 150                 155                 160

Gly Ser Ser Pro Asp Leu Pro Glu Ala Ser Ala Cys Pro Pro Gly Leu
                165                 170                 175

Leu Lys Ala Ser Gly Ser Gly Pro Ser Tyr Ser Asn Asn Leu Ala Lys
            180                 185                 190

Ala Gly Leu Asn Gly Ala Ser Cys His Leu Glu Tyr Ser Pro Glu Arg
        195                 200                 205

Gly Lys Ala Glu Gly Arg Glu Ser Phe Tyr Ser Thr Gly Ser Gln Leu
    210                 215                 220

Thr Pro Asp Arg Cys Gly Leu Arg Phe Glu Glu His Arg His Pro Gly
225                 230                 235                 240

Leu Gly Glu Leu Gly Gln Gly Pro Asp Ser Tyr Gly Ser Pro Ser Phe
                245                 250                 255

Arg Ser Thr Pro Glu Ala Pro Tyr Ala Ser Leu Thr Glu Ile Glu His
            260                 265                 270

Leu Val Gln Ser Val Cys Lys Ser Tyr Arg Glu Thr Cys Gln Leu Arg
        275                 280                 285
```

```
Leu Glu Asp Leu Leu Arg Gln Arg Ser Asn Ile Phe Ser Arg Glu Glu
    290                 295                 300

Val Thr Gly Tyr Gln Arg Lys Ser Met Trp Glu Met Trp Glu Arg Cys
305                 310                 315                 320

Ala His His Leu Thr Glu Ala Ile Gln Tyr Val Val Glu Phe Ala Lys
                325                 330                 335

Arg Leu Ser Gly Phe Met Glu Leu Cys Gln Asn Asp Gln Ile Val Leu
            340                 345                 350

Leu Lys Ala Gly Ala Met Glu Val Val Leu Val Arg Met Cys Arg Ala
        355                 360                 365

Tyr Asn Ala Asp Asn Arg Thr Val Phe Phe Glu Gly Lys Tyr Gly Gly
    370                 375                 380

Met Glu Leu Phe Arg Ala Leu Gly Cys Ser Glu Leu Ile Ser Ser Ile
385                 390                 395                 400

Phe Asp Phe Ser His Ser Leu Ser Ala Leu His Phe Ser Glu Asp Glu
                405                 410                 415

Ile Ala Leu Tyr Thr Ala Leu Val Leu Ile Asn Ala His Arg Pro Gly
            420                 425                 430

Leu Gln Glu Lys Arg Lys Val Glu Gln Leu Gln Tyr Asn Leu Glu Leu
        435                 440                 445

Ala Phe His His His Leu Cys Lys Thr His Arg Gln Ser Ile Leu Ala
    450                 455                 460

Lys Leu Pro Pro Lys Gly Lys Leu Arg Ser Leu Cys Ser Gln His Val
465                 470                 475                 480

Glu Arg Leu Gln Ile Phe Gln His Leu His Pro Ile Val Val Gln Ala
                485                 490                 495

Ala Phe Pro Pro Leu Tyr Lys Glu Leu Phe Ser Thr Glu Thr Glu Ser
            500                 505                 510

Pro Val Gly Leu Ser Lys
        515
```

<210> SEQ ID NO 56
<211> LENGTH: 516
<212> TYPE: PRT
<213> ORGANISM: Murine sp.

<400> SEQUENCE: 56

```
Met Asp Arg Ala Pro Gln Arg His His Arg Thr Ser Arg Glu Leu Leu
1               5                   10                  15

Ala Ala Lys Lys Thr His Thr Ser Gln Ile Glu Val Ile Pro Cys Lys
            20                  25                  30

Ile Cys Gly Asp Lys Ser Ser Gly Ile His Tyr Gly Val Ile Thr Cys
        35                  40                  45

Glu Gly Cys Lys Gly Phe Phe Arg Arg Ser Gln Gln Cys Asn Val Ala
    50                  55                  60

Tyr Ser Cys Thr Arg Gln Gln Asn Cys Pro Ile Asp Arg Thr Ser Arg
65                  70                  75                  80

Asn Arg Cys Gln His Cys Arg Leu Gln Lys Cys Leu Ala Leu Gly Met
                85                  90                  95

Ser Arg Asp Ala Val Lys Phe Gly Arg Met Ser Lys Lys Gln Arg Asp
            100                 105                 110

Ser Leu His Ala Glu Val Gln Lys Gln Leu Gln Gln Gln Gln Gln Gln
        115                 120                 125

Glu Gln Val Ala Lys Thr Pro Pro Ala Gly Ser Arg Gly Ala Asp Thr
```

```
    130                 135                 140

Leu Thr Tyr Thr Leu Gly Leu Ser Asp Gly Gln Leu Pro Leu Gly Ala
145                 150                 155                 160

Ser Pro Asp Leu Pro Glu Ala Ser Ala Cys Pro Pro Gly Leu Leu Arg
                165                 170                 175

Ala Ser Gly Ser Gly Pro Pro Tyr Ser Asn Thr Leu Ala Lys Thr Glu
            180                 185                 190

Val Gln Gly Ala Ser Cys His Leu Glu Tyr Ser Pro Glu Arg Gly Lys
        195                 200                 205

Ala Glu Gly Arg Asp Ser Ile Tyr Ser Thr Asp Gly Gln Leu Thr Leu
    210                 215                 220

Gly Arg Cys Gly Leu Arg Phe Glu Glu Thr Arg His Pro Glu Leu Gly
225                 230                 235                 240

Glu Pro Glu Gln Gly Pro Asp Ser His Cys Ile Pro Ser Phe Cys Ser
                245                 250                 255

Ala Pro Glu Val Pro Tyr Ala Ser Leu Thr Asp Ile Glu Tyr Leu Val
            260                 265                 270

Gln Asn Val Cys Lys Ser Phe Arg Glu Thr Cys Gln Leu Arg Leu Glu
        275                 280                 285

Asp Leu Leu Arg Gln Arg Thr Asn Leu Phe Ser Arg Glu Glu Val Thr
    290                 295                 300

Ser Tyr Gln Arg Lys Ser Met Trp Glu Met Trp Glu Arg Cys Ala His
305                 310                 315                 320

His Leu Thr Glu Ala Ile Gln Tyr Val Val Glu Phe Ala Lys Arg Leu
                325                 330                 335

Ser Gly Phe Met Glu Leu Cys Gln Asn Asp Gln Ile Ile Leu Leu Lys
            340                 345                 350

Ala Gly Ala Met Glu Val Val Leu Val Arg Met Cys Arg Ala Tyr Asn
        355                 360                 365

Ala Asn Asn His Thr Val Phe Phe Glu Gly Lys Tyr Gly Gly Val Glu
    370                 375                 380

Leu Phe Arg Ala Leu Gly Cys Ser Glu Leu Ile Ser Ser Ile Phe Asp
385                 390                 395                 400

Phe Ser His Phe Leu Ser Ala Leu Cys Phe Ser Glu Asp Glu Ile Ala
                405                 410                 415

Leu Tyr Thr Ala Leu Val Leu Ile Asn Ala Asn Arg Pro Gly Leu Gln
            420                 425                 430

Glu Lys Arg Arg Val Glu His Leu Gln Tyr Asn Leu Glu Leu Ala Phe
        435                 440                 445

His His His Leu Cys Lys Thr His Arg Gln Gly Leu Leu Ala Lys Leu
    450                 455                 460

Pro Pro Lys Gly Lys Leu Arg Ser Leu Cys Ser Gln His Val Glu Lys
465                 470                 475                 480

Leu Gln Ile Phe Gln His Leu His Pro Ile Val Val Gln Ala Ala Phe
                485                 490                 495

Pro Pro Leu Tyr Lys Glu Leu Phe Ser Thr Asp Val Glu Ser Pro Glu
            500                 505                 510

Gly Leu Ser Lys
        515
```

<210> SEQ ID NO 57
<211> LENGTH: 218
<212> TYPE: PRT
<213> ORGANISM: Homo sapiens

<400> SEQUENCE: 57

```
Met Ala Thr Arg Ser Pro Gly Val Val Ile Ser Asp Asp Glu Pro Gly
1               5                   10                  15

Tyr Asp Leu Asp Leu Phe Cys Ile Pro Asn His Tyr Ala Glu Asp Leu
            20                  25                  30

Glu Arg Val Phe Ile Pro His Gly Leu Ile Met Asp Arg Thr Glu Arg
        35                  40                  45

Leu Ala Arg Asp Val Met Lys Glu Met Gly Gly His His Ile Val Ala
    50                  55                  60

Leu Cys Val Leu Lys Gly Gly Tyr Lys Phe Phe Ala Asp Leu Leu Asp
65                  70                  75                  80

Tyr Ile Lys Ala Leu Asn Arg Asn Ser Asp Arg Ser Ile Pro Met Thr
                85                  90                  95

Val Asp Phe Ile Arg Leu Lys Ser Tyr Cys Asn Asp Gln Ser Thr Gly
            100                 105                 110

Asp Ile Lys Val Ile Gly Gly Asp Asp Leu Ser Thr Leu Thr Gly Lys
        115                 120                 125

Asn Val Leu Ile Val Glu Asp Ile Ile Asp Thr Gly Lys Thr Met Gln
    130                 135                 140

Thr Leu Leu Ser Leu Val Arg Gln Tyr Asn Pro Lys Met Val Lys Val
145                 150                 155                 160

Ala Ser Leu Leu Val Lys Arg Thr Pro Arg Ser Val Gly Tyr Lys Pro
                165                 170                 175

Asp Phe Val Gly Phe Glu Ile Pro Asp Lys Phe Val Val Gly Tyr Ala
            180                 185                 190

Leu Asp Tyr Asn Glu Tyr Phe Arg Asp Leu Asn His Val Cys Val Ile
        195                 200                 205

Ser Glu Thr Gly Lys Ala Lys Tyr Lys Ala
    210                 215
```

<210> SEQ ID NO 58
<211> LENGTH: 218
<212> TYPE: PRT
<213> ORGANISM: Murine sp.

<400> SEQUENCE: 58

```
Met Pro Thr Arg Ser Pro Ser Val Val Ile Ser Asp Asp Glu Pro Gly
1               5                   10                  15

Tyr Asp Leu Asp Leu Phe Cys Ile Pro Asn His Tyr Ala Glu Asp Leu
            20                  25                  30

Glu Lys Val Phe Ile Pro His Gly Leu Ile Met Asp Arg Thr Glu Arg
        35                  40                  45

Leu Ala Arg Asp Val Met Lys Glu Met Gly Gly His His Ile Val Ala
    50                  55                  60

Leu Cys Val Leu Lys Gly Gly Tyr Lys Phe Phe Ala Asp Leu Leu Asp
65                  70                  75                  80

Tyr Ile Lys Ala Leu Asn Arg Asn Ser Asp Arg Ser Ile Pro Met Thr
                85                  90                  95

Val Asp Phe Ile Arg Leu Lys Ser Tyr Cys Asn Asp Gln Ser Thr Gly
            100                 105                 110

Asp Ile Lys Val Ile Gly Gly Asp Asp Leu Ser Thr Leu Thr Gly Lys
        115                 120                 125

Asn Val Leu Ile Val Glu Asp Ile Ile Asp Thr Gly Lys Thr Met Gln
    130                 135                 140
```

```
Thr Leu Leu Ser Leu Val Lys Gln Tyr Ser Pro Lys Met Val Lys Val
145                 150                 155                 160

Ala Ser Leu Leu Val Lys Arg Thr Ser Arg Ser Val Gly Tyr Arg Pro
                165                 170                 175

Asp Phe Val Gly Phe Glu Ile Pro Asp Lys Phe Val Val Gly Tyr Ala
            180                 185                 190

Leu Asp Tyr Asn Glu Tyr Phe Arg Asp Leu Asn His Val Cys Val Ile
        195                 200                 205

Ser Glu Thr Gly Lys Ala Lys Tyr Lys Ala
    210                 215


<210> SEQ ID NO 59
<211> LENGTH: 375
<212> TYPE: PRT
<213> ORGANISM: Homo sapiens

<400> SEQUENCE: 59

Met Asp Asp Asp Ile Ala Ala Leu Val Val Asp Asn Gly Ser Gly Met
1               5                   10                  15

Cys Lys Ala Gly Phe Ala Gly Asp Asp Ala Pro Arg Ala Val Phe Pro
            20                  25                  30

Ser Ile Val Gly Arg Pro Arg His Gln Gly Val Met Val Gly Met Gly
        35                  40                  45

Gln Lys Asp Ser Tyr Val Gly Asp Glu Ala Gln Ser Lys Arg Gly Ile
    50                  55                  60

Leu Thr Leu Lys Tyr Pro Ile Glu His Gly Ile Val Thr Asn Trp Asp
65                  70                  75                  80

Asp Met Glu Lys Ile Trp His His Thr Phe Tyr Asn Glu Leu Arg Val
                85                  90                  95

Ala Pro Glu Glu His Pro Val Leu Leu Thr Glu Ala Pro Leu Asn Pro
            100                 105                 110

Lys Ala Asn Arg Glu Lys Met Thr Gln Ile Met Phe Glu Thr Phe Asn
        115                 120                 125

Thr Pro Ala Met Tyr Val Ala Ile Gln Ala Val Leu Ser Leu Tyr Ala
    130                 135                 140

Ser Gly Arg Thr Thr Gly Ile Val Met Asp Ser Gly Asp Gly Val Thr
145                 150                 155                 160

His Thr Val Pro Ile Tyr Glu Gly Tyr Ala Leu Pro His Ala Ile Leu
                165                 170                 175

Arg Leu Asp Leu Ala Gly Arg Asp Leu Thr Asp Tyr Leu Met Lys Ile
            180                 185                 190

Leu Thr Glu Arg Gly Tyr Ser Phe Thr Thr Thr Ala Glu Arg Glu Ile
        195                 200                 205

Val Arg Asp Ile Lys Glu Lys Leu Cys Tyr Val Ala Leu Asp Phe Glu
    210                 215                 220

Gln Glu Met Ala Thr Ala Ala Ser Ser Ser Ser Leu Glu Lys Ser Tyr
225                 230                 235                 240

Glu Leu Pro Asp Gly Gln Val Ile Thr Ile Gly Asn Glu Arg Phe Arg
                245                 250                 255

Cys Pro Glu Ala Leu Phe Gln Pro Ser Phe Leu Gly Met Glu Ser Cys
            260                 265                 270

Gly Ile His Glu Thr Thr Phe Asn Ser Ile Met Lys Cys Asp Val Asp
        275                 280                 285

Ile Arg Lys Asp Leu Tyr Ala Asn Thr Val Leu Ser Gly Gly Thr Thr
```

```
    290                 295                 300

Met Tyr Pro Gly Ile Ala Asp Arg Met Gln Lys Glu Ile Thr Ala Leu
305                 310                 315                 320

Ala Pro Ser Thr Met Lys Ile Lys Ile Ile Ala Pro Pro Glu Arg Lys
                325                 330                 335

Tyr Ser Val Trp Ile Gly Gly Ser Ile Leu Ala Ser Leu Ser Thr Phe
            340                 345                 350

Gln Gln Met Trp Ile Ser Lys Gln Glu Tyr Asp Glu Ser Gly Pro Ser
        355                 360                 365

Ile Val His Arg Lys Cys Phe
    370                 375


<210> SEQ ID NO 60
<211> LENGTH: 375
<212> TYPE: PRT
<213> ORGANISM: Murine sp.

<400> SEQUENCE: 60

Met Asp Asp Asp Ile Ala Ala Leu Val Val Asp Asn Gly Ser Gly Met
1               5                   10                  15

Cys Lys Ala Gly Phe Ala Gly Asp Asp Ala Pro Arg Ala Val Phe Pro
            20                  25                  30

Ser Ile Val Gly Arg Pro Arg His Gln Gly Val Met Val Gly Met Gly
        35                  40                  45

Gln Lys Asp Ser Tyr Val Gly Asp Glu Ala Gln Ser Lys Arg Gly Ile
    50                  55                  60

Leu Thr Leu Lys Tyr Pro Ile Glu His Gly Ile Val Thr Asn Trp Asp
65                  70                  75                  80

Asp Met Glu Lys Ile Trp His His Thr Phe Tyr Asn Glu Leu Arg Val
                85                  90                  95

Ala Pro Glu Glu His Pro Val Leu Leu Thr Glu Ala Pro Leu Asn Pro
            100                 105                 110

Lys Ala Asn Arg Glu Lys Met Thr Gln Ile Met Phe Glu Thr Phe Asn
        115                 120                 125

Thr Pro Ala Met Tyr Val Ala Ile Gln Ala Val Leu Ser Leu Tyr Ala
    130                 135                 140

Ser Gly Arg Thr Thr Gly Ile Val Met Asp Ser Gly Asp Gly Val Thr
145                 150                 155                 160

His Thr Val Pro Ile Tyr Glu Gly Tyr Ala Leu Pro His Ala Ile Leu
                165                 170                 175

Arg Leu Asp Leu Ala Gly Arg Asp Leu Thr Asp Tyr Leu Met Lys Ile
            180                 185                 190

Leu Thr Glu Arg Gly Tyr Ser Phe Thr Thr Thr Ala Glu Arg Glu Ile
        195                 200                 205

Val Arg Asp Ile Lys Glu Lys Leu Cys Tyr Val Ala Leu Asp Phe Glu
    210                 215                 220

Gln Glu Met Ala Thr Ala Ala Ser Ser Ser Ser Leu Glu Lys Ser Tyr
225                 230                 235                 240

Glu Leu Pro Asp Gly Gln Val Ile Thr Ile Gly Asn Glu Arg Phe Arg
                245                 250                 255

Cys Pro Glu Ala Leu Phe Gln Pro Ser Phe Leu Gly Met Glu Ser Cys
            260                 265                 270

Gly Ile His Glu Thr Thr Phe Asn Ser Ile Met Lys Cys Asp Val Asp
        275                 280                 285
```

-continued

```
Ile Arg Lys Asp Leu Tyr Ala Asn Thr Val Leu Ser Gly Gly Thr Thr
    290                 295                 300

Met Tyr Pro Gly Ile Ala Asp Arg Met Gln Lys Glu Ile Thr Ala Leu
305                 310                 315                 320

Ala Pro Ser Thr Met Lys Ile Lys Ile Ile Ala Pro Pro Glu Arg Lys
                325                 330                 335

Tyr Ser Val Trp Ile Gly Gly Ser Ile Leu Ala Ser Leu Ser Thr Phe
            340                 345                 350

Gln Gln Met Trp Ile Ser Lys Gln Glu Tyr Asp Glu Ser Gly Pro Ser
        355                 360                 365

Ile Val His Arg Lys Cys Phe
    370                 375


<210> SEQ ID NO 61
<211> LENGTH: 29
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 61

tgttggatac aggccagact ttgttggat                                    29


<210> SEQ ID NO 62
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 62

ctggtgaaaa ggacctctcg                                              20


<210> SEQ ID NO 63
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 63

tgaagtactc attatagtca agggca                                       26


<210> SEQ ID NO 64
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 64

agccaccccc actcctaaga ggagg                                        25


<210> SEQ ID NO 65
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
```

<400> SEQUENCE: 65
gaagtccctc accctcccaa 20

<210> SEQ ID NO 66
<211> LENGTH: 16
<212> TYPE: DNA
<213> ORGANISM: Artificial Sequence
<220> FEATURE:
<223> OTHER INFORMATION: Description of Artificial Sequence: Synthetic primer

<400> SEQUENCE: 66
ggcatggacg cgacca 16

<210> SEQ ID NO 67
<211> LENGTH: 28
<212> TYPE: DNA
<213> ORGANISM: Artificial Sequence
<220> FEATURE:
<223> OTHER INFORMATION: Description of Artificial Sequence: Synthetic probe

<400> SEQUENCE: 67
tctgcaagag acttccatcc agttgcct 28

<210> SEQ ID NO 68
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 68
ccagaaaccg ctatgaagtt cc 22

<210> SEQ ID NO 69
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 69
tcaccagcat cagtcccaag 20

<210> SEQ ID NO 70
<211> LENGTH: 27
<212> TYPE: DNA
<213> ORGANISM: Artificial Sequence
<220> FEATURE:
<223> OTHER INFORMATION: Description of Artificial Sequence: Synthetic probe

<400> SEQUENCE: 70
tctgggaagc tcagtgccgc caccagc 27

<210> SEQ ID NO 71
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 71
ctccagaagg ccctcagact ac 22

<210> SEQ ID NO 72
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 72
agctttccct ccgcattgac acag 24

<210> SEQ ID NO 73
<211> LENGTH: 28
<212> TYPE: DNA
<213> ORGANISM: Artificial Sequence
<220> FEATURE:
<223> OTHER INFORMATION: Description of Artificial Sequence: Synthetic probe

<400> SEQUENCE: 73
atcctaccca ctgctggcaa atggagtc 28

<210> SEQ ID NO 74
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 74
cccaggaaag acagcaacct t 21

<210> SEQ ID NO 75
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 75
ttctcacaac caggccactt g 21

<210> SEQ ID NO 76
<211> LENGTH: 27
<212> TYPE: DNA
<213> ORGANISM: Artificial Sequence
<220> FEATURE:
<223> OTHER INFORMATION: Description of Artificial Sequence: Synthetic probe

<400> SEQUENCE: 76
aagggcttct tccgccgcag ccagcag 27

<210> SEQ ID NO 77
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 77

```
ccgctgagag ggcttcac                                                18


<210> SEQ ID NO 78
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 78

tgcaggagta ggccacatta ca                                           22


<210> SEQ ID NO 79
<211> LENGTH: 27
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 79

ccgggagaac tttgagtcca tgtacgc                                      27


<210> SEQ ID NO 80
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 80

caacaacccc tttgccaaag                                              20


<210> SEQ ID NO 81
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 81

tcccccaagc agttgacagt                                              20


<210> SEQ ID NO 82
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 82

tgagcacctg cttcatcagg tagca                                        25


<210> SEQ ID NO 83
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 83

tccgaggagt cagtgctaaa                                              20
```

<210> SEQ ID NO 84
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 84
agaacgtctt ccagggtgaa 20

<210> SEQ ID NO 85
<211> LENGTH: 23
<212> TYPE: DNA
<213> ORGANISM: Artificial Sequence
<220> FEATURE:
<223> OTHER INFORMATION: Description of Artificial Sequence: Synthetic probe

<400> SEQUENCE: 85
tgcagcaagt gggcatgtgt tcc 23

<210> SEQ ID NO 86
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 86
ctcaggatcg ctattacaat tcctc 25

<210> SEQ ID NO 87
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 87
ttccaacgtt gcatcctagg atc 23

<210> SEQ ID NO 88
<211> LENGTH: 22
<212> TYPE: DNA
<213> ORGANISM: Artificial Sequence
<220> FEATURE:
<223> OTHER INFORMATION: Description of Artificial Sequence: Synthetic probe

<400> SEQUENCE: 88
tctggccgtc ttcaccatgt ca 22

<210> SEQ ID NO 89
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 89
cttagccagt cccgaaacct 20

<210> SEQ ID NO 90
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 90
ttggtcccgt gtgatgtct 19

<210> SEQ ID NO 91
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 91

```
Ile Ser Gln Ala Val His Ala Ala His Ala Glu Ile Asn Glu Ala Gly
1               5                   10                  15

Arg
```

<210> SEQ ID NO 92
<211> LENGTH: 189
<212> TYPE: PRT
<213> ORGANISM: Homo sapiens

<400> SEQUENCE: 92

```
Met Leu Gly Ser Arg Ala Val Met Leu Leu Leu Leu Leu Pro Trp Thr
1               5                   10                  15

Ala Gln Gly Arg Ala Val Pro Gly Gly Ser Ser Pro Ala Trp Thr Gln
            20                  25                  30

Cys Gln Gln Leu Ser Gln Lys Leu Cys Thr Leu Ala Trp Ser Ala His
        35                  40                  45

Pro Leu Val Gly His Met Asp Leu Arg Glu Glu Gly Asp Glu Glu Thr
    50                  55                  60

Thr Asn Asp Val Pro His Ile Gln Cys Gly Asp Gly Cys Asp Pro Gln
65                  70                  75                  80

Gly Leu Arg Asp Asn Ser Gln Phe Cys Leu Gln Arg Ile His Gln Gly
                85                  90                  95

Leu Ile Phe Tyr Glu Lys Leu Leu Gly Ser Asp Ile Phe Thr Gly Glu
            100                 105                 110

Pro Ser Leu Leu Pro Asp Ser Pro Val Gly Gln Leu His Ala Ser Leu
        115                 120                 125

Leu Gly Leu Ser Gln Leu Leu Gln Pro Glu Gly His His Trp Glu Thr
    130                 135                 140

Gln Gln Ile Pro Ser Leu Ser Pro Ser Gln Pro Trp Gln Arg Leu Leu
145                 150                 155                 160

Leu Arg Phe Lys Ile Leu Arg Ser Leu Gln Ala Phe Val Ala Val Ala
                165                 170                 175

Ala Arg Val Phe Ala His Gly Ala Ala Thr Leu Ser Pro
            180                 185
```

<210> SEQ ID NO 93
<211> LENGTH: 196
<212> TYPE: PRT
<213> ORGANISM: Murine sp.

```
<400> SEQUENCE: 93

Met Leu Asp Cys Arg Ala Val Ile Met Leu Trp Leu Leu Pro Trp Val
1               5                   10                  15

Thr Gln Gly Leu Ala Val Pro Arg Ser Ser Ser Pro Asp Trp Ala Gln
            20                  25                  30

Cys Gln Gln Leu Ser Arg Asn Leu Cys Met Leu Ala Trp Asn Ala His
        35                  40                  45

Ala Pro Ala Gly His Met Asn Leu Leu Arg Glu Glu Glu Asp Glu Glu
    50                  55                  60

Thr Lys Asn Asn Val Pro Arg Ile Gln Cys Glu Asp Gly Cys Asp Pro
65                  70                  75                  80

Gln Gly Leu Lys Asp Asn Ser Gln Phe Cys Leu Gln Arg Ile Arg Gln
                85                  90                  95

Gly Leu Ala Phe Tyr Lys His Leu Leu Asp Ser Asp Ile Phe Lys Gly
            100                 105                 110

Glu Pro Ala Leu Leu Pro Asp Ser Pro Met Glu Gln Leu His Thr Ser
        115                 120                 125

Leu Leu Gly Leu Ser Gln Leu Leu Gln Pro Glu Asp His Pro Arg Glu
    130                 135                 140

Thr Gln Gln Met Pro Ser Leu Ser Ser Ser Gln Gln Trp Gln Arg Pro
145                 150                 155                 160

Leu Leu Arg Ser Lys Ile Leu Arg Ser Leu Gln Ala Phe Leu Ala Ile
                165                 170                 175

Ala Ala Arg Val Phe Ala His Gly Ala Ala Thr Leu Thr Glu Pro Leu
            180                 185                 190

Val Pro Thr Ala
        195
```